United States Patent
Bedi et al.

(10) Patent No.: US 12,295,968 B2
(45) Date of Patent: *May 13, 2025

(54) COMPOSITIONS AND METHODS FOR TARGETED IMMUNOMODULATORY ANTIBODIES AND FUSION PROTEINS

(71) Applicant: The Johns Hopkins University, Baltimore, MD (US)

(72) Inventors: Atul Bedi, Timonium, MD (US); Rajani Ravi, Ruxton, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/883,719

(22) Filed: Sep. 12, 2024

(65) Prior Publication Data

US 2025/0009772 A1 Jan. 9, 2025

Related U.S. Application Data

(60) Continuation of application No. 17/694,541, filed on Mar. 14, 2022, which is a continuation of application
(Continued)

(51) Int. Cl.
| | | |
|---|---|---|
| C07K 14/71 | (2006.01) | |
| A61K 31/704 | (2006.01) | |
| A61K 38/17 | (2006.01) | |
| A61K 39/395 | (2006.01) | |
| A61K 45/06 | (2006.01) | |
| A61K 47/68 | (2017.01) | |
| C07K 14/495 | (2006.01) | |
| C07K 14/705 | (2006.01) | |
| C07K 16/28 | (2006.01) | |
| C07K 16/30 | (2006.01) | |

(Continued)

(52) U.S. Cl.
CPC .......... *A61K 31/704* (2013.01); *A61K 38/179* (2013.01); *A61K 39/3955* (2013.01); *A61K 39/39558* (2013.01); *A61K 45/06* (2013.01); *A61K 47/6803* (2017.08); *C07K 14/495* (2013.01); *C07K 14/70532* (2013.01); *C07K 14/70575* (2013.01); *C07K 14/70578* (2013.01); *C07K 14/70596* (2013.01); *C07K 14/71* (2013.01); *C07K 16/28* (2013.01); *C07K 16/2812* (2013.01); *C07K 16/2815* (2013.01); *C07K 16/2827* (2013.01); *C07K 16/2851* (2013.01); *C07K 16/2863* (2013.01); *C07K 16/2866* (2013.01); *C07K 16/30* (2013.01); *C07K 19/00* (2013.01); *A61K 2039/505* (2013.01); *A61K 2039/572* (2013.01); *C07K 2317/33* (2013.01); *C07K 2317/526* (2013.01); *C07K 2317/622* (2013.01); *C07K 2317/73* (2013.01); *C07K 2317/76* (2013.01); *C07K 2319/00* (2013.01); *C07K 2319/70* (2013.01)

(58) Field of Classification Search
CPC .... C07K 16/2863; C07K 14/71; C07K 19/00; C07K 2319/00; C07K 2319/31; C07K 2319/32; C07K 2319/33; C07K 2319/35; C07K 14/70596; C07K 14/70578; C07K 14/70575; C07K 16/2866; C07K 16/30; A61K 39/3955; A61K 2039/505; A61K 38/1793; A61K 38/179
See application file for complete search history.

(56) References Cited

U.S. PATENT DOCUMENTS

| | | |
|---|---|---|
| 7,317,091 B2 | 1/2008 | Lazar et al. |
| 7,527,791 B2 | 5/2009 | Adams et al. |

(Continued)

FOREIGN PATENT DOCUMENTS

| | | |
|---|---|---|
| WO | WO 2009/062399 A1 | 5/2009 |
| WO | WO 2009/152610 A1 | 12/2009 |
| WO | WO 2010/003118 A1 | 1/2010 |

OTHER PUBLICATIONS

Huang et al. A Yeast Platform for the Production of Single-Chain Antibody—Green Fluorescent Protein Fusions. Appl Environmental Microbiol 72(12): 7748-7759, 2006.*
Schmidt et al. Suppression of metastasis formation by a recombinant single chain antibody-toxin targeted to full-length and oncogenic variant EGF receptors. Oncogene 18: 1711-1721, 1999.*
Alignment of SEQ ID No. 10 of D3 with SEQ ID No. 87 of B1.
Alignment of SEQ ID No. 744 of D2 with SEQ ID No. 87 of B1.
Canadian Office Action dated Mar. 28, 2018, regarding CA 2,791,383.

(Continued)

*Primary Examiner* — Bridget E Bunner
(74) *Attorney, Agent, or Firm* — DLA Piper LLP (US)

(57) ABSTRACT

The present invention is based on the seminal discovery that targeted immunomodulatory antibodies and fusion proteins can counter act or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immunosuppressive mechanisms include immunosuppressive cytokines (for example, Transforming growth factor beta (TGF-β)) and regulatory T cells and/or immunosuppressive myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor immunity against resistant or disseminated cancer cells.

9 Claims, 75 Drawing Sheets

Specification includes a Sequence Listing.

Related U.S. Application Data

No. 16/601,347, filed on Oct. 14, 2019, now Pat. No. 11,274,156, which is a continuation of application No. 15/362,632, filed on Nov. 28, 2016, now Pat. No. 10,442,860, which is a division of application No. 15/231,309, filed on Aug. 8, 2016, now Pat. No. 9,850,306, which is a continuation of application No. 14/645,282, filed on Mar. 11, 2015, now Pat. No. 9,441,044, which is a continuation of application No. 13/582,717, filed as application No. PCT/US2011/027317 on Mar. 4, 2011, now Pat. No. 8,993,524.

(60) Provisional application No. 61/435,671, filed on Jan. 24, 2011, provisional application No. 61/311,255, filed on Mar. 5, 2010.

(51) Int. Cl.
*C07K 19/00* (2006.01)
*A61K 38/18* (2006.01)
*A61K 39/00* (2006.01)

(56) References Cited

U.S. PATENT DOCUMENTS

| | | | |
|---|---|---|---|
| 7,795,389 B2 | 9/2010 | Sun et al. | |
| 7,803,378 B2 | 9/2010 | Tranchanf-Bunel | |
| 7,820,165 B2 | 10/2010 | McKenna et al. | |
| 8,101,720 B2 | 1/2012 | Lazar et al. | |
| 8,114,845 B2 | 2/2012 | Langermann et al. | |
| 8,399,618 B2 | 3/2013 | Lazar et al. | |
| 8,815,247 B2 | 8/2014 | Govindappa et al. | |
| 8,993,524 B2 * | 3/2015 | Bedi | C07K 16/2866 514/19.2 |
| 9,441,044 B2 * | 9/2016 | Bedi | A61K 39/39558 |
| 9,850,306 B2 * | 12/2017 | Bedi | C07K 16/2866 |
| 11,274,156 B2 * | 3/2022 | Bedi | A61K 45/06 |
| 2005/0054832 A1 | 3/2005 | Lazar et al. | |
| 2006/0135459 A1 | 6/2006 | Epstein et al. | |
| 2006/0193849 A1 | 8/2006 | Krauss et al. | |
| 2006/0263368 A1 | 11/2006 | Rosenblum et al. | |
| 2007/0212337 A1 | 9/2007 | Bedi et al. | |
| 2007/0244042 A1 | 10/2007 | Sun et al. | |
| 2008/0075717 A1 | 3/2008 | Tranchand-Bunel | |
| 2009/0053240 A1 | 2/2009 | Lazar et al. | |
| 2009/0214533 A1 | 8/2009 | Clynes | |
| 2009/0226435 A1 | 9/2009 | Sanjay | |
| 2011/0052585 A1 | 3/2011 | Scaria et al. | |
| 2013/0017199 A1 | 1/2013 | Langermann | |

OTHER PUBLICATIONS

Carter et al., "Identification and Validation of Cell Surface Antigens for Antibody Targeting in Oncology", Endocr. Relat. Cancer, Dec. 2004, 11(4):659-687.
Coffelt et al., "Angiopoietin 2 Stimulates TIE2-Expressing Monocytes to Suppress T Cell Activation and to Promote Regulatory T Cell Expression"; The Journal of Immunology 2011, 186 (7), p. 4183-4190.
Contardi et al., Int. J. Cancer: 117, 538-550; 2005.
EP Communication dated Sep. 5, 2018, pursuant to Rule 114(2) EPC regarding EP 2542590.
EP Third Party Observation in European Application No. EP20200205164 dated Apr. 5, 2022, 10 pages.
European Search Report and Search Opinion Received for EP Application No. 17168491.3, mailed on Nov. 24, 2017, 5 pages.
Fernandez-Botran et al., "Soluble cytokine receptors in biological therapy"; Expert Opinion on Biological Therapy, 2002, vol. 2, Issue 6, p. 585-605.
Fonseca et al., "Capitalizing on the immunogenicity of Dying Tumor Cells"; Clinical Cancer Research 2008, 14 (6), p. 1603-1608.

Francisco et al, "PD-L1 Regulates the Development, Maintenance, and Function of Induced Regulatory T Cells", J. Exp. Med., Dec. 2009, 206(13):3015-3029.
Haier et al., "Cell Surface Molecules and Their Prognostic Values in Assessing Colorectal Carcinomas", Annal Surgery, Jan. 2000, 231(1):11-24.
IN Examination Report in Indian Application No. 201948021756 dated Jan. 24, 2022, 6 pages.
International Preliminary Report on Patentability received for PCT Patent Application No. PCT/US2011/027317, mailed on Sep. 20, 2012, 9 pages.
International Search Report and Written Opinion received for PCT Patent Application No. PCT/US2011/027317, mailed on Feb. 8, 2012, 11 pages.
Japanese Office Action issued on May 27, 2020, regarding JP 2018-140050.
JP Office Action in Japanese Application No. 2021-094042 dated Aug. 1, 2022, 6 pages (with English translation).
Jones et al., "Degree of CD25 expression in T-Cell lymphoma is dependent on tissue site: implications for targeted therapy", Clinical Cancer Research, 2004, 10:5587-5594.
Jung et al.: "Double anti-angiogenic and anti-inflammatory protein valpha targeting VEGF-A and TNF-.alpha. in retinopathy and psoriasis"; JBC, vol. 286, No. 16, Feb. 23, 2011, pp. 14410-14418.
Koh et al.: "Double anti-angiogenic protein, DAAP, targeting VEGF-A and angiopoietins in tumor angiogenesis, metastasis, and vascular leakage"; Cancer Cell, vol. 18, Issue 2, Aug. 16, 2010, p. 171-184. Supplementary data, 28 pages.
Kwiatkowska et al.: "Expression of soluble recombinant TGF-.beta. type II receptor fused with the Fc portion of human IgG1 (sT.beta. 11-Fc) in NSO cells"; Acta Biochimica Polonica, 2006, 53(2), pp. 361-369.
Letourneau et al,: "IL-2- and CD25-dependent immunoregulatory mechanisms in the homeostasis of T-cell subsets"; J Allergy Clin Immunol. 2009, 123(4), pp. 758-762.
Malek et al.: "Interleukin-2 receptor signaling: at the interface between tolerance and immunity"; Immunity 2010, vol. 33, Issue 2, p. 153-165.
Office Action received for European Application No. 11751481.0, mailed on Jan. 22, 2016, 3 pages.
Podar et al.: "Inhibition of the TGF-.beta. signaling pathway in tumor cells"; Recent Results in Cancer Research, 2007, vol. 172, p. 77-97.
Regnault et al.: "Fc.gamma. Receptor-mediated Induction of Dendritic Cell Maturation and Major Histocompatibility Complex Class I-restricted Antigen Presentation after Immune Complex Internalization"; J. Exp. Med., 1999, vol. 189, No. 2, p. 371-380.
Rose-John et al. 2007. Expert Opinion in Therapeutic Targets. 11:613-624.
Schrama et al.: "Antibody targeted drugs as cancer therapeutics"; Nature Reviews Drug Discovery, Jan. 20, 2006, vol. 5, p. 147-159.
Supplementary European Search Report received for EP Patent Application No. 11751481.0, mailed on Jun. 27, 2013, 16 pages.
Trail et al.: "Monoclonal antibody drug conjugates in the treatment of cancer"; Current Opinion in Immunology, 1999, vol. 11, Issue 5, p. 584-588.
U.S. Appl. No. 61/311;255, Mar. 5, 2010, Atul Bedi.
U.S. Appl. No. 61/435,671, filed Jan. 24, 2011, Atul Bedi.
Wang et al.: "Tumor necrosis factor and cancer, buddies or foes?"; Acta Pharmacologica Sinica, 2008, 29 (11), p. 1275-1288.
Yang et al.: "The role of T.sub.reg in the cancer immunological response"; American Journal of Immunology, 2009, 5 (1), p. 17-28.
Yao and Chen: "Contribution of B7-H1/PD-1 Co-inhibitory Pathway to T-Cell Dysfunction in Cancer"; D.I. Gabrilovich, A.A. Hurwitz (eds.), Tumor-Induced Immune Suppression. pp. 29-40 .COPYRGT. Springer 2008.
Zhang et al., "Design and Optimization of a Linker for Fusion Protein Construction," Prog. Natural Sci. (2009), 19:1197-1200, Elsevier.

(56) References Cited

OTHER PUBLICATIONS

Zhang et al: "Expression of a Soluble TGF-.beta. Receptor by Tumor Cells Enhances Dendritic Cell/Tumor FusionVaccine Efficacy. sup.1"; J. Immunology, 2008, 181, pp. 3690-3697.

* cited by examiner

1. Amino acid sequences of transforming growth factor beta receptor type II (TGF-β-RII) or TGF-β-RIIB or a fragment thereof:

(i) Transforming growth factor beta receptor type II (TGF-β-RII) (SEQ ID NO: 79):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDN VLRDRGRPEI PSFWLNHQGI QMVCETLTEC WDHDPEARLT AQCVAERFSE
LEHLDRLSGR SCSEEKIPED GSLNTTK
```

[Italic — Extracellular domain of Transforming growth factor beta Receptor II (TGFβ RII)]
[Underlined = TGFβ RII Extracellular domain (ECD) region that binds TGF-β)]

(ii) Transforming growth factor beta receptor type IIB (TGF-β-RIIB) (SEQ ID NO: 80):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSSTWETGK TRKLMEFSEH
CAIILEDDRS DISSTCANNI NHNTELLPIE LDTLVGKGRF AEVYKAKLKQ NTSEQFETVA VKI FP
YEEYASWKTE KDIFSDINLK HENILQFLTA EERKTELGKQ YWLITAFHAK GNLQEYLTRH
VISWEDLRKL GSSLARGIAH LHSDHTPCGR PKMPIVHRDL KSSNILVKND LTCCLCDFGL
SLRLDPTLSV DDLANSGQVG TARYMAPEVL ESRMNLENVE SFKQTDVYSM ALVLWEMTSR
CNAVGEVKDY EPPFGSKVRE HPCVESMKDN VLRDRGRPEI PSFWLNHQGI QMVCETLTEC
WDHDPEARLT AQCVAERFSE LEHLDRLSGR SCSEEKIPED GSLNTTK
```

[Italic — Extracellular domain of Transforming growth factor beta Receptor IIB (TGFβ RIIB)]
[Underlined = TGFβ RIIB Extracellular domain (ECD) region that binds TGF-β)]

2. Truncated mutants of Transforming growth factor beta Receptor II (TGF-β-RII) or TGF-β-RIIB comprising the Extracellular domain (ECD) region that binds TGF-β

(i) TGF-β R-II (ΔC terminus): TGFβ RII lacking the last 38 amino acids from the C-terminus (SEQ ID NO: 81):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDN VLRDRGRPEI PSFWLNHQGI QMVCETLTEC WDHDPEARL
```

FIG. 1A

TGF-β R-IIB (ΔC terminus): TGFβ RIIB lacking the last 38 aa from the C-terminus (SEQ ID NO: 82):

```
      MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSSTWETGK TRKLMEFSEH
CAIILEDDRS DISSTCANNI NHNTELLPIE LDTLVGKGRF AEVYKAKLKQ NTSEQFETVA VKI FP
YEEYASWKTE KDIFSDINLK HENILQFLTA EERKTELGKQ YWLITAFHAK GNLQEYLTRH
VISWEDLRKL GSSLARGIAH LHSDHTPCGR PKMPIVHRDL KSSNILVKND LTCCLCDFGL
SLRLDPTLSV DDLANSGQVG TARYMAPEVL ESRMNLENVE SFKQTDVYSM ALVLWEMTSR
CNAVGEVKDY EPPFGSKVRE HPCVESMKDN VLRDRGRPEI PSFWLNHQGI QMVCETLTEC
WDHDPEARL
```

(ii) TGF-βR-II (Δcyt): TGFβRII lacking the kinase domain & juxtamembrane region (SEQ ID NO: 83):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSS
```

TGF-βR-IIB (Δcyt): TGFβRIIB lacking the kinase domain & juxtamembrane region (SEQ ID NO: 84):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF QVTGISLLPP LGVAISVIII FYCYRVNRQQ KLSS
```

(iii) TGF-β R-II containing the N-terminus region including the extracellular domain (SEQ ID NO: 85):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQ
```

TGF-β R-IIB containing the N-terminus region including the extracellular domain (SEQ ID NO: 86):

```
MGRGLLRGLW PLHIVLWTRI ASTIPPHVQK SDVEMEAQKD EIICPSCNRT AHPLRHINND
MIVTDNNGAV KFPQLCKFCD VRFSTCDNQK SCMSNCSITS ICEKPQEVCV AVWRKNDENI
TLETVCHDPK LPYHDFILED AASPKCIMKE KKKPGETFFM CSCSSDECND NIIFSEEYNT
SNPDLLLVIF Q
```

(iv) TGF-β R-II containing the extracellular domain that binds TGF-β (SEQ ID NO: 87):

```
TIPPHVQK SVNNDMIVTD NNGAVKFPQL CKFCDVRFST CDNQKSCMSN CSITSICEKP
QEVCVAVWRK NDENITLETV CHDPKLPYHD FILEDAASPK CIMKEKKKPG ETFFMCSCSS
DECNDNIIFS EEYNTSNPD
```

TGF-β R-IIB containing the extracellular domain that binds TGF-β (SEQ ID NO: 88):

```
TIPPHVQK SDVEMEAQKD EIICPSCNRT AHPLRHINND MIVTDNNGAV KFPQLCKFCD
VRFSTCDNQK SCMSNCSITS ICEKPQEVCV AVWRKNDENI TLETVCHDPK LPYHDFILED
AASPKCIMKE KKKPGETFFM CSCSSDECND NIIFSEEYNT SNPD
```

(v) TGF-β R-II containing the region of the extracellular domain that binds TGF-β (SEQ ID NO: 89):

```
PQL CKFCDVRFST CDNQKSCMSN CSITSICEKP QEVCVAVWRK NDENITLETV CHDPKLPYHD
FILEDAASPK CIMKEKKKPG ETFFMCSCSS DECNDNIIFS EEYNTSNPD
```

FIG. 1B

3. Kinase-deficient mutants, deletion mutants, or point mutants of Transforming growth factor beta Receptor II (TGFβ-RII) or TGFβ-RIIB or a fragment thereof which binds TGF-β

(i) Transforming growth factor beta Receptor II containing point mutations:

Amino acid sequence of TGF-β R-II (K277R) contains a point mutation in its ATP-binding site and is inactive as a kinase (SEQ ID NO: 90):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVRIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
LEHLDRLSGR SCSEEKIPED GSLNTTK
```

(ii) Transforming growth factor beta Receptor II containing deletions in the amino acid sequence (deletion mutants): Transforming growth factor beta Receptor II (Δi)

TGF-β R-II (Δi2) contains a deletion of amino acids 498 to 508 and is inactive as a kinase (SEQ ID NO: 91):

```
MGRGLLRGLW PLHIVLWTRI ASTIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPDL LLVIFQVTGI SLLPPLGVAI
SVIIIFYCYR VNRQQKLSST WETGKTRKLM EFSEHCAIIL EDDRSDISST CANNINHNTE
LLPIELDTLV GKGRFAEVYK AKLKQNTSEQ FETVAVKIFP YEEYASWKTE KDIFSDINLK
HENILQFLTA EERKTELGKQ YWLITAFHAK GNLQEYLTRH VISWEDLRKL GSSLARGIAH
LHSDHTPCGR PKMPIVHRDL KSSNILVKND LTCCLCDFGL SLRLDPTLSV DDLANSGQVG
TARYMAPEVL ESRMNLENVE SFKQTDVYSM ALVLWEMTSR CNAVGEVKDY EPPFGSKVRE
HPCVESMKDA SGIQMVCETL TECWDHDPEA RLTAQCVAER FSELEHLDRL SGRSCSEEKI
PEDGSLNTTK
```

4. Amino acid sequences of transforming growth factor beta receptor type III (TGF-β-RIII) or or a fragment thereof.

5. Hybrid or fusion proteins containing amino acid sequences of transforming growth factor beta receptor type II (TGF-β-RII) and TGF-β-RIII.

6. Hybrid or fusion proteins containing amino acid sequences of transforming growth factor beta receptor type IIB (TGF-β-RIIB) and TGF-β-RIII.

Linker sequence used in fusion proteins (SEQ ID NO: 104):

GGGGSGGGGSGGGGS

FIG. 1C

Fusion proteins comprising Anti-HER2/neu antibody and Transforming growth factor-beta receptor II (TGFβ-RII) Extracellular domain (ECD).

Anti-HER2/neu heavy chain + TGFβ-RII ECD fusion amino acid sequence (SEQ ID NO: 1):

<u>EVQLVESGGGLVQPGGSLRLSCAASGFNIKDTYIHWVRQAPGKGLEWVARIYPTNGYTRYADSVKG</u>
<u>RFTISADTSKNTAYLQMNSLRAEDTAVYYCSRWGGDGFYAMDYWGQGTLVTVSS</u>ASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-HER2/neu light chain amino acid sequence (SEQ ID NO: 70):
<u>DIQMTQSPSSLSASVGDRVTITCRASQDVNTAVAWYQQKPGKAPKLLIYSASFLYSGVPSRFSGSR</u>
<u>SGTDFTLTISSLQPEDFATYYCQQHYTTPPTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: <u>Anti-HER2 antibody variable region</u>
Plain: Anti-HER2 antibody constant region
*Italic: Linker*
Bold: TGFβRII ectodomain

FIG. 2

Fusion proteins comprising Anti-EGFR1 antibody and Transforming growth factor-beta receptor II (TGFβ-RII) Extracellular domain (ECD).

Anti-EGFR1 heavy chain + TGFβ-RII ECD fusion amino acid sequence
(SEQ ID NO: 2):

<u>QVQLKQSGPGLVQPSQSLSITCTVSGFSLTNYGVHWVRQSPGKGLEWLGVIWSGGNTDYNTPFTSR</u>
<u>LSINKDNSKSQVFFKMNSLQSNDTAIYYCARALTYYDYEFAYWGQGTLVTVSA</u>ASTKGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK
*GGGGSGGGGSGGGGS* **TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD**

Anti-EGFR1 light chain amino acid sequence (SEQ ID NO: 71):
<u>DILLTQSPVILSVSPGERVSFSCRASQSIGTNIHWYQQRTNGSPRLLIKYASESISGIPSRFSGSG
SGTDFTLSINSVESEDIADYYCQQNNNWPTTFGAGTKLELK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: <u>Anti-EGFR antibody variable region</u>
Plain: Anti-EGFR antibody constant region
*Italic: Linker*
Bold: TGFβRII ectodomain

FIG. 3

Fusion proteins comprising Anti-CD20 antibody and Transforming growth factor-beta receptor II (TGFβ-RII) Extracellular domain (ECD).

Anti-CD20 heavy chain+ TGFβ-RII ECD fusion amino acid sequence
(SEQ ID NO: 3):

<u>QVQLQQPGAELVKPGASVKMSCKASGYTFTSYNMHWVKQTPGRGLEWIGAIYPGNGDTSYNQKFKG</u>
<u>KATLTADKSSSTAYMQLSSLTSEDSAVYYCARSTYYGGDWYFNVWGAGTTVTVSA</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-CD20 light chain amino acid sequence (SEQ ID NO: 72):
<u>QIVLSQSPAILSASPGEKVTMTCRASSSVSYIHWFQQKPGSSPKPWIYATSNLASGVPVRFSGSGS</u>
<u>GTSYSLTISRVEAEDAATYYCQQWTSNPPTFGGGTKLEIK</u>RTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC <u>Underlined</u>: <u>Anti-CD20 antibody variable region</u>
    Plain: Anti-CD20 antibody constant region
    *Italic: Linker*
    Bold: TGFβRII ectodomain

FIG. 4

Fusion proteins comprising anti-VEGF antibody and Transforming growth factor-beta receptor II (TGFβ-RII) Extracellular domain (ECD).

Anti-VEGF heavy chain+ TGFβ-RII ECD fusion amino acid sequence
(SEQ ID NO: 4):

<u>EVQLVESGGGLVQPGGSLRLSCAASGYTFTNYGMNWVRQAPGKGLEWVGWINTYTGEPTYAADFKR</u>
<u>RFTFSLDTSKSTAYLQMNSLRAEDTAVYYCAKYPHYYGSSHWYFDVWGQGTLVTVSS</u>ASTKGPSVF
PLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK
*GGGGSGGGGSGGGGS* TIPPHVQK SVNNDMIVTD NNGAVKFPQL CKFCDVRFST
CDNQKSCMSN CSITSICEKP QEVCVAVWRK NDENITLETV CHDPKLPYHD FILEDAASPK
CIMKEKKKPG ETFFMCSCSS DECNDNIIFS EEYNTSNPD

Anti-VEGF Light chain sequence (SEQ ID NO: 73):
<u>DIQMTQSPSSLSASVGDRVTITCSASQDISNYLNWYQQKPGKAPKVLIYFTSSLHSGVPSRFSGSG</u>
<u>SGTDFTLTISSLQPEDFATYYCQQYSTVPWTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: <u>Anti-VEGF antibody variable region</u>
Plain: Anti-VEGF antibody constant region
*Italic: Linker*
Bold: TGFβRII ectodomain

FIG. 5

Fusion proteins comprising anti-human CTLA-4 antibody and Transforming growth factor-beta receptor II (TGFβ-RII) Extracellular domain (ECD).

Anti-CTLA-4 heavy chain + TGFβ-RII Extracellular domain fusion amino acid sequence (SEQ ID NO: 5):

<u>QVQLVESGGG VVQPGRSLRL SCAASGFTFS SYTMHWVRQA PGKGLEWVTF ISYDGNNKYY</u>
<u>ADSVKGRFTI SRDNSKNTLY LQMNSLRAED TAIYYCARTG WLGPFDYWGQ GTLVTVSSAS</u>
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPELLGGPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ
GNVFSCSVMH EALHNHYTQK SLSLSPGK *GGGGSGGGGSGGGGS* TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFS EEYNTSNPD

Anti-CTLA-4 light chain (SEQ ID NO: 74):

<u>EIVLTQSPGT LSLSPGERAT LSCRASQSVG SSYLAWYQQK PGQAPRLLIY GAFSRATGIP</u>
<u>DRFSGSGSGT DFTLTISRLE PEDFAVYYCQ QYGSSPWTFG</u> QGTKVEIKRT VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC

<u>Underlined</u>: <u>Anti-CTLA-4 antibody heavy chain variable region</u>
Plain: Anti-CTLA-4 antibody heavy chain constant region
*Italic: Linker*
Bold: TGFβRII ectodomain

FIG. 6

Fusion proteins comprising IL-2, Fc, and Transforming growth factor-beta receptor II (TGFβ-RII) Extracellular domain (ECD).

IL-2 + Fc + TGFβ-RII Extracellular domain (SEQ ID NO: 6):

<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>EEM</u>TKNQVSLTCLVKGFYPSDIAVEWESNGQPENNYKTTPPVLSDGSFFLYSKLTVDKSRWQQG
NVFSCSVMHEALHNHYTQKSLSLSPGK *GGGGSGGGGSGGGGS* TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFSEEYNTSNPD

TGFβ-RII Extracellular domain + Fc + IL-2 (SEQ ID NO: 7):

TIPPHVQK SVNNDMIVTD NNGAVKFPQL CKFCDVRFST CDNQKSCMSN CSITSICEKP
QEVCVAVWRK NDENITLETV CHDPKLPYHD FILEDAASPK CIMKEKKKPG ETFFMCSCSS
DECNDNIIFS EEYNTSNPD *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>EEM</u>TKNQVSLTCLVKGFYPSDIAVEWESNGQPENNYKTTPPVLSDGSFFLYSKLTVDKSRWQQG
NVFSCSVMHEALHNHYTQKSLSLSPGK *GGGGSGGGGSGGGGS*
<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u>

Bold: TGFβRII ectodomain
*Italic: Linker (Optional; other linker sequences)*
Plain: Fc
<u>Underlined: IL-2 fragment</u>
(Note: Can replace linker *GGGGSGGGGSGGGGS* SEQ ID NO: 104 with *EPKSCDK* SEQ ID NO: 105)
(Note: Can replace underlined aa in Fc: <u>E</u> with D and <u>M</u> with L in Fc)

FIG. 7

Fusion proteins comprising anti-CD25 antibody and Transforming growth factor-beta receptor II (TGFβ-RII) Extracellular domain (ECD).

Anti-CD25 (Daclizumab) heavy chain and TGFβ-RII Extracellular domain
(SEQ ID NO: 8):

```
QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK GGGGSGGGGSGGGGS TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFS EEYNTSNPD
```

Anti-CD25 (Daclizumab) light chain (SEQ ID NO: 75):

```
DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC
```

Plain: Anti-CD25 antibody
*Italic: Linker*
Bold: TGFβRII ectodomain

FIG. 8A

Anti-CD25 (Basiliximab) heavy chain and TGFβ-RII Extracellular domain
(SEQ ID NO: 9):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS* **TIPPHVQK SVNNDMIVTD
NNGAVKFPQL CKFCDVRFST CDNQKSCMSN CSITSICEKP QEVCVAVWRK NDENITLETV
CHDPKLPYHD FILEDAASPK CIMKEKKKPG ETFFMCSCSS DECNDNIIFS EEYNTSNPD**

Anti-CD25 (Basiliximab) light chain (SEQ ID NO: 76):
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGE Plain: Anti-CD25 antibody
*Italic: Linker*
Bold: TGFβRII ectodomain

FIG. 8B

Fusion proteins comprising anti-CD4 antibody and Transforming growth factor-beta receptor II (TGFβ-RII) Extracellular domain (ECD).

Anti-CD4 heavy chain and TGFβ-RII Extracellular domain (SEQ ID NO: 10):

Heavy chain fusion protein:

QVQLQEAGPGLVKPSETLSLTCSVSGGSISGDYYWFWIRQSPGKGLEWIGYIYGSGGGTNYNPSLN
NRVSISIDTSKNLFSLKLRSVTAADTAVYYCASNILKYLHWLLYWGQGVLVTVSSASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* TIPPHVQKSVNNDMIVTDNNGAVKFPQLCKFCDVRF
STCDNQKSCMSNCSITSICEKPQEVCVAVWRKNDENITLETVCHDPKLPYHDFILEDAASPKCIMK
EKKKPGETFFMCSCSSDECNDNIIFSEEYNTSNPD

Anti-CD4 light chain (SEQ ID NO: 77):

Light chain:

SYELSQPRSVSVSPGQTAGFTCGGDNVGRKSVQWYQQKPPQAPVLVIYADSERPSGIPARFSGSNS
GNTATLTISGVEAGDEADYYCQVWDSTADHWVFGGGTRLTVLGRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

Plain: Anti-CD4 antibody (variable region – underlined)

*Italic*: *Linker*

Bold: TGFβRII ectodomain

FIG. 9

Fusion proteins comprising PD-1 Ectodomain, Fc, and Transforming growth factor-beta receptor II (TGFβ-RII) Extracellular domain (ectodomain).

PD-1 ectodomain + Fc + TGFβRII ectodomain (SEQ ID NO: 11):

<u>PGWFLDSPDRPWNPPTFSPALLVVTEGDNATFTCSFSNTSESFVLNWYRMSPSNQTDKLAAFPEDR</u>
<u>SQPGQDCRFRVTQLPNGRDFHMSVVRARRNDSGTYLCGAISLAPKAQIKESLRAELRVTERRAEVP</u>
<u>TAHPSPSPRPAGQFQTLV</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD

TGFβRII ectodomain + Fc + PD-1 ectodomain (SEQ ID NO: 12):

TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>PGWFLDSPDRPWNPPTFSPALLVVTEGDNATFTCSFSNTSESFVLNWYRMSPSNQTDKLAAFPEDR</u>
<u>SQPGQDCRFRVTQLPNGRDFHMSVVRARRNDSGTYLCGAISLAPKAQIKESLRAELRVTERRAEVP</u>
<u>TAHPSPSPRPAGQFQTLV</u>

<u>Underlined</u>: PD-1 ectodomain
*Italic*: Linkers
Plain: IgG1 Fc
Bold: TGFβRII ectodomain
(Note: The first linker sequence *GGGGSGGGGSGGGGS* is optional and may be replaced with *EPKSCDK* SEQ ID NO: 105 or deleted)

FIG. 10

Fusion proteins comprising Transforming growth factor-beta receptor II (TGFβ-RII) ectodomain, Fc, and Receptor activator of nuclear factor–κB (RANK) Ectodomain:

TGFβRII ectodomain – Fc - RANK ectodomain (SEQ. ID. NO: 13):

**TIPPHVQKSVNNDMIVTDNNGAVKFPQLCKFCDVRFSTCDNQKSCMSNCSITSICEKPQEVCVAVW
RKNDENITLETVCHDPKLPYHDFILEDAASPKCIMKEKKKPGETFFMCSCSSDECNDNIIFSEEYN
TSNPD***GGGGSGGGGSGGGGS*THTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK *GGGGSGGGGSGGGGS* <u>QI
APPCTSEKHY  EHLGRCCNKC  EPGKYMSSKC  TTTSDSVCLP  CGPDEYLDSW  NEEDKCLLHK
VCDTGKALVA  VVAGNSTTPR  RCACTAGYHW  SQDCECCRRN  TECAPGLGAQ  HPLQLNKDTV
CKPCLAGYFS  DAFSSTDKCR  PWTNCTFLGK  RVEHHGTEKS  DAVCSSSLPA  RKPPNEPHVY  LPG</u>

RANK ectodomain – Fc - TGFβRII ectodomain (SEQ. ID. NO: 14):

<u>QI  APPCTSEKHY  EHLGRCCNKC  EPGKYMSSKC  TTTSDSVCLP  CGPDEYLDSW  NEEDKCLLHK
VCDTGKALVA  VVAGNSTTPR  RCACTAGYHW  SQDCECCRRN  TECAPGLGAQ  HPLQLNKDTV
CKPCLAGYFS  DAFSSTDKCR  PWTNCTFLGK  RVEHHGTEKS  DAVCSSSLPA  RKPPNEPHVY  LPG</u>
*GGGGSGGGGSGGGGS*THTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGKGGGGSGGGGSGGGGS**TIPPHVQKS
VNNDMIVTDNNGAVKFPQLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNIIFSEEYNTSNPD**

Bold: TGFβRII ectodomain

Plain: IgG1 Fc

*Italics: Linker*

<u>Underlined: RANK ectodomain</u>

(optional linker 1 may be deleted or replaced with another linker such as IEGRDMD (SEQ. ID. NO:106) or EPKSCDK (SEQ.ID. NO: 105))

FIG. 11

(i)  Full-length PD-1 or fragment thereof (SEQ ID NO: 92):

```
1    MQIPQAPWPV VWAVLQLGWR PGWFLDSPDR PWNPPTFSPA LLVVTEGDNA TFTCSFSNTS
61   ESFVLNWYRM SPSNQTDKLA AFPEDRSQPG QDCRFRVTQL PNGRDFHMSV VRARRNDSGT
121  YLCGAISLAP KAQIKESLRA ELRVTERRAE VPTAHPSPSP RPAGQFQTLV VGVVGGLLGS
181  LVLLVWVLAV ICSRAARGTI GARRTGQPLK EDPSAVPVFS VDYGELDFQW REKTPEPPVP
241  CVPEQTEYAT IVFPSGMGTS SPARRGSADG PRSAQPLRPE DGHCSWPL
```

*Italic: PD-1 ectodomain*
*Underlined Italic: ligand-binding domain*

(ii)  PD-1 extracellular domain (ectodomain) or fragment thereof (SEQ ID NO: 93):

PGWFLDSPDR PWNPPTFSPA LLVVTEGDNA TFTCSFSNTS ESFVLNWYRM SPSNQTDKLA
AFPEDRSQPG QDCRFRVTQL PNGRDFHMSV VRARRNDSGT YLCGAISLAP KAQIKESLRA
ELRVTERRAE VPTAHPSPSP RPAGQFQTLV (iii)  PD-1 extracellular domain (ectodomain) ligand-binding region (SEQ ID NO: 94):

DSPDR PWNPPTFSPA LLVVTEGDNA TFTCSFSNTS ESFVLNWYRM SPSNQTDKLA
AFPEDRSQPG QDCRFRVTQL PNGRDFHMSV VRARRNDSGT YLCGAISLAP KAQIKESLRA
ELRVTERRAE VPTAHPSPSP RPAGQFQ (iv).  Mutant of PD-1 or a fragment thereof which binds Programmed Death-1 ligand [PD-L1 (B7-H1) or PD-L2 (B7-DC)]

FIG. 12

Fusion proteins comprising Anti-HER2/neu antibody and PD-1 Ectodomain.

Anti-HER2/neu heavy chain + PD-1 ectodomain fusion amino acid sequence
(SEQ ID NO: 15):

<u>EVQLVESGGGLVQPGGSLRLSCAASGFNIKDTYIHWVRQAPGKGLEWVARIYPTNGYTRYADSVKG</u>
<u>RFTISADTSKNTAYLQMNSLRAEDTAVYYCSRWGGDGFYAMDYWGQGTLVTVSS</u>ASTKGPSVFPLA
PSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-HER2/neu light chain amino acid sequence (SEQ ID NO: 70):
<u>DIQMTQSPSSLSASVGDRVTITCRASQDVNTAVAWYQQKPGKAPKLLIYSASFLYSGVPSRFSGSR</u>
<u>SGTDFTLTISSLQPEDFATYYCQQHYTTPPTFGQGTKVEIK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC <u>Underlined</u>: Anti-HER2/neu Variable region
Plain: Anti-HER2/neu Constant region
*Italic*: Linker
Bold: PD-1 ectodomain

FIG. 13

Fusion proteins comprising Anti-EGFR1 antibody and PD-1 Ectodomain.

Anti-EGFR heavy chain + PD-1 ectodomain fusion amino acid sequence
(SEQ ID NO: 16):

<u>QVQLKQSGPGLVQPSQSLSITCTVSGFSLTNYGVHWVRQSPGKGLEWLGVIWSGGNTDYNTPFTSR</u>
<u>LSINKDNSKSQVFFKMNSLQSNDTAIYYCARALTYYDYEFAYWGQGTLVTVSAAST</u>KGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-EGFR light chain amino acid sequence (SEQ ID NO: 71):

<u>DILLTQSPVILSVSPGERVSFSCRASQSIGTNIHWYQQRTNGSPRLLIKYASESISGIPSRFSGSG</u>
<u>SGTDFTLSINSVESEDIADYYCQQNNNWPTTFGAGTKLELK</u>RTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

<u>Underlined</u>: <u>Anti-EGFR Variable region</u>
Plain: Anti-EGFR Constant region
*Italic: Linker*
Bold: PD-1 ectodomain

FIG. 14

Fusion proteins comprising Anti-CD20 antibody and PD-1 Ectodomain.

Anti-CD20 heavy chain + PD-1 ectodomain fusion amino acid sequence
(SEQ ID NO: 17):

<u>QVQLQQPGAELVKPGASVKMSCKASGYTFTSYNMHWVKQTPGRGLEWIGAIYPGNGDTSYNQKFKG
KATLTADKSSSTAYMQLSSLTSEDSAVYYCARSTYYGGDWYFNVWGAGTTVTVSA</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* **PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV**

Anti-CD20 light chain amino acid sequence (SEQ ID NO: 72):
<u>QIVLSQSPAILSASPGEKVTMTCRASSSVSYIHWFQQKPGSSPKPWIYATSNLASGVPVRFSGSGS
GTSYSLTISRVEAEDAATYYCQQWTSNPPTFGGGTKLEIK</u>RTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC > <u>Underlined:</u> Anti-CD20 Variable region
> Plain: Anti-CD20 Constant region
> *Italic: Linker*
> Bold: PD-1 ectodomain

FIG. 15

Fusion proteins comprising Anti-VEGF antibody and PD-1 Ectodomain.

Anti-VEGF heavy chain + PD-1 ectodomain fusion amino acid sequence
(SEQ ID NO: 18):

EVQLVESGGGLVQPGGSLRLSCAASGYTFTNYGMNWVRQAPGKGLEWVGWINTYTGEPTYAADFKR
RFTFSLDTSKSTAYLQMNSLRAEDTAVYYCAKYPHYYGSSHWYFDVWGQGTLVTVSSASTKGPSVF
PLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK
*GGGGSGGGGSGGGGS* PGWFLDSPDR PWNPPTFSPA LLVVTEGDNA TFTCSFSNTS
ESFVLNWYRM SPSNQTDKLA AFPEDRSQPG QDCRFRVTQL PNGRDFHMSV VRARRNDSGT
YLCGAISLAP KAQIKESLRA ELRVTERRAE VPTAHPSPSP RPAGQFQTLV

Anti-VEGF Light chain sequence (SEQ ID NO: 73):

DIQMTQSPSSLSASVGDRVTITCSASQDISNYLNWYQQKPGKAPKVLIYFTSSLHSGVPSRFSGSG
SGTDFTLTISSLQPEDFATYYCQQYSTVPWTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

Underlined: Anti-VEGF Variable region
Plain: Anti-VEGF Constant region
*Italic: Linker*
Bold: PD-1 ectodomain

FIG. 16

Fusion proteins comprising anti-human CTLA-4 antibody and PD-1 Ectodomain.

Anti-(human CTLA-4) (human γ1-chain)-PD-1 ectodomain fusion protein, disulfide with human κ-chain, dimer Anti-CTLA-4 heavy chain + PD-1 ectodomain fusion amino acid sequence (SEQ ID NO: 19):

<u>QVQLVESGGG VVQPGRSLRL SCAASGFTFS SYTMHWVRQA PGKGLEWVTF ISYDGNNKYY</u>
<u>ADSVKGRFTI SRDNSKNTLY LQMNSLRAED TAIYYCARTG WLGPFDYWGQ GTLVTVSSAS</u>
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPELLGGPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ
GNVFSCSVMH EALHNHYTQKSLSLSPGK *GGGGSGGGGSGGGGS* PGWFLDSPDR
PWNPPTFSPA LLVVTEGDNA TFTCSFSNTS ESFVLNWYRM SPSNQTDKLA AFPEDRSQPG
QDCRFRVTQL PNGRDFHMSV VRARRNDSGT YLCGAISLAP KAQIKESLRA ELRVTERRAE
VPTAHPSPSP RPAGQFQTLV

Anti-CTLA-4 light chain (SEQ ID NO: 74):

<u>EIVLTQSPGT LSLSPGERAT LSCRASQSVG SSYLAWYQQK PGQAPRLLIY GAFSRATGIP</u>
<u>DRFSGSGSGT DFTLTISRLE PEDFAVYYCQ QYGSSPWTFG QGTKVEIKRT</u> VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC

<u>Underlined</u>: Anti-CTLA-4 Variable region
  Plain: Anti-CTLA-4 Constant region
  *Italic: Linker*
  Bold: PD-1 ectodomain

FIG. 17

Fusion proteins comprising anti-CD25 antibody and PD-1 Ectodomain.

Anti-CD25 (Daclizumab) heavy chain and PD-1 ectodomain (SEQ ID NO: 20):

QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS*
PGWFLDSPDRPWNPPTFSPALLVVTEGDNATFTCSFSNT
SESFVLNWYRMSPSNQTDKLAAFPEDRSQPGQDCRFRVTQLPNGRDFHMSVVRAR
RNDSGTYLCGAISLAPKAQIKESLRAELRVTERRAEVPTAHPSPSRPAGQFQTLV

Anti-CD25 (Daclizumab) light chain (SEQ ID NO: 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: Anti-CD25 antibody
*Italic: Linker*
Bold: PD-1 ectodomain

FIG. 18A

Anti-CD25 (Basiliximab) heavy chain and PD-1 ectodomain (SEQ ID NO: 21):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS*
PGWFLDSPDRPWNPPTFSPALLVVTEGDNATFTCSFSNT
SESFVLNWYRMSPSNQTDKLAAFPEDRSQPGQDCRFRVTQLPNGRDFHMSVVRAR
RNDSGTYLCGAISLAPKAQIKESLRAELRVTERRAEVPTAHPSPSRPAGQFQTLV

Anti-CD25 (Basiliximab) light chain (SEQ ID NO: 76):

QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGE

Plain: Anti-CD25 antibody
*Italic: Linker*
Bold: PD-1 ectodomain

FIG. 18B

Fusion proteins comprising IL-2, Fc, and PD-1 ectodomain.

IL-2 + Fc + PD-1 ectodomain (SEQ ID NO: 22):

<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u><u>E</u><u>M</u>TKNQVSLTCLVKGFYPSDIAVEWESNGQPENNYKTTPPVLSDGSFFLYSKLTVDKSRWQQG
NVFSCSVMHEALHNHYTQKSLSLSPGK *GGGGSGGGGSGGGGS*
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSRPAGQFQTLV

PD-1 ectodomain + Fc + IL-2 (SEQ ID NO: 23):

PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSRPAGQFQTLV *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u><u>E</u><u>M</u>TKNQVSLTCLVKGFYPSDIAVEWESNGQPENNYKTTPPVLSDGSFFLYSKLTVDKSRWQQG
NVFSCSVMHEALHNHYTQKSLSLSPGK *GGGGSGGGGSGGGGS*
<u>APTSSSTKKTQLQLEHLLLDLQMILNGINNYKNPKLTRMLTFKFYMPKKATELKHLQCLEEELKPL</u>
<u>EEVLNLAQSKNFHLRPRDLISNINVIVLELKGSETTFMCEYADETATIVEFLNRWITFCQSIISTL</u>
<u>T</u>

Underlined: IL-2 fragment
    *Italic: Linker*
    Plain: Fc
    Bold: human PD-1 ectodomain
    (Note: Can replace optional linker 1 *GGGGSGGGGSGGGGS* SEQ ID NO: 104 with *EPKSCDK* SEQ ID NO: 105)
    (Note: Can replace underlined aa in Fc: <u>E</u> with D and <u>M</u> with L)

FIG. 19

Fusion proteins comprising anti-CD4 antibody and PD-1 Extracellular domain

Anti-CD4 heavy chain and PD-1 Extracellular domain (SEQ ID NO: 24):
Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV

Anti-CD4 light chain (SEQ ID NO: 77):
Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTVL</u>GRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

Plain: Anti-CD4 antibody (Variable region – underlined)
    *Italic: Linker*
    Bold: PD-1 ectodomain

FIG. 20

Fusion proteins comprising PD-1 Ectodomain, Fc, and Receptor activator of nuclear factor-κB (RANK) Extracellular domain (ectodomain):

RANK ectodomain – Fc - PD-1 ectodomain (SEQ. ID. NO: 25):

<u>QI APPCTSEKHY EHLGRCCNKC EPGKYMSSKC TTTSDSVCLP CGPDEYLDSW NEEDKCLLHK</u>
<u>VCDTGKALVA VVAGNSTTPR RCACTAGYHW SQDCECCRRN TECAPGLGAQ HPLQLNKDTV</u>
<u>CKPCLAGYFS DAFSSTDKCR PWTNCTFLGK RVEHHGTEKS DAVCSSSLPA RKPPNEPHVY LPG</u>
*GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
PGWFLDSPDRPWNPPTFSPALLVVTEGDNATFTCSFSNTSESFVLNWYRMSPSNQTDKLAAFPEDR
SQPGQDCRFRVTQLPNGRDFHMSVVRARRNDSGTYLCGAISLAPKAQIKESLRAELRVTERRAEVP
TAHPSPSPRPAGQFQTLV

PD-1 ectodomain – Fc - RANK ectodomain (SEQ. ID. NO: 26):

PGWFLDSPDRPWNPPTFSPALLVVTEGDNATFTCSFSNTSESFVLNWYRMSPSNQTDKLAAFPEDR

SQPGQDCRFRVTQLPNGRDFHMSVVRARRNDSGTYLCGAISLAPKAQIKESLRAELRVTERRAEVP

TAHPSPSPRPAGQFQTLV*GGGGSGGGGSGGGGS*

THTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVDKSRWQQG

NVFSCSVMHEALHNHYTQKSLSLSPGK *GGGGSGGGGSGGGGS* <u>QI APPCTSEKHY EHLGRCCNKC</u>

<u>EPGKYMSSKC TTTSDSVCLP CGPDEYLDSW NEEDKCLLHK VCDTGKALVA VVAGNSTTPR</u>

<u>RCACTAGYHW SQDCECCRRN TECAPGLGAQ HPLQLNKDTV CKPCLAGYFS DAFSSTDKCR</u>

<u>PWTNCTFLGK RVEHHGTEKS DAVCSSSLPA RKPPNEPHVY LPG</u>

Bold: PD-1 ectodomain
*Italics: Linker* <u>(optional: may delete linker 1 or replace with IEGRDMD (SEQ. ID. NO: 106) or</u>
<u>EPKSCDK (SEQ. ID. NO: 105))</u>
Plain: IgG1 Fc
<u>Underlined:    RANK ectodomain</u>

FIG. 21

Moieties that bind Receptor activator of nuclear factor–κB (RANK) ligand

(i) <u>Full-length RANK (TNFRSF11A) or fragment thereof (SEQ. ID. NO: 95)</u>:

```
1   MAPRARRRRP LFALLLLCAL LARLQVALQI APPCTSEKHY EHLGRCCNKC EPGKYMSSKC
61  TTTSDSVCLP CGPDEYLDSW NEEDKCLLHK VCDTGKALVA VVAGNSTTPR RCACTAGYHW
121 SQDCECCRRN TECAPGLGAQ HPLQLNKDTV CKPCLAGYFS DAFSSTDKCR PWTNCTFLGK
181 RVEHHGTEKS DAVCSSSLPA RKPPNEPHVY LPGLIILLLF ASVALVAAII FGVCYRKKGK
241 ALTANLWHWI NEACGRLSGD KESSGDSCVS THTANFGQQG ACEGVLLLTL EEKTFPEDMC
301 YPDQGGVCQG TCVGGGPYAQ GEDARMLSLV SKTEIEEDSF RQMPTEDEYM DRPSQPTDQL
361 LFLTEPGSKS TPPFSEPLEV GENDSLSQCF TGTQSTVGSE SCNCTEPLCR TDWTPMSSEN
421 YLQKEVDSGH CPHWAASPSP NWADVCTGCR NPPGEDCEPL VGSPKRGPLP QCAYGMGLPP
481 EEEASRTEAR DQPEDGADGR LPSSARAGAG SGSSPGGQSP ASGNVTGNSN STFISSGQVM
541 NFKGDIIVVY VSQTSQEGAA AAAEPMGRPV QEETLARRDS FAGNGPRFPD PCGGPEGLRE
601 PEKASRPVQE QGGAKA
```

Bold: RANK extracellular domain (RANK ligand-binding domain)

(ii) <u>RANK extracellular domain (ectodomain) or fragment thereof (SEQ. ID. NO: 96)</u>:

QI APPCTSEKHY EHLGRCCNKC EPGKYMSSKC TTTSDSVCLP CGPDEYLDSW NEEDKCLLHK VCDTGKALVA VVAGNSTTPR RCACTAGYHW SQDCECCRRN TECAPGLGAQ HPLQLNKDTV CKPCLAGYFS DAFSSTDKCR PWTNCTFLGK RVEHHGTEKS DAVCSSSLPA RKPPNEPHVY LPG

(iii) <u>Peptide sequences in RANKL binding domains of RANK or peptides containing key RANKL-binding residues of RANK (SEQ. ID. NO: 97)</u>:

```
1   MAPRARRRRP LFALLLLCAL LARLQVALQI APPCTSEKHY EHLGRCCNKC EPGKYMSSKC
61  TTTSDSVCLP CGPDEYLDSW NEEDKCLLHK VC_DTGKALVA_ VVAGNSTTPR RCACTAGYH_W_
121 _SQDCECCRRN_ TECAPGLGAQ HPLQLNKDTV CKPCLAGYFS DAFSSTDKCR PWTNCTFLGK
181 RVEHHGTEKS DAVCSSSLPA RKPPNEPHVY LPG
```

Bold: RANK extracellular domain (RANK ligand-binding domain)
RANK peptide sequences (Underlined) and residues (Italics) involved in binding RANKL.

(iv). <u>Mutant of RANK or a fragment thereof which binds Receptor activator of nuclear factor–κB (RANK) ligand (RANKL)</u>

(v) <u>Full-length Osteoprotegerin (OPG, TNFRSF11B) or fragment thereof (SEQ. ID. NO: 98)</u>:

```
1   MNKLLCCALV FLDISIKWTT QETFPPKYLH YDEETSHQLL CDKCPPGTYL KQHCTAKWKT
61  VCAPCPDHYY TDSWHTSDEC LYCSPVCKEL QYVKQECNRT HNRVCECKEG RYLEIEFCLK
121 HRSCPPGFGV VQAGTPERNT VCKRCPDGFF SNETSSKAPC RKHTNCSVFG LLLTQKGNAT
181 HDNICSGNSE STQKCGIDVT LCEEAFFRFA VPTKFTPNWL SVLVDNLPGT KVNAESVERI
241 KRQHSSQEQT FQLLKLWKHQ NKAQDIVKKI IQDIDLCENS VQRHIGHANL TFEQLRSLME
301 SLPGKKVGAE DIEKTIKACK PSDQILKLLS LWRIKNGDQD TLKGLMHALK HSKTYHFPKT
361 VTQSLKKTIR FLHSFTMYKL YQKLFLEMIG NQVQSVKISC L
```

Bold: RANK ligand-binding domain

FIG. 22

Fusion proteins comprising Anti-HER2/neu antibody and Receptor activator of nuclear factor–κB (RANK) Extracellular domain (ECD).

Anti-HER2/neu heavy chain+ RANK ECD fusion amino acid sequence (SEQ. ID. NO: 27):

EVQLVESGGGLVQPGGSLRLSCAASGFNIKDTYIHWVRQAPGKGLEWVARIYPTNGYTRYADSVKGRFTISA
DTSKNTAYLQMNSLRAEDTAVYYCSRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMH
EALHNHYTQKSLSLSPGK *GGGGSGGGGSGGGGS* **QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG**

Anti-HER2/neu light chain amino acid sequence (SEQ. ID. NO: 70):

DIQMTQSPSSLSASVGDRVTITCRASQDVNTAVAWYQQKPGKAPKLLIYSASFLYSGVPSRFSGSRSGTDFT
LTISSLQPEDFATYYCQQHYTTPPTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

<u>Underlined</u>: Anti-HER2 antibody variable region
Plain: Anti-HER2 antibody constant region
*Italics: Linker*
Bold: RANK ectodomain

FIG. 23

Fusion proteins comprising Anti-EGFR1 antibody and Receptor activator of nuclear factor–κB (RANK) Extracellular domain (ECD).

Anti-EGFR1 heavy chain + RANK ECD fusion amino acid sequence (SEQ. ID. NO: 28):

<u>QVQLKQSGPGLVQPSQSLSITCTVSGFSLTNYGVHWVRQSPGKGLEWLGVIWSGGNTDYNTPFTSRLSINKD</u>
<u>NSKSQVFFKMNSLQSNDTAIYYCARALTYYDYEFAYWGQGTLVTVSA</u>ASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCSVMHE
ALHNHYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

Anti-EGFR1 light chain amino acid sequence (SEQ. ID. NO: 71):

<u>DILLTQSPVILSVSPGERVSFSCRASQSIGTNIHWYQQRTNGSPRLLIKYASESISGIPSRFSGSGSGTDFT</u>
<u>LSINSVESEDIADYYCQQNNNWPTTFGAGTKLELK</u>RTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

<u>Underlined: Anti-EGFR antibody variable region</u>
Plain: Anti-EGFR antibody constant region
Italics: Linker
Bold: RANK ectodomain

FIG. 24

Fusion proteins comprising Anti-CD20 antibody and Receptor activator of nuclear factor-κB (RANK) Extracellular domain (ECD).

Anti-CD20 heavy chain+ RANK ECD fusion amino acid sequence (SEQ. ID. NO: 29):

<u>QVQLQQPGAELVKPGASVKMSCKASGYTFTSYNMHWVKQTPGRGLEWIGAIYPGNGDTSYNQKFKGKATLTA</u>
<u>DKSSSTAYMQLSSLTSEDSAVYYCARSTYYGGDWYFNVWGAGTTVTVSA</u>ASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVD
KKAEPKSCDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVM
HEALHNHYTQKSLSLSPGK *GGGGSGGGGSGGGGS* QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG

Anti-CD20 light chain amino acid sequence (SEQ. ID. NO: 72):

<u>QIVLSQSPAILSASPGEKVTMTCRASSSVSYIHWFQQKPGSSPKPWIYATSNLASGVPVRFSGSGSGTSYSL</u>
<u>TISRVEAEDAATYYCQQWTSNPPTFGGGTKLEIKR</u>TVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<u>Underlined</u>: Anti-CD20 antibody variable region
Plain: Anti-CD20 antibody constant region
*Italics*: Linker
Bold: RANK ectodomain

FIG. 25

Fusion proteins comprising anti-VEGF antibody and Receptor activator of nuclear factor-κB (RANK) Extracellular domain (ECD).

Anti-VEGF heavy chain+ RANK ECD fusion amino acid sequence (SEQ. ID. NO: 30):

<u>EVQLVESGGGLVQPGGSLRLSCAASGYTFTNYGMNWVRQAPGKGLEWVGWINTYTGEPTYAADF
KRRFTFSLDTSKSTAYLQMNSLRAEDTAVYYCAKYPHYYGSSHWYFDVWGQGTLVTVS</u>SASTKG
PSVFPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSPGK
*GGGGSGGGGSGGGGS* **QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG**

Anti-VEGF Light chain sequence (SEQ. ID. NO: 73):

<u>DIQMTQSPSSLSASVGDRVTITCSASQDISNYLNWYQQKPGKAPKVLIYFTSSLHSGVPSRFSGSGSG
TDFTLTISSLQPEDFATYYCQQYSTVPWTFGQGTKVEIK</u>RTVAAPSVFIFPPSDEQLKSGTASVVCLL
NNFYPREAKVQWKVDNALQSGNSQESVTEQDSKDSTYSLSSTLTLSKADYEKHKVYACEVTHQG
LSSPVTKSFNRGEC

<u>Underlined: Anti-VEGF antibody variable region</u>
Plain: Anti-VEGF antibody constant region
Italics: Linker
Bold: RANK ectodomain

FIG. 26

Fusion proteins comprising anti-human CTLA-4 antibody and Receptor activator of nuclear factor–κB (RANK) Extracellular domain (ECD).

Anti-CTLA-4 heavy chain + RANK ECD fusion sequence (SEQ. ID. NO: 31):

<u>QVQLVESGGG VVQPGRSLRL SCAASGFTFS SYTMHWVRQA PGKGLEWVTF ISYDGNNKYY</u>
<u>ADSVKGRFTI SRDNSKNTLY LQMNSLRAED TAIYYCARTG WLGPFDYWGQ GTLVTVSSAS</u>
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPELLGGPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ
GNVFSCSVMH EALHNHYTQK SLSLSPGK *GGGGSGGGGSGGGGS* QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG

Anti-CTLA-4 light chain (SEQ. ID. NO: 74):

<u>EIVLTQSPGT LSLSPGERAT LSCRASQSVG SSYLAWYQQK PGQAPRLLIY GAFSRATGIP</u>
<u>DRFSGSGSGT DFTLTISRLE PEDFAVYYCQ QYGSSPWTFG QGTKVEIKRT</u> VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC

<u>Underlined: Anti-CTLA-4 antibody variable region</u>
Plain: Anti-CTLA-4 antibody constant region
*Italics: Linker*
Bold: RANK ectodomain

FIG. 27

Fusion proteins comprising anti-CD25 antibody and Receptor activator of nuclear factor-κB (RANK) Extracellular domain (ECD).

Anti-CD25 and RANK ectodomain - Heavy chain (SEQ. ID. NO: 32):

QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS* **QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG**

Anti-CD25 - Light chain (SEQ. ID. NO. 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: Anti-CD25 antibody
*Italics: Linker*
Bold: RANK ectodomain

FIG. 28A

Fusion proteins comprising anti-CD25 antibody and Receptor activator of nuclear factor–κB (RANK) Extracellular domain (ECD).

Anti-CD25 and RANK ectodomain – Heavy chain (SEQ. ID. NO: 33):

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS* QI APPCTSEKHY EHLGRCCNKC
EPGKYMSSKC TTTSDSVCLP CGPDEYLDSW NEEDKCLLHK VCDTGKALVA VVAGNSTTPR
RCACTAGYHW SQDCECCRRN TECAPGLGAQ HPLQLNKDTV CKPCLAGYFS DAFSSTDKCR
PWTNCTFLGK RVEHHGTEKS DAVCSSSLPA RKPPNEPHVY LPG

Anti-CD25 – Light chain (SEQ. ID. NO: 76):

QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGEC

Plain: Anti-CD25 antibody
*Italics: Linker*
Bold: RANK ectodomain

FIG. 28B

Fusion proteins comprising IL-2, Fc, and Receptor activator of nuclear factor–κB (RANK) Extracellular domain (ECD).

IL2 – Fc – RANK ECD (SEQ. ID. NO: 34):

<u>APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLT</u>*GGGGSGGGGSG
GGGS*THTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPS<u>R</u>EE<u>M</u>TKNQ
VSLTCLVKGFYPSDIAVEWESNGQPENNYKTTPPVLDSDGSFFLYSKLTVDKSRWQQGNVFSCSVMHEALHN
HYTQKSLSLSPGK *GGGGSGGGGSGGGGS* **QI APPCTSEKHY EHLGRCCNKC EPGKYMSSKC
TTTSDSVCLP CGPDEYLDSW NEEDKCLLHK VCDTGKALVA VVAGNSTTPR RCACTAGYHW
SQDCECCRRN TECAPGLGAQ HPLQLNKDTV CKPCLAGYFS DAFSSTDKCR PWTNCTFLGK
RVEHHGTEKS DAVCSSSLPA RKPPNEPHVY LPG**

RANK ECD – Fc – IL-2 (SEQ. ID. NO: 35):

**QI APPCTSEKHY EHLGRCCNKC EPGKYMSSKC TTTSDSVCLP CGPDEYLDSW NEEDKCLLHK
VCDTGKALVA VVAGNSTTPR RCACTAGYHW SQDCECCRRN TECAPGLGAQ HPLQLNKDTV
CKPCLAGYFS DAFSSTDKCR PWTNCTFLGK RVEHHGTEKS DAVCSSSLPA RKPPNEPHVY LPG**
*GGGGSGGGGSGGGGS*THTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVYTL
PPS<u>R</u>EE<u>M</u>TKNQVSLTCLVKGFYPSDIAVEWESNGQPENNYKTTPPVLDSDGSFFLYSKLTVDKSRWQQGNVF
SCSVMHEALHNHYTQKSLSLSPGK*GGGGSGGGGSGGGGS*<u>APTSSSTKKTQLQLEHLLLDLQMILNGINNYKN
PKLTRMLTFKFYMPKKATELKHLQCLEEELKPLEEVLNLAQSKNFHLRPRDLISNINVIVLELKGSETTFMC
EYADETATIVEFLNRWITFCQSIISTLT</u>

Bold: RANK ectodomain
*Italics: Linker* (Optional; any linker sequence)
Plain: Fc
<u>Underlined: IL2 fragment that binds CD25 (IL-2Rα)</u>

(Can replace linker 1 with <u>EPKSCDK</u> (SEQ. ID. NO: 105) or <u>IEGRDMD</u> (SEQ. ID. NO: 106))
(Can replace underlined aa in Fc: <u>E</u> with D and <u>M</u> with L)

FIG. 29

Fusion protein comprising anti-CD4 antibody and Receptor activator of nuclear factor–κB (RANK) Extracellular domain (ECD)

Anti-CD4 heavy chain and RANK Extracellular domain (SEQ ID NO: 36):

Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS* **QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG**

Anti-CD4 light chain (SEQ ID NO: 77):

Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTV</u>LGRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

<u>Underlined: Anti-CD4 antibody variable region</u>

*Italic: Linker*

Bold: PD-1 ectodomain

FIG. 30

(i) Full-length human PD-1 ligand 1 (B7-H1; PDCD1L1; PDL1; CD274) protein or a fragment thereof (SEQ ID NO: 99):

MRIFAVFIFM TYWHLLNAFT VTVPKDLYVV EYGSNMTIEC KFPVEKQLDL AALIVYWEME
DKNIIQFVHG EEDLKVQHSS YRQRARLLKD QLSLGNAALQ ITDVKLQDAG VYRCMISYGG
ADYKRITVKV NAPYNKINQR ILVVDPVTSE HELTCQAEGY PKAEVIWTSS DHQVLSGKTT
TTNSKREEKL FNVTSTLRIN TTTNEIFYCT FRRLDPEENH TAELVIPELP LAHPPNERTH
LVILGAILLC LGVALTFIFR LRKGRMMDVK KCGIQDTNSK KQSDTHLEET (ii) PD-L1 extracellular binding domain (ectodomain) or fragment thereof (SEQ ID NO: 100):

**AFT VTVPKDLYVV EYGSNMTIEC KFPVEKQLDL AALIVYWEME DKNIIQFVHG
EEDLKVQHSS YRQRARLLKD QLSLGNAALQ ITDVKLQDAG VYRCMISYGG ADYKRITVKV
NAPYNKINQR ILVVDPVTSE HELTCQAEGY PKAEVIWTSS DHQVLSGKTT TTNSKREEKL
FNVTSTLRIN TTTNEIFYCT FRRLDPEENH TAELVI**

(iii) Human PD-1 ligand 2 [PD-L2 (B7-DC)] or a fragment thereof.

(iv). Mutant of Programmed Death-1 ligand [PD-L1 (B7-H1) or PD-L2 (B7-DC)] or a fragment thereof which binds Programmed Death-1 (PD-1).

Sequence used in fusion proteins (SEQ ID NO: 101):

RIFAVFIFM TYWHLLNAFT **VTVPKDLYVV EYGSNMTIEC KFPVEKQLDL AALIVYWEME
DKNIIQFVHG EEDLKVQHSS YRQRARLLKD QLSLGNAALQ ITDVKLQDAG VYRCMISYGG
ADYKRITVKV NAPYNKINQR ILVVDPVTSE HELTCQAEGY PKAEVIWTSS DHQVLSGKTT
TTNSKREEKL FNVTSTLRIN TTTNEIFYCT FRRLDPEENH TAELVI**PELP LAHPPNERTH
LVILGAILLC LGVALTFIFR LRKGRMMDVK KCGIQDTNSK KQSDTHLEET

Bold: PD-L1 extracellular domain (ectodomain)
<u>Underlined Bold: Ligand Binding domain</u>

FIG. 31

Fusion proteins comprising anti-tumor necrosis factor (TNFα) antibody and PD-1 ligand 1 or PD-1 ligand 2

Anti-TNFα heavy chain + PD-L1 (SEQ ID NO: 37):

<u>EVQLVESGGGLVQPGRSLRLSCAASGFTFDDYAMHWVRQAPGKGLEWVSAITWNSGHIDYADSVEG</u>
<u>RFTISRDNAKNSLYLQMNSLRAEDTAVYYCALVSYLSTASSLDYWGQGTLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Anti-TNFα light chain (SEQ ID NO: 78):

<u>DIQMTQSPSSLSASVGDRVTITCRASQGIRNYLAWYQQLPGKAPKLLIYAASTLQSGVPSRFSGSG</u>
<u>SGTDFTLTISSLQPEDVATYYCQRYNRAPYTFGQGTKVEIKR</u>TVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

<u>Underlined: anti-TNFα antibody variable region</u>
Plain: anti-TNFα antibody constant region
*Italic: Linker*
Bold: human PD-1 ligand 1 (PD-L1)
(Note: Fc region KKAE SEQ ID NO: 107 can be replaced with KRVE SEQ ID NO: 108 or KKVE SEQ ID NO: 109)

FIG. 32

Fusion proteins comprising TNFR2 Extracellular ligand binding domain, Fc, and PD-1 ligand: (TNFR2 ECD + IgG Cγ1 + PD-L1)

TNFR2 ECD + IgG Cγ1 + PD-L1 (SEQ ID NO: 38):

<u>LPAQVAFTPYAPEPGSTCRLREYYDQTAQMCCSKCSPGQHAKVFCTKTSDTVCDSCEDSTYTQLWN</u>
<u>WVPECLSCGSRCSSDQVETQACTREQNRICTCRPGWYCALSKQEGCRLCAPLRKCRPGFGVARPGT</u>
<u>ETSDVVCKPCAPGTFSNTTSSTDICRPHQICNVVAIPGNASMDAVCTSTSPTRSMAPGAVHLPQPV</u>
<u>STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Fusion proteins comprising PD-1 ligand, Fc, and TNFR2 Extracellular ligand binding domain: (PD-L1 + IgG Cγ1 + TNFR2 ECD)

PD-L1 + IgG Cγ1 + TNFR2 ECD (SEQ ID NO: 39):

MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFR
LRKGRMMDVKKCGIQDTNSKKQSDTHLEET *GGGGSGGGGSGGGGS* *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN</u>
<u>WVPECLSCGSRCSSDQVETQACTREQNRICTCRPGWYCALSKQEGCRLCAPLRKCRPGFGVARPGT</u>
<u>ETSDVVCKPCAPGTFSNTTSSTDICRPHQICNVVAIPGNASMDAVCTSTSPTRSMAPGAVHLPQPV</u>
<u>STRSQHTQPTPEPSTAPSTSFLLPMGPSPPAEGSTGD</u>

<u>Underlined</u>: TNFR2 ligand-binding domain
Plain: human IgG1 heavy chain constant region (IgG Cγ1 domain = H, CH2, CH3)
*Italic*: Linker (Linker 1 is optional and may be replaced with another linker such as EPKSCDK (SEQ. ID. NO: 105) or GGGGSGGGGSGGGGS (SEQ. ID. NO: 104))
Bold: human PD-1 ligand 1 or extracellular binding domain of PD-L1

FIG. 33

Fusion proteins comprising anti-CD20 antibody and PD-1 ligand 1 (PD-L1).

Anti-CD20 heavy chain + PD-L1 sequence (SEQ ID NO: 40):

<u>QVQLQQPGAELVKPGASVKMSCKASGYTFTSYNMHWVKQTPGRGLEWIGAIYPGNGDTSYNQKFKG</u>
<u>KATLTADKSSSTAYMQLSSLTSEDSAVYYCARSTYYGGDWYFNVWGAGTTVTVSAA</u>STKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET

Anti-CD20 light chain sequence (SEQ ID NO: 72):

<u>QIVLSQSPAILSASPGEKVTMTCRASSSVSYIHWFQQKPGSSPKPWIYATSNLASGVPVRFSGSGS</u>
<u>GTSYSLTISRVEAEDAATYYCQQWTSNPPTFGGGTKLEIK</u>RTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC

<u>Underlined</u>: anti-CD20 antibody variable region
Plain: anti-CD20 antibody constant region
*Italic*: Linker
Bold: human PD-1 ligand 1 or extracellular binding domain of PD-L1

FIG. 34

Fusion proteins comprising anti-CD25 antibody and PD-1 ligand 1 (PD-L1).

Anti-CD25 (Daclizumab) heavy chain and PD-L1 (SEQ ID NO: 41):

```
QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK
```
*GGGGSGGGGSGGGGS*

RIFAVFIFMTYWHLLNAFTVTVPKDLYVVEYGSNMTIECK
FPVEKQLDLAALIVYWEMEDKNIIQFVHGEEDLKVQHSSYRQRARLLKDQLSLGNA
ALQITDVKLQDAGVYRCMISYGGADYKRITVKVNAPYNKINQRILVVDPVTSEHEL
TCQAEGYPKAEVIWTSSDHQVLSGKTTTTNSKREEKLFNVTSTLRINTTTNEIFYC
TFRRLDPEENHTAELVIPELPLAHPPNERTHLVILGAILLCLGVALTFIFRLRKGR
MMDVKKCGIQDTNSKKQSDTHLEET

Anti-CD25 (Daclizumab) light chain (SEQ ID NO: 75):

```
DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC
```

Plain: anti-CD25 antibody
*Italic: Linker* (optional and may be replaced)
Bold: human PD-1 ligand 1 or extracellular binding domain of PD-L1 (underlined)

FIG. 35A

Anti-CD25 (Basiliximab) heavy chain and PD-1 ectodomain (SEQ ID NO: 42)

QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK *GGGGSGGGGSGGGGS*
RIFAVFIFMTYWHLLNAFTVTVPKDLYVVEYGSNMTIECK
FPVEKQLDLAALIVYWEMEDKNIIQFVHGEEDLKVQHSSYRQRARLLKDQLSLGNA
ALQITDVKLQDAGVYRCMISYGGADYKRITVKVNAPYNKINQRILVVDPVTSEHEL
TCQAEGYPKAEVIWTSSDHQVLSGKTTTTNSKREEKLFNVTSTLRINTTTNEIFYC
TFRRLDPEENHTAELVIPELPLAHPPNERTHLVILGAILLCLGVALTFIFRLRKGR
MMDVKKCGIQDTNSKKQSDTHLEET

Anti-CD25 (Basiliximab) light chain (SEQ ID NO: 76):

QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGE

Plain: anti-CD25 antibody
*Italic: Linker*
Bold: human PD-1 ligand 1 or extracellular binding domain of PD-L1 (underlined)

FIG. 35B

Fusion proteins comprising IL-2, Fc, and PD-1 ligand 1 (PD-L1)

Fusion protein: hPD-1 ligand 1 + Fc + IL-2 (SEQ ID NO: 43):

**MRIFAVFIFMTYWHLLNAFTVTVPKDLYVVEYGSNMTIECKFPVEKQLDLAALIVYWEMEDKNIIQFVHGEE
DLKVQHSSYRQRARLLKDQLSLGNAALQITDVKLQDAGVYRCMISYGGADYKRITVKV
NAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERTHLVILGAILLCLGVALTFIFR
LRKGRMMDVKKCGIQDTNSKKQSDTHLEET** *GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
<u>APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLT</u>

Fusion protein: IL-2 + Fc + PD-1 ligand 1 (SEQ ID NO: 44):

<u>APTSSSTKKTQLQLEHLLLDLQMILNGINNYKNPKLTRMLTFKFYMPKKATELKHLQCLEEELKPLEEVLNL
AQSKNFHLRPRDLISNINVIVLELKGSETTFMCEYADETATIVEFLNRWITFCQSIISTLT</u>
*GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
**RIFAVFIFMTYWHLLNAFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVKVNAPYNKINQRILVVD
PVTSEHELTCQAEGYPKAEVIWTSSDHQVLSGKTTTTNSKREEKLFNVTSTLRINTTTNEIFYCTFRRLDPE
ENHTAELVIPELPLAHPPNERTHLVILGAILLCLGVALTFIFRLRKGRMMDVKKCGIQDTNSKKQSDTHLEE
T**

<u>Underlined: IL-2 fragment</u>
*Italic: Linker (optional)*
Plain: Fc
Bold: human PD-1 ligand 1 or extracellular binding domain of PD-1L (underlined)
(Note: Can replace linker 1 *GGGGSGGGGSGGGGS* SEQ ID NO: 104 with
*EPKSCDK* SEQ ID NO: 105)
(Note: Can replace underlined aa in Fc: E with D and M with L)

FIG. 36

Fusion protein comprising anti-CD4 antibody and PD-1 ligand 1 (PD-L1)

Anti-CD4 heavy chain and PD-1 ligand 1 (SEQ ID NO: 45)

Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
RIFAVFIFMTYWHLLN<u>AFTVTVPKDLYVVEYGSNMTIECKFPVEKQLDLAALIVYWEMEDKNIIQF</u>
<u>VHGEEDLKVQHSSYRQRARLLKDQLSLGNAALQITDVKLQDAGVYRCMISYGGADYKRITVKVNAP</u>
<u>YNKINQRILVVDPVTSEHELTCQAEGYPKAEVIWTSSDHQVLSGKTTTTNSKREEKLFNVTSTLRI</u>
<u>NTTTNEIFYCTFRRLDPEENHTAELVI</u>PELPLAHPPNERTHLVILGAILLCLGVALTFIFRLRKGR
MMDVKKCGIQDTNSKKQSDTHLEET

Anti-CD4 light chain (SEQ ID NO: 77)

Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTVL</u>GRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

<u>Underlined: Anti-CD4 antibody variable region</u>
Plain: Anti-CD4 antibody constant region
*Italic: Linker*
Bold: human PD-1 ligand 1 or extracellular binding domain of PD-1L (underlined)

FIG. 37

Fusion proteins comprising the extracellular domain of CTLA-4, Immunoglobulin Fc (IgG Cγ1), and a sequence from PD-1 ligand (PD-L1)

Oncostatin M signal peptide + CTLA-4 ECD + IgG Cγ1 + PD-L1 (SEQ ID NO: 46):

*MGVLLTQRTLLSLVLALLFPSMASM*AMHVAQPAVVLASSRGIASFVCEYASPGKATEVRVTVLRQA
DSQVTEVCAATYMMGNELTFLDDSICTGTSSGNQVNLTIQGLRAMDTGLYICKVELMYPPPYYLGI
GNGTQIYVIDPEPCPDSD *QEPKSCDKT*HT*C*PP*C*PAPELLGGPSVFLFPPKPKDTLM
ISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
*GGGGSGGGGSGGGGS*
**RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET**

Fusion proteins comprising the extracellular domain of PD-1 ligand (PD-L1), Immunoglobulin Fc (IgG Cγ1), and a sequence from the extracellular domain of CTLA-4.

PD-L1 + IgG Cγ1 + CTLA-4 ECD (SEQ ID NO: 47):

**MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFR
LRKGRMMDVKKCGIQDTNSKKQSDTHLEET** *GGGGSGGGGSGGGGS*
*QEPKSC̲DK*THT*C̲*PP*C̲*PAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK *GGGGSGGGGSGGGGS*
AMHVAQPAVVLASSRGIASFVCEYASPGKATEVRVTVLRQADSQVTEVCAATYMMGNELTFLDDSI
CTGTSSGNQVNLTIQGLRAMDTGLYICKVELMYPPPYYLGIGNGTQIYVIDPEPCPDSD

<u>*Underlined Italic*</u>: <u>*Oncostatin M Signal Peptide (-25 to -1)*</u>
Underlined: CTLA-4 extracellular domain (1-125)
Plain: human IgG1 heavy chain constant region (IgG Cγ1 domain = H, CH2, CH3)
*Italic: Linker (optional)*
Bold: human PD-1 ligand 1 (PD-1L) or extracellular binding domain of PD-1L (underlined)
(Note: Optional C to S conversion in IgG sequence (bold underlined))
(Note: The linker *QEPKSCDK* SEQ ID NO: 110 can be replaced with *EPKSCDK* SEQ ID NO: 105 or another linker sequence)

FIG. 38

Fusion proteins comprising a sequence of transforming growth factor-β (TGF-β), Immunoglobulin Fc (IgG Cβ1), and a sequence of PD-1 ligand (PD-L1)

TGFβ-1 + Fc + PD-L1 (SEQ ID NO: 48):
<u>ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RE<u>E</u>MTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**RIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRI
NTTTNEIFYCTFRRLDPEENHTAELVIPELPLAHPPNERTHLVILGAILLCLGVALTFIFRLRKGR
MMDVKKCGIQDTNSKKQSDTHLEET**

Fusion protein comprising a sequence of PD-1 ligand (PD-L1), Immunoglobulin Fc (IgG Cγ1), and a sequence of Transforming growth factor beta (TGF-β)

PD-L1 + Fc + TGFβ-1 (SEQ ID NO: 49):
**MRIFAVFIFMTYWHLLNAFTVTVPKDLYVVEYGSNMTIECKFPVEKQLDLAALIVYWEMEDKNIIQ
FVHGEEDLKVQHSSYRQRARLLKDQLSLGNAALQITDVKLQDAGVYRCMISYGGADYKRITVKVNA
PYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERTHLVILGAILLCLGVALTFIFRLRKG
RMMDVKKCGIQDTNSKKQSDTHLEET** *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RE<u>E</u>MTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS</u>

<u>Underlined</u>: TGFβ-1
*Italic: Linker (optional)*
Plain: Fc
Bold: human PD-1 ligand 1 or extracellular binding domain of PD-1L (underlined)
(Note: Can replace linker *GGGGSGGGGSGGGGS* SEQ ID NO: 104 with
*EPKSCDK* SEQ ID NO: 105)
(Note: Can replace underlined aa in Fc: <u>E</u> with D and <u>M</u> with L)

FIG. 39

(i) Transforming growth factor-beta (TGF-β1, TGF-β2, or TGF-β3 or a fragment thereof:

TGF-β1 full sequence (SEQ ID NO: 102):

```
1   MPPSGLRLLP LLLPLLRLLV LTPGRPAAGL STCKTIDMEL VKRKRIEAIR GQILSKLRLS
61  SPPSQGEVPP VPLPEAVLAL YNSTRDRVAG ESAEPEPEPE ADYYAKEVTR VLMVENTNKI
121 YEKVKKSPHS IYMLFNTSEL REAVPEPVLL SRAELRLLRL KLKAEQHVEL YQKYSNDSWR
181 YLSNRLLAPS DTPEWLSFDV TGVVRQWLSH GGEVEGFRLS AHCSCDSKDN TLQVDINGFS
241 SSRRGDLATI HGMNRPFLLL MATPLERAQH LHSSRQRRAL DTNYCFSSTE KNCCVRQLYI
301 DFRKDLGWKW IHEPKGYHAN FCLGPCPYIW SLDTQYSKVL ALYNQHNPGA SAAPCCVPQA
361 LEPLPIVYYV GRKPKVEQLS NMIVRSCKCS
```

Underlined: Mature (active) TGF-β1 sequence (Ala 279 – Ser 390; 112 aa).

(ii) Mature (active) TGF-β1 sequence (Ala 279 – Ser 390; 112 aa) (SEQ ID NO: 103):

AL DTNYCFSSTE KNCCVRQLYI DFRKDLGWKW IHEPKGYHAN FCLGPCPYIW
SLDTQYSKVL ALYNQHNPGA SAAPCCVPQA LEPLPIVYYV GRKPKVEQLS NMIVRSCKCS

FIG. 40

Fusion proteins comprising an antibody that binds TNF-α, and a sequence of transforming growth factor-β (TGF-β).

Anti-TNFα heavy chain + TGF-β1 (SEQ ID NO: 50):

<u>EVQLVESGGGLVQPGRSLRLSCAASGFTFDDYAMHWVRQAPGKGLEWVSAITWNSGHIDYADSVEG</u>
<u>RFTISRDNAKNSLYLQMNSLRAEDTAVYYCALVSYLSTASSLDYWGQGTLVTVSS</u>ASTKGPSVFPL
APSSKSTSGGTAALGCLVKDYFPEPVTV

Fusion proteins comprising TNFR2 Extracellular ligand binding domain, Fc, and a sequence from transforming growth factor-β (TGF-β)

TNFR2 ECD + IgG Cγ1 + TGF-β1 (SEQ ID NO: 51):

<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u>E<u>M</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS**

Fusion proteins comprising a sequence from transforming growth factor-β (TGF-β), Fc, and TNFR2 Extracellular ligand binding domain:

TGF-β1 + IgG Cγ1 + TNFR2 ECD (SEQ ID NO: 52):

**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *GGGGSGGGGSGGGGS*
THTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKT
ISKAKGQPREPQVYTLPPSR<u>E</u>E<u>M</u>TKNQVSLTCLVKGFYPSDIAVEWESNGQPENNYKTTPPVLDSD
GSFFLYSKLTVDKSRWQQGNVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN
WVPECLSCGSRCSSDQVETQACTREQNRICTCRPGWYCALSKQEGCRLCAPLRKCRPGFGVARPGT
ETSDVVCKPCAPGTFSNTTSSTDICRPHQICNVVAIPGNASMDAVCTSTSPTRSMAPGAVHLPQPV
STRSQHTQPTPEPSTAPSTSFLLPMGPSPPAEGSTGD</u>

Underlined: TNFR2 ligand-binding domain

Plain: human IgG1 heavy chain constant region (IgG Cγ1 domain = H, CH2, CH3)

*Italic: Linker*

Bold: Mature (active) human TGF-β1

(Note: Can replace linker 1 with *GGGGSGGGGSGGGGS* SEQ ID NO: 104 or *EPKSCDK* SEQ ID NO: 105)
(Note: Can replace underlined aa in Fc: <u>E</u> with D and <u>M</u> with L)

FIG. 42

Fusion proteins comprising anti-CD20 antibody and a sequence from transforming growth factor-β (TGF-β)

Anti-CD20 heavy chain + mature TGFβ1 sequence (SEQ ID NO: 53):

QVQLQQPGAELVKPGASVKMSCKASGYTFTSYNMHWVKQTPGRGLEWIGAIYPGNGDTSYNQKFKG
KATLTADKSSSTAYMQLSSLTSEDSAVYYCARSTYYGGDWYFNVWGAGTTVTVSAASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS

Anti-CD20 light chain sequence (SEQ ID NO: 72):

QIVLSQSPAILSASPGEKVTMTCRASSSVSYIHWFQQKPGSSPKPWIYATSNLASGVPVRFSGSGS
GTSYSLTISRVEAEDAATYYCQQWTSNPPTFGGGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC

Underlined: anti-CD20 antibody variable region

Plain: anti-CD20 antibody constant region

*Italic: Linker*

Bold: Mature (active) human TGF-β1

FIG. 43

Fusion proteins comprising anti-CD25 antibody and a sequence from transforming growth factor-β (TGF-β).

Anti-CD25 (Daclizumab) heavy chain and TGF-β1 (SEQ ID NO: 54):
QVQLVQSGAE VKKPGSSVKV SCKASGYTFT SYRMHWVRQA PGQGLEWIGY INPSTGYTEY
NQKFKDKATI TADESTNTAY MELSSLRSED TAVYYCARGG GVFDYWGQGT LVTVSSASTK
GPSVFPLAPS SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCPPCPA PELLGGPSVF
LFPPKPKDTL MISRTPEVTC VVVDVSHEDP EVKFNWYVDG VEVHNAKTKP REEQYNSTYR
VVSVLTVLHQ DWLNGKEYKC KVSNKALPAP IEKTISKAKG QPREPQVYTL PPSRDELTKN
QVSLTCLVKG FYPSDIAVEW ESNGQPENNY KTTPPVLDSD GSFFLYSKLT VDKSRWQQGN
VFSCSVMHEA LHNHYTQKSL SLSPGK *GGGGSGGGGSGGGGS* ALDTNYCFSSTEKNCCVRQLY IDFRKDLGWKWIHEPKGYHANFCLGPCPYIWSLDTQYSKVLALYNQHNPGASAAPCCVPQALEPLP IVYYVGRKPKVEQLSNMIVRSCKCS

Anti-CD25 (Daclizumab) light chain (SEQ ID NO: 75):

DIQMTQSPST LSASVGDRVT ITCSASSSIS YMHWYQQKPG KAPKLLIYTT SNLASGVPAR
FSGSGSGTEF TLTISSLQPD DFATYYCHQR STYPLTFGQG TKVEVKRTVA APSVFIFPPS
DEQLKSGTAS VVCLLNNFYP REAKVQWKVD NALQSGNSQE SVTEQDSKDS TYSLSSTLTL
SKADYEKHKV YACEVTHQGL SSPVTKSFNR GEC

Plain: anti-CD25 antibody

*Italic*: *Linker*

Bold: Mature (active) human TGF-β1

FIG. 44A

Anti-CD25 (Basiliximab) heavy chain and TGF-β1 (SEQ ID NO: 55):

```
QLQQSGTVLA RPGASVKMSC KASGYSFTRY WMHWIKQRPG QGLEWIGAIY PGNSDTSYNQ
KFEGKAKLTA VTSASTAYME LSSLTHEDSA VYYCSRDYGY YFDFWGQGTT LTVSSASTKG
PSVFPLAPSS KSTSGGTAAL GCLVKDYFPE PVTVSWNSGA LTSGVHTFPA VLQSSGLYSL
SSVVTVPSSS LGTQTYICNV NHKPSNTKVD KRVEPKSCDK THTCPPCPAP ELLGGPSVFL
FPPKPKDTLM ISRTPEVTCV VVDVSHEDPE VKFNWYVDGV EVHNAKTKPR EEQYNSTYRV
VSVLTVLHQD WLNGKEYKCK VSNKALPAPI EKTISKAKGQ PREPQVYTLP PSRDELTKNQ
VSLTCLVKGF YPSDIAVEWE SNGQPENNYK TTPPVLDSDG SFFLYSKLTV DKSRWQQGNV
FSCSVMHEAL HNHYTQKSLS LSPGK
```
*GGGGSGGGGSGGGGS*
ALDTNYCFSSTEKNCCVRQLYIDFRKDLGWKWIHEPKGYHAN
FCLGPCPYIWSLDTQYSKVLALYNQHNPGASAAPCCVPQALEPLPIVYYVGRKPKVEQ
LSNMIVRSCKCS

Anti-CD25 (Basiliximab) light chain (SEQ ID NO: 76):
```
QIVSTQSPAI MSASPGEKVT MTCSASSSRS YMQWYQQKPG TSPKRWIYDT SKLASGVPAR
FSGSGSGTSY SLTISSMEAE DAATYYCHQR SSYTFGGGTK LEIKRTVAAP SVFIFPPSDE
QLKSGTASVV CLLNNFYPRE AKVQWKVDNA LQSGNSQESV TEQDSKDSTY SLSSTLTLSK
ADYEKHKVYA CEVTHQGLSS PVTKSFNRGE
```

Plain: anti-CD25 antibody
*Italic: Linker*
Bold: Mature (active) human TGF-β1

FIG. 44B

Fusion proteins comprising IL-2, Fc, and a sequence from transforming growth factor-β (TGF-β).

TGF-β1 + Fc + IL-2 (SEQ ID NO: 56):

**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *GGGGSGGGGSGGGGS*
THTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQG NVFSCSVMHEALHNHYTQKSLSLSPGK *GGGGSGGGGSGGGGS*
APTSSSTKKTQLQLEHLLLDLQMILNGINNYKNPKLTRMLTFKFYMPKKATELKHLQCLEEELKPL EEVLNLAQSKNFHLRPRDLISNINVIVLELKGSETTFMCEYADETATIVEFLNRWITFCQSIISTL T

IL-2 + Fc + TGF-β1 (SEQ ID NO: 57):

APTSSSTKKTQLQLEHLLLDLQMILNGINNYKNPKLTRMLTFKFYMPKKATELKHLQCLEEELKPL EEVLNLAQSKNFHLRPRDLISNINVIVLELKGSETTFMCEYADETATIVEFLNRWITFCQSIISTL T *GGGGSGGGGSGGGGS*
THTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYSKLTVDKSRWQQG NVFSCSVMHEALHNHYTQKSLSLSPGK *GGGGSGGGGSGGGGS*
ALDTNYCFSSTEKNCCVRQLYIDFRKDLGWKWIHEPKGYHANFCLGPCPYIWSLDTQYSKVLALYN QHNPGASAAPCCVPQALEPLPIVYYVGRKPKVEQLSNMIVRSCKCS

Underlined: IL-2 fragment
*Italic: Linker (optional)*
Plain: Fc
Bold: Mature (active) human TGF-β1
(Note: Can replace linker 1 *GGGGSGGGGSGGGGS* SEQ ID NO: 104 with *EPKSCDK* SEQ ID NO: 105)
(Note: Can replace underlined aa in Fc: E with D and M with L)

FIG. 45

Fusion protein comprising anti-CD4 antibody and a sequence from transforming growth factor-β (TGF-β).

Anti-CD4 heavy chain and TGF-β1 (SEQ ID NO: 58)

Heavy chain fusion protein:

<u>QVQLQEAGPGLVKPSETLSLTCSVSGGSISGDYYWFWIRQSPGKGLEWIGYIYGSGGGTNYNPSLN</u>
<u>NRVSISIDTSKNLFSLKLRSVTAADTAVYYCASNILKYLHWLLYWGQGVLVTVSS</u>ASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK
*GGGGSGGGGSGGGGS*
ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS

Anti-CD4 light chain (SEQ ID NO: 77)

Light chain:

<u>SYELSQPRSVSVSPGQTAGFTCGGDNVGRKSVQWYQQKPPQAPVLVIYADSERPSGIPARFSGSNS</u>
<u>GNTATLTISGVEAGDEADYYCQVWDSTADHWVFGGGTRLTVL</u>GRTVAAPSVFIFPPSDEQLKSGTA
SVVCLLNNFYPREAKVQWKVDNALQSGNSQESVTEQDSKDSTYSLSSTLTLSKADYEKHKVYACEV
THQGLSSPVTKSFNRGEC

<u>Underlined: Anti-CD4 antibody variable region</u>
Plain: Anti-CD4 antibody constant region
*Italic: Linker*
Bold: Mature (active) human TGF-β1

FIG. 46

Fusion proteins comprising the extracellular domain of CTLA-4, Immunoglobulin Fc (IgG Cγ1), and a sequence from a sequence from transforming growth factor-β (TGF-β)

Oncostatin M signal peptide + CTLA-4 ECD + IgG Cγ1 + TGF-β1 (SEQ ID NO: 59):

*MGVLLTQRTLLSLVLALLFPSMASM*AMHVAQPAVVLASSRGIASFVCEYASPGKATEVRVTVLRQA
DSQVTEVCAATYMMGNELTFLDDSICTGTSSGNQVNLTIQGLRAMDTGLYICKVELMYPPPYYLGI
GNGTQIYVIDPEPCPDSD*QEPKSCDK* THTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWESN
GQPENNYKTTPPVLDSDGSFFLYSKLTVDKSRWQQGNVFSCSVMHEALHNHYTQKSLSLSPGK
*GGGGSGGGGSGGGGS*
**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS**

Fusion proteins comprising a sequence from transforming growth factor-β (TGF-β), Immunoglobulin Fc (IgG Cγ1), and a sequence from the extracellular domain of CTLA-4

TGF-β1 + IgG Cγ1 + CTLA-4 ECD (SEQ ID NO: 60):

**ALDTNYCFSSTEKNCCVRQLYIDFRKDLGWKWIHEPKGYHANFCLGPCPYIWSLDTQYSKVLALYN
QHNPGASAAPCCVPQALEPLPIVYYVGRKPKVEQLSNMIVRSCKCS** *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
AMHVAQPAVVLASSRGIASFVCEYASPGKATEVRVTVLRQADSQVTEVCAATYMMGNELTFLDDSI
CTGTSSGNQVNLTIQGLRAMDTGLYICKVELMYPPPYYLGIGNGTQIYVIDPEPCPDSD

*Underlined Italic*: Oncostatin M Signal Peptide (-25 to -1)
Underlined: CTLA-4 extracellular domain (1-125)
Plain: human IgG1 heavy chain constant region (IgG Cγ1 domain = H, CH2, CH3)
*Italic: Linker (optional)*
Bold: Mature (active) human TGF-β1
(Note: Optional C to S conversion in IgG sequence (bold underlined))
(Note: The linker *QEPKSCDK* SEQ ID NO: 110 can be replaced with *EPKSCDK* SEQ ID NO: 105 or another linker sequence)

FIG. 47

Fusion proteins comprising an antibody that binds TNF-α, and a RANKL-binding sequence of receptor activator of nuclear factor-kB (RANK)

Anti-TNFα heavy chain + RANK ectodomain (SEQ ID NO: 61):

<u>EVQLVESGGGLVQPGRSLRLSCAASGFTFDDYAMHWVRQAPGKGLEWVSAITWNSGHIDYADSVEG</u>
<u>RFTISRDNAKNSLYLQMNSLRAEDTAVYYCALVSYLSTASSLDYWGQGTLVTVSS</u>ASTKGPSVFPL
APSSKSTSGGTAALGCLVKDYFPEP

Fusion proteins comprising TNFR2 Extracellular ligand binding domain, Fc, and a RANKL-binding sequence of receptor activator of nuclear factor-kB (RANK)

TNFR2 ECD + IgG Cγ1 + RANK ectodomain (SEQ ID NO: 62):

<u>LPAQVAFTPYAPEPGSTCRLREYYDQTAQMCCSKCSPGQHAKVFCTKTSDTVCDSCEDSTYTQLWN</u>
<u>WVPECLSCGSRCSSDQVETQACTREQNRICTCRPGWYCALSKQEGCRLCAPLRKCRPGFGVARPGT</u>
<u>ETSDVVCKPCAPGTFSNTTSSTDICRPHQICNVVAIPGNASMDAVCTSTSPTRSMAPGAVHLPQPV</u>
<u>STRSQHTQPTPEPSTAPSTSFLLPMGPSPPAEGSTGD</u> *EPKSCDK*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u><u>E</u><u>M</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS* QI APPCTSEKHY
EHLGRCCNKC EPGKYMSSKC TTTSDSVCLP CGPDEYLDSW NEEDKCLLHK VCDTGKALVA
VVAGNSTTPR RCACTAGYHW SQDCECCRRN TECAPGLGAQ HPLQLNKDTV CKPCLAGYFS
DAFSSTDKCR PWTNCTFLGK RVEHHGTEKS DAVCSSSLPA RKPPNEPHVY LPG

Fusion proteins comprising a RANKL-binding sequence of receptor activator of nuclear factor-kB (RANK), Fc, and TNFR2 Extracellular ligand binding domain:

RANK ectodomain + IgG Cγ1 + TNFR2 ECD (SEQ ID NO: 63):

QI APPCTSEKHY EHLGRCCNKC EPGKYMSSKC TTTSDSVCLP CGPDEYLDSW
NEEDKCLLHK VCDTGKALVA VVAGNSTTPR RCACTAGYHW SQDCECCRRN TECAPGLGAQ
HPLQLNKDTV CKPCLAGYFS DAFSSTDKCR PWTNCTFLGK RVEHHGTEKS DAVCSSSLPA
RKPPNEPHVY LPG
*GGGGSGGGGSGGGGS* THTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKT
ISKAKGQPREPQVYTLPPSR<u>E</u><u>E</u><u>M</u>TKNQVSLTCLVKGFYPSDIAVEWESNGQPENNYKTTPPVLDSD
GSFFLYSKLTVDKSRWQQGNVFSCSVMHEALHNHYTQKSLSLSPGK *GGGGSGGGGSGGGGS*
<u>LPAQVAFTPYAPEPGSTCRLREYYDQTAQMCCSKCSPGQHAKVFCTKTSDTVCDSCEDSTYTQLWN</u>
<u>WVPECLSCGSRCSSDQVETQACTREQNRICTCRPGWYCALSKQEGCRLCAPLRKCRPGFGVARPGT</u>
<u>ETSDVVCKPCAPGTFSNTTSSTDICRPHQICNVVAIPGNASMDAVCTSTSPTRSMAPGAVHLPQPV</u>
<u>STRSQHTQPTPEPSTAPSTSFLLPMGPSPPAEGSTGD</u>

Underlined: TNFR2 ligand-binding domain

Plain: human IgG1 heavy chain constant region (IgG Cγ1 domain = H, CH2, CH3)

*Italic: Linker*

Bold: RANK ectodomain

(Note: Can replace linker 1 with *GGGGSGGGGSGGGGS* SEQ ID NO: 104 or *EPKSCDK* SEQ ID NO: 105)
(Note: Can replace underlined aa in Fc: E with D and M with L)

FIG. 49

Fusion proteins comprising the extracellular domain of CTLA-4, Immunoglobulin Fc (IgG Cγ1), and a RANKL-binding sequence of receptor activator of nuclear factor-kB (RANK)

Oncostatin M signal peptide + CTLA-4 ECD + IgG Cγ1 + RANK ectodomain (SEQ ID NO: 64):

<u>*MGVLLTQRTLLSLVLALLFPSMASM*AMHVAQPAVVLASSRGIASFVCEYASPGKATEVRVTVLRQA DSQVTEVCAATYMMGNELTFLDDSICTGTSSGNQVNLTIQGLRAMDTGLYICKVELMYPPPYYLGI GNGTQIYVIDPEPCPDSD</u>*QEPKSCDK* THTCPPCPAPELLGGPSVFLFPPKPKDTLM ISRTPEVTCVVVDVSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQKSLSLSPGK *GGGGSGGGGSGGGGS* QI APPCTSEKHY EHLGRCCNKC EPGKYMSSKC TTTSDSVCLP CGPDEYLDSW NEEDKCLLHK VCDTGKALVA VVAGNSTTPR RCACTAGYHW SQDCECCRRN TECAPGLGAQ HPLQLNKDTV CKPCLAGYFS DAFSSTDKCR PWTNCTFLGK RVEHHGTEKS DAVCSSSLPA RKPPNEPHVY LPG

Fusion proteins comprising a RANKL-binding sequence of receptor activator of nuclear factor-kB (RANK), Immunoglobulin Fc (IgG Cγ1), and a sequence from the extracellular domain of CTLA-4

RANK ectodomain + IgG Cγ1 + CTLA-4 ECD (SEQ ID NO: 65):

QI APPCTSEKHY EHLGRCCNKC EPGKYMSSKC TTTSDSVCLP CGPDEYLDSW NEEDKCLLHK VCDTGKALVA VVAGNSTTPR RCACTAGYHW SQDCECCRRN TECAPGLGAQ HPLQLNKDTV CKPCLAGYFS DAFSSTDKCR PWTNCTFLGK RVEHHGTEKS DAVCSSSLPA RKPPNEPHVY LPG *EPKSCDK* THTCPPCPAPELLGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSKLTVDKSRWQQG NVFSCSVMHEALHNHYTQKSLSLSPGK *GGGGSGGGGSGGGGS* <u>AMHVAQPAVVLASSRGIASFVCEYASPGKATEVRVTVLRQADSQVTEVCAATYMMGNELTFLDDSI CTGTSSGNQVNLTIQGLRAMDTGLYICKVELMYPPPYYLGIGNGTQIYVIDPEPCPDSD</u>

<u>*Underlined Italic*</u>: <u>*Oncostatin M Signal Peptide (-25 to -1)*</u>
<u>Underlined</u>: <u>CTLA-4 extracellular domain (1-125)</u>
Plain: human IgG1 heavy chain constant region (IgG Cγ1 domain = H, CH2, CH3)
*Italic: Linker (optional)*
Bold: RANK ectodomain
(Note: Optional C to S conversion in IgG sequence (bold underlined))
(Note: The linker *QEPKSCDK* SEQ ID NO: 110 can be replaced with *EPKSCDK* SEQ ID NO: 105 or another linker sequence)

FIG. 50

Fusion proteins comprising a RANKL-binding sequence of receptor activator of nuclear factor-kB (RANK), Fc, and a sequence from transforming growth factor-β (TGF-β).

TGF-β1 + Fc + RANK ectodomain (SEQ ID NO: 66):

<u>ALDTNYCFSSTEKNCCVRQLYIDFRKDLGWKWIHEPKGYHANFCLGPCPYIWSLDTQYSKVLALYN</u>
<u>QHNPGASAAPCCVPQALEPLPIVYYVGRKPKVEQLSNMIVRSCKCS</u> *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u>E<u>M</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS* QI APPCTSEKHY
EHLGRCCNKC EPGKYMSSKC TTTSDSVCLP CGPDEYLDSW NEEDKCLLHK VCDTGKALVA
VVAGNSTTPR RCACTAGYHW SQDCECCRRN TECAPGLGAQ HPLQLNKDTV CKPCLAGYFS
DAFSSTDKCR PWTNCTFLGK RVEHHGTEKS DAVCSSSLPA RKPPNEPHVY LPG

RANK ectodomain + Fc + TGF-β1 (SEQ ID NO: 67):

QI APPCTSEKHY EHLGRCCNKC EPGKYMSSKC TTTSDSVCLP CGPDEYLDSW
NEEDKCLLHK VCDTGKALVA VVAGNSTTPR RCACTAGYHW SQDCECCRRN TECAPGLGAQ
HPLQLNKDTV CKPCLAGYFS DAFSSTDKCR PWTNCTFLGK RVEHHGTEKS DAVCSSSLPA
RKPPNEPHVY LPG *GGGGSGGGGSGGGGS*
THTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPS
R<u>E</u>E<u>M</u>TKNQVSLTCLVKGFYPSDIAVEWESNGQPENNYKTTPPVLDSDGSFFLYSKLTVDKSRWQQG
NVFSCSVMHEALHNHYTQKSLSLSPGK *GGGGSGGGGSGGGGS*
<u>ALDTNYCFSSTEKNCCVRQLYIDFRKDLGWKWIHEPKGYHANFCLGPCPYIWSLDTQYSKVLALYN</u>
<u>QHNPGASAAPCCVPQALEPLPIVYYVGRKPKVEQLSNMIVRSCKCS</u>

Underlined: Mature (active) human TGF-β1
*Italic: Linker (optional)*
Plain: Fc
Bold: RANK ectodomain
(Note: Can replace linker 1 *GGGGSGGGGSGGGGS* SEQ ID NO: 104 with
*EPKSCDK* SEQ ID NO: 105)
(Note: Can replace underlined aa in Fc: <u>E</u> with D and <u>M</u> with L)

FIG. 51

Fusion proteins comprising a RANKL-binding sequence of receptor activator of nuclear factor-kB (RANK), Fc, and a sequence from PD-1 ligand 1

PD-1L1 + Fc + RANK ectodomain (SEQ ID NO: 68):
**RIFAVFIFMTYWHLLNAFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVKVNAPYNKINQRILVVD
PVTSEHELTCQAEGYPKAEVIWTSSDHQVLSGKTTTTNSKREEKLFNVTSTLRINTTTNEIFYCTFRRLDPE
ENHTAELVIPELPLAHPPNERTHLVILGAILLCLGVALTFIFRLRKGRMMDVKKCGIQDTNSKKQSDTHLEE
T** *GGGGSGGGGSGGGGS*

THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSR<u>EEM</u>TKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS* QI APPCTSEKHY EHLGRCCNKC EPGKYMSSKC TTTSDSVCLP
CGPDEYLDSW NEEDKCLLHK VCDTGKALVA VVAGNSTTPR RCACTAGYHW SQDCECCRRN
TECAPGLGAQ HPLQLNKDTV CKPCLAGYFS DAFSSTDKCR PWTNCTFLGK RVEHHGTEKS
DAVCSSSLPA RKPPNEPHVY LPG

RANK ectodomain + Fc + PD-1L1 (SEQ ID NO: 69):
QI APPCTSEKHY EHLGRCCNKC EPGKYMSSKC TTTSDSVCLP CGPDEYLDSW NEEDKCLLHK
VCDTGKALVA VVAGNSTTPR RCACTAGYHW SQDCECCRRN TECAPGLGAQ HPLQLNKDTV
CKPCLAGYFS DAFSSTDKCR PWTNCTFLGK RVEHHGTEKS DAVCSSSLPA RKPPNEPHVY LPG
*GGGGSGGGGSGGGGS*
THTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSR<u>EEM</u>TKNQVSLT
CLVKGFYPSDIAVEWESNGQPENNYKTTPPVLDSDGSFFLYSKLTVDKSRWQQGNVFSCSVMHEALHNHYTQ
KSLSLSPGK *GGGGSGGGGSGGGGS*
**RIFAVFIFMTYWHLLNAFTVTVPKDLYVVEYGSNMTIECKFPVEKQLDLAALIVYWEMEDKNIIQFVHGEED
LKVQHSSYRQRARLLKDQLSLGNAALQITDVKLQDAGVYRCMISYGGADYKRITVKVNAPYNKINQRILVVD
PVTSEHELTCQAEGYPKAEVIWTSSDHQVLSGKTTTTNSKREEKLFNVTSTLRINTTTNEIFYCTFRRLDPE
ENHTAELVIPELPLAHPPNERTHLVILGAILLCLGVALTFIFRLRKGRMMDVKKCGIQDTNSKKQSDTHLEE
T**

Bold: PD-1L1 (May use PD-1L1 extracellular domain – underlined)

FIG. 52

```
                           SEQUENCE LISTING

Sequence total quantity: 124
SEQ ID NO: 1            moltype = AA   length = 602
FEATURE                 Location/Qualifiers
source                  1..602
                        mol_type = protein
                        organism = synthetic construct
SEQUENCE: 1
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS GGGGSTIPPH VQKSVNNDMI  480
VTDNNGAVKF PQLCKFCDVR FSTCDNQKSC MSNCSITSIC EKPQEVCVAV WRKNDENITL  540
ETVCHDPKLP YHDFILEDAA SPKCIMKEKK KPGETFFMCS CSSDECNDNI IFSEEYNTSN  600
PD                                                                602

SEQ ID NO: 2            moltype = AA   length = 601
FEATURE                 Location/Qualifiers
source                  1..601
                        mol_type = protein
                        organism = synthetic construct
SEQUENCE: 2
QVQLKQSGPG LVQPSQSLSI TCTVSGFSLT NYGVHWVRQS PGKGLEWLGV IWSGGNTDYN   60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGSG GGGSTIPPHV QKSVNNDMIV  480
TDNNGAVKFP QLCKFCDVRF STCDNQKSCM SNCSITSICE KPQEVCVAVW RKNDENITLE  540
TVCHDPKLPY HDFILEDAAS PKCIMKEKKK PGETFFMCSC SSDECNDNII FSEEYNTSNP  600
D                                                                 601

SEQ ID NO: 3            moltype = AA   length = 603
FEATURE                 Location/Qualifiers
source                  1..603
                        mol_type = protein
                        organism = synthetic construct
SEQUENCE: 3
QVQLQQPGAE LVKPGASVKM SCKASGYTFT SYNMHWVKQT PGRGLEWIGA IYPGNGDTSY   60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG SGGGGSTIPP HVQKSVNNDM  480
IVTDNNGAVK FPQLCKFCDV RFSTCDNQKS CMSNCSITSI CEKPQEVCVA VWRKNDENIT  540
LETVCHDPKL PYHDFILEDA ASPKCIMKEK KKPGETFFMC SCSSDECNDN IIFSEEYNTS  600
NPD                                                               603

SEQ ID NO: 4            moltype = AA   length = 605
FEATURE                 Location/Qualifiers
source                  1..605
                        mol_type = protein
                        organism = synthetic construct
SEQUENCE: 4
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
```

```
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSTI PPHVQKSVNN  480
DMIVTDNNGA VKFPQLCKFC DVRFSTCDNQ KSCMSNCSIT SICEKPQEVC VAVWRKNDEN  540
ITLETVCHDP KLPYHDFILE DAASPKCIMK EKKKPGETFF MCSCSSDECN DNIIFSEEYN  600
TSNPD                                                              605

SEQ ID NO: 5         moltype = AA   length = 600
FEATURE              Location/Qualifiers
source               1..600
                     mol_type = protein
                     organism = synthetic construct
SEQUENCE: 5
QVQLVESGGG VVQPGRSLRL SCAASGFTFS SYTMHWVRQA PGKGLEWVTF ISYDGNNKYY   60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGKGG GGSGGGGSGG GGSTIPPHVQ KSVNNDMIVT  480
DNNGAVKFPQ LCKFCDVRFS TCDNQKSCMS NCSITSICEK PQEVCVAVWR KNDENITLET  540
VCHDPKLPYH DFILEDAASP KCIMKEKKKP GETFFMCSCS SDECNDNIIF SEEYNTSNPD  600

SEQ ID NO: 6         moltype = AA   length = 525
FEATURE              Location/Qualifiers
source               1..525
                     mol_type = protein
                     organism = synthetic construct
SEQUENCE: 6
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSTH TCPPCPAPEL LGGPSVFLFP PKPKDTLMIS  180
RTPEVTCVVV DVSHEDPEVK FNWYVDGVEV HNAKTKPREE QYNSTYRVVS VLTVLHQDWL  240
NGKEYKCKVS NKALPAPIEK TISKAKGQPR EPQVYTLPPS REEMTKNQVS LTCLVKGFYP  300
SDIAVEWESN GQPENNYKTT PPVLDSDGSF FLYSKLTVDK SRWQQGNVFS CSVMHEALHN  360
HYTQKSLSLS PGKGGGGSGG GGSGGGGSTI PPHVQKSVNN DMIVTDNNGA VKFPQLCKFC  420
DVRFSTCDNQ KSCMSNCSIT SICEKPQEVC VAVWRKNDEN ITLETVCHDP KLPYHDFILE  480
DAASPKCIMK EKKKPGETFF MCSCSSDECN DNIIFSEEYN TSNPD                  525

SEQ ID NO: 7         moltype = AA   length = 525
FEATURE              Location/Qualifiers
source               1..525
                     mol_type = protein
                     organism = synthetic construct
SEQUENCE: 7
TIPPHVQKSV NNDMIVTDNN GAVKFPQLCK FCDVRFSTCD NQKSCMSNCS ITSICEKPQE   60
VCVAVWRKND ENITLETVCH DPKLPYHDFI LEDAASPKCI MKEKKKPGET FFMCSCSSDE  120
CNDNIIFSEE YNTSNPDGGG GSGGGGSGGG GSTHTCPPCP APELLGGPSV FLFPPKPKDT  180
LMISRTPEVT CVVVDVSHED PEVKFNWYVD GVEVHNAKTK PREEQYNSTY RVVSVLTVLH  240
QDWLNGKEYK CKVSNKALPA PIEKTISKAK GQPREPQVYT LPPSREEMTK NQVSLTCLVK  300
GFYPSDIAVE WESNGQPENN YKTTPPVLDS DGSFFLYSKL TVDKSRWQQG NVFSCSVMHE  360
ALHNHYTQKS LSLSPGKGGG GSGGGGSGGG GSAPTSSSTK TQLQLEHLLL DLDQMILNGI  420
NNYKNPKLTR MLTFKFYMPK KATELKHLQC LEEELKPLEE VLNLAQSKNF HLRPRDLISN  480
INVIVLELKG SETTFMCEYA DETATIVEFL NRWITFCQSI ISTLT                  525

SEQ ID NO: 8         moltype = AA   length = 598
FEATURE              Location/Qualifiers
source               1..598
                     mol_type = protein
                     organism = synthetic construct
SEQUENCE: 8
QVQLVQSGAE VKKPGSSVKV SCKASGYTFT SYRMHWVRQA PGQGLEWIGY INPSTGYTEY   60
NQKFKDKATI TADESTNTAY MELSSLRSED TAVYYCARGG GVFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKGGGG SGGGGSGGGG STIPPHVQKS VNNDMIVTDN  480
NGAVKFPQLC KFCDVRFSTC DNQKSCMSNC SITSICEKPQ EVCVAVWRKN DENITLETVC  540
HDPKLPYHDF ILEDAASPKC IMKEKKKPGE TFFMCSCSSD ECNDNIIFSE EYNTSNPD    598

SEQ ID NO: 9         moltype = AA   length = 597
FEATURE              Location/Qualifiers
source               1..597
                     mol_type = protein
```

```
                                organism = synthetic construct
SEQUENCE: 9
QLQQSGTVLA RPGASVKMSC KASGYSFTRY WMHWIKQRPG QGLEWIGAIY PGNSDTSYNQ    60
KFEGKAKLTA VTSASTAYME LSSLTHEDSA VYYCSRDYGY YFDFWGQGTT LTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGVN   420
FSCSVMHEAL HNHYTQKSLS LSPGKGGGGS GGGGSGGGGS TIPPHVQKSV NNDMIVTDNN   480
GAVKFPQLCK FCDVRFSTCD NQKSCMSNCS ITSICEKPQE VCVAVWRKND ENITLETVCH   540
DPKLPYHDFI LEDAASPKCI MKEKKKPGET FFMCSCSSDE CNDNIIFSEE YNTSNPD     597

SEQ ID NO: 10           moltype = AA   length = 603
FEATURE                 Location/Qualifiers
source                  1..603
                        mol_type = protein
                        organism = synthetic construct
SEQUENCE: 10
QVQLQEAGPG LVKPSETLSL TCSVSGGSIS GDYYWFWIRQ SPGKGLEWIG YIYGSGGGTN    60
YNPSLNNRVS ISIDTSKNLF SLKLRSVTAA DTAVYYCASN ILKYLHWLLY WGQGVLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLPPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSTIPP HVQKSVNNDM   480
IVTDNNGAVK FPQLCKFCDV RFSTCDNQKS CMSNCSITSI CEKPQEVCVA VWRKNDENIT   540
LETVCHDPKL PYHDFILEDA ASPKCIMKEK KKPGETFFMC SCSSDECNDN IIFSEEYNTS   600
NPD                                                                 603

SEQ ID NO: 11           moltype = AA   length = 542
FEATURE                 Location/Qualifiers
source                  1..542
                        mol_type = protein
                        organism = synthetic construct
SEQUENCE: 11
PGWFLDSPDR PWNPPTFSPA LLVVTEGDNA TFTCSFSNTS ESFVLNWYRM SPSNQTDKLA    60
AFPEDRSQPG QDCRFRVTQL PNGRDFHMSV VRARRNDSGT YLCGAISLAP KAQIKESLRA   120
ELRVTERRAE VPTAHPSPSP RPAGQFQTLV GGGGSGGGGS GGGGSTHTCP PCPAPELLGG   180
PSVFLFPPKP KDTLMISRTP EVTCVVVDVS HEDPEVKFNW YVDGVEVHNA KTKPREEQYN   240
STYRVVSVLT VLHQDWLNGK EYKCKVSNKA LPAPIEKTIS KAKGQPREPQ VYTLPPSREE   300
MTKNQVSLTC LVKGFYPSDI AVEWESNGQP ENNYKTTPPV LDSDGSFFLY SKLTVDKSRW   360
QQGNVFSCSV MHEALHNHYT QKSLSLSPGK GGGGSGGGGS GGGGSTIPPH VQKSVNNDMI   420
VTDNNGAVKF PQLCKFCDVR FSTCDNQKSC MSNCSITSIC EKPQEVCVAV WRKNDENITL   480
ETVCHDPKLP YHDFILEDAA SPKCIMKEKK KPGETFFMCS CSSDECNDNI IFSEEYNTSN   540
PD                                                                  542

SEQ ID NO: 12           moltype = AA   length = 542
FEATURE                 Location/Qualifiers
source                  1..542
                        mol_type = protein
                        organism = synthetic construct
SEQUENCE: 12
TIPPHVQKSV NNDMIVTDNN GAVKFPQLCK FCDVRFSTCD NQKSCMSNCS ITSICEKPQE    60
VCVAVWRKND ENITLETVCH DPKLPYHDFI LEDAASPKCI MKEKKKPGET FFMCSCSSDE   120
CNDNIIFSEE YNTSNPDGGG GSGGGGSGGG GSTHTCPPCP APELLGGPSV FLFPPKPKDT   180
LMISRTPEVT CVVVDVSHED PEVKFNWYVD GVEVHNAKTK PREEQYNSTY RVVSVLTVLH   240
QDWLNGKEYK CKVSNKALPA PIEKTISKAK GQPREPQVYT LPPSREEMTK NQVSLTCLVK   300
GFYPSDIAVE WESNGQPENN YKTTPPVLDS DGSFFLYSKL TVDKSRWQQG NVFSCSVMHE   360
ALHNHYTQKS LSLSPGKGGG GSGGGGSGGG GSPGWFLDSP DRPWNPPTFS PALLVVTEGD   420
NATFTCSFSN TSESFVLNWY RMSPSNQTDK LAAFPEDRSQ PGQDCRFRVT QLPNGRDFHM   480
SVVRARRNDS GTYLCGAISL APKAQIKESL RAELRVTERR AEVPTAHPSP SPRPAGQFQT   540
LV                                                                  542

SEQ ID NO: 13           moltype = AA   length = 577
FEATURE                 Location/Qualifiers
source                  1..577
                        mol_type = protein
                        organism = synthetic construct
SEQUENCE: 13
TIPPHVQKSV NNDMIVTDNN GAVKFPQLCK FCDVRFSTCD NQKSCMSNCS ITSICEKPQE    60
VCVAVWRKND ENITLETVCH DPKLPYHDFI LEDAASPKCI MKEKKKPGET FFMCSCSSDE   120
CNDNIIFSEE YNTSNPDGGG GSGGGGSGGG GSTHTCPPCP APELLGGPSV FLFPPKPKDT   180
LMISRTPEVT CVVVDVSHED PEVKFNWYVD GVEVHNAKTK PREEQYNSTY RVVSVLTVLH   240
QDWLNGKEYK CKVSNKALPA PIEKTISKAK GQPREPQVYT LPPSREEMTK NQVSLTCLVK   300
GFYPSDIAVE WESNGQPENN YKTTPPVLDS DGSFFLYSKL TVDKSRWQQG NVFSCSVMHE   360
ALHNHYTQKS LSLSPGKGGG GSGGGGSGGG GSQIAPPCTS EKHYEHLGRC CNKCEPGKYM   420
SSKCTTTSDS VCLPCGPDEY LDSWNEEDKC LLHKVCDTGK ALVAVVAGNS TTPRRCACTA   480
```

```
GYHWSQDCEC CRRNTECAPG LGAQHPLQLN KDTVCKPCLA GYFSDAFSST DKCRPWTNCT   540
FLGKRVEHHG TEKSDAVCSS SLPARKPPNE PHVYLPG                            577

SEQ ID NO: 14           moltype = AA  length = 577
FEATURE                 Location/Qualifiers
source                  1..577
                        mol_type = protein
                        organism = synthetic construct
SEQUENCE: 14
QIAPPCTSEK HYEHLGRCCN KCEPGKYMSS KCTTTSDSVC LPCGPDEYLD SWNEEDKCLL   60
HKVCDTGKAL VAVVAGNSTT PRRCACTAGY HWSQDCECCR RNTECAPGLG AQHPLQLNKD   120
TVCKPCLAGY FSDAFSSTDK CRPWTNCTFL GKRVEHHGTE KSDAVCSSSL PARKPPNEPH   180
VYLPGGGGGS GGGGSGGGGS THTCPPCPAP ELLGGPSVFL FPPKPKDTLM ISRTPEVTCV   240
VVDVSHEDPE VKFNWYVDGV EVHNAKTKPR EEQYNSTYRV VSVLTVLHQD WLNGKEYKCK   300
VSNKALPAPI EKTISKAKGQ PREPQVYTLP PSREEMTKNQ VSLTCLVKGF YPSDIAVEWE   360
SNGQPENNYK TTPPVLDSDG SFFLYSKLTV DKSRWQQGNV FSCSVMHEAL HNHYTQKSLS   420
LSPGKGGGGS GGGGSGGGGS TIPPHVQKSV NNDMIVTDNN GAVKFPQLCK FCDVRFSTCD   480
NQKSCMSNCS ITSICEKPQE VCVAVWRKND ENITLETVCH DPKLPYHDFI LEDAASPKCI   540
MKEKKKPGET FFMCSCSSDE CNDNIIFSEE YNTSNPD                            577

SEQ ID NO: 15           moltype = AA  length = 615
FEATURE                 Location/Qualifiers
source                  1..615
                        mol_type = protein
                        organism = synthetic construct
SEQUENCE: 15
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSPGWFL DSPDRPWNPP   480
TFSPALLVVT EGDNATFTCS FSNTSESFVL NWYRMSPSNQ TDKLAAFPED RSQPGQDCRF   540
RVTQLPNGRD FHMSVVRARR NDSGTYLCGA ISLAPKAQIK ESLRAELRVT ERRAEVPTAH   600
PSPSPRPAGQ FQTLV                                                   615

SEQ ID NO: 16           moltype = AA  length = 614
FEATURE                 Location/Qualifiers
source                  1..614
                        mol_type = protein
                        organism = synthetic construct
SEQUENCE: 16
QVQLKQSGPG LVQPSQSLSI TCTVSGFSLT NYGVHWVRQS PGKGLEWLGV IWSGGNTDYN   60
TPFTSRLSIN KDNSKSQVFF KMNSLQSNDT AIYYCARALT YYDYEFAYWG QGTLVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGKG GGGSGGGGSG GGGSPGWFLD SPDRPWNPPT   480
FSPALLVVTE GDNATFTCSF SNTSESFVLN WYRMSPSNQT DKLAAFPEDR SQPGQDCRFR   540
VTQLPNGRDF HMSVVRARRN DSGTYLCGAI SLAPKAQIKE SLRAELRVTE RRAEVPTAHP   600
SPSPRPAGQF QTLV                                                    614

SEQ ID NO: 17           moltype = AA  length = 616
FEATURE                 Location/Qualifiers
source                  1..616
                        mol_type = protein
                        organism = synthetic construct
SEQUENCE: 17
QVQLQQPGAE LVKPGASVKM SCKASGYTFT SYNMHWVKQT PGRGLEWIGA IYPGNGDTSY   60
NQKFKGKATL TADKSSSTAY MQLSSLTSED SAVYYCARST YYGGDWYFNV WGAGTTVTVS   120
AASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKAE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSPGWF LDSPDRPWNP   480
PTFSPALLVV TEGDNATFTC SFSNTSESFV LNWYRMSPSN QTDKLAAFPE DRSQPGQDCR   540
FRVTQLPNGR DFHMSVVRAR RNDSGTYLCG AISLAPKAQI KESLRAELRV TERRAEVPTA   600
HPSPSPRPAG QFQTLV                                                  616

SEQ ID NO: 18           moltype = AA  length = 618
FEATURE                 Location/Qualifiers
source                  1..618
                        mol_type = protein
                        organism = synthetic construct
```

```
SEQUENCE: 18
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT     120
VSSASTKGPS VFPLAPSSKS TSGGTAALGC LVKDYFPEPV TVSWNSGALT SGVHTFPAVL     180
QSSGLYSLSS VVTVPSSSLG TQTYICNVNH KPSNTKVDKK VEPKSCDKTH TCPPCPAPEL     240
LGGPSVFLFP PKPKDTLMIS RTPEVTCVVV DVSHEDPEVK FNWYVDGVEV HNAKTKPREE     300
QYNSTYRVVS VLTVLHQDWL NGKEYKCKVS NKALPAPIEK TISKAKGQPR EPQVYTLPPS     360
REEMTKNQVS LTCLVKGFYP SDIAVEWESN GQPENNYKTT PPVLDSDGSF FLYSKLTVDK     420
SRWQQGNVFS CSVMHEALHN HYTQKSLSLS PGKGGGGSGG GGSGGGGSPG WFLDSPDRPW     480
NPPTFSPALL VVTEGDNATF TCSFSNTSES FVLNWYRMSP SNQTDKLAAF PEDRSQPGQD     540
CRFRVTQLPN GRDFHMSVVR ARRNDSGTYL CGAISLAPKA QIKESLRAEL RVTERRAEVP     600
TAHPSPSRP  AGQFQTLV                                                   618

SEQ ID NO: 19           moltype = AA   length = 613
FEATURE                 Location/Qualifiers
source                  1..613
                        mol_type = protein
                        organism = synthetic construct
SEQUENCE: 19
QVQLVESGGG VVQPGRSLRL SCAASGFTFS SYTMHWVRQA PGKGLEWVTF ISYDGNNKYY      60
ADSVKGRFTI SRDNSKNTLY LQMNSLRAED TAIYYCARTG WLGPFDYWGQ GTLVTVSSAS     120
TKGPSVFPLA PSSKSTSGGT AALGCLVKDY FPEPVTVSWN SGALTSGVHT FPAVLQSSGL     180
YSLSSVVTVP SSSLGTQTYI CNVNHKPSNT KVDKRVEPKS CDKTHTCPPC PAPELLGGPS     240
VPLFPPKPKD TLMISRTPEV TCVVVDVSHE DPEVKFNWYV DGVEVHNAKT KPREEQYNST     300
YRVVSVLTVL HQDWLNGKEY KCKVSNKALP APIEKTISKA KGQPREPQVY TLPPSRDELT     360
KNQVSLTCLV KGFYPSDIAV EWESNGQPEN NYKTTPPVLD SDGSFFLYSK LTVDKSRWQQ     420
GNVFSCSVMH EALHNHYTQK SLSLSPGKGG GGSGGGGSGG GGSPGWFLDS PDRPWNPPTF     480
SPALLVVTEG DNATFTCSFS NTSESFVLNW YRMSPSNQTD KLAAFPEDRS QPGQDCRFRV     540
TQLPNGRDFH MSVVRARRND SGTYLCGAIS LAPKAQIKES LRAELRVTER RAEVPTAHPS     600
PSPRPAGQFQ TLV                                                        613

SEQ ID NO: 20           moltype = AA   length = 611
FEATURE                 Location/Qualifiers
source                  1..611
                        mol_type = protein
                        organism = synthetic construct
SEQUENCE: 20
QVQLVQSGAE VKKPGSSVKV SCKASGYTFT SYRMHWVRQA PGQGLEWIGY INPSTGYTEY      60
NQKFKDKATI TADESTNTAY MELSSLRSED TAVYYCARGG GVFDYWGQGT LVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCPPCPA PELLGGPSVF     240
LFPPKPKDTL MISRTPEVTC VVVDVSHEDP EVKFNWYVDG VEVHNAKTKP REEQYNSTYR     300
VVSVLTVLHQ DWLNGKEYKC KVSNKALPAP IEKTISKAKG QPREPQVYTL PPSRDELTKN     360
QVSLTCLVKG FYPSDIAVEW ESNGQPENNY KTTPPVLDSD GSFFLYSKLT VDKSRWQQGN     420
VFSCSVMHEA LHNHYTQKSL SLSPGKGGGG SGGGGSGGGG SPGWFLDSPD RPWNPPTFSP     480
ALLVVTEGDN ATFTCSFSNT SESFVLNWYR MSPSNQTDKL AAFPEDRSQP GQDCRFRVTQ     540
LPNGRDFHMS VVRARRNDSG TYLCGAISLA PKAQIKESLR AELRVTERRA EVPTAHPSPS     600
PRPAGQFQTL V                                                          611

SEQ ID NO: 21           moltype = AA   length = 610
FEATURE                 Location/Qualifiers
source                  1..610
                        mol_type = protein
                        organism = synthetic construct
SEQUENCE: 21
QLQQSGTVLA RPGASVKMSC KASGYSFTRY WMHWIKQRPG QGLEWIGAIY PGNSDTSYNQ      60
KFEGKAKLTA VTSASTAYME LSSLTHEDSA VYYCSRDYGY YFDFWGQGTT LTVSSASTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KRVEPKSCDK THTCPPCPAP ELLGGPSVFL     240
FPPKPKDTLM ISRTPEVTCV VVDVSHEDPE VKFNWYVDGV EVHNAKTKPR EEQYNSTYRV     300
VSVLTVLHQD WLNGKEYKCK VSNKALPAPI EKTISKAKGQ PREPQVYTLP PSRDELTKNQ     360
VSLTCLVKGF YPSDIAVEWE SNGQPENNYK TTPPVLDSDG SFFLYSKLTV DKSRWQQGNV     420
FSCSVMHEAL HNHYTQKSLS LSPGKGGGGS GGGGSGGGGS PGWFLDSPDR PWNPPTFSPA     480
LLVVTEGDNA TFTCSFSNTS ESFVLNWYRM SPSNQTDKLA AFPEDRSQPG QDCRFRVTQL     540
PNGRDFHMSV VRARRNDSGT YLCGAISLAP KAQIKESLRA ELRVTERRAE VPTAHPSPSP     600
RPAGQFQTLV                                                            610

SEQ ID NO: 22           moltype = AA   length = 538
FEATURE                 Location/Qualifiers
source                  1..538
                        mol_type = protein
                        organism = synthetic construct
SEQUENCE: 22
APTSSSTKKT QLQLEHLLLD LQMILNGINN YKNPKLTRML TFKFYMPKKA TELKHLQCLE      60
EELKPLEEVL NLAQSKNFHL RPRDLISNIN VIVLELKGSE TTFMCEYADE TATIVEFLNR     120
WITFCQSIIS TLTGGGGSGG GGSGGGGSTH TCPPCPAPEL LGGPSVFLFP PKPKDTLMIS     180
RTPEVTCVVV DVSHEDPEVK FNWYVDGVEV HNAKTKPREE QYNSTYRVVS VLTVLHQDWL     240
NGKEYKCKVS NKALPAPIEK TISKAKGQPR EPQVYTLPPS REEMTKNQVS LTCLVKGFYP     300
SDIAVEWESN GQPENNYKTT PPVLDSDGSF FLYSKLTVDK SRWQQGNVFS CSVMHEALHN     360
```

```
HYTQKSLSLS PGKGGGGSGG GGSGGGGSPG WFLDSPDRPW NPPTFSPALL VVTEGDNATF    420
TCSFSNTSES FVLNWYRMSP SNQTDKLAAF PEDRSQPGQD CRFRVTQLPN GRDFHMSVVR    480
ARRNDSGTYL CGAISLAPKA QIKESLRAEL RVTERRAEVP TAHPSPSPRP AGQFQTLV     538

SEQ ID NO: 23           moltype = AA  length = 538
FEATURE                 Location/Qualifiers
source                  1..538
                        mol_type = protein
                        organism = synthetic construct
SEQUENCE: 23
PGWFLDSPDR PWNPPTFSPA LLVVTEGDNA TFTCSFSNTS ESFVLNWYRM SPSNQTDKLA    60
AFPEDRSQPG QDCRFRVTQL PNGRDFHMSV VRARRNDSGT YLCGAISLAP KAQIKESLRA   120
ELRVTERRAE VPTAHPSPSP RPAGQFQTLV GGGGSGGGGS GGGGSTHTCP PCPAPELLGG   180
PSVFLFPPKP KDTLMISRTP EVTCVVVDVS HEDPEVKFNW YVDGVEVHNA KTKPREEQYN   240
STYRVVSVLT VLHQDWLNGK EYKCKVSNKA LPAPIEKTIS KAKGQPREPQ VYTLPPSREE   300
MTKNQVSLTC LVKGFYPSDI AVEWESNGQP ENNYKTTPPV LDSDGSFFLY SKLTVDKSRW   360
QQGNVFSCSV MHEALHNHYT QKSLSLSPGK GGGGSGGGGS GGGGSAPTSS STKKTQLQLE   420
HLLLDLQMIL NGINNYKNPK LTRMLTFKFY MPKKATELKH LQCLEEELKP LEEVLNLAQS   480
KNFHLRPRDL ISNINIVLE LKGSETTFMC EYADETATIV EFLNRWITFC QSIISTLT      538

SEQ ID NO: 24           moltype = AA  length = 616
FEATURE                 Location/Qualifiers
source                  1..616
                        mol_type = protein
                        organism = synthetic construct
SEQUENCE: 24
QVQLQEAGPG LVKPSETLSL TCSVSGGSIS GDYYWFWIRQ SPGKGLEWIG YIYGSGGGTN    60
YNPSLNNRVS ISIDTSKNLF SLKLRSVTAA DTAVYYCASN ILKYLHWLLY WGQGVLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSPGWF LDSPDRPWNP   480
PTFSPALLVV TEGDNATFTC SFSNTSESFV LNWYRMSPSN QTDKLAAFPE DRSQPGQDCR   540
FRVTQLPNGR DFHMSVVRAR RNDSGTYLCG AISLAPKAQI KESLRAELRV TERRAEVPTA   600
HPSPSPRPAG QFQTLV                                                  616

SEQ ID NO: 25           moltype = AA  length = 590
FEATURE                 Location/Qualifiers
source                  1..590
                        mol_type = protein
                        organism = synthetic construct
SEQUENCE: 25
QIAPPCTSEK HYEHLGRCCN KCEPGKYMSS KCTTTSDSVC LPCGPDEYLD SWNEEDKCLL    60
HKVCDTGKAL VAVVAGNSTT PRRCACTAGY HWSQDCECCR RNTECAPGLG AQHPLQLNKD   120
TVCKPCLAGY FSDAFSSTDK CRPWTNCTFL GKRVEHHGTE KSDAVCSSSL PARKPPNEPH   180
VYLPGGGGGS GGGGSGGGGS THTCPPCPAP ELLGGPSVFL FPPKPKDTLM ISRTPEVTCV   240
VVDVSHEDPE VKFNWYVDGV EVHNAKTKPR EEQYNSTYRV VSVLTVLHQD WLNGKEYKCK   300
VSNKALPAPI EKTISKAKGQ PREPQVYTLP PSREEMTKNQ VSLTCLVKGF YPSDIAVEWE   360
SNGQPENNYK TTPPVLDSDG SFFLYSKLTV DKSRWQQGNV FSCSVMHEAL HNHYTQKSLS   420
LSPGKGGGGS GGGGSGGGGS PGWFLDSPDR PWNPPTFSPA LLVVTEGDNA TFTCSFSNTS   480
ESFVLNWYRM SPSNQTDKLA AFPEDRSQPG QDCRFRVTQL PNGRDFHMSV VRARRNDSGT   540
YLCGAISLAP KAQIKESLRA ELRVTERRAE VPTAHPSPSP RPAGQFQTLV              590

SEQ ID NO: 26           moltype = AA  length = 590
FEATURE                 Location/Qualifiers
source                  1..590
                        mol_type = protein
                        organism = synthetic construct
SEQUENCE: 26
PGWFLDSPDR PWNPPTFSPA LLVVTEGDNA TFTCSFSNTS ESFVLNWYRM SPSNQTDKLA    60
AFPEDRSQPG QDCRFRVTQL PNGRDFHMSV VRARRNDSGT YLCGAISLAP KAQIKESLRA   120
ELRVTERRAE VPTAHPSPSP RPAGQFQTLV GGGGSGGGGS GGGGSTHTCP PCPAPELLGG   180
PSVFLFPPKP KDTLMISRTP EVTCVVVDVS HEDPEVKFNW YVDGVEVHNA KTKPREEQYN   240
STYRVVSVLT VLHQDWLNGK EYKCKVSNKA LPAPIEKTIS KAKGQPREPQ VYTLPPSREE   300
MTKNQVSLTC LVKGFYPSDI AVEWESNGQP ENNYKTTPPV LDSDGSFFLY SKLTVDKSRW   360
QQGNVFSCSV MHEALHNHYT QKSLSLSPGK GGGGSGGGGS GGGGSQIAPP CTSEKHYEHL   420
GRCCNKCEPG KYMSSKCTTT SDSVCLPCGP DEYLDSWNEE DKCLLHKVCD TGKALVAVVA   480
GNSTTPRRCA CTAGYHWSQD CECCRRNTEC APGLGAQHPL QLNKDTVCKP CLAGYFSDAF   540
SSTDKCRPWT NCTFLGKRVE HHGTEKSDAV CSSSLPARKP PNEPHVYLPG              590

SEQ ID NO: 27           moltype = AA  length = 650
FEATURE                 Location/Qualifiers
source                  1..650
                        mol_type = protein
                        organism = synthetic construct
SEQUENCE: 27
EVQLVESGGG LVQPGGSLRL SCAASGFNIK DTYIHWVRQA PGKGLEWVAR IYPTNGYTRY    60
```

```
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS GGGGSQIAPP CTSEKHYEHL  480
GRCCNKCEPG KYMSSKCTTT SDSVCLPCGP DEYLDSWNEE DKCLLHKVCD TGKALVAVVA  540
GNSTTPRRCA CTAGYHWSQD CECCRRNTEC APGLGAQHPL QLNKDTVCKP CLAGYFSDAF  600
SSTDKCRPWT NCTFLGKRVE HHGTEKSDAV CSSSLPARKP PNEPHVYLPG            650

SEQ ID NO: 28           moltype = AA   length = 649
FEATURE                 Location/Qualifiers
source                  1..649
                        mol_type = protein
                        organism = synthetic construct
SEQUENCE: 28
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGSG GGGSQIAPPC TSEKHYEHLG  480
RCCNKCEPGK YMSSKCTTTS DSVCLPCGPD EYLDSWNEED KCLLHKVCDT GKALVAVVAG  540
NSTTPRRCAC TAGYHWSQDC ECCRRNTECA PGLGAQHPLQ LNKDTVCKPC LAGYFSDAFS  600
STDKCRPWTN CTFLGKRVEH HGTEKSDAVC SSSLPARKPP NEPHVYLPG             649

SEQ ID NO: 29           moltype = AA   length = 651
FEATURE                 Location/Qualifiers
source                  1..651
                        mol_type = protein
                        organism = synthetic construct
SEQUENCE: 29
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG SGGGGSQIAP PCTSEKHYEH  480
LGRCCNKCEP GKYMSSKCTT TSDSVCLPCG PDEYLDSWNE EDKCLLHKVC DTGKALVAVV  540
AGNSTTPRRC ACTAGYHWSQ DCECCRRNTE CAPGLGAQHP LQLNKDTVCK PCLAGYFSDA  600
FSSTDKCRPW TNCTFLGKRV EHHGTEKSDA VCSSSLPARK PPNEPHVYLP G          651

SEQ ID NO: 30           moltype = AA   length = 653
FEATURE                 Location/Qualifiers
source                  1..653
                        mol_type = protein
                        organism = synthetic construct
SEQUENCE: 30
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSQI APPCTSEKHY  480
EHLGRCCNKC EPGKYMSSKC TTTSDSVCLP CGPDEYLDSW NEEDKCLLHK VCDTGKALVA  540
VVAGNSTTPR RCACTAGYHW SQDCECCRRN TECAPGLGAQ HPLQLNKDTV CKPCLAGYFS  600
DAFSSTDKCR PWTNCTFLGK RVEHHGTEKS DAVCSSSLPA RKPPNEPHVY LPG         653

SEQ ID NO: 31           moltype = AA   length = 648
FEATURE                 Location/Qualifiers
source                  1..648
                        mol_type = protein
                        organism = synthetic construct
SEQUENCE: 31
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGKGG GGSGGGGSGG GSQIAPPCT SEKHYEHLGR   480
```

```
CCNKCEPGKY MSSKCTTTSD SVCLPCGPDE YLDSWNEEDK CLLHKVCDTG KALVAVVAGN   540
STTPRRCACT AGYHWSQDCE CCRRNTECAP GLGAQHPLQL NKDTVCKPCL AGYFSDAFSS   600
TDKCRPWTNC TFLGKRVEHH GTEKSDAVCS SSLPARKPPN EPHVYLPG               648

SEQ ID NO: 32              moltype = AA  length = 646
FEATURE                    Location/Qualifiers
source                     1..646
                           mol_type = protein
                           organism = synthetic construct
SEQUENCE: 32
QVQLVQSGAE VKKPGSSVKV SCKASGYTFT SYRMHWVRQA PGQGLEWIGY INPSTGYTEY    60
NQKFKDKATI TADESTNTAY MELSSLRSED TAVYYCARGG GVFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGKGGGG SGGGGSGGGG SQIAPPCTSE KHYEHLGRCC   480
NKCEPGKYMS SKCTTTSDSV CLPCGPDEYL DSWNEEDKCL LHKVCDTGKA LVAVVAGNST   540
TPRRCACTAG YHWSQDCECC RRNTECAPGL GAQHPLQLNK DTVCKPCLAG YFSDAFSSTD   600
KCRPWTNCTF LGKRVEHHGT EKSDAVCSSS LPARKPPNEP HVYLPG                 646

SEQ ID NO: 33              moltype = AA  length = 645
FEATURE                    Location/Qualifiers
source                     1..645
                           mol_type = protein
                           organism = synthetic construct
SEQUENCE: 33
QLQQSGTVLA RPGASVKMSC KASGYSFTRY WMHWIKQRPG QGLEWIGAIY PGNSDTSYNQ    60
KFEGKAKLTA VTSASTAYME LSSLTHEDSA VYYCSRDYGY YFDFWGQGTT LTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGKGGGGS GGGGSGGGGS QIAPPCTSEK HYEHLGRCCN   480
KCEPGKYMSS KCTTTSDSVC LPCGPDEYLD SWNEEDKCLL HKVCDTGKAL VAVVAGNSTT   540
PRRCACTAGY HWSQDCECCR RNTECAPGLG AQHPLQLNKD TVCKPCLAGY FSDAFSSTDK   600
CRPWTNCTFL GKRVEHHGTE KSDAVCSSSL PARKPPNEPH VYLPG                  645

SEQ ID NO: 34              moltype = AA  length = 573
FEATURE                    Location/Qualifiers
source                     1..573
                           mol_type = protein
                           organism = synthetic construct
SEQUENCE: 34
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSTH TCPPCPAPEL LGGPSVFLFP PKPKDTLMIS   180
RTPEVTCVVV DVSHEDPEVK FNWYVDGVEV HNAKTKPREE QYNSTYRVVS VLTVHQDWL   240
NGKEYKCKVS NKALPAPIEK TISKAKGQPR EPQVYTLPPS REEMTKNQVS LTCLVKGFYP   300
SDIAVEWESN GQPENNYKTT PPVLDSDGSF FLYSKLTVDK SRWQQGNVFS CSVMHEALHN   360
HYTQKSLSLS PGKGGGGSGG GGSGGGGSQI APPCTSEKHY EHLGRCCNKC EPGKYMSSKC   420
TTTSDSVCLP CGPDEYLDSW NEEDKCLLHK VCDTGKALVA VVAGNSTTPR RCACTAGYHW   480
SQDCECCRRN TECAPGLGAQ HPLQLNKDTV CKPCLAGYFS DAFSSTDKCR PWTNCTFLGK   540
RVEHHGTEKS DAVCSSSLPA RKPPNEPHVY LPG                               573

SEQ ID NO: 35              moltype = AA  length = 573
FEATURE                    Location/Qualifiers
source                     1..573
                           mol_type = protein
                           organism = synthetic construct
SEQUENCE: 35
QIAPPCTSEK HYEHLGRCCN KCEPGKYMSS KCTTTSDSVC LPCGPDEYLD SWNEEDKCLL    60
HKVCDTGKAL VAVVAGNSTT PRRCACTAGY HWSQDCECCR RNTECAPGLG AQHPLQLNKD   120
TVCKPCLAGY FSDAFSSTDK CRPWTNCTFL GKRVEHHGTE KSDAVCSSSL PARKPPNEPH   180
VYLPGGGGGS GGGGSGGGGS THTCPPCPAP ELLGGPSVFL FPPKPKDTLM ISRTPEVTCV   240
VVDVSHEDPE VKFNWYVDGV EVHNAKTKPR EEQYNSTYRV VSVLTVLHQD WLNGKEYKCK   300
VSNKALPAPI EKTISKAKGQ PREPQVYTLP PSREEMTKNQ VSLTCLVKGF YPSDIAVEWE   360
SNGQPENNYK TTPPVLDSDG SFFLYSKLTV DKSRWQQGNV FSCSVMHEAL HNHYTQKSLS   420
LSPGKGGGGS GGGGSGGGGS APTSSSTKKT QLQLEHLLLD LQMILNGINN YKNPKLTRML   480
TFKFYMPKKA TELKHLQCLE EELKPLEEVL NLAQSKNFHL RPRDLISNIN VIVLELKGSE   540
TTFMCEYADE TATIVEFLNR WITFCQSIIS TLT                               573

SEQ ID NO: 36              moltype = AA  length = 651
FEATURE                    Location/Qualifiers
source                     1..651
                           mol_type = protein
                           organism = synthetic construct
```

```
SEQUENCE: 36
QVQLQEAGPG LVKPSETLSL TCSVSGGSIS GDYYWFWIRQ SPGKGLEWIG YIYGSGGGTN    60
YNPSLNNRVS ISIDTSKNLF SLKLRSVTAA DTAVYYCASN ILKYLHWLLY WGQGVLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQIAP PCTSEKHYEH   480
LGRCCNKCEP GKYMSSKCTT TSDSVCLPCG PDEYLDSWNE EDKCLLHKVC DTGKALVAVV   540
AGNSTTPRRC ACTAGYHWSQ DCECCRRNTE CAPGLGAQHP LQLNKDTVCK PCLAGYFSDA   600
FSSTDKCRPW TNCTFLGKRV EHHGTEKSDA VCSSSLPARK PPNEPHVYLP G            651

SEQ ID NO: 37           moltype = AA  length = 755
FEATURE                 Location/Qualifiers
source                  1..755
                        mol_type = protein
                        organism = synthetic construct
SEQUENCE: 37
EVQLVESGGG LVQPGRSLRL SCAASGFTFD DYAMHWVRQA PGKGLEWVSA ITWNSGHIDY    60
ADSVEGRFTI SRDNAKNSLY LQMNSLRAED TAVYYCALVS YLSTASSLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKAE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSRIFA VFIFMTYWHL   480
LNAFTVTVPK DLYVVEYGSN MTIECKFPVE KQLDLAALIV YWEMEDKNII QFVHGEEDLK   540
VQHSSYRQRA RLLKDQLSLG NAALQITDVK LQDAGVYRCM ISYGGADYKR ITVKVNAPYN   600
KINQRILVVD PVTSEHELTC QAEGYPKAEV IWTSSDHQVL SGKTTTTNSK REEKLFNVTS   660
TLRINTTTNE IFYCTFRRLD PEENHTAELV IPELPLAHPP NERTHLVILG AILLCLGVAL   720
TFIFRLRKGR MMDVKKCGIQ DTNSKKQSDT HLEET                              755

SEQ ID NO: 38           moltype = AA  length = 771
FEATURE                 Location/Qualifiers
source                  1..771
                        mol_type = protein
                        organism = synthetic construct
SEQUENCE: 38
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSNT TSSTDICRPH QICNVVAIPG NASMDAVCTS   180
TSPTRSMAPG AVHLPQPVST RSQHTQPTPE PSTAPSTSFL LPMGPSPPAE GSTGDEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGKGGG GSGGGGSGGG   480
GSRIFAVFIF MTYWHLLNAF TVTVPKDLYV VEYGSNMTIE CKFPVEKQLD LAALIVYWEM   540
EDKNIIQFVH GEEDLKVQHS SYRQRARLLK DQLSLGNAAL QITDVKLQDA GVYRCMISYG   600
GADYKRITVK VNAPYNKINQ RILVVDPVTS EHELTCQAEG YPKAEVIWTS SDHQVLSGKT   660
TTTNSKREEK LFNVTSTLRI NTTTNEIFYC TFRRLDPEEN HTAELVIPEL PLAHPPNERT   720
HLVILGAILL CLGVALTFIF RLRKGRMMDV KKCGIQDTNS KKQSDTHLEE T            771

SEQ ID NO: 39           moltype = AA  length = 787
FEATURE                 Location/Qualifiers
source                  1..787
                        mol_type = protein
                        organism = synthetic construct
SEQUENCE: 39
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET GGGGSGGGGS   300
GGGGSEPKSC DKTHTCPPCP APELLGGPSV FLFPPKPKDT LMISRTPEVT CVVVDVSHED   360
PEVKFNWYVD GVEVHNAKTK PREEQYNSTY RVVSVLTVLH QDWLNGKEYK CKVSNKALPA   420
PIEKTISKAK GQPREPQVYT LPPSREEMTK NQVSLTCLVK GFYPSDIAVE WESNGQPENN   480
YKTTPPVLDS DGSFFLYSKL TVDKSRWQQG NVFSCSVMHE ALHNHYTQKS LSLSPGKGGG   540
GSGGGGSGGG GSLPAQVAFT PYAPEPGSTC RLREYYDQTA QMCCSKCSPG QHAKVFCTKT   600
SDTVCDSCED STYTQLWNWV PECLSCGSRC SSDQVETQAC TREQNRICTC RPGWYCALSK   660
QEGCRLCAPL RKCRPGFGVA RPGTETSDVV CKPCAPGTFS NTTSSTDICR PHQICNVVAI   720
PGNASMDAVC TSTSPTRSMA PGAVHLPQPV STRSQHTQPT PEPSTAPSTS FLLPMGPSPP   780
AEGSTGD                                                             787

SEQ ID NO: 40           moltype = AA  length = 755
FEATURE                 Location/Qualifiers
source                  1..755
                        mol_type = protein
                        organism = synthetic construct
```

```
SEQUENCE: 40
QVQLQQPGAE LVKPGASVKM SCKASGYTFT SYNMHWVKQT PGRGLEWIGA IYPGNGDTSY    60
NQKFKGKATL TADKSSSTAY MQLSSLTSED SAVYYCARST YYGGDWYFNV WGAGTTVTVS   120
AASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKAE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSRIFA VPIFMTYWHL   480
LNAFTVTVPK DLYVVEYGSN MTIECKFPVE KQLDLAALIV YWEMEDKNII QFVHGEEDLK   540
VQHSSYRQRA RLLKDQLSLG NAALQITDVK LQDAGVYRCM ISYGGADYKR ITVKVNAPYN   600
KINQRILVVD PVTSEHELTC QAEGYPKAEV IWTSSDHQVL SGKTTTTNSK REEKLFNVTS   660
TLRINTTTNE IFYCTFRRLD PEENHTAELV IPELPLAHPP NERTHLVILG AILLCLGVAL   720
TFIFRLRKGR MMDVKKCGIQ DTNSKKQSDT HLEET                             755

SEQ ID NO: 41          moltype = AA  length = 750
FEATURE                Location/Qualifiers
source                 1..750
                       mol_type = protein
                       organism = synthetic construct
SEQUENCE: 41
QVQLVQSGAE VKKPGSSVKV SCKASGYTFT SYRMHWVRQA PGQGLEWIGY INPSTGYTEY    60
NQKFKDKATI TADESTNTAY MELSSLRSED TAVYYCARGG GVFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGKGGGG SGGGGSGGGG SRIFAVFIFM TYWHLLNAFT   480
VTVPKDLYVV EYGSNMTIEC KFPVEKQLDL AALIVYWEME DKNIIQFVHG EEDLKVQHSS   540
YRQRARLLKD QLSLGNAALQ ITDVKLQDAG VYRCMISYGG ADYKRITVKV NAPYNKINQR   600
ILVVDPVTSE HELTCQAEGY PKAEVIWTSS DHQVLSGKTT TTNSKREEKL FNVTSTLRIN   660
TTTNEIFYCT FRRLDPEENH TAELVIPELP LAHPPNERTH LVILGAILLC LGVALTFIFR   720
LRKGRMMDVK KCGIQDTNSK KQSDTHLEET                                   750

SEQ ID NO: 42          moltype = AA  length = 749
FEATURE                Location/Qualifiers
source                 1..749
                       mol_type = protein
                       organism = synthetic construct
SEQUENCE: 42
QLQQSGTVLA RPGASVKMSC KASGYSFTRY WMHWIKQRPG QGLEWIGAIY PGNSDTSYNQ    60
KFEGKAKLTA VTSASTAYME LSSLTHEDSA VYYCSRDYGY YFDFWGQGTT LTVSSASTKG   120
PSVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP ELLGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALPAPI EKTISKAKGQ PREPQVYTLP PSRDELTKNQ   360
VSLTCLVKGF YPSDIAVEWE SNGQPENNYK TTPPVLDSDG SFFLYSKLTV DKSRWQQGNV   420
FSCSVMHEAL HNHYTQKSLS LSPGKGGGGS GGGGSGGGGS RIFAVFIFMT YWHLLNAFTV   480
TVPKDLYVVE YGSNMTIECK FPVEKQLDLA ALIVYWEMED KNIIQFVHGE EDLKVQHSSY   540
RQRARLLKDQ LSLGNAALQI TDVKLQDAGV YRCMISYGGA DYKRITVKVN APYNKINQRI   600
LVVDPVTSEH ELTCQAEGYP KAEVIWTSSD HQVLSGKTTT TNSKREEKLF NVTSTLRINT   660
TTNEIFYCTF RRLDPEENHT AELVIPELPL AHPPNERTHL VILGAILLCL GVALTFIFRL   720
RKGRMMDVKK CGIQDTNSKK QSDTHLEET                                    749

SEQ ID NO: 43          moltype = AA  length = 678
FEATURE                Location/Qualifiers
source                 1..678
                       mol_type = protein
                       organism = synthetic construct
SEQUENCE: 43
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET GGGGSGGGGS   300
GGGGSTHTCP PCPAPELLGG PSVFLFPPKP KDTLMISRTP EVTCVVVDVS HEDPEVKFNW   360
YVDGVEVHNA KTKPREEQYN STYRVVSVLT VLHQDWLNGK EYKCKVSNKA LPAPIEKTIS   420
KAKGQPREPQ VYTLPPSREE MTKNQVSLTC LVKGFYPSDI AVEWESNGQP ENNYKTTPPV   480
LDSDGSFFLY SKLTVDKSRW QQGNVFSCSV MHEALHNHYT QKSLSLSPGK GGGGSGGGGS   540
GGGGSAPTSS STKKTQLQLE HLLLDLQMIL NGINNYKNPK LTRMLTFKFY MPKKATELKH   600
LQCLEEELKP LEEVLNLAQS KNFHLRPRDL ISNINVVLE LKGSETTFMC EYADETATIV   660
EFLNRWITFC QSIISTLT                                                678

SEQ ID NO: 44          moltype = AA  length = 677
FEATURE                Location/Qualifiers
source                 1..677
                       mol_type = protein
                       organism = synthetic construct
```

```
SEQUENCE: 44
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSTH TCPPCPAPEL LGGPSVFLFP PKPKDTLMIS   180
RTPEVTCVVV DVSHEDPEVK FNWYVDGVEV HNAKTKPREE QYNSTYRVVS VLTVLHQDWL   240
NGKEYKCKVS NKALPAPIEK TISKAKGQPR EPQVYTLPPS REEMTKNQVS LTCLVKGFYP   300
SDIAVEWESN GQPENNYKTT PPVLDSDGSF FLYSKLTVDK SRWQQGNVFS CSVMHEALHN   360
HYTQKSLSLS PGKGGGGSGG GGSGGGGSRI FAVFIFMTYW HLLNAFTVTV PKDLYVVEYG   420
SNMTIECKFP VEKQLDLAAL IVYWEMEDKN IIQFVHGEENH LKVQHSSYRQ RARLLKDQLS   480
LGNAALQITD VKLQDAGVYR CMISYGGADY KRITVKVNAP YNKINQRILV VDPVTSEHEL   540
TCQAEGYPKA EVIWTSSDHQ VLSGKTTTTN SKREEKLFNV TSTLRINTTT NEIFYCTFRR   600
LDPEENHTAE LVIPELPLAH PPNERTHLVI LGAILLCLGV ALTFIFRLRK GRMMDVKKCG   660
IQDTNSKKQS DTHLEET                                                 677

SEQ ID NO: 45           moltype = AA  length = 755
FEATURE                 Location/Qualifiers
source                  1..755
                        mol_type = protein
                        organism = synthetic construct
SEQUENCE: 45
QVQLQEAGPG LVKPSETLSL TCSVSGGSIS GDYYWFWIRQ SPGKGLEWIG YIYGSGGGTN    60
YNPSLNNRVS ISIDTSKNLF SLKLRSVTAA DTAVYYCASN ILKYLHWLLY WGQGVLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSRIFA VPIFMTYWHL   480
LNAFTVTVPK DLYVVEYGSN MTIECKFPVE KQLDLAALIV YWEMEDKNII QFVHGEEDLK   540
VQHSSYRQRA RLLKDQLSLG NAALQITDVK LQDAGVYRCM ISYGGADYKR ITVKVNAPYN   600
KINQRILVVD PVTSEHELTC QAEGYPKAEV IWTSSDHQVL SGKTTTTNSK REEKLFNVTS   660
TLRINTTTNE IFYCTFRRLD PEENHTAELV IPELPLAHPP NERTHLVILG AILLCLGVAL   720
TFIFRLRKGR MMDVKKCGIQ DTNSKKQSDT HLEET                              755

SEQ ID NO: 46           moltype = AA  length = 687
FEATURE                 Location/Qualifiers
source                  1..687
                        mol_type = protein
                        organism = synthetic construct
SEQUENCE: 46
MGVLLTQRTL LSLVLALLFP SMASMAMHVA QPAVVLASSR GIASFVCEYA SPGKATEVRV    60
TVLRQADSQV TEVCAATYMM GNELTFLDDS ICTGTSSGNQ VNLTIQGLRA MDTGLYICKV   120
ELMYPPPYYL GIGNGTQIYV IDPEPCPDSD QEPKSCDKTH TCPPCPAPEL LGGPSVFLFP   180
PKPKDTLMIS RTPEVTCVVV DVSHEDPEVK FNWYVDGVEV HNAKTKPREE QYNSTYRVVS   240
VLTVLHQDWL NGKEYKCKVS NKALPAPIEK TISKAKGQPR EPQVYTLPPS RDELTKNQVS   300
LTCLVKGFYP SDIAVEWESN GQPENNYKTT PPVLDSDGSF FLYSKLTVDK SRWQQGNVFS   360
CSVMHEALHN HYTQKSLSLS PGKGGGGSGG GGSGGGGSRI FAVFIFMTYW HLLNAFTVTV   420
PKDLYVVEYG SNMTIECKFP VEKQLDLAAL IVYWEMEDKN IIQFVHGEED LKVQHSSYRQ   480
RARLLKDQLS LGNAALQITD VKLQDAGVYR CMISYGGADY KRITVKVNAP YNKINQRILV   540
VDPVTSEHEL TCQAEGYPKA EVIWTSSDHQ VLSGKTTTTN SKREEKLFNV TSTLRINTTT   600
NEIFYCTFRR LDPEENHTAE LVIPELPLAH PPNERTHLVI LGAILLCLGV ALTFIFRLRK   660
GRMMDVKKCG IQDTNSKKQS DTHLEET                                      687

SEQ ID NO: 47           moltype = AA  length = 678
FEATURE                 Location/Qualifiers
source                  1..678
                        mol_type = protein
                        organism = synthetic construct
SEQUENCE: 47
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET GGGGSGGGGS   300
GGGGSQEPKS CDKTHTCPPC PAPELLGGPS VFLFPPKPKD TLMISRTPEV TCVVVDVSHE   360
DPEVKFNWYV DGVEVHNAKT KPREEQYNST YRVVSVLTVL HQDWLNGKEY KCKVSNKALP   420
APIEKTISKA KGQPREPQVY TLPPSRDELT KNQVSLTCLV KGFYPSDIAV EWESNGQPEN   480
NYKTTPPVLD SDGSFFLYSK LTVDKSRWQQ GNVFSCSVMH EALHNHYTQK SLSLSPGKGG   540
GGSGGGGSGG GGSAMHVAQP AVVLASSRGI ASFVCEYASP GKATEVRVRV LRQADSQVTE   600
VCAATYMMGN ELTFLDDSIC TGTSSGNQVN LTIQGLRAMD TGLYICKVEL MYPPPYYLGI   660
GNGTQIYVID PEPCPDSD                                                678

SEQ ID NO: 48           moltype = AA  length = 656
FEATURE                 Location/Qualifiers
source                  1..656
                        mol_type = protein
                        organism = synthetic construct
SEQUENCE: 48
ALDTNYCFSS TEKNCCVRQL YIDFRKDLGW KWIHEPKGYH ANFCLGPCPY IWSLDTQYSK    60
```

```
VLALYNQHNP GASAAPCCVP QALEPLPIVY YVGRKPKVEQ LSNMIVRSCK CSGGGGSGGG   120
GSGGGGSTHT CPPCPAPELL GGPSVFLFPP KPKDTLMISR TPEVTCVVVD VSHEDPEVKF   180
NWYVDGVEVH NAKTKPREEQ YNSTYRVVSV LTVLHQDWLN GKEYKCKVSN KALPAPIEKT   240
ISKAKGQPRE PQVYTLPPSR EEMTKNQVSL TCLVKGFYPS DIAVEWESNG QPENNYKTTP   300
PVLDSDGSFF LYSKLTVDKS RWQQGNVFSC SVMHEALHNH YTQKSLSLSP GKGGGSGGGG   360
GSGGGGSRIF AVFIFMTYWH LLNAFTVTVP KDLYVVEYGS NMTIECKFPV EKQLDLAALI   420
VYWEMEDKNI IQFVHGEEDL KVQHSSYRQR ARLLKDQLSL GNAALQITDV KLQDAGVYRC   480
MISYGGADYK RITVKVNAPY NKINQRILVV DPVTSEHELT CQAEGYPKAE VIWTSSDHQV   540
LSGKTTTTNS KREEKLFNVT STLRINTTTN EIFYCTFRRL DPEENHTAEL VIPELPLAHP   600
PNERTHLVIL GAILLCLGVA LTFIFRLRKG RMMDVKKCGI QDTNSKKQSD THLEET      656

SEQ ID NO: 49           moltype = AA   length = 657
FEATURE                 Location/Qualifiers
source                  1..657
                        mol_type = protein
                        organism = synthetic construct
SEQUENCE: 49
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET GGGGSGGGGS  300
GGGGSTHTCP PCPAPELLGG PSVFLFPPKP KDTLMISRTP EVTCVVVDVS HEDPEVKFNW  360
YVDGVEVHNA KTKPREEQYN STYRVVSVLT VLHQDWLNGK EYKCKVSNKA LPAPIEKTIS  420
KAKGQPREPQ VYTLPPSREE MTKNQVSLTC LVKGFYPSDI AVEWESNGQP ENNYKTTPPV  480
LDSDGSFFLY SKLTVDKSRW QQGNVFSCSV MHEALHNHYT QKSLSLSPGK GGGSGGGGSG  540
GGGGSALDTN YCFSSTEKNC CVRQLYIDFR KDLGWKWIHE PKGYHANFCL GPCPYIWSLD  600
TQYSKVLALY NQHNPGASAA PCCVPQALEP LPIVYYVGRK PKVEQLSNMI VRSCKCS    657

SEQ ID NO: 50           moltype = AA   length = 578
FEATURE                 Location/Qualifiers
source                  1..578
                        mol_type = protein
                        organism = synthetic construct
SEQUENCE: 50
EVQLVESGGG LVQPGRSLRL SCAASGFTFD DYAMHWVRQA PGKGLEWVSA ITWNSGHIDY   60
ADSVEGRFTI SRDNAKNSLY LQMNSLRAED TAVYYCALVS YLSTASSLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG SGGGGSALDT NYCFSSTEKN  480
CCVRQLYIDF RKDLGWKWIH EPKGYHANFC LGPCPYIWSL DTQYSKVLAL YNQHNPGASA  540
APCCVPQALE PLPIVYYVGR KPKVEQLSNM IVRSCKCS                         578

SEQ ID NO: 51           moltype = AA   length = 594
FEATURE                 Location/Qualifiers
source                  1..594
                        mol_type = protein
                        organism = synthetic construct
SEQUENCE: 51
LPAQVAFTPY APEPGSTCRL REYYDQTAQM CCSKCSPGQH AKVFCTKTSD TVCDSCEDST   60
YTQLWNWVPE CLSCGSRCSS DQVETQACTR EQNRICTCRP GWYCALSKQE GCRLCAPLRK  120
CRPGFGVARP GTETSDVVCK PCAPGTFSNT TSSTDICRPH QICNVVAIPG NASMDAVCTS  180
TSPTRSMAPG AVHLPQPVST RSQHTQPTPE PSTAPSTSFL LPMGPSPPAE GSTGDEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKGGG GSGGGGSGGG  480
GSALDTNYCF SSTEKNCCVR QLYIDFRKDL GWKWIHEPKG YHANFCLGPC PYIWSLDTQY  540
SKVLALYNQH NPGASAAPCC VPQALEPLPI VYYVGRKPKV EQLSNMIVRS CKCS        594

SEQ ID NO: 52           moltype = AA   length = 602
FEATURE                 Location/Qualifiers
source                  1..602
                        mol_type = protein
                        organism = synthetic construct
SEQUENCE: 52
ALDTNYCFSS TEKNCCVRQL YIDFRKDLGW KWIHEPKGYH ANFCLGPCPY IWSLDTQYSK   60
VLALYNQHNP GASAAPCCVP QALEPLPIVY YVGRKPKVEQ LSNMIVRSCK CSGGGGSGGG  120
GSGGGGSTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GKGGGGSGGG  360
GSGGGGSLPA QVAFTPYAPE PGSTCRLREY YDQTAQMCCS KCSPGQHAKV FCTKTSDTVC  420
DSCEDSTYTQ LWNWVPECLS CGSRCSSDQV ETQACTREQN RICTCRPGWY CALSKQEGCR  480
LCAPLRKCRP GFGVARPGTE TSDVVCKPCA PGTFSNTTSS TDICRPHQIC NVVAIPGNAS  540
MDAVCTSTSP TRSMAPGAVH LPQPVSTRSQ HTQPTPEPST APSTSFLLPM GPSPPAEGST  600
```

```
GD                                                               602

SEQ ID NO: 53           moltype = AA  length = 578
FEATURE                 Location/Qualifiers
source                  1..578
                        mol_type = protein
                        organism = synthetic construct
SEQUENCE: 53
QVQLQQPGAE LVKPGASVKM SCKASGYTFT SYNMHWVKQT PGRGLEWIGA IYPGNGDTSY   60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKAE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSGGGG SGGGGSALDT NYCFSSTEKN  480
CCVRQLYIDF RKDLGWKWIH EPKGYHANFC LGPCPYIWSL DTQYSKVLAL YNQHNPGASA  540
APCCVPQALE PLPIVYYVGR KPKVEQLSNM IVRSCKCS                         578

SEQ ID NO: 54           moltype = AA  length = 573
FEATURE                 Location/Qualifiers
source                  1..573
                        mol_type = protein
                        organism = synthetic construct
SEQUENCE: 54
QVQLVQSGAE VKKPGSSVKV SCKASGYTFT SYRMHWVRQA PGQGLEWIGY INPSTGYTEY   60
NQKFKDKATI TADESTNTAY MELSSLRSED TAVYYCARGG GVFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGKGGGG SGGGGSGGGG SALDTNYCFS STEKNCCVRQ  480
LYIDFRKDLG WKWIHEPKGY HANFCLGPCP YIWSLDTQYS KVLALYNQHN PGASAAPCCV  540
PQALEPLPIV YYVGRKPKVE QLSNMIVRSC KCS                              573

SEQ ID NO: 55           moltype = AA  length = 572
FEATURE                 Location/Qualifiers
source                  1..572
                        mol_type = protein
                        organism = synthetic construct
SEQUENCE: 55
QLQQSGTVLA RPGASVKMSC KASGYSFTRY WMHWIKQRPG QGLEWIGAIY PGNSDTSYNQ   60
KFEGKAKLTA VTSASTAYME LSSLTHEDSA VYYCSRDYGY YFDFWGQGTT LTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKGGGGS GGGGSGGGGS ALDTNYCFSS TEKNCCVRQL  480
YIDFRKDLGW KWIHEPKGYH ANFCLGPCPY IWSLDTQYSK VLALYNQHNP GASAAPCCVP  540
QALEPLPIVY YVGRKPKVEQ LSNMIVRSCK CS                               572

SEQ ID NO: 56           moltype = AA  length = 500
FEATURE                 Location/Qualifiers
source                  1..500
                        mol_type = protein
                        organism = synthetic construct
SEQUENCE: 56
ALDTNYCFSS TEKNCCVRQL YIDFRKDLGW KWIHEPKGYH ANFCLGPCPY IWSLDTQYSK   60
VLALYNQHNP GASAAPCCVP QALEPLPIVY YVGRKPKVEQ LSNMIVRSCK CSGGGGSGGG  120
GSGGGGSTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GKGGGGSGGG  360
GSGGGGSAPT SSSTKKTQLQ LEHLLLDLQM ILNGINNYKN PKLTRMLTFK FYMPKKATEL  420
KHLQCLEEEL KPLEEVLNLA QSKNFHLRPR DLISNINVIV LELKGSETTF MCEYADETAT  480
IVEFLNRWIT FCQSIISTLT                                             500

SEQ ID NO: 57           moltype = AA  length = 500
FEATURE                 Location/Qualifiers
source                  1..500
                        mol_type = protein
                        organism = synthetic construct
SEQUENCE: 57
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSTH TCPPCPAPEL LGGPSVFLFP PKPKDTLMIS  180
RTPEVTCVVV DVSHEDPEVK FNWYVDGVEV HNAKTKPREE QYNSTYRVVS VLTVLHQDWL  240
```

```
NGKEYKCKVS NKALPAPIEK TISKAKGQPR EPQVYTLPPS REEMTKNQVS LTCLVKGFYP   300
SDIAVEWESN GQPENNYKTT PPVLDSDGSF FLYSKLTVDK SRWQQGNVFS CSVMHEALHN   360
HYTQKSLSLS PGKGGGGSGG GGSGGGGSAL DTNYCFSSTE KNCCVRQLYI DFRKDLGWKW   420
IHEPKGYHAN FCLGPCPYIW SLDTQYSKVL ALYNQHNPGA SAAPCCVPQA LEPLPIVYYV   480
GRKPKVEQLS NMIVRSCKCS                                              500

SEQ ID NO: 58           moltype = AA  length = 578
FEATURE                 Location/Qualifiers
source                  1..578
                        mol_type = protein
                        organism = synthetic construct
SEQUENCE: 58
QVQLQEAGPG LVKPSETLSL TCSVSGGSIS GDYYWFWIRQ SPGKGLEWIG YIYGSGGGTN    60
YNPSLNNRVS ISIDTSKNLF SLKLRSVTAA DTAVYYCASN ILKYLHWLLY WGQGVLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSALDT NYCFSSTEKN   480
CCVRQLYIDF RKDLGWKWIH EPKGYHANFC LGPCPYIWSL DTQYSKVLAL YNQHNPGASA   540
APCCVPQALE PLPIVYYVGR KPKVEQLSNM IVRSCKCS                          578

SEQ ID NO: 59           moltype = AA  length = 510
FEATURE                 Location/Qualifiers
source                  1..510
                        mol_type = protein
                        organism = synthetic construct
SEQUENCE: 59
MGVLLTQRTL LSLVLALLFP SMASMAMHVA QPAVVLASSR GIASFVCEYA SPGKATEVRV    60
TVLRQADSQV TEVCAATYMM GNELTFLDDS ICTGTSSGNQ VNLTIQGLRA MDTGLYICKV   120
ELMYPPPYYL GIGNGTQIYV IDPEPCPDSD QEPKSCDKTH TCPPCPAPEL LGGPSVFLFP   180
PKPKDTLMIS RTPEVTCVVV DVSHEDPEVK FNWYVDGVEV HNAKTKPREE QYNSTYRVVS   240
VLTVHQDWL NGKEYKCKVS NKALPAPIEK TISKAKGQPR EPQVYTLPPS RDELTKNQVS   300
LTCLVKGFYP SDIAVEWESN GQPENNYKTT PPVLDSDGSF FLYSKLTVDK SRWQQGNVFS   360
CSVMHEALHN HYTQKSLSLS PGKGGGGSGG GGSGGGGSAL DTNYCFSSTE KNCCVRQLYI   420
DFRKDLGWKW IHEPKGYHAN FCLGPCPYIW SLDTQYSKVL ALYNQHNPGA SAAPCCVPQA   480
LEPLPIVYYV GRKPKVEQLS NMIVRSCKCS                                   510

SEQ ID NO: 60           moltype = AA  length = 484
FEATURE                 Location/Qualifiers
source                  1..484
                        mol_type = protein
                        organism = synthetic construct
SEQUENCE: 60
ALDTNYCFSS TEKNCCVRQL YIDFRKDLGW KWIHEPKGYH ANFCLGPCPY IWSLDTQYSK    60
VLALYNQHNP GASAAPCCVP QALEPLPIVY YVGRKPKVEQ LSNMIVRSCK CSEPKSCDKT   120
HTCPPCPAPE LLGGPSVFLF PPKPKDTLMI SRTPEVTCVV VDVSHEDPEV KFNWYVDGVE   180
VHNAKTKPRE EQYNSTYRVV SVLTVLHQDW LNGKEYKCKV SNKALPAPIE KTISKAKGQP   240
REPQVYTLPP SRDELTKNQV SLTCLVKGFY PSDIAVEWES NGQPENNYKT TPPVLDSDGS   300
FFLYSKLTVD KSRWQQGNVF SCSVMHEALH NHYTQKSLSL SPGKGGGGSG GGGSGGGGSM   360
MHVAQPAVVL ASSRGIASFV CEYASPGKAT EVRVTVLRQA DSQVTEVCAA TYMMGNELTF   420
LDDSICTGTS SGNQVNLTIQ GLRAMDTGLY ICKVELMYPP PYYLGIGNGT QIYVIDPEPC   480
PDSD                                                               484

SEQ ID NO: 61           moltype = AA  length = 651
FEATURE                 Location/Qualifiers
source                  1..651
                        mol_type = protein
                        organism = synthetic construct
SEQUENCE: 61
EVQLVESGGG LVQPGRSLRL SCAASGFTFD DYAMHWVRQA PGKGLEWVSA ITWNSGHIDY    60
ADSVEGRFTI SRDNAKNSLY LQMNSLRAED TAVYYCALVS YLSTASSLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKAE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG KGGGGSGGGG SGGGGSQIAP PCTSEKHYEH   480
LGRCCNKCEP GKYMSKCTT TSDSVCLPCG PDEYLDSWNE EDKCLLHKVC DTGKALVAVV   540
AGNSTTPRRC ACTAGYHWSQ DCECCRRNTE CAPGLGAQHP LQLNKDTVCK PCLAGYFSDA   600
FSSTDKCRPW TNCTFLGKRV EHHGTEKSDA VCSSSLPARK PPNEPHVYLP G           651

SEQ ID NO: 62           moltype = AA  length = 667
FEATURE                 Location/Qualifiers
source                  1..667
                        mol_type = protein
                        organism = synthetic construct
SEQUENCE: 62
```

```
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSNT TSSTDICRPH QICNVVAIPG NASMDAVCTS   180
TSPTRSMAPG AVHLPQPVST RSQHTQPTPE PSTAPSTSFL LPMGPSPPAE GSTGDEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGKGGG GSGGGGSGGG   480
GSQIAPPCTS EKHYEHLGRC CNKCEPGKYM SSKCTTTSDS VCLPCGPDEY LDSWNEEDKC   540
LLHKVCDTGK ALVAVVAGNS TTPRRCACTA GYHWSQDCEC CRRNTECAPG LGAQHPLQLN   600
KDTVCKPCLA GYFSDAFSST DKCRPWTNCT FLGKRVEHHG TEKSDAVCSS SLPARKPPNE   660
PHVYLPG                                                            667

SEQ ID NO: 63           moltype = AA   length = 675
FEATURE                 Location/Qualifiers
source                  1..675
                        mol_type = protein
                        organism = synthetic construct
SEQUENCE: 63
QIAPPCTSEK HYEHLGRCCN KCEPGKYMSS KCTTTSDSVC LPCGPDEYLD SWNEEDKCLL    60
HKVCDTGKAL VAVVAGNSTT PRRCACTAGY HWSQDCECCR RNTECAPGLG AQHPLQLNKD   120
TVCKPCLAGY FSDAFSSTDK CRPWTNCTFL GKRVEHHGTE KSDAVCSSSL PARKPPNEPH   180
VYLPGGGGGS GGGGSGGGGS THTCPPCPAP ELLGGPSVFL FPPKPKDTLM ISRTPEVTCV   240
VVDVSHEDPE VKFNWYVDGV EVHNAKTKPR EEQYNSTYRV VSVLTVLHQD WLNGKEYKCK   300
VSNKALPAPI EKTISKAKGQ PREPQVYTLP PSREEMTKNQ VSLTCLVKGF YPSDIAVEWE   360
SNGQPENNYK TTPPVLDSDG SFFLYSKLTV DKSRWQQGNV FSCSVMHEAL HNHYTQKSLS   420
LSPGKGGGGS GGGGSGGGGS LPAQVAFTPY APEPGSTCRL REYYDQTAQM CCSKCSPGQH   480
AKVFCTKTSD TVCDSCEDST YTQLWNWVPE CLSCGSRCSS DQVETQACTR EQNRICTCRP   540
GWYCALSKQE GCRLCAPLRK CRPGFGVARP GTETSDVVCK PCAPGTFSNT TSSTDICRPH   600
QICNVVAIPG NASMDAVCTS TSPTRSMAPG AVHLPQPVST RSQHTQPTPE PSTAPSTSFL   660
LPMGPSPPAE GSTGD                                                   675

SEQ ID NO: 64           moltype = AA   length = 583
FEATURE                 Location/Qualifiers
source                  1..583
                        mol_type = protein
                        organism = synthetic construct
SEQUENCE: 64
MGVLLTQRTL LSLVLALLFP SMASMAMHVA QPAVVLASSR GIASFVCEYA SPGKATEVRV    60
TVLRQADSQV TEVCAATYMM GNELTFLDDS ICTGTSSGNQ VNLTIQGLRA MDTGLYICKV   120
ELMYPPPYYL GIGNGTQIYV IDPEPCPDSD QEPKSCDKTH TCPPCPAPEL LGGPSVFLFP   180
PKPKDTLMIS RTPEVTCVVV DVSHEDPEVK FNWYVDGVEV HNAKTKPREE QYNSTYRVVS   240
VLTVLHQDWL NGKEYKCKVS NKALPAPIEK TISKAKGQPR EPQVYTLPPS RDELTKNQVS   300
LTCLVKGFYP SDIAVEWESN GQPENNYKTT PPVLDSDGSF FLYSKLTVDK SRWQQGNVFS   360
CSVMHEALHN HYTQKSLSLS PGKGGGGSGG GGSGGGGSQI APPCTSEKHY EHLGRCCNKC   420
EPGKYMSSKC TTTSDSVCLP CGPDEYLDSW NEEDKCLLHK VCDTGKALVA VVAGNSTTPR   480
RCACTAGYHW SQDCECCRRN TECAPGLGAQ HPLQLNKDTV CKPCLAGYFS DAFSSTDKCR   540
PWTNCTFLGK RVEHHGTEKS DAVCSSSLPA RKPPNEPHVY LPG                     583

SEQ ID NO: 65           moltype = AA   length = 557
FEATURE                 Location/Qualifiers
source                  1..557
                        mol_type = protein
                        organism = synthetic construct
SEQUENCE: 65
QIAPPCTSEK HYEHLGRCCN KCEPGKYMSS KCTTTSDSVC LPCGPDEYLD SWNEEDKCLL    60
HKVCDTGKAL VAVVAGNSTT PRRCACTAGY HWSQDCECCR RNTECAPGLG AQHPLQLNKD   120
TVCKPCLAGY FSDAFSSTDK CRPWTNCTFL GKRVEHHGTE KSDAVCSSSL PARKPPNEPH   180
VYLPGEPKSC DKTHTCPPCP APELLGGPSV FLFPPKPKDT LMISRTPEVT CVVVDVSHED   240
PEVKFNWYVD GVEVHNAKTK PREEQYNSTY RVVSVLTVLH QDWLNGKEYK CKVSNKALPA   300
PIEKTISKAK GQPREPQVYT LPPSRDELTK NQVSLTCLVK GFYPSDIAVE WESNGQPENN   360
YKTTPPVLDS DGSFFLYSKL TVDKSRWQQG NVFSCSVMHE ALHNHYTQKS LSLSPGKGGG   420
GSGGGGSGGG GSAMHVAQPA VVLASSRGIA SFVCEYASPG KATEVRVTVL RQADSQVTEV   480
CAATYMMGNE LTFLDDSICT GTSSGNQVNL TIQGLRAMDT GLYICKVELM YPPPYYLGIG   540
NGTQIYVIDP EPCPDSD                                                 557

SEQ ID NO: 66           moltype = AA   length = 552
FEATURE                 Location/Qualifiers
source                  1..552
                        mol_type = protein
                        organism = synthetic construct
SEQUENCE: 66
ALDTNYCFSS TEKNCCVRQL YIDFRKDLGW KWIHEPKGYH ANFCLGPCPY IWSLDTQYSK    60
VLALYNQHNP GASAAPCCVP QALEPLPIVY YVGRKPKVEQ LSNMIVRSCK CSGGGGSGGG   120
GSGGGGSTHT CPPCPAPELL GGPSVFLFPP KPKDTLMISR TPEVTCVVVD VSHEDPEVKF   180
NWYVDGVEVH NAKTKPREEQ YNSTYRVVSV LTVLHQDWLN GKEYKCKVSN KALPAPIEKT   240
ISKAKGQPRE PQVYTLPPSR EEMTKNQVSL TCLVKGFYPS DIAVEWESNG QPENNYKTTP   300
PVLDSDGSFF LYSKLTVDKS RWQQGNVFSC SVMHEALHNH YTQKSLSLSP GKGGGGSGGG   360
GSGGGGSQIA PPCTSEKHYE HLGRCCNKCE PGKYMSSKCT TTSDSVCLPC GPDEYLDSWN   420
```

```
EEDKCLLHKV CDTGKALVAV VAGNSTTPRR CACTAGYHWS QDCECCRRNT ECAPGLGAQH    480
PLQLNKDTVC KPCLAGYFSD AFSSTDKCRP WTNCTFLGKR VEHHGTEKSD AVCSSSLPAR    540
KPPNEPHVYL PG                                                       552

SEQ ID NO: 67          moltype = AA  length = 552
FEATURE                Location/Qualifiers
source                 1..552
                       mol_type = protein
                       organism = synthetic construct
SEQUENCE: 67
QIAPPCTSEK HYEHLGRCCN KCEPGKYMSS KCTTTDSVC LPCGPDEYLD SWNEEDKCLL      60
HKVCDTGKAL VAVVAGNSTT PRRCACTAGY HWSQDCECCR RNTECAPGLG AQHPLQLNKD    120
TVCKPCLAGY FSDAFSSTDK CRPWTNCTFL GKRVEHHGTE KSDAVCSSSL PARKPPNEPH    180
VYLPGGGGGS GGGGSGGGGS THTCPPCPAP ELLGGPSVFL FPPKPKDTLM ISRTPEVTCV    240
VVDVSHEDPE VKFNWYVDGV EVHNAKTKPR EEQYNSTYRV VSVLTVLHQD WLNGKEYKCK    300
VSNKALPAPI EKTISKAKGQ PREPQVYTLP PSREEMTKNQ VSLTCLVKGF YPSDIAVEWE    360
SNGQPENNYK TTPPVLDSDG SFFLYSKLTV DKSRWQQGNV FSCSVMHEAL HNHYTQKSLS    420
LSPGKGGGGS GGGGSGGGGS ALDTNYCFSS TEKNCCVRQL YIDFRKDLGW KWIHEPKGYH    480
ANFCLGPCPY IWSLDTQYSK VLALYNQHNP GASAAPCCVP QALEPLPIVY YVGRKPKVEQ    540
LSNMIVRSCK CS                                                       552

SEQ ID NO: 68          moltype = AA  length = 729
FEATURE                Location/Qualifiers
source                 1..729
                       mol_type = protein
                       organism = synthetic construct
SEQUENCE: 68
RIFAVFIFMT YWHLLNAFTV TVPKDLYVVE YGSNMTIECK FPVEKQLDLA ALIVYWEMED     60
KNIIQFVHGE EDLKVQHSSY RQRARLLKDQ LSLGNAALQI TDVKLQDAGV YRCMISYGGA    120
DYKRITVKVN APYNKINQRI LVVDPVTSEH ELTCQAEGYP KAEVIWTSSD HQVLSGKTTT    180
TNSKREEKLF NVTSTLRINT TTNEIFYCTF RRLDPEENHT AELVIPELPL AHPPNERTHL    240
VILGAILLCL GVALTFIFRL RKGRMMDVKK CGIQDTNSKK QSDTHLEETG GGGSGGGGSG    300
GGGSTHTCPP CPAPELLGGP SVFLFPPKPK DTLMISRTPE VTCVVVDVSH EDPEVKFNWY    360
VDGVEVHNAK TKPREEQYNS TYRVVSVLTV LHQDWLNGKE YKCKVSNKAL PAPIEKTISK    420
AKGQPREPQV YTLPPSREEM TKNQVSLTCL VKGFYPSDIA VEWESNGQPE NNYKTTPPVL    480
DSDGSFFLYS KLTVDKSRWQ QGNVFSCSVM HEALHNHYTQ KSLSLSPGKG GGGSGGGGSG    540
GGGSQIAPPC TSEKHYEHLG RCCNKCEPGK YMSSKCTTTS DSVCLPCGPD EYLDSWNEED    600
KCLLHKVCDT GKALVAVVAG NSTTPRRCAC TAGYHWSQDC ECCRRNTECA PGLGAQHPLQ    660
LNKDTVCKPC LAGYFSDAFS STDKCRPWTN CTFLGKRVEH HGTEKSDAVC SSSLPARKPP    720
NEPHVYLPG                                                           729

SEQ ID NO: 69          moltype = AA  length = 729
FEATURE                Location/Qualifiers
source                 1..729
                       mol_type = protein
                       organism = synthetic construct
SEQUENCE: 69
QIAPPCTSEK HYEHLGRCCN KCEPGKYMSS KCTTTDSVC LPCGPDEYLD SWNEEDKCLL      60
HKVCDTGKAL VAVVAGNSTT PRRCACTAGY HWSQDCECCR RNTECAPGLG AQHPLQLNKD    120
TVCKPCLAGY FSDAFSSTDK CRPWTNCTFL GKRVEHHGTE KSDAVCSSSL PARKPPNEPH    180
VYLPGGGGGS GGGGSGGGGS THTCPPCPAP ELLGGPSVFL FPPKPKDTLM ISRTPEVTCV    240
VVDVSHEDPE VKFNWYVDGV EVHNAKTKPR EEQYNSTYRV VSVLTVLHQD WLNGKEYKCK    300
VSNKALPAPI EKTISKAKGQ PREPQVYTLP PSREEMTKNQ VSLTCLVKGF YPSDIAVEWE    360
SNGQPENNYK TTPPVLDSDG SFFLYSKLTV DKSRWQQGNV FSCSVMHEAL HNHYTQKSLS    420
LSPGKGGGGS GGGGSGGGGS RIFAVFIFMT YWHLLNAFTV TVPKDLYVVE YGSNMTIECK    480
FPVEKQLDLA ALIVYWEMED KNIIQFVHGE EDLKVQHSSY RQRARLLKDQ LSLGNAALQI    540
TDVKLQDAGV YRCMISYGGA DYKRITVKVN APYNKINQRI LVVDPVTSEH ELTCQAEGYP    600
KAEVIWTSSD HQVLSGKTTT TNSKREEKLF NVTSTLRINT TTNEIFYCTF RRLDPEENHT    660
AELVIPELPL AHPPNERTHL VILGAILLCL GVALTFIFRL RKGRMMDVKK CGIQDTNSKK    720
QSDTHLEET                                                           729

SEQ ID NO: 70          moltype = AA  length = 214
FEATURE                Location/Qualifiers
source                 1..214
                       mol_type = protein
                       organism = synthetic construct
SEQUENCE: 70
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 71          moltype = AA  length = 214
FEATURE                Location/Qualifiers
source                 1..214
                       mol_type = protein
                       organism = synthetic construct
SEQUENCE: 71
DILLTQSPVI LSVSPGERVS FSCRASQSIG TNIHWYQQRT NGSPRLLIKY ASESISGIPS     60
```

```
RFSGSGSGTD FTLSINSVES EDIADYYCQQ NNNWPTTFGA GTKLELKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 72           moltype = AA   length = 213
FEATURE                 Location/Qualifiers
source                  1..213
                        mol_type = protein
                        organism = synthetic construct
SEQUENCE: 72
QIVLSQSPAI LSASPGEKVT MTCRASSSVS YIHWFQQKPG SSPKPWIYAT SNLASGVPVR    60
FSGSGSGTSY SLTISRVEAE DAATYYCQQW TSNPPTFGGG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 73           moltype = AA   length = 214
FEATURE                 Location/Qualifiers
source                  1..214
                        mol_type = protein
                        organism = synthetic construct
SEQUENCE: 73
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 74           moltype = AA   length = 215
FEATURE                 Location/Qualifiers
source                  1..215
                        mol_type = protein
                        organism = synthetic construct
SEQUENCE: 74
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                               215

SEQ ID NO: 75           moltype = AA   length = 213
FEATURE                 Location/Qualifiers
source                  1..213
                        mol_type = protein
                        organism = synthetic construct
SEQUENCE: 75
DIQMTQSPST LSASVGDRVT ITCSASSSIS YMHWYQQKPG KAPKLLIYTT SNLASGVPAR    60
FSGSGSGTEF TLTISSLQPD DFATYYCHQR STYPLTFGQG TKVEVKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 76           moltype = AA   length = 210
FEATURE                 Location/Qualifiers
source                  1..210
                        mol_type = protein
                        organism = synthetic construct
SEQUENCE: 76
QIVSTQSPAI MSASPGEKVT MTCSASSSRS YMQWYQQKPG TSPKRWIYDT SKLASGVPAR    60
FSGSGSGTSY SLTISSMEAE DAATYYCHQR SSYTFGGGTK LEIKRTVAAP SVFIFPPSDE    120
QLKSGTASVV CLLNNFYPRE AKVQWKVDNA LQSGNSQESV TEQDSKDSTY SLSSTLTLSK    180
ADYEKHKVYA CEVTHQGLSS PVTKSFNRGE                                     210

SEQ ID NO: 77           moltype = AA   length = 216
FEATURE                 Location/Qualifiers
source                  1..216
                        mol_type = protein
                        organism = synthetic construct
SEQUENCE: 77
SYELSQPRSV SVSPGQTAGF TCGGDNVGRK SVQWYQQKPP QAPVLVIYAD SERPSGIPAR    60
FSGSNSGNTA TLTISGVEAG DEADYYCQVW DSTADHWVFG GGTRLTVLGR TVAAPSVFIF    120
PPSDEQLKSG TASVVCLLNN FYPREAKVQW KVDNALQSGN SQESVTEQDS KDSTYSLSST    180
LTLSKADYEK HKVYACEVTH QGLSSPVTKS FNRGEC                              216

SEQ ID NO: 78           moltype = AA   length = 214
FEATURE                 Location/Qualifiers
source                  1..214
                        mol_type = protein
                        organism = synthetic construct
SEQUENCE: 78
DIQMTQSPSS LSASVGDRVT ITCRASQGIR NYLAWYQQLP GKAPKLLIYA ASTLQSGVPS    60
RFSGSGSGTD FTLTISSLQP EDVATYYCQR YNRAPYTFGQ GTKVEIKRTV AAPSVFIFPP    120
SDEQLKSGTA SVVCLLNNFY PREAKVQWKV DNALQSGNSQ ESVTEQDSKD STYSLSSTLT    180
```

```
LSKADYEKHK VYACEVTHQG LSSPVTKSFN RGEC                              214

SEQ ID NO: 79           moltype = AA   length = 567
FEATURE                 Location/Qualifiers
source                  1..567
                        mol_type = protein
                        organism = synthetic construct
SEQUENCE: 79
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQVTGI SLLPPLGVAI   180
SVIIIFYCYR VNRQQKLSST WETGKTRKLM EFSEHCAIIL EDDRSDISST CANNINHNTE   240
LLPIELDTLV GKGRFAEVYK AKLKQNTSEQ FETVAVKIFP YEEYASWKTE KDIFSDINLK   300
HENILQFLTA EERKTELGKQ YWLITAFHAK GNLQEYLTRH VISWEDLRKL GSSLARGIAH   360
LHSDHTPCGR PKMPIVHRDL KSSNILVKND LTCCLCDFGL SLRLDPTLSV DDLANSGQVG   420
TARYMAPEVL ESRMNLENVE SFKQTDVYSM ALVLWEMTSR CNAVGEVKDY EPPFGSKVRE   480
HPCVESMKDN VLRDRGRPEI PSFWLNHQGI QMVCETLTEC WDHDPEARLT AQCVAERFSE   540
LEHLDRLSGR SCSEEKIPED GSLNTTK                                      567

SEQ ID NO: 80           moltype = AA   length = 592
FEATURE                 Location/Qualifiers
source                  1..592
                        mol_type = protein
                        organism = synthetic construct
SEQUENCE: 80
MGRGLLRGLW PLHIVLWTRI ASTIPPHVQK SDVEMEAQKD EIICPSCNRT AHPLRHINND   60
MIVTDNNGAV KFPQLCKFCD VRFSTCDNQK SCMSNCSITS ICEKPQEVCV AVWRKNDENI   120
TLETVCHDPK LPYHDFILED AASPKCIMKE KKKPGETFFM CSCSSDECND NIIFSEEYNT   180
SNPDLLLVIF QVTGISLLPP LGVAISVIII FYCYRVNRQQ KLSSTWETGK TRKLMEFSEH   240
CAIILEDDRS DISSTCANNI NHNTELLPIE LDTLVGKGRF AEVYKAKLKQ NTSEQFETVA   300
VKIFPYEEYA SWKTEKDIFS DINLKHENIL QFLTAEERKT ELGKQYWLIT AFHAKGNLQE   360
YLTRHVISWE DLRKLGSSLA RGIAHLHSDH TPCGRPKMPI VHRDLKSSNI LVKNDLTCCL   420
CDFGLSLRLD PTLSVDDLAN SGQVGTARYM APEVLESRMN LENVESFKQT DVYSMALVLW   480
EMTSRCNAVG EVKDYEPPFG SKVREHPCVE SMKDNVLRDR GRPEIPSFWL NHQGIQMVCE   540
TLTECWDHDP EARLTAQCVA ERFSELEHLD RLSGRSCSEE KIPEDGSLNT TK           592

SEQ ID NO: 81           moltype = AA   length = 529
FEATURE                 Location/Qualifiers
source                  1..529
                        mol_type = protein
                        organism = synthetic construct
SEQUENCE: 81
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQVTGI SLLPPLGVAI   180
SVIIIFYCYR VNRQQKLSST WETGKTRKLM EFSEHCAIIL EDDRSDISST CANNINHNTE   240
LLPIELDTLV GKGRFAEVYK AKLKQNTSEQ FETVAVKIFP YEEYASWKTE KDIFSDINLK   300
HENILQFLTA EERKTELGKQ YWLITAFHAK GNLQEYLTRH VISWEDLRKL GSSLARGIAH   360
LHSDHTPCGR PKMPIVHRDL KSSNILVKND LTCCLCDFGL SLRLDPTLSV DDLANSGQVG   420
TARYMAPEVL ESRMNLENVE SFKQTDVYSM ALVLWEMTSR CNAVGEVKDY EPPFGSKVRE   480
HPCVESMKDN VLRDRGRPEI PSFWLNHQGI QMVCETLTEC WDHDPEARL              529

SEQ ID NO: 82           moltype = AA   length = 554
FEATURE                 Location/Qualifiers
source                  1..554
                        mol_type = protein
                        organism = synthetic construct
SEQUENCE: 82
MGRGLLRGLW PLHIVLWTRI ASTIPPHVQK SDVEMEAQKD EIICPSCNRT AHPLRHINND   60
MIVTDNNGAV KFPQLCKFCD VRFSTCDNQK SCMSNCSITS ICEKPQEVCV AVWRKNDENI   120
TLETVCHDPK LPYHDFILED AASPKCIMKE KKKPGETFFM CSCSSDECND NIIFSEEYNT   180
SNPDLLLVIF QVTGISLLPP LGVAISVIII FYCYRVNRQQ KLSSTWETGK TRKLMEFSEH   240
CAIILEDDRS DISSTCANNI NHNTELLPIE LDTLVGKGRF AEVYKAKLKQ NTSEQFETVA   300
VKIFPYEEYA SWKTEKDIFS DINLKHENIL QFLTAEERKT ELGKQYWLIT AFHAKGNLQE   360
YLTRHVISWE DLRKLGSSLA RGIAHLHSDH TPCGRPKMPI VHRDLKSSNI LVKNDLTCCL   420
CDFGLSLRLD PTLSVDDLAN SGQVGTARYM APEVLESRMN LENVESFKQT DVYSMALVLW   480
EMTSRCNAVG EVKDYEPPFG SKVREHPCVE SMKDNVLRDR GRPEIPSFWL NHQGIQMVCE   540
TLTECWDHDP EARL                                                    554

SEQ ID NO: 83           moltype = AA   length = 199
FEATURE                 Location/Qualifiers
source                  1..199
                        mol_type = protein
                        organism = synthetic construct
SEQUENCE: 83
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK   120
CIMKEKKKPG ETFFMCSCSS DECNDNIIFS EEYNTSNPDL LLVIFQVTGI SLLPPLGVAI   180
SVIIIFYCYR VNRQQKLSS                                               199
```

```
SEQ ID NO: 84            moltype = AA  length = 224
FEATURE                  Location/Qualifiers
source                   1..224
                         mol_type = protein
                         organism = synthetic construct
SEQUENCE: 84
MGRGLLRGLW PLHIVLWTRI ASTIPPHVQK SDVEMEAQKD EIICPSCNRT AHPLRHINND    60
MIVTDNNGAV KFPQLCKFCD VRFSTCDNQK SCMSNCSITS ICEKPQEVCV AVWRKNDENI   120
TLETVCHDPK LPYHDFILED AASPKCIMKE KKKPGETFFM CSCSSDECND NIIFSEEYNT   180
SNPDLLLVIF QVTGISLLPP LGVAISVIII FYCYRVNRQQ KLSS                    224

SEQ ID NO: 85            moltype = AA  length = 166
FEATURE                  Location/Qualifiers
source                   1..166
                         mol_type = protein
                         organism = synthetic construct
SEQUENCE: 85
MGRGLLRGLW PLHIVLWTRI ASTIPPHVQK SVNNDMIVTD NNGAVKFPQL CKFCDVRFST    60
CDNQKSCMSN CSITSICEKP QEVCAVWRK NDENITLETV CHDPKLPYHD FILEDAASPK   120
CIMKEKKKPG ETFFMCSCSS DECNDNIIFS EEYNTSNPDL LLVIFQ                  166

SEQ ID NO: 86            moltype = AA  length = 191
FEATURE                  Location/Qualifiers
source                   1..191
                         mol_type = protein
                         organism = synthetic construct
SEQUENCE: 86
MGRGLLRGLW PLHIVLWTRI ASTIPPHVQK SDVEMEAQKD EIICPSCNRT AHPLRHINND    60
MIVTDNNGAV KFPQLCKFCD VRFSTCDNQK SCMSNCSITS ICEKPQEVCV AVWRKNDENI   120
TLETVCHDPK LPYHDFILED AASPKCIMKE KKKPGETFFM CSCSSDECND NIIFSEEYNT   180
SNPDLLLVIF Q                                                        191

SEQ ID NO: 87            moltype = AA  length = 137
FEATURE                  Location/Qualifiers
source                   1..137
                         mol_type = protein
                         organism = synthetic construct
SEQUENCE: 87
TIPPHVQKSV NNDMIVTDNN GAVKFPQLCK FCDVRFSTCD NQKSCMSNCS ITSICEKPQE    60
VCVAVWRKND ENITLETVCH DPKLPYHDFI LEDAASPKCI MKEKKKPGET FFMCSCSSDE   120
CNDNIIFSEE YNTSNPD                                                  137

SEQ ID NO: 88            moltype = AA  length = 162
FEATURE                  Location/Qualifiers
source                   1..162
                         mol_type = protein
                         organism = synthetic construct
SEQUENCE: 88
TIPPHVQKSD VEMEAQKDEI ICPSCNRTAH PLRHINNDMI VTDNNGAVKF PQLCKFCDVR    60
FSTCDNQKSC MSNCSITSIC EKPQEVCVAV WRKNDENITL ETVCHDPKLP YHDFILEDAA   120
SPKCIMKEKK KPGETFFMCS CSSDECNDNI IFSEEYNTSN PD                      162

SEQ ID NO: 89            moltype = AA  length = 112
FEATURE                  Location/Qualifiers
source                   1..112
                         mol_type = protein
                         organism = synthetic construct
SEQUENCE: 89
PQLCKFCDVR FSTCDNQKSC MSNCSITSIC EKPQEVCVAV WRKNDENITL ETVCHDPKLP    60
YHDFILEDAA SPKCIMKEKK KPGETFFMCS CSSDECNDNI IFSEEYNTSN PD           112

SEQ ID NO: 90            moltype = AA  length = 507
FEATURE                  Location/Qualifiers
source                   1..507
                         mol_type = protein
                         organism = synthetic construct
SEQUENCE: 90
MGRGLLRGLW PLHIVLWTRI ASTIPPHVQK SVNNDMIVTD NNGAVKFPQL CKFCDVRFST    60
CDNQKSCMSN CSITSICEKP QEVCAVWRK NDENITLETV CHDPKLPYHD FILEDAASPK   120
CIMKEKKKPG ETFFMCSCSS DECNDNIIFS EEYNTSNPDL LLVIFQVTGI SLLPPLGVAI   180
SVIIIFYCYR VNRQQKLSST WETGKTRKLM EFSEHCAIIL EDDRSDISST CANNINHNTE   240
LLPIELDTLV GKGRFAEVYK AKLKQNTSEQ FETVAVRIPP YEEYASWKTE KDIFSDINLK   300
HENILQFLTA EERKTELGKQ YWLITAFHAK GNLQEYLTRH VISWEDLRKL GSSLARGIAH   360
LHSDHTPCGR PKMPIVHRDL KSSNILVKND LTCCLCDFGL SLRLDPTLSV DDLANSGQVG   420
TARYMAPEVL ESRMNLENVE SFKQTDVYSM ALVLWEMTSR CNAVGEVKDY EPPFGSKVRE   480
LEHLDRLSGR SCSEEKIPED GSLNTTK                                       507

SEQ ID NO: 91            moltype = AA  length = 550
```

| FEATURE | Location/Qualifiers |
| --- | --- |
| source | 1..550 |
| | mol_type = protein |
| | organism = synthetic construct |

SEQUENCE: 91
```
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQQKLSST WETGKTRKLM EFSEHCAIIL EDDRSDISST CANNINHNTE  240
LLPIELDTLV GKGRFAEVYK AKLKQNTSEQ FETVAVKIFP YEEYASWKTE KDIFSDINLK  300
HENILQFLTA EERKTELGKQ YWLITAFHAK GNLQEYLTRH VISWEDLRKL GSSLARGIAH  360
LHSDHTPCGR PKMPIVHRDL KSSNILVKND LTCCLCDFGL SLRLDPTLSV DDLANSGQVG  420
TARYMAPEVL ESRMNLENVE SFKQTDVYSM ALVLWEMTSR CNAVGEVKDY EPPFGSKVRE  480
HPCVESMKDA SGIQMVCETL TECWDHDPEA RLTAQCVAER FSELEHLDRL SGRSCSEEKI  540
PEDGSLNTTK                                                         550
```

| SEQ ID NO: 92 | moltype = AA length = 288 |
| --- | --- |
| FEATURE | Location/Qualifiers |
| source | 1..288 |
| | mol_type = protein |
| | organism = synthetic construct |

SEQUENCE: 92
```
MQIPQAPWPV VWAVLQLGWR PGWFLDSPDR PWNPPTFSPA LLVVTEGDNA TFTCSFSNTS   60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL              288
```

| SEQ ID NO: 93 | moltype = AA length = 150 |
| --- | --- |
| FEATURE | Location/Qualifiers |
| source | 1..150 |
| | mol_type = protein |
| | organism = synthetic construct |

SEQUENCE: 93
```
PGWFLDSPDR PWNPPTFSPA LLVVTEGDNA TFTCSFSNTS ESFVLNWYRM SPSNQTDKLA   60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV                                   150
```

| SEQ ID NO: 94 | moltype = AA length = 142 |
| --- | --- |
| FEATURE | Location/Qualifiers |
| source | 1..142 |
| | mol_type = protein |
| | organism = synthetic construct |

SEQUENCE: 94
```
DSPDRPWNPP TFSPALLVVT EGDNATFTCS FSNTSESFVL NWYRMSPSNQ TDKLAAFPED   60
RSQPGQDCRF RVTQLPNGRD FHMSVVRARR NDSGTYLCGA ISLAPKAQIK ESLRAELRVT  120
ERRAEVPTAH PSPSPRPAGQ FQ                                           142
```

| SEQ ID NO: 95 | moltype = AA length = 616 |
| --- | --- |
| FEATURE | Location/Qualifiers |
| source | 1..616 |
| | mol_type = protein |
| | organism = synthetic construct |

SEQUENCE: 95
```
MAPRARRRRP LFALLLLCAL LARLQVALQI APPCTSEKHY EHLGRCCNKC EPGKYMSSKC   60
TTTSDSVCLP CGPDEYLDSW NEEDKCLLHK VCDTGKALVA VVAGNSTTPR RCACTAGYHW  120
SQDCECCRRN TECAPGLGAQ HPLQLNKDTV CKPCLAGYFS DAFSSTDKCR PWTNCTFLGK  180
RVEHHGTEKS DAVCSSSLPA RKPPNEPHVY LPGLIILLLF ASVALVAAII FGVCYRKKGK  240
ALTANLWHWI NEACGRLSGD KESSGDSCVS THTANFGQQG ACEGVLLLTL EEKTFPEDMC  300
YPDQGGVCQG TCVGGGPYAQ GEDARMLSLV SKTEIEEDSF RQMPTEDEYM DRPSQPTDQL  360
LFLTEPGSKS TPPFSEPLEV GENDSLSQCF TGTQSTVGSE SCNCTEPLCR TDWTPMSSEN  420
YLQKEVDSGH CPHWAASPSP NWADVCTGCR NPPGEDCEPL VGSPKRGPLP QCAYGMGLPP  480
EEEASRTEAR DQPEDGADGR LPSSARAGAG SGSSPGGQSP ASGNVTGNSN STFISSGQVM  540
NFKGDIIVVY VSQTSQEGAA AAAEPMGRPV QEETLARRDS FAGNGPRFPD PCGGPEGLRE  600
PEKASRPVQE QGGAKA                                                  616
```

| SEQ ID NO: 96 | moltype = AA length = 185 |
| --- | --- |
| FEATURE | Location/Qualifiers |
| source | 1..185 |
| | mol_type = protein |
| | organism = synthetic construct |

SEQUENCE: 96
```
QIAPPCTSEK HYEHLGRCCN KCEPGKYMSS KCTTTSDSVC LPCGPDEYLD SWNEEDKCLL   60
HKVCDTGKAL VAVVAGNSTT PRRCACTAGY HWSQDCECCR RNTECAPGLG AQHPLQLNKD  120
TVCKPCLAGY FSDAFSSTDK CRPWTNCTFL GKRVEHHGTE KSDAVCSSSL PARKPPNEPH  180
VYLPG                                                              185
```

| SEQ ID NO: 97 | moltype = AA length = 213 |
| --- | --- |
| FEATURE | Location/Qualifiers |

```
source                  1..213
                        mol_type = protein
                        organism = synthetic construct
SEQUENCE: 97
MAPRARRRRP LFALLLLCAL LARLQVALQI APPCTSEKHY EHLGRCCNKC EPGKYMSSKC    60
TTTSDSVCLP CGPDEYLDSW NEEDKCLLHK VCDTGKALVA VVAGNSTTPR RCACTAGYHW   120
SQDCECCRRN TECAPGLGAQ HPLQLNKDTV CKPCLAGYFS DAFSSTDKCR PWTNCTFLGK   180
RVEHHGTEKS DAVCSSSLPA RKPPNEPHVY LPG                                213

SEQ ID NO: 98           moltype = AA   length = 401
FEATURE                 Location/Qualifiers
source                  1..401
                        mol_type = protein
                        organism = synthetic construct
SEQUENCE: 98
MNKLLCCALV FLDISIKWTT QETFPPKYLH YDEETSHQLL CDKCPPGTYL KQHCTAKWKT    60
VCAPCPDHYY TDSWHTSDEC LYCSPVCKEL QYVKQECNRT HNRVCECKEG RYLEIEFCLK   120
HRSCPPGFGV VQAGTPERNT VCKRCPDGFF SNETSSKAPC RKHTNCSVFG LLLTQKGNAT   180
HDNICSGNSE STQKCGIDVT LCEEAFFRFA VPTKFTPNWL SVLVDNLPGT KVNAESVERI   240
KRQHSSQEQT FQLLKLWKHQ NKAQDIVKKI IQDIDLCENS VQRHIGHANL TFEQLRSLME   300
SLPGKKVGAE DIEKTIKACK PSDQILKLLS LWRIKNGDQD TLKGLMHALK HSKTYHFPKT   360
VTQSLKKTIR FLHSFTMYKL YQKLFLEMIG NQVQSVKISC L                       401

SEQ ID NO: 99           moltype = AA   length = 290
FEATURE                 Location/Qualifiers
source                  1..290
                        mol_type = protein
                        organism = synthetic construct
SEQUENCE: 99
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET              290

SEQ ID NO: 100          moltype = AA   length = 209
FEATURE                 Location/Qualifiers
source                  1..209
                        mol_type = protein
                        organism = synthetic construct
SEQUENCE: 100
AFTVTVPKDL YVVEYGSNMT IECKFPVEKQ LDLAALIVYW EMEDKNIIQF VHGEEDLKVQ    60
HSSYRQRARL LKDQLSLGNA ALQITDVKLQ DAGVYRCMIS YGGADYKRIT VKVNAPYNKI   120
NQRILVVDPV TSEHELTCQA EGYPKAEVIW TSSDHQVLSG KTTTTNSKRE EKLFNVTSTL   180
RINTTTNEIF YCTFRRLDPE ENHTAELVI                                     209

SEQ ID NO: 101          moltype = AA   length = 289
FEATURE                 Location/Qualifiers
source                  1..289
                        mol_type = protein
                        organism = synthetic construct
SEQUENCE: 101
RIFAVFIFMT YWHLLNAFTV TVPKDLYVVE YGSNMTIECK FPVEKQLDLA ALIVYWEMED    60
KNIIQFVHGE EDLKVQHSSY RQRARLLKDQ LSLGNAALQI TDVKLQDAGV YRCMISYGGA   120
DYKRITVKVN APYNKINQRI LVVDPVTSEH ELTCQAEGYP KAEVIWTSSD HQVLSGKTTT   180
TNSKREEKLF NVTSTLRINT TTNEIFYCTF RRLDPEENHT AELVIPELPL AHPPNERTHL   240
VILGAILLCL GVALTFIFRL RKGRMMDVKK CGIQDTNSKK QSDTHLEET               289

SEQ ID NO: 102          moltype = AA   length = 390
FEATURE                 Location/Qualifiers
source                  1..390
                        mol_type = protein
                        organism = synthetic construct
SEQUENCE: 102
MPPSGLRLLP LLLPLLRLLV LTPGRPAAGL STCKTIDMEL VKRKRIEAIR GQILSKLRLS    60
SPPSQGEVPP VPLPEAVLAL YNSTRDRVAG ESAEPEPEPE ADYYAKEVTR VLMVENTNKI   120
YEKVKKSPHS IYMLFNTSEL REAVPEPVLL SRAELRLLRL KLKAEQHVEL YQKYSNDSWR   180
YLSNRLLAPS DTPEWLSFDV TGVVRQWLSH GGEVEGFRLS AHCSCDSKDN TLQVDINGFS   240
SSRRGDLATI HGMNRPFLLL MATPLERAQH LHSSRQRRAL DTNYCFSSTE KNCCVRQLYI   300
DFRKDLGWKW IHEPKGYHAN FCLGPCPYIW SLDTQYSKVL ALYNQHNPGA SAAPCCVPQA   360
LEPLPIVYYV GRKPKVEQLS NMIVRSCKCS                                    390

SEQ ID NO: 103          moltype = AA   length = 112
FEATURE                 Location/Qualifiers
source                  1..112
                        mol_type = protein
                        organism = synthetic construct
SEQUENCE: 103
ALDTNYCFSS TEKNCCVRQL YIDFRKDLGW KWIHEPKGYH ANFCLGPCPY IWSLDTQYSK    60
```

VLALYNQHNP GASAAPCCVP QALEPLPIVY YVGRKPKVEQ LSNMIVRSCK CS                112

SEQ ID NO: 104          moltype = AA   length = 15
FEATURE                 Location/Qualifiers
REGION                  1..15
                        note = Synthetic construct
source                  1..15
                        mol_type = protein
                        organism = synthetic construct
SEQUENCE: 104
GGGGSGGGGS GGGGS                                                         15

SEQ ID NO: 105          moltype = AA   length = 7
FEATURE                 Location/Qualifiers
REGION                  1..7
                        note = Synthetic construct
source                  1..7
                        mol_type = protein
                        organism = synthetic construct
SEQUENCE: 105
EPKSCDK                                                                  7

SEQ ID NO: 106          moltype = AA   length = 7
FEATURE                 Location/Qualifiers
REGION                  1..7
                        note = Synthetic construct
source                  1..7
                        mol_type = protein
                        organism = synthetic construct
SEQUENCE: 106
IEGRDMD                                                                  7

SEQ ID NO: 107          moltype = AA   length = 4
FEATURE                 Location/Qualifiers
REGION                  1..4
                        note = Synthetic construct
source                  1..4
                        mol_type = protein
                        organism = synthetic construct
SEQUENCE: 107
KKAE                                                                     4

SEQ ID NO: 108          moltype = AA   length = 4
FEATURE                 Location/Qualifiers
REGION                  1..4
                        note = Synthetic construct
source                  1..4
                        mol_type = protein
                        organism = synthetic construct
SEQUENCE: 108
KRVE                                                                     4

SEQ ID NO: 109          moltype = AA   length = 4
FEATURE                 Location/Qualifiers
REGION                  1..4
                        note = Synthetic construct
source                  1..4
                        mol_type = protein
                        organism = synthetic construct
SEQUENCE: 109
KKVE                                                                     4

SEQ ID NO: 110          moltype = AA   length = 8
FEATURE                 Location/Qualifiers
REGION                  1..8
                        note = Synthetic construct
source                  1..8
                        mol_type = protein
                        organism = synthetic construct
SEQUENCE: 110
QEPKSCDK                                                                 8

SEQ ID NO: 111          moltype = DNA   length = 21
FEATURE                 Location/Qualifiers
misc_feature            1..21
                        note = Primer
source                  1..21
                        mol_type = other DNA
                        organism = synthetic construct

```
SEQUENCE: 111
ctagtgccac ctgggaattc a                                              21

SEQ ID NO: 112          moltype = DNA   length = 24
FEATURE                 Location/Qualifiers
misc_feature            1..24
                        note = Primer
source                  1..24
                        mol_type = other DNA
                        organism = synthetic construct
SEQUENCE: 112
catcattagc tgatctccag ctca                                           24

SEQ ID NO: 113          moltype = DNA   length = 38
FEATURE                 Location/Qualifiers
misc_feature            1..38
                        note = Synthetic construct
source                  1..38
                        mol_type = other DNA
                        organism = synthetic construct
SEQUENCE: 113
catcagtgac agttacttct tcaccttcta cacagaga                            38

SEQ ID NO: 114          moltype = DNA   length = 1821
FEATURE                 Location/Qualifiers
source                  1..1821
                        mol_type = other DNA
                        organism = Homo sapiens
SEQUENCE: 114
gagctcgagg tgcagctggt ggaatccggc ggaggactgg tgcagcctgg cggatccctg    60
agactgtctt gcgccgcctc cggcttcaac atcaaggaca cctacatcca ctgggtgcga   120
caggcccctg gcaagggact ggaatgggtg gcccggatct accccaccaa cggctacacc   180
agatacgccg actccgtgaa gggccggttc accatctccg ccgacacctc caagaacacc   240
gcctacctgc agatgaactc cctgcgggcc gaggacacca ccgtgtacta ctgctccaga   300
tggggaggcg acggcttcta cgccatggac tactgggcc agggcaccct ggtgacagtg   360
tcctctgcct ccaccaaggg cccctctgtg ttccctctgg cccttccag caagtccaca   420
tctggcggca ccgccgctct gggctgcctg gtgaaagact acttcccga gcccgtgacc   480
gtgtcctgga actctggcgc cctgacctcc ggcgtgcaca cctttccagc cgtgctgcag   540
tcctccggcc tgtactccct gtcctccgtg gtgaccgtgc cctccagctc tctgggcacc   600
cagacctaca tctgcaacgt gaaccacaag ccctccaaca ccaaggtgga caagaaggtg   660
gaacccaagt cctgcgacaa gacccacacc tgtccccctt gccctgctcc tgaactgctg   720
ggcggaccct ccgtgttcct gttcccccca agcccaagg acaccctgat gatctcccgg   780
acccccgaag tgacctgcgt ggtggtggac gtgtcccacg aggaccctga agtgaagttc   840
aattggtatg tggacggcgt ggaagtgcac aacgccaaga ccaagccag agaggaacag   900
tacaactcca cctaccgggt ggtgtctgtg ctgaccgtgc tgcaccagga ctggctgaac   960
ggcaaagagt acaagtgcaa ggtgtccaac aaggccctgc ctgcccccat cgaaaagacc  1020
atctccaagg ccaagggcca gcctcgcgag cctcaggtgt acacactgcc ccctagccgg  1080
gaagagatga ccaagaacca ggtgtccctg acctgtctgg tgaaaggctt ctacccctcc  1140
gatatcgccg tggaatggga gtccaacggc cagcccgaga caactacaa gaccacccc   1200
cctgtgctga ctccgacgg ctcattcttc ctgtactcca gctgaccgt ggacaagtcc   1260
cggtggcagc agggcaacgt gttctcctgc tccgtgatgc acgaggccct gcacaaccac  1320
tacacccaga gtccctgtc cctgagccct ggaaagggcg aggcggctc tggtggtgga  1380
ggctctggag gcgaggctc taccatccct ccacacgtgc agaaatccgt gaacaacgac  1440
atgatcgtga ccgacaacaa cggcgccgtg aagttccccc agctgtgcaa gttctgcgac  1500
gtgcggttct ctacctgcga caaccagaaa tcctgcatgt ccaactgctc catcacctcc  1560
atctgcgaga agcccagga agtgtgcgtg gccgtgtggc ggaagaacga cgagaacatc  1620
accctggaaa ccgtgtgcca cgaccccaag ctgccctacc acgacttcat cctgaaggat  1680
gccgcctccc ccaagtgcat catgaaggaa aagaagaagc ccggcgagac attcttcatg  1740
tgcagctgct cctccgacga gtgcaacgac aacatcatct ctcccgaaga gtacaacacc  1800
tccaaccccg actgaggtac c                                            1821

SEQ ID NO: 115          moltype = DNA   length = 657
FEATURE                 Location/Qualifiers
source                  1..657
                        mol_type = other DNA
                        organism = Homo sapiens
SEQUENCE: 115
gagctcgaca tccagatgac ccagtccccc tccagcctgt ccgctctgt gggcgacaga    60
gtgaccatca cctgtcgggc ctctcaggac gtgaacaccg ccgtggcctg gtatcagcag   120
aagcctggca aggcccccaa gctgctgatc tactccgcct ccttcctgta ctccggggtg   180
ccatcccggt tctccggctc tagatccggc accgacttca ccctgaccat ctccagcctg   240
cagcccgagg acttcgccac ctactactgc cagcagcact acaccacccc cctgaccttc   300
ggccagggca ccaaggtgga aatcaagcgg accgtggccc tccctccgt gttcatcttc   360
ccaccctccg acgagcagct gaagtctggc accgctgtgt gtgcct gctgaacaac     420
ttctacccc gcgaggccaa ggtgcagtgg aaggtggaca acgccctgca gtccggcaac   480
tcccaggaat ccgtgaccga gcaggactcc aaggacagca cctactccct gtcctccacc   540
ctgaccctgt ccaaggccga ctacgagaag cacaaggtgt acgcctgcga agtgacccac   600
cagggcctgt ccagccccgt gaccaagtcc ttcaaccggg cgagtgctg aggtacc      657
```

| SEQ ID NO: 116 | moltype = DNA length = 1818 |
|---|---|
| FEATURE | Location/Qualifiers |
| source | 1..1818 |
| | mol_type = other DNA |
| | organism = Homo sapiens |

SEQUENCE: 116

```
gagctccagg tgcagctgaa gcagtccggc ccaggactgg tgcagccttc ccagtccctg   60
tccatcacct gtaccgtgtc cggcttctcc ctgaccaact acggcgtgca ctgggtccga  120
cagtccccag gcaagggcct ggaatggctg ggagtgattt ggagcggcgg caacaccgac  180
tacaacaccc ccttcacctc ccggctgtcc atcaacaagg acaactccaa gtcccaggtg  240
ttcttcaaga tgaactccct gcagtccaac gacaccgcca tctactactg cgccagagcc  300
ctgacctact atgactacga gttcgcctac tggggacagg gcaccctggt caccgtgtct  360
gccgcctcta ccaagggccc ctccgtgttt ccctggccc cctccagcaa gtccacatct  420
ggcggcaccg ccgctctggg ctgcctggtc aaggactact tccccgagcc cgtgaccgtg  480
tcctggaact ctggcgccct gacctccggc gtgcacacct tccagcgcgt gctgcagtcc  540
tccggcctgt actccctgtc ctccgtcgtg accgtgccct ccagctctct gggcacccag  600
acctacatct gcaacgtgaa ccacaagccc tccaacacca aggtggacaa gcgggtggaa  660
cccaagtcct gcgacaagac ccacacctgt cccccctgcc ctgcccctga actgctggga  720
ggcccttccg tgttcctgtt ccccccaaag cccaaggaca ccctgatgat ctcccggacc  780
cccgaagtga cctgcgtggt ggtggacgtg tcccacgagg accctgaagt gaagttcaat  840
tggtacgtgg acggcgtgga agtgcacaac gccaagacca gcccagaga ggaacagtac  900
aactccaact accgggtggt gtccgtgctg accgtgctgc accaggacgg gctgaacggc  960
aaagagtaca agtgcaaggt ctccaacaag gccctgcctg ccccatcga aaagaccatc 1020
tccaaggcca agggccagcc ccgcgagcct caggtgtaca ctctgcctcc cagccgggac 1080
gagctgacca gaaccaggt gtccctgacc tgtctggtca agggcttcta cccctccgat 1140
atcgccgtgg aatgggagtc caacggccag cccgagaaca actacaagac cacccccct 1200
gtgctggact ccgacggctc attcttcctg tactccaagc tgaccgtgga caagtcccgg 1260
tggcagcagg gcaacgtgtt ctcctgctcc gtgatgcacg aggccctgca caaccactac 1320
acccagaagt ccctgtctct gagccccggc aagggcggag cggatctgg tggtggtggc 1380
tctggtggcg gaggctctac catccctcca cacgtgcaga aatccgtgaa caacgacatg 1440
atcgtgaccg acaacaacgg cgccgtgaag ttcccccagc tgtgcaagtt ctgcgacgtg 1500
cggttctcta cctgcgacaa ccagaaatcc tgcatgtcca actgctccat cacctccatc 1560
tgcgagaagc cccaggaagt gtgcgtcgcc gtctggcgga gaacgacga gaacatcacc 1620
ctggaaaccg tgtgccacga ccccaagctg ccctaccacg acttcatcct ggaagatgcc 1680
gcctccccca agtgcatcat gaaggaaaag aagaagcccg cgagacttt cttcatgtgc 1740
agctgctcct ccgacgagtg caacgacaac atcatcttct ccgaagagta caacacctcc 1800
aaccccgact gaggtacc                                                1818
```

| SEQ ID NO: 117 | moltype = DNA length = 657 |
|---|---|
| FEATURE | Location/Qualifiers |
| source | 1..657 |
| | mol_type = other DNA |
| | organism = Homo sapiens |

SEQUENCE: 117

```
gagctcgata tcctgctgac ccagtccccc gtgatcctgt ccgtgtctcc tggcgagcgg   60
gtgtccttct cctgccgggc ctcccagtcc atcggcacca acatccactg gtatcagcag  120
cggaccaacg gctcccctcg gctgctgatt aagtacgcct ccgagtctat ctccggcatc  180
ccctcccggt tctccggctc tggctccggc accgacttca ccctgtccat caactccgtg  240
gaatccgagg atatcgccga ctactactgc cagcagaaca caaactggcc caccaccttc  300
ggcgctggca ccaagctgga actgaagcgg accgtggccg ctcccctccgt gttcatcttc  360
ccacccctccg acgagcagct gaagtccggc accgcctcc tcgtgtgcct gctgaacaac  420
ttctacccc gcgaggccaa ggtgcagtgg aaggtggaca acgccctgca gtccggcaac  480
tcccaggaat ccgtcaccga gcaggactcc aaggacagca cctactccct gtcctccacc  540
ctgaccctgt ccaaggccga ctacgagaag cacaaggtgt acgcctgcga agtgacccac  600
cagggcctgt ccagccccgt gaccaagtcc ttcaaccggg gcgagtgctg aggtacc      657
```

| SEQ ID NO: 118 | moltype = DNA length = 1824 |
|---|---|
| FEATURE | Location/Qualifiers |
| source | 1..1824 |
| | mol_type = other DNA |
| | organism = Homo sapiens |

SEQUENCE: 118

```
gagctccagg tgcagctgca gcagcctggc gccgagctgg tcaagcctgg cgcttccgtg   60
aagatgtcct gcaaggcctc cggctacacc ttcaccagct acaacatgca ctgggtcaag  120
cagaccccccg gcagaggcct ggaatggatc ggcgccatct accccggcaa cggcgacacc  180
tcctacaacc agaagttcaa gggaaaggcc accctgaccg ccgacaagtc ctcctccacc  240
gcctacatgc agctgtcctc cctgacctcc gaggactccg ccgtgtacta ctgcgcccgg  300
tccacctact acggcggcga ctggtacttc aacgtgtggg gcgctggcac caccgtgacc  360
gtgtctgccg cctctaccaa gggccctcc gtgtttccc tggccccctc cagcaagtcc  420
acatctggcg gcaccgccgc tctgggctgc ctggtcaagg actacttccc cgagcccgtg  480
acagtgtcct ggaactctgg cgccctgacc agcggcgtgc acacctttcc agccgtgctg  540
cagtcctctg gcctgtactc cctgtccagc gtcgtgaccg tgccctccag ctctctgggc  600
acccagacct acatctgcaa cgtgaaccac aagccctcca acaccaaggt ggacaagaag  660
gccgagccca agtcctgcga caagacccac acctgtccc ctgccctaactg  720
ctgggaggcc cttctgtgtt cctgttcccc caaagcccaa aggacaccct gatgatctcc  780
cggacccccg aagtgacctg cgtggtggt gacgtgtccc acgaggaccc tgaagtgaag  840
ttcaattggt acgtggacgg cgtggaagtg cacaacgcca agaccaagcc cagagaggaa  900
cagtacaact ccacctaccg ggtggtgtcc gtgctgaccg tgctgcacca ggactggctg  960
aacggcaaag agtacaagtg caaggtgtcc aacaaggccc tgcctgcccc catcgaaaag 1020
```

```
accatctcca aggccaaggg ccagccccgc gagcctcagg tgtacactct gcctcccagc  1080
cgggacgagc tgaccaagaa ccaggtgtcc ctgacctgtc tggtcaaggg cttctacccc  1140
tccgatatcg ccgtggaatg ggagtccaac ggccagcccg agaacaacta caagaccacc  1200
cccctgtgc tggactccga cggctcattc ttcctgtact ccaagctgac cgtggacaag  1260
tcccggtggc agcagggcaa cgtgttctcc tgctccgtga tgcacgaggc cctgcacaac  1320
cactacaccc agaagtccct gtccctgagc cccggaaagg gcggaggcgg atctggtggt  1380
ggaggatcag gcggcggagg ctctaccatc ccccacacg tgcagaaatc cgtgaacaac  1440
gacatgatcg tgaccgacaa caacggcgcc gtgaagttcc cccagctgtg caagttctgc  1500
gacgtgcggt tctctacctg cgacaaccag aaatcctgca tgtccaactg ctccatcacc  1560
tccatctgcg agaagcccca ggaagtgtgc gtcgccgtct ggccgaagaa cgacgagaac  1620
atcaccctgg aaaccgtgtg ccacgacccc aagcgcccct accacgactt catcctggaa  1680
gatgccgcct cccccaagtg catcatgaag gaaaagaaga agcccggcga gactttcttc  1740
atgtgctctt gctcctccga cgagtgcaac gacaacatca tcttctccga agagtacaac  1800
acctccaacc ccgactgagg tacc                                         1824

SEQ ID NO: 119         moltype = DNA   length = 654
FEATURE                Location/Qualifiers
source                 1..654
                       mol_type = other DNA
                       organism = Homo sapiens
SEQUENCE: 119
gagctccaga tcgtgctgtc ccagtccccc gccatcctgt ctgctagccc tggcgagaaa  60
gtgacaatga cctgccgggc ctcctcctcc gtgtcctaca tccactggtt ccagcagaag  120
cccggctcca gccccaagcc ctggatctac gccacctcca acctggcctc cggcgtgcca  180
gtgcggttct ctggctccgg ctccggcacc tcctactccc tgaccatctc cgggtgaa  240
gccgaggacg ccgccaccta ctactgccag cagtggacca ccaaccccgc caccttggc  300
ggaggcacca agctggaaat caagcgggacc gtggccgctc cctccgtgtt catcttccca  360
ccctccgacg agcagctgaa gtccggcacc gcctccgtcg tgtgcctgct gaacaacttc  420
taccccgcg aggccaaggt gcagtggaag gtggacaacg ccctgcagtc cggcaactcc  480
caggaatccg tcaccgagca ggactccaag gacagccacct acagcctgtc ctccaccctg  540
accctgtcca aggccgacta cgagaagcac aaggtgtacg cctgcgaagt gacccaccag  600
ggcctgtcca gccccgtgac caagtccttc aaccgggggcg agtgctgagg tacc        654

SEQ ID NO: 120         moltype = DNA   length = 1830
FEATURE                Location/Qualifiers
source                 1..1830
                       mol_type = other DNA
                       organism = Homo sapiens
SEQUENCE: 120
gagctcgagg tgcagctggt ggaatccggc ggaggcctgg tccagcctgg cggatccctg  60
agactgtcct gtgccgcctc cggctacacc ttcaccaact acggcatgaa ctgggtccga  120
caggcccctg gcaagggcct ggaatgggtc ggatggatca cacctacac cggcgagccc  180
acctacgccg ccgacttcaa gcggcggttc accttctcca tggacacctc caagtccacc  240
gcctacctgc agatgaactc cctgcgggcc gaggacaccg ccgtgtacta ctgcgccaag  300
taccccact actacggctc ctcccactgg tacttcgacg tgtggggcca gggcaccctg  360
gtcaccgtgt cctccgcctc taccaagggc ccctccgtgt tccctctggc ccctccagc  420
aagtccacat ctgggggcac cgccgctctg ggctgcctgg tcaaggacta cttccccgag  480
cccgtgaccg tgtcctggaa ctctggcgcc ctgacctccg gcgtgcacac ctttccagcc  540
gtgctgcagt cctccggcct gtactccctg tcctccgtcg tgaccgtgcc ctccagctct  600
ctgggcaccc agacctacat ctgcaacgtg aaccacaagc cctccaacac caaggtggac  660
aagaaggtgg aacccaagtc ctgcgacaag acccacacct gtccccctg gcctgccct  720
gaactgctgg gaggccctag cgtgttcctg ttccccccaa agcccaagga caccctgatg  780
atctcccgga ccccgaagt gacctgcgtg tggtggacg tgtcccacga ggaccctgaa  840
gtgaagttca attggtacgt ggacggcgtg gaagtgcaca acgccaagac caagcccaga  900
gaggaacagt acaactccac ctaccgggtg gtgtccgtgc tgaccgtgct gcaccaggac  960
tggctgaacg gcaaagagta caagtgcaag gtgtccaaca aggccctgcc tgccccatc  1020
gaaaagacca tctccaaggc caagggccag ccccgcgagc ctcaggtgta cactctgccc  1080
cctagccggg aagagatgac caagaaccag gtgtccctga cctgtctggt caagggcttc  1140
tacccctccg atatcgccgt ggaatgggag tccaacggcc agcccgagaa caactacaag  1200
accaccccc ctgtgctgga ctccgacggc tcattcttcc tgtactccaa gctgaccgtg  1260
gacaagtccc ggtggcagca gggcaacgtg ttcctcctgct ccgtgatgca cgaggccctg  1320
cacaaccact acacccagaa gtccctgtcc ctgagcccag gcaagggcgg aggcggatct  1380
ggtggtggag gatcaggcgg cggaggctct accatccccc acacgtgca gaaatccgtg  1440
aacaacgaca tgatcgtgac cgacaacaac ggccgcgtga agttccccca gctgtgcaag  1500
ttctgcgacg tgcggttctc tacctgcgac aaccagaaat cctgcatgtc caactgctcc  1560
atcacctcca tctgcgagaa gccccaggaa gtgtgcgtcg ccgtctgcg gaagaacgac  1620
gagaacatca ccctggaaac cgtgtgccac gaccccaagc gcccctacca cgacttcatc  1680
ctggaagatg ccgcctcccc caagtgcatc atgaaggaaa gaagaagcc ggcgagact  1740
ttcttcatgt gcagctgctc ctccgacgag tgcaacgaca acatcatctt ctccgaagag  1800
tacaacacct ccaacccga ctgaggtacc                                    1830

SEQ ID NO: 121         moltype = DNA   length = 657
FEATURE                Location/Qualifiers
source                 1..657
                       mol_type = other DNA
                       organism = Homo sapiens
SEQUENCE: 121
gagctcgata tccagatgac ccagtccccc tccagcctgt ccgcctctgt gggcgacaga  60
gtgaccatca cctgttccgc cagccaggac atctccaact acctgaactg gtatcagcag  120
```

```
aagcccggca aggccccataa ggtgctgatc tacttcacct cctccctgca ctccggcgtg    180
ccctccagat tctccggctc tggctccggc accgactta ccctgaccat ctccagcctg    240
cagcccgagg acttcgccac ctactactgc cagcagtact ccaccgtgcc ctggaccttc    300
ggccagggca ccaaggtgga aatcaagcgg accgtggccg ctccctccgt gttcatcttc    360
ccaccctccg acgagcagct gaagtccggc accgcctccg tcgtgtgcct gctgaacaac    420
ttctaccccc gcgaggccaa ggtgcagtgg aaggtggaca acgccctgca gtccggcaac    480
tcccaggaat ccgtcaccga gcaggactcc aaggacagca cctactccct gtcctccacc    540
ctgaccctgt ccaaggccga ctacgagaag cacaaggtgt acgcctgcga agtgaccac     600
cagggcctgt ccagccccgt gaccaagtcc ttcaaccggg gcgagtgctg aggtacc       657

SEQ ID NO: 122         moltype = AA  length = 40
FEATURE                Location/Qualifiers
REGION                 1..40
                       note = Synthetic construct
source                 1..40
                       mol_type = protein
                       organism = synthetic construct
SEQUENCE: 122
GGGGSGGGGS GGGGSGGGGS GGGGSGGGGS GGGGSGGGGS                           40

SEQ ID NO: 123         moltype = AA  length = 5
FEATURE                Location/Qualifiers
source                 1..5
                       mol_type = protein
                       organism = synthetic construct
VARIANT                1..5
                       note = The entire sequence of amino acids 1-5 can be
                         repeated one to eight times.
SEQUENCE: 123
GGGGS                                                                  5

SEQ ID NO: 124         moltype = AA  length = 211
FEATURE                Location/Qualifiers
source                 1..211
                       mol_type = protein
                       organism = synthetic construct
SEQUENCE: 124
QIVSTQSPAI MSASPGEKVT MTCSASSSRS YMQWYQQKPG TSPKRWIYDT SKLASGVPAR     60
FSGSGSGTSY SLTISSMEAE DAATYYCHQR SSYTFGGGTK LEIKRTVAAP SVFIFPPSDE    120
QLKSGTASVV CLLNNFYPRE AKVQWKVDNA LQSGNSQESV TEQDSKDSTY SLSSTLTLSK    180
ADYEKHKVYA CEVTHQGLSS PVTKSFNRGE C                                   211
```

COMPOSITIONS AND METHODS FOR TARGETED IMMUNOMODULATORY ANTIBODIES AND FUSION PROTEINS

CROSS-REFERENCE TO RELATED APPLICATIONS

This application is a continuation application of U.S. application Ser. No. 17/694,541 filed Mar. 14, 2022, now pending; which is a continuation application of U.S. application Ser. No. 16/601,347 filed Oct. 14, 2019, now issued as U.S. Pat. No. 11,274,156; which is a continuation application of U.S. application Ser. No. 15/362,632 filed Nov. 28, 2016, now issued as U.S. Pat. No. 10,442,860; which is a divisional application of U.S. application Ser. No. 15/231,309 filed Aug. 8, 2016, now issued as U.S. Pat. No. 9,850,306; which is a continuation application of U.S. application Ser. No. 14/645,282 filed Mar. 11, 2015, now issued as U.S. Pat. No. 9,441,044; which is a continuation application of U.S. application Ser. No. 13/582,717 filed Oct. 17, 2012, now issued as U.S. Pat. No. 8,993,524; which is a 35 USC § 371 National Stage application of International Application No. PCT/US2011/027317 filed Mar. 4, 2011, now expired; which claims the benefit under 35 USC § 119 (c) to U.S. Application Ser. No. 61/435,671 filed Jan. 24, 2011 and to U.S. Application Ser. No. 61/311,255 filed Mar. 5, 2010. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. CA123277 awarded by the National Institutes of Health. The government has certain rights in the invention.

INCORPORATION BY REFERENCE OF SEQUENCE LISTING

The material in the accompanying sequence listing is hereby incorporated by reference into this application. The accompanying sequence listing text file, named JHU3260-10.xml, was created on Sep. 23, 2024 and is 174,970 bytes in size.

BACKGROUND OF THE INVENTION

Field of the Invention

The present invention relates generally to the field of targeted immunomodulatory antibodies and fusion proteins for cancer therapy and more specifically to composition and methods for targeted immunostimulatory or immunosuppressive antibodies and fusion proteins to counteract or induce immune tolerance of cancer cells.

BACKGROUND INFORMATION

The immune system provides the human body with a means to recognize and defend itself against microorganisms and substances recognized as foreign or potentially harmful. While passive immunotherapy of cancer with monoclonal antibodies and passive transfer of T cells to attack tumor cells have demonstrated clinical efficacy, the goal of active therapeutic vaccination to induce these immune effectors and establish immunological memory against tumor cells has remained challenging. Several tumor-specific and tumor-associated antigens have been identified, yet these antigens are generally weakly immunogenic and tumors employ diverse mechanisms to create a tolerogenic environment that allows them to evade immunologic attack. Strategies to overcome such immune tolerance and activating robust levels of antibody and/or T cell responses hold the key to effective cancer immunotherapy.

SUMMARY OF THE INVENTION

The present invention is based on the seminal discovery that targeted immunomodulatory antibodies and fusion proteins can counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. Such immunosuppressive mechanisms include immunosuppressive cytokines (for example, Transforming growth factor beta (TGF-β)) and regulatory T cells and/or immunosuppressive myeloid dendritic cells (DCs). By counteracting tumor-induced immune tolerance, the present invention provides effective compositions and methods for cancer treatment, optional in combination with another existing cancer treatment. The present invention provides strategies to counteract tumor-induced immune tolerance and enhance the antitumor efficacy of chemotherapy by activating and leveraging T cell-mediated adaptive antitumor immunity against resistant or disseminated cancer cells.

In one embodiment, the present invention provides a molecule including a targeting moiety fused with an immunomodulatory moiety. The targeting moiety specifically binds a target molecule, and the immunomodulatory moiety specifically binds one of the following molecules: (i) Transforming growth factor-beta (TGF-β); (ii) Programmed death-1 ligand 1 (PD-L1) or Programmed death-1 ligand 2 (PD-L2); (iii) Receptor activator of nuclear factor-κB (RANK) ligand (RANKL); (iv) Transforming growth factor-beta receptor (TGF-βR); (v) Programmed death-1 (PD-1); and (vi) Receptor activator of nuclear factor-κB (RANK).

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-B1), HER2/neu (Erb-B2), CD20, Vascular endothelial growth factor (VEGF), insulin-like growth factor receptor (IGF-1R), TRAIL-receptor, epithelial cell adhesion molecule, carcino-embryonic antigen, Prostate-specific membrane antigen, Mucin-1, CD30, CD33, or CD40.

In one aspect, the targeting moiety specifically binds a component of a regulatory T cell, myeloid suppressor cell, or dendritic cell. In another aspect, the targeting moiety specifically binds one of the following molecules: (i) CD4; (ii) CD25 (IL-2α receptor; IL-2αR); (iii) cytotoxic T-lymphocyte antigen-4 (CTLA-4; CD152); (iv) Interleukin-10 (IL-10); (v) Transforming growth factor-beta receptor (TGF-βR); (vi) Transforming growth factor-beta (TGF-β); (vii) Programmed Death-1 (PD-1); (viii) Programmed death-1 ligand (PD-L1 or PD-L2); (ix) Receptor activator of nuclear factor-κB (RANK); or (x) Receptor activator of nuclear factor-κB (RANK) ligand (RANKL).

In one aspect, the immunomodulatory moiety specifically binds one of the following molecules: (i) Transforming growth factor-beta (TGF-β); (ii) Programmed death-1 ligand (PD-L1 or PD-L2); or (iii) Receptor activator of nuclear factor-κB (RANK) ligand (RANKL).

In one aspect, the immunomodulatory moiety includes a molecule that binds TGF-β. In another aspect, the immunomodulatory moiety includes an extracellular ligand-binding domain of Transforming growth factor-beta receptor TGF-βRII, TGF-βRIIb, or TGF-βRIII. In another aspect, the immunomodulatory moiety includes an extracellular ligand-binding domain of TGF-βRII. In an additional aspect, the immunomodulatory moiety inhibits the activity or function of TGF-β.

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain of TGF-βRII. In another aspect, the molecule includes an amino acid sequence corresponding to SEQ ID NO: 1, 2, 3, 4, 5, 6, 7, 8, 9 or 10.

In one aspect, the targeting moiety includes an antibody, antibody fragment, or polypeptide that specifically binds to Programmed Death-1 (PD-1), Programmed death-1 ligand 1 (PD-L1), or Programmed death-1 ligand 2 (PD-L2). In another aspect, the targeting moiety includes an extracellular ligand-binding domain or ectodomain of Programmed Death-1 (PD-1). In an additional aspect, the immunomodulatory moiety includes an extracellular ligand-binding domain of TGF-βRII. In another aspect, the molecule includes PD-1 ectodomain, immunoglobulin Fc region, and TGFβRII ectodomain. In another aspect, the molecule includes an amino acid sequence corresponding to SEQ ID NO: 11 or 12.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of TGF-βRII. In another aspect, the molecule includes RANK ectodomain, immunoglobulin Fc region, and TGFβRII ectodomain. In another aspect, the molecule includes an amino acid sequence corresponding to SEQ ID NO: 13 or 14.

In one aspect, the immunomodulatory moiety includes a molecule that specifically binds to Programmed death-1 ligand 1 (PD-L1) or Programmed death-1 ligand 2 (PD-L2). In another aspect, the immunomodulatory moiety includes an extracellular ligand-binding domain or ectodomain of Programmed Death-1 (PD-1). In an additional aspect, the immunomodulatory moiety inhibits the activity or function of Programmed death-1 ligand 1 (PD-L1).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Programmed Death-1 (PD-1). In another aspect, the molecule includes an amino acid sequence corresponding to SEQ ID NO: 15, 16, 17, 18, 19, 20, 21, 22, 23, or 24.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of Programmed Death-1 (PD-1). In another aspect, the molecule includes RANK ectodomain, immunoglobulin Fc region, and PD-1 ectodomain. In another aspect, the molecule includes an amino acid sequence corresponding to SEQ ID NO: 25 or 26.

In one aspect, the immunomodulatory moiety includes a molecule that specifically binds to Receptor activator of nuclear factor-κB ligand (RANKL). In another aspect, the immunomodulatory moiety includes an extracellular ligand-binding domain or ectodomain of Receptor activator of nuclear factor-κB (RANK). In an additional aspect, the immunomodulatory moiety inhibits the activity or function of Receptor activator of nuclear factor-κB ligand (RANKL).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Receptor activator of nuclear factor-κB (RANK). In another aspect, the molecule includes an amino acid sequence corresponding to SEQ ID NO: 27, 28, 29, 30, 31, 32, 33, 34, 35, or 36.

In one aspect, the immunomodulatory moiety includes a sequence from Programmed death-1 ligand 1 (PD-L1) or Programmed death-1 ligand 2 (PD-L2). In an additional aspect, the immunomodulatory moiety increases the function of PD-1.

In one aspect, the targeting moiety specifically binds to Tumor Necrosis Factor-α (TNF-α), and the immunomodulatory moiety includes a sequence from Programmed death-1 ligand 1 (PD-L1) or Programmed death-1 ligand 2 (PD-L2). In an additional aspect, the targeting moiety includes an antibody that binds TNF-α, and the immunomodulatory moiety includes a sequence from PD-1 ligand 1 (PD-L1 or B7-H1). In another aspect, the molecule includes an amino acid sequence corresponding to SEQ ID NO: 37. In another aspect, the targeting moiety includes an extracellular ligand-binding domain of tumor necrosis factor receptor 2 (TNFR2), and the immunomodulatory moiety includes a sequence from PD-1 ligand 1 (PD-L1 or B7-H1). In another aspect, the molecule includes TNFR2 Extracellular ligand binding domain, immunoglobulin Fc region, and a sequence from PD-L1. In another aspect, the molecule includes an amino acid sequence corresponding to SEQ ID NO: 38 or 39.

In one aspect, the targeting moiety includes an antibody or antibody fragment that specifically binds to CD20, CD25, or CD4, and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 40, 41, 42, 43, 44, or 45.

In one aspect, the targeting moiety includes the extracellular domain of CTLA-4 and immunoglobulin Fc region (IgG Cγ1), and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 46 or 47.

In one aspect, the targeting moiety includes transforming growth factor-β (TGF-β) and immunoglobulin Fc region (IgG Cγ1), and the immunomodulatory moiety includes a sequence from Programmed death-1 ligand 1 (PD-L1) or Programmed death-1 ligand 2 (PD-L2). In an additional aspect, the molecule includes an amino acid sequence corresponding to SEQ ID NO: 48 or 49.

In one aspect, the immunomodulatory moiety includes a sequence from transforming growth factor-β (TGF-β). In an additional aspect, the immunomodulatory moiety activates the signaling function of transforming growth factor-β (TGF-β) receptor.

In one aspect, the targeting moiety includes an antibody, antibody fragment, or polypeptide that specifically binds to Tumor Necrosis Factor-α (TNF-α), and the immunomodulatory moiety includes a sequence from transforming growth factor-β (TGF-β). In an additional aspect, the targeting moiety includes an antibody that binds TNF-α, and the immunomodulatory moiety includes a sequence from TGF-β. In another aspect, the molecule includes an amino acid sequence corresponding to SEQ ID NO: 50. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from transforming growth factor-β (TGF-β). In another aspect, the molecule includes an amino acid sequence corresponding to SEQ ID NO: 51 or 52.

In one aspect, the targeting moiety includes an antibody or antibody fragment that specifically binds to CD20, CD25 (IL-2α receptor; IL-2αR), or CD4, and the immunomodulatory moiety includes a sequence from transforming growth factor-β (TGF-β). In an additional aspect, the molecule includes an amino acid sequence corresponding to SEQ ID NO: 53, 54, 55, 56, 57 or 58.

In one aspect, the targeting moiety includes an extracellular domain of CTLA-4 and immunoglobulin Fc region (IgG Cγ1), and the immunomodulatory moiety includes a sequence from transforming growth factor-β (TGF-β). In another aspect, the molecule includes an amino acid sequence corresponding to SEQ ID NO: 59 or 60.

In one aspect, the targeting moiety includes an antibody, antibody fragment, or polypeptide that specifically binds to Tumor Necrosis Factor-α (TNF-α), and the immunomodulatory moiety includes an extracellular RANKL-binding domain or ectodomain of Receptor activator of nuclear factor-κB (RANK). In an additional aspect, the targeting moiety includes an antibody that binds TNF-α, and the immunomodulatory moiety includes a sequence from an extracellular RANKL-binding domain or ectodomain of RANK. In another aspect, the molecule includes an amino acid sequence corresponding to SEQ ID NO: 61. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from an extracellular RANK-binding domain or ectodomain of RANK. In another aspect, the molecule includes an amino acid sequence corresponding to SEQ ID NO: 62 or 63.

In one aspect, the targeting moiety includes an extracellular domain of CTLA-4 and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 64 or 65.

In one aspect, the targeting moiety includes a sequence from transforming growth factor-β (TGF-β) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 66 or 67.

In one aspect, the targeting moiety includes a sequence from Programmed death-1 ligand 1 (PD-L1) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 68 or 69.

In various aspects, the molecule is fused or directly linked to one or more antigen, antigenic determinant, or epitope.

In another embodiment, the present invention provides a composition including the molecule of the invention and a cell, wherein the cell is a tumor cell, immune cell, or dendritic cell.

In another embodiment, the present invention provides a method of counteracting or overcoming immune tolerance. The method includes administering to a subject in need thereof one or more molecule of the invention.

In another embodiment, the present invention provides a method of preventing or treating a neoplastic disease. The method includes administration to a subject in need thereof one or more molecule of the invention. In various aspects, the subject is administered one or more molecule of the invention in combination with another anticancer therapy. In one aspect, the anticancer therapy includes a chemotherapeutic molecule, antibody, small molecule kinase inhibitor, hormonal agent or cytotoxic agent. In another aspect, the anticancer therapy includes ionizing radiation, ultraviolet radiation, cryoablation, thermal ablation, or radiofrequency ablation.

In another embodiment, the present invention provides a method of preventing or treating a neoplastic disease. The method includes administration to a subject in need thereof an antibody that targets and depletes CD4+ regulatory T cells (Tregs) in combination with another cytotoxic anticancer therapy. In one aspect, the antibody that targets and depletes Tregs is an anti-CD4 antibody. In various aspects, the cytotoxic anticancer therapy includes a chemotherapeutic molecule, tumor-targeted antibody, small molecule kinase inhibitor, hormonal agent or tumor-targeted cytotoxic agent. In another aspect, the cytotoxic anticancer therapy includes ionizing radiation, ultraviolet radiation, cryoablation, thermal ablation, or radiofrequency ablation.

In another embodiment, the subject is administered one or more molecule of the invention in combination with any vaccine. In another aspect, the vaccine includes a tumor antigen, tumor-associated antigen, tumor epitope, tumor antigen-containing fusion protein, tumor cell, or dendritic cell. In another aspect, the vaccine includes a pathogen antigen, pathogen-associated antigen, pathogen epitope, or pathogen antigen-containing fusion protein.

In another embodiment, the present invention provides a method for treating immune cells wherein the cells are contacted ex vivo or in vitro with a molecule of the invention. In another embodiment, the present invention provides a method of treatment of a neoplastic disease. The method includes administering to a subject in need thereof a composition of immune cells contacted with a molecule of the invention.

In another embodiment, the present invention provides a method of inducing or promoting immune tolerance. The method includes administering to a subject in need thereof one or more molecule of the invention.

In another embodiment, the present invention provides a method of preventing or treating an autoimmune or inflammatory disease including administering to a subject in need thereof one or more molecule of the invention. In one aspect, the subject is administered one or more molecule of the invention in combination with another anti-inflammatory or immunosuppressive therapy. In another embodiment, the present invention provides a method of treatment of immune cells wherein the cells are contacted ex vivo or in vitro with a molecule of the invention. In another embodiment, the present invention provides a method of treating an autoimmune or inflammatory disease or preventing rejection of grafted cells or tissue. The method includes administering to a subject in need thereof a composition of immune cells contacted with a molecule of the invention.

BRIEF DESCRIPTION OF THE DRAWINGS

FIGS. 1A-1C show exemplary amino acid sequences of transforming growth factor beta receptor type II (TGF-β-RII) or TGF-β-RIIB or a fragment thereof, including (i) Transforming growth factor beta receptor type II (TGF-β-RII) (SEQ ID NO: 79); and (ii) Transforming growth factor beta receptor type IIB (TGF-β-RIIB) (SEQ ID NO: 80).

Figure 53A:
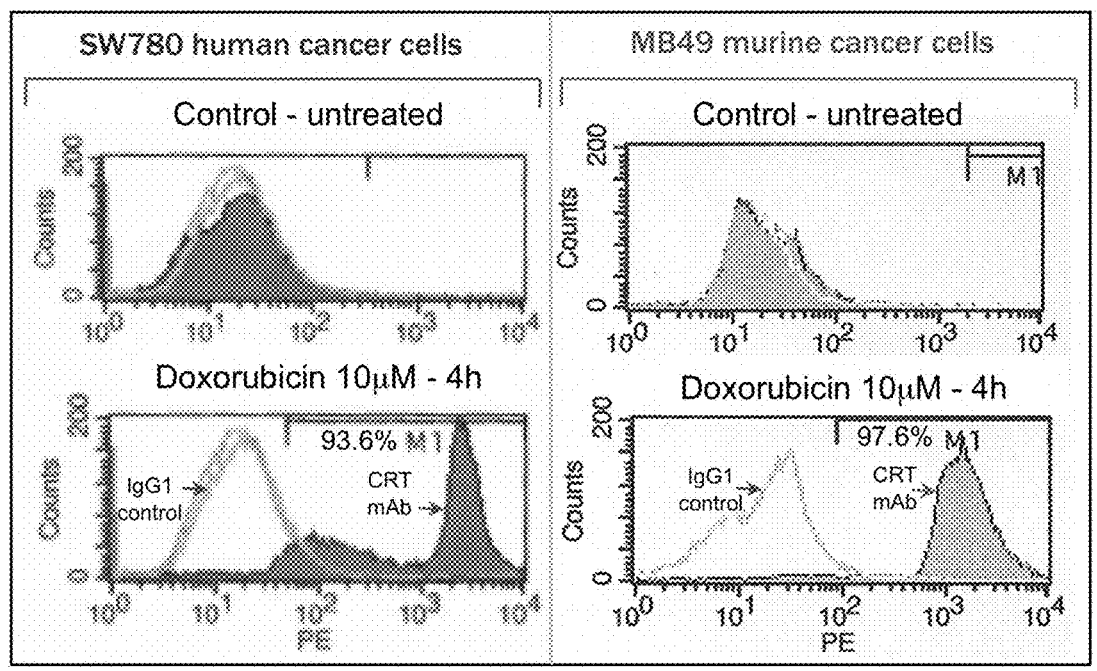

Also shown in FIGS. 1A-1C are exemplary truncated mutants of Transforming growth factor beta Receptor II (TGF-β-RII) or TGF-β-RIIB including the Extracellular domain (ECD) region that binds TGF-β, including (i) TGF-β R-II (ΔC terminus): TGFβ RII lacking the last 38 amino acids from the C-terminus (SEQ ID NO: 81) and TGF-β R-IIB (ΔC terminus): TGFβ RIIB lacking the last 38 aa from the C-terminus (SEQ ID NO: 82); (ii) TGF-βR-II (Δcyt): TGFβRII lacking the kinase domain & juxtamembrane region (SEQ ID NO: 83) and TGF-βR-IIB (Δcyt): TGFβRIIB lacking the kinase domain & juxtamembrane region (SEQ ID NO: 84); (iii) TGF-β R-II containing the N-terminus region including the extracellular domain (SEQ ID NO: 85) and TGF-β R-IIB containing the N-terminus region including the extracellular domain (SEQ ID NO: 86); (iv) TGF-β R-II containing the extracellular domain that binds TGF-β (SEQ ID NO: 87) and TGF-β R-IIB containing the extracellular domain that binds TGF-β (SEQ ID NO: 88); and (v) TGF-β R-II containing the region of the extracellular domain that binds TGF-β (SEQ ID NO: 89).

In addition, FIGS. 1A-1C also show exemplary kinase-deficient mutants, deletion mutants, or point mutants of Transforming growth factor beta Receptor II (TGFβ-RII) or TGFβ-RIIB or a fragment thereof which binds TGF-β, including (i) Transforming growth factor beta Receptor II containing point mutations-amino acid sequence of TGF-β R-II (K277R) contains a point mutation in its ATP-binding site and is inactive as a kinase (SEQ ID NO: 90); and (ii) Transforming growth factor beta Receptor II containing deletions in the amino acid sequence (deletion mutants)—Transforming growth factor beta Receptor II (Δi)-TGF-β R-II (Δi2) contains a deletion of amino acids 498 to 508 and is inactive as a kinase (SEQ ID NO: 91).

FIG. 2 shows exemplary fusion proteins including anti-HER2/neu antibody and Transforming growth factor-beta receptor II (TGFβ-RII) Extracellular domain (ECD), including anti-HER2/neu heavy chain+TGFβ-RII ECD fusion amino acid sequence (SEQ ID NO: 1) and anti-HER2/neu light chain amino acid sequence (SEQ ID NO: 70).

FIG. 3 shows exemplary fusion proteins including anti-EGFR1 antibody and Transforming growth factor-beta receptor II (TGFβ-RII) Extracellular domain (ECD), including anti-EGFR1 heavy chain+TGFβ-RII ECD fusion amino acid sequence (SEQ ID NO: 2) and anti-EGFR1 light chain amino acid sequence (SEQ ID NO: 71).

FIG. 4 shows exemplary fusion proteins including anti-CD20 antibody and Transforming growth factor-beta receptor II (TGFβ-RII) Extracellular domain (ECD), including anti-CD20 heavy chain+TGFβ-RII ECD fusion amino acid sequence (SEQ ID NO: 3) and anti-CD20 light chain amino acid sequence (SEQ ID NO: 72).

FIG. 5 shows exemplary fusion proteins including anti-VEGF antibody and Transforming growth factor-beta receptor II (TGFβ-RII) Extracellular domain (ECD), including anti-VEGF heavy chain+TGFβ-RII ECD fusion amino acid sequence (SEQ ID NO: 4) and anti-VEGF Light chain sequence (SEQ ID NO: 73).

FIG. 6 shows exemplary fusion proteins including anti-human CTLA-4 antibody and Transforming growth factor-beta receptor II (TGFβ-RII) Extracellular domain (ECD), including Anti-CTLA-4 heavy chain+TGFβ-RII Extracellular domain fusion amino acid sequence (SEQ ID NO: 5) and Anti-CTLA-4 light chain (SEQ ID NO: 74).

FIG. 7 shows exemplary fusion proteins including IL-2, Fc, and Transforming growth factor-beta receptor II (TGFβ-RII) Extracellular domain (ECD), including IL-2+Fc+TGFβ-RII Extracellular domain (SEQ ID NO: 6) and TGFβ-RII Extracellular domain+Fc+IL-2 (SEQ ID NO: 7). The linker GGGGGGGGSGGGGS (SEQ ID NO: 104) is optional and can be replaced with EPKSCDK (SEQ ID NO: 105) or another linker sequence well known in the art. Certain amino acid sequences can be replaced in Fc, including underlined E with D and underlined M with L.

FIGS. 8A-8B show exemplary fusion proteins including anti-CD25 antibody and Transforming growth factor-beta receptor II (TGFβ-RII) Extracellular domain (ECD), including anti-CD25 (Daclizumab) heavy chain and TGFβ-RII Extracellular domain (SEQ ID NO: 8) and anti-CD25 (Daclizumab) light chain (SEQ ID NO: 75) (FIG. 8A); and anti-CD25 (Basiliximab) heavy chain and TGFβ-RII Extracellular domain (SEQ ID NO: 9) and anti-CD25 (Basiliximab) light chain (SEQ ID NO: 76).

FIG. 9 shows exemplary fusion proteins including anti-CD4 antibody and Transforming growth factor-beta receptor II (TGFβ-RII) Extracellular domain (ECD), including anti-CD4 heavy chain and TGFβ-RII Extracellular domain (SEQ ID NO: 10) and anti-CD4 light chain (SEQ ID NO: 77).

FIG. 10 shows exemplary fusion proteins including Programmed Death-1 (PD-1) Ectodomain, Fc, and Transforming growth factor-beta receptor II (TGFβ-RII) Extracellular domain (ectodomain), including PD-1 ectodomain+Fc+TGFβRII ectodomain (SEQ ID NO: 11) and TGFβRII ectodomain+Fc+PD-1 ectodomain (SEQ ID NO: 12). The linker sequence EPKSCDK (SEQ ID NO: 105) is optional and can be deleted or replaced with another linker.

FIG. 11 shows exemplary fusion proteins including Receptor activator of nuclear factor-kB (RANK) Ectodomain, Fc, and Transforming growth factor-beta receptor II (TGFβ-RII) Extracellular domain (ectodomain), including RANK ectodomain+Fc+TGFβRII ectodomain (SEQ ID NO: 13) and TGFβRII ectodomain+Fc+RANK ectodomain (SEQ ID NO: 14). The linker sequence EPKSCDK (SEQ ID NO: 105) is optional and can be deleted or replaced with another linker.

FIG. 12 shows exemplary immunomodulatory moiety that binds Programmed Death-1 ligand 1 (PD-L1 or B7-H1) or Programmed Death-1 ligand 2 (PD-L2 or B7-DC), including full-length PD-1 or fragment thereof (SEQ ID NO: 92), PD-1 extracellular domain (ectodomain) or fragment thereof (SEQ ID NO: 93), and PD-1 extracellular domain (ectodomain) ligand-binding region (SEQ ID NO: 94).

FIG. 13 shows exemplary fusion proteins including anti-HER2/neu antibody and PD-1 Ectodomain, including anti-HER2/neu heavy chain+PD-1 ectodomain fusion amino acid sequence (SEQ ID NO: 15) and anti-HER2/neu light chain amino acid sequence (SEQ ID NO: 70).

FIG. 14 shows exemplary fusion proteins including anti-EGFR1 antibody and PD-1 Ectodomain, including anti-EGFR heavy chain+PD-1 ectodomain fusion amino acid sequence (SEQ ID NO: 16) and anti-EGFR light chain amino acid sequence (SEQ ID NO: 71).

FIG. 15 shows exemplary fusion proteins including anti-CD20 antibody and PD-1 Ectodomain, including anti-CD20 heavy chain+PD-1 ectodomain fusion amino acid sequence (SEQ ID NO: 17) and anti-CD20 light chain amino acid sequence (SEQ ID NO: 72).

FIG. 16 shows exemplary fusion proteins including anti-VEGF antibody and PD-1 Ectodomain, including anti-VEGF heavy chain+PD-1 ectodomain fusion amino acid sequence (SEQ ID NO: 18) and anti-VEGF Light chain sequence (SEQ ID NO: 73).

FIG. 17 shows exemplary fusion proteins including anti-human CTLA-4 antibody and PD-1 Ectodomain, including anti-CTLA-4 heavy chain+PD-1 ectodomain fusion amino acid sequence (SEQ ID NO: 19) and anti-CTLA-4 light chain (SEQ ID NO: 74).

FIGS. 18A-18B show exemplary fusion proteins including anti-CD25 antibody and PD-1 Ectodomain, including anti-CD25 (Daclizumab) heavy chain and PD-1 ectodomain (SEQ ID NO: 20) and anti-CD25 (Daclizumab) light chain (SEQ ID NO: 75) (FIG. 18A), and anti-CD25 (Basiliximab) heavy chain and PD-1 ectodomain (SEQ ID NO: 21) and anti-CD25 (Basiliximab) light chain (SEQ ID NO: 76) (FIG. 18B).

FIG. 19 shows exemplary fusion proteins including IL-2, Fc, and PD-1 ectodomain, including IL-2+Fc+PD-1 ectodomain (SEQ ID NO: 22) and PD-1 ectodomain+Fc+IL-2 (SEQ ID NO: 23). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 20 shows exemplary fusion proteins including anti-CD4 antibody and PD-1 ectodomain, including anti-CD4 heavy chain and PD-1 ectodomain (SEQ ID NO: 24) and anti-CD4 light chain (SEQ ID NO: 77).

FIG. 21 shows exemplary fusion proteins including Receptor activator of nuclear factor-kB (RANK) Ectodomain, Fc, and PD-1 ectodomain, including RANK ectodomain+Fc+PD-1 ectodomain (SEQ ID NO: 25) and PD-1 ectodomain+Fc+RANK ectodomain (SEQ ID NO: 26). The linker sequence EPKSCDK (SEQ ID NO: 105) is optional and can be deleted or replaced with another linker.

FIG. 22 shows exemplary immunomodulatory moiety that binds Receptor activator of nuclear factor-kB (RANK) ligand (RANKL) including full-length RANK or fragment thereof (SEQ ID NO: 95), extracellular ligand-binding domain or ectodomain of RANK (SEQ ID NO: 96), RANKL-binding sequences or residues of RANK (SEQ ID NO: 93), or RANKL-binding sequences of Osteoprotegerin (OPG) (SEQ ID NO: 98).

FIG. 23 shows exemplary fusion proteins including anti-HER2/neu antibody and RANK Ectodomain, including anti-HER2/neu heavy chain+RANK ectodomain fusion amino acid sequence (SEQ ID NO: 27) and anti-HER2/neu light chain amino acid sequence (SEQ ID NO: 70).

FIG. 24 shows exemplary fusion proteins including anti-EGFR1 antibody and RANK Ectodomain, including anti-EGFR heavy chain+RANK ectodomain fusion amino acid sequence (SEQ ID NO: 28) and anti-EGFR light chain amino acid sequence (SEQ ID NO: 71).

FIG. 25 shows exemplary fusion proteins including anti-CD20 antibody and RANK Ectodomain, including anti-CD20 heavy chain+RANK ectodomain fusion amino acid sequence (SEQ ID NO: 29) and anti-CD20 light chain amino acid sequence (SEQ ID NO: 72).

FIG. 26 shows exemplary fusion proteins including anti-VEGF antibody and RANK Ectodomain, including anti-VEGF heavy chain+RANK ectodomain fusion amino acid sequence (SEQ ID NO: 30) and anti-VEGF Light chain sequence (SEQ ID NO: 73).

FIG. 27 shows exemplary fusion proteins including anti-human CTLA-4 antibody and RANK Ectodomain, including anti-CTLA-4 heavy chain+RANK ectodomain fusion amino acid sequence (SEQ ID NO: 31) and anti-CTLA-4 light chain (SEQ ID NO: 74).

FIGS. 28A-28B show exemplary fusion proteins including anti-CD25 antibody and RANK Ectodomain, including anti-CD25 (Daclizumab) heavy chain and RANK ectodomain (SEQ ID NO: 32) and anti-CD25 (Daclizumab) light chain (SEQ ID NO: 75) (FIG. 28A), and anti-CD25 (Basiliximab) heavy chain and RANK ectodomain (SEQ ID NO: 33) and anti-CD25 (Basiliximab) light chain (SEQ ID NO: 76) (FIG. 28B).

FIG. 29 shows exemplary fusion proteins including IL-2, Fc, and RANK ectodomain, including IL-2+Fc+RANK ectodomain (SEQ ID NO: 34) and RANK ectodomain+Fc+IL-2 (SEQ ID NO: 35). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 30 shows exemplary fusion proteins including anti-CD4 antibody and RANK ectodomain, including anti-CD4 heavy chain and RANK ectodomain (SEQ ID NO: 36) and anti-CD4 light chain (SEQ ID NO: 77).

FIG. 31 shows exemplary immunomodulatory moiety that binds Programmed Death-1 (PD-1) including a PD-1 ligand 1 (PD-L1 or B7-H1) or PD-1 ligand 2 (PD-L2 or B7-DC) or a fragment thereof (for example, SEQ ID NO: 101), full-length human PD-1 ligand 1 (B7-H1; PDCD1L1; PD-L1; or CD274) protein or a fragment thereof (SEQ ID NO: 99), and PD-L1 extracellular binding domain (ectodomain) or fragment thereof (SEQ ID NO: 100).

FIG. 32 shows exemplary fusion proteins including anti-tumor necrosis factor (TNFα) antibody and PD-1 ligand, including anti-TNFα heavy chain+PD-1L (SEQ ID NO: 37) and anti-TNFα light chain (SEQ ID NO: 78). The sequence KKAE (SEQ ID NO: 107) can be replaced with KRVE (SEQ ID NO: 108) or KKVE (SEQ ID NO: 109).

FIG. 33 shows exemplary fusion proteins including TNFR2 Extracellular ligand binding domain, Fc, and PD-1 ligand, including TNFR2 ECD+IgG Cγ1+PD-L1 (SEQ ID NO: 38) and PD-L1+IgG Cγ1-TNFR2 ECD (SEQ ID NO: 39).

FIG. 34 shows exemplary fusion proteins including anti-CD20 antibody and PD-1 ligand 1 (PD-L1), including anti-CD20 heavy chain+PD-L1 sequence (SEQ ID NO: 40) and anti-CD20 light chain sequence (SEQ ID NO: 72).

FIGS. 35A-35B show exemplary fusion proteins including anti-CD25 antibody and PD-1 ligand 1 (PD-L1), including anti-CD25 (Daclizumab) heavy chain and PD-L1 (SEQ ID NO: 41) and anti-CD25 (Daclizumab) light chain (SEQ ID NO: 75) (FIG. 35A), and anti-CD25 (Basiliximab) heavy chain and PD-1 ectodomain (SEQ ID NO: 42) and anti-CD25 (Basiliximab) light chain (SEQ ID NO: 76) (FIG. 35B).

FIG. 36 shows exemplary fusion proteins including IL-2, Fc, and PD-1 ligand 1 (PD-L1), including fusion protein hPD-1 ligand 1+Fc+IL-2 (SEQ ID NO: 43) and fusion protein IL-2+Fc+PD-1 ligand 1 (SEQ ID NO: 44). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 37 shows exemplary fusion proteins including anti-CD4 antibody and PD-1 ligand 1 (PD-L1), including anti-CD4 heavy chain and PD-1 ligand 1 (PD-L1) (SEQ ID NO: 45) and anti-CD4 light chain (SEQ ID NO: 77).

FIG. 38 shows exemplary fusion proteins including the extracellular domain of CTLA-4, Immunoglobulin Fc (IgG Cγ1), and a sequence from PD-1 ligand (PD-L1) including Oncostatin M signal peptide+CTLA-4 ECD+IgG Cγ1+PD-L1 (SEQ ID NO: 46) and PD-1L1+IgG Cγ1+CTLA-4 ECD (SEQ ID NO: 47). The IgG sequence shown can have optional C to S conversion in (bold underlined). The linker QEPKSCDK SEQ ID NO: 110 is optional and can be replaced with EPKSCDK SEQ ID NO: 105 or another linker sequence.

FIG. 39 shows exemplary fusion proteins including a sequence of transforming growth factor-β (TGF-β), Immunoglobulin Fc (IgG Cγ1), and a sequence of PD-1 ligand (PD-L1) including TGFβ-1+Fc+PD-L1 (SEQ ID NO: 48), and PD-1L1+Fc+TGFβ-1 (SEQ ID NO: 49). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 40 shows exemplary immunomodulatory moiety that binds Transforming growth factor-beta receptor (TGF-βR) including Transforming growth factor-beta (TGF-β1, TGF-β2, or TGF-β3 or a fragment thereof, TGF-β1 full sequence (SEQ ID NO: 102), and mature (active) TGF-β1 sequence (Ala 279-Ser 390; 112 amino acids) (SEQ ID NO: 103).

FIG. 41 shows exemplary fusion proteins including an antibody that binds TNF-α, and a sequence of transforming growth factor-β (TGF-β), including anti-TNFα heavy chain+TGF-β1 (SEQ ID NO: 50) and anti-TNFα light chain (SEQ ID NO: 78). The sequence KKAE (SEQ ID NO: 107) can be replaced with KRVE (SEQ ID NO: 108) or KKVE (SEQ ID NO: 109).

FIG. 42 shows exemplary fusion proteins including TNFR2 Extracellular ligand binding domain (TNFR2 ECD), immunoglobulin Fc (IgG Cγ1), and a sequence from transforming growth factor-β (TGF-β) including TNFR2 ECD+IgG Cγ1+TGF-β1 (SEQ ID NO: 51), and TGF-β1+IgG Cγ1+TNFR2 ECD (SEQ ID NO: 52).

FIG. 43 shows exemplary fusion proteins including anti-CD20 antibody and a sequence from transforming growth factor-β (TGF-β), including anti-CD20 heavy chain+mature TGFβ1 sequence (SEQ ID NO: 53) and anti-CD20 light chain sequence (SEQ ID NO: 72).

FIGS. 44A-44B show exemplary fusion proteins including anti-CD25 antibody and a sequence from transforming growth factor-β (TGF-β), including anti-CD25 (Daclizumab) heavy chain and TGF-β1 (SEQ ID NO: 54) and anti-CD25 (Daclizumab) light chain (SEQ ID NO: 75) (FIG. 44A), and anti-CD25 (Basiliximab) heavy chain and TGF-β1 (SEQ ID NO: 55) and anti-CD25 (Basiliximab) light chain (SEQ ID NO: 76) (FIG. 44B).

FIG. 45 shows exemplary fusion proteins including IL-2, Fc, and a sequence from transforming growth factor-β (TGF-β), including TGF-β1+Fc+IL-2 (SEQ ID NO: 56) and IL-2+Fc+TGF-1 (SEQ ID NO: 57). The linker GGGGSGGGGSGGGGS SEQ ID NO: 104 is optional and can be replaced with EPKSCDK SEQ ID NO: 105 or another linker sequence well known in the art. Certain amino acid sequences can be replaced in Fc, including underlined E with D and underlined M with L.

FIG. 46 shows exemplary fusion proteins including anti-CD4 antibody and a sequence from transforming growth factor-β (TGF-β), including anti-CD4 heavy chain and TGF-β (SEQ ID NO: 58) and anti-CD4 light chain (SEQ ID NO: 77).

FIG. 47 shows exemplary Fusion proteins including the extracellular domain of CTLA-4, Immunoglobulin Fc (IgG Cγ1), and a sequence from transforming growth factor-β (TGF-β) including Oncostatin M signal peptide+CTLA-4 ECD+IgG Cγ1+TGF-β1 (SEQ ID NO: 59), and TGF-β1+IgG Cγ1+CTLA-4 ECD (SEQ ID NO: 60). The IgG sequence shown can have optional C to S conversion in (bold underlined). The linker QEPKSCDK SEQ ID NO: 110 is optional and can be replaced with EPKSCDK SEQ ID NO: 105 or another linker sequence.

FIG. 48 shows exemplary fusion proteins including an antibody that binds TNF-α, and a sequence of RANK ectodomain, including anti-TNFα heavy chain+RANK ectodomain (SEQ ID NO: 61) and anti-TNFα light chain (SEQ ID NO: 78). The sequence KKAE (SEQ ID NO: 107) can be replaced with KRVE (SEQ ID NO: 108) or KKVE (SEQ ID NO: 109).

FIG. 49 shows exemplary fusion proteins including TNFR2 Extracellular ligand binding domain (TNFR2 ECD), immunoglobulin Fc (IgG Cγ1), and a sequence from RANK ectodomain including TNFR2 ECD+IgG Cγ1+RANK ectodomain (SEQ ID NO: 62), and RANK ectodomain+IgG Cγ1+TNFR2 ECD (SEQ ID NO: 63).

FIG. 50 shows exemplary Fusion proteins including the extracellular domain of CTLA-4, Immunoglobulin Fc (IgG Cγ1), and a sequence from RANK ectodomain including Oncostatin M signal peptide+CTLA-4 ECD+IgG Cγ1+RANK ectodomain (SEQ ID NO: 64), and RANK ectodomain+IgG Cγ1+CTLA-4 ECD (SEQ ID NO: 65). The IgG sequence shown can have optional C to S conversion in (bold underlined). The linker QEPKSCDK SEQ ID NO: 110 is optional and can be replaced with EPKSCDK SEQ ID NO: 105 or another linker sequence.

FIG. 51 shows exemplary fusion proteins including a sequence from transforming growth factor-β (TGF-β), immunoglobulin Fc (IgG Cγ1), and a sequence from RANK ectodomain including TGF-β+IgG Cγ1+RANK ectodomain (SEQ ID NO: 66), and RANK ectodomain+IgG Cγ1+TGF-β (SEQ ID NO: 67).

FIG. 52 shows exemplary fusion proteins including a sequence from PD-1 ligand (PD-L1), immunoglobulin Fc (IgG Cγ1), and a sequence from RANK ectodomain including PD-L1+IgG Cγ1+RANK ectodomain (SEQ ID NO: 68), and RANK ectodomain+IgG Cγ1+PD-L1 (SEQ ID NO: 69).

FIGS. 53A-53G show Regulatory T cells (Treg) accumulate in the tumor microenvironment and counteract the ability of chemotherapy to activate CD8+ T cell-mediated antitumor immunity. (FIG. 53A) Surface exposure of calreticulin (CRT) in response to treatment of human (SW780) and murine (MB49) cancer cells with doxorubicin (10 μM) for 4 h. The surface exposure of CRT was determined by immunofluorescence cytometry of untreated control or doxorubicin-treated cells stained with Dylight-labeled anti-CRT antibody or an isotype control (IgG1) antibody. (FIG. 53B) Priming of tumor-reactive immune responses by MB49 tumor cells treated with doxorubicin ex vivo or in vivo. $5 \times 10^6$ MB49 cells that were pre-treated ex vivo with doxorubicin (10 μM) for 4 h were injected into one flank of syngeneic immunocompetent C57BL/6 mice. Alternatively, C57BL/6 mice were injected with $5 \times 10^5$ live MB49 tumor cells and then administered intratumoral doxorubicin (10 μg) at 10 d following tumor inoculation. Tumor-reactive immune responses were determined by measuring production of IFN-γ by draining lymph node (DLN) cells in response to in vitro re-challenge with either MB49 cell lysates, an irrelevant peptide (Hemagglutinin-HA), or medium alone. (FIG. 53C) Vaccination with doxorubicin-treated tumor cells induces CD8$^+$ T cell-mediated antitumor immunity that prevents tumor formation following re-challenge with live tumor cells. MB49 cells ($5 \times 10^6$) that were pre-treated in vitro with doxorubicin (10 μM) for 4 h were injected subcutaneously into one flank of syngeneic immunocompetent C57BL/6 mice. Naïve or vaccinated mice were challenged with untreated live MB49 tumor cells injected into the opposite flank with or without pre-treatment with an anti-CD8 antibody (Clone GK2.43) (5 μg×2 doses, iv) to deplete CD8$^+$ T cells. (FIG. 53D) Delayed administration of chemotherapy in mice with pre-established tumors decreases its immunogenicity and antitumor efficacy. C57BL/6 mice were injected with $5 \times 10^5$ live syngeneic MB49 tumor cells and then administered intratumoral doxorubicin (10 μg) at d3, d7, or d10 following tumor inoculation. (FIG. 53E) Tumors foster the accumulation of CD4$^+$CD25$^+$FoxP3$^+$ cells (Tregs) in their microenvironment. Flow cytometric analyses of the percentage of CD4$^+$CD25$^+$FoxP3$^+$ cells (Tregs) among CD4$^+$ T lymphocytes isolated from the spleen, draining lymph nodes (DLN), and tumors of immunocompetent C57BL/6 mice at d0 and d14 after subcutaneous inoculation of $5 \times 10^5$ live MB49 tumor cells. (FIG. 53F) Tregs infiltrating the tumor microenvironment suppress priming of tumor-reactive immune responses by doxorubicin-treated tumor cells. Naïve C57BL/6 mice were vaccinated with $5 \times 10^6$ doxorubicin-killed MB49 cells with or without intravenous adoptive transfer of $5 \times 10^6$ CD4$^+$CD25$^+$ cells isolated from tumors and DLN of tumor-bearing mice via immunomagnetic separation. Tumor-reactive immune responses were determined by measuring production of IFN-γ by draining lymph node (DLN) cells in response to in vitro re-challenge with either MB49 cell lysates, an irrelevant peptide (Hemagglutinin-HA), or medium alone. (FIG. 53G) Tregs infiltrating the tumor microenvironment suppress the activation of adaptive antitumor immunity in response to chemotherapy-induced tumor cell death. Naïve C57BL/6 mice were vaccinated with $5 \times 10^6$ doxorubicin-killed MB49 cells (left flank) with or without pre-treatment with either an anti-CD8 antibody (Clone GK2.43) (5 μg×2 doses, iv) to deplete CD8$^+$ T cells or adoptive transfer of $5 \times 10^6$ CD4$^+$CD25$^+$ cells isolated from tumors and DLN of tumor-bearing mice. Protective antitumor immunity in vaccinated mice was determined by assessment of tumor growth upon challenge with untreated live MB49 tumor cells injected into the opposite flank.

Figure 54A:
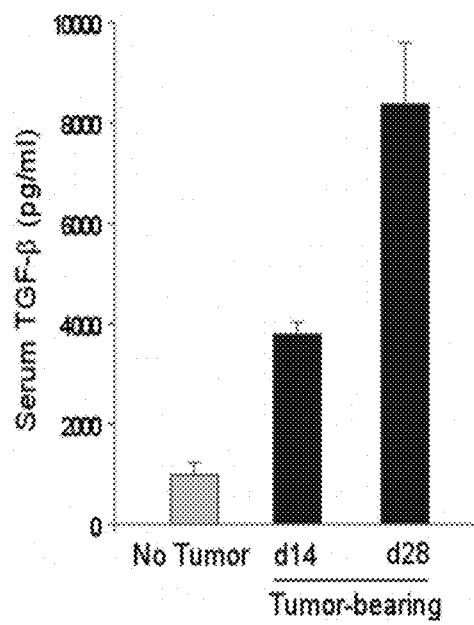
Figure 54B:
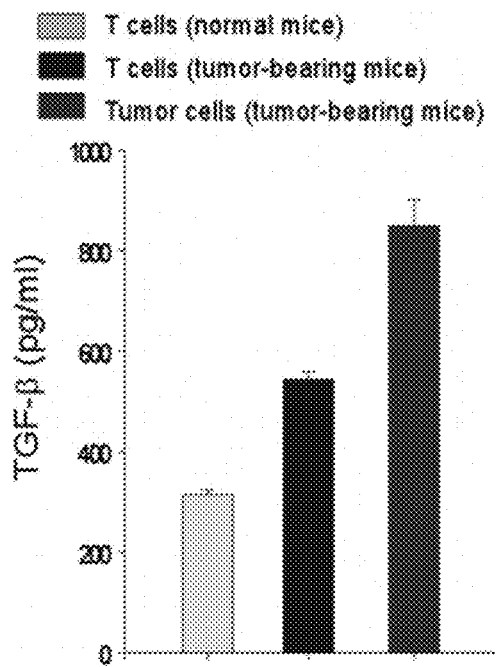
Figure 54C:
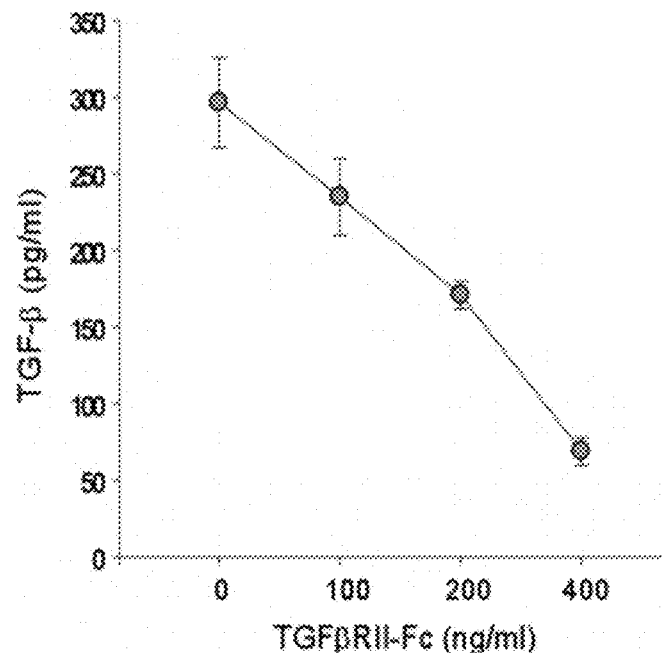
Figure 54D:
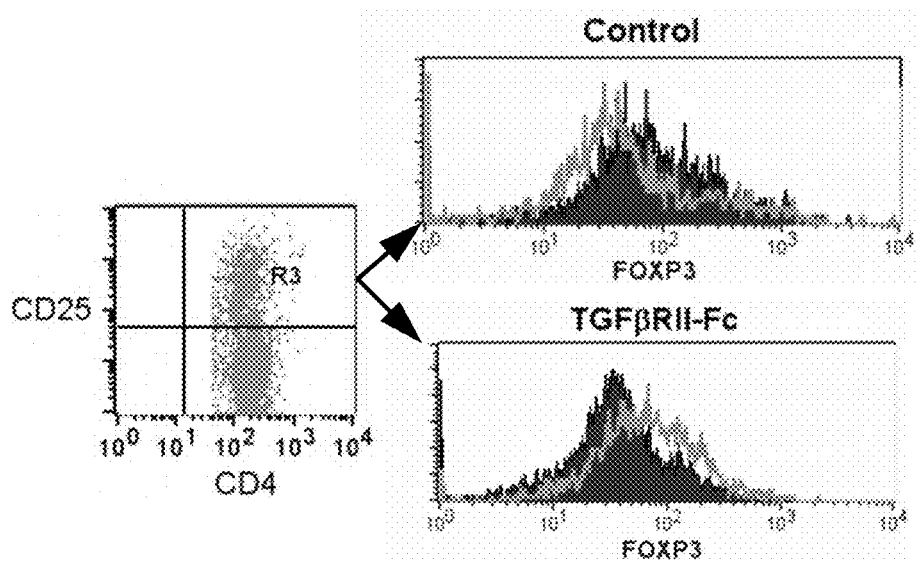
Figure 54E:
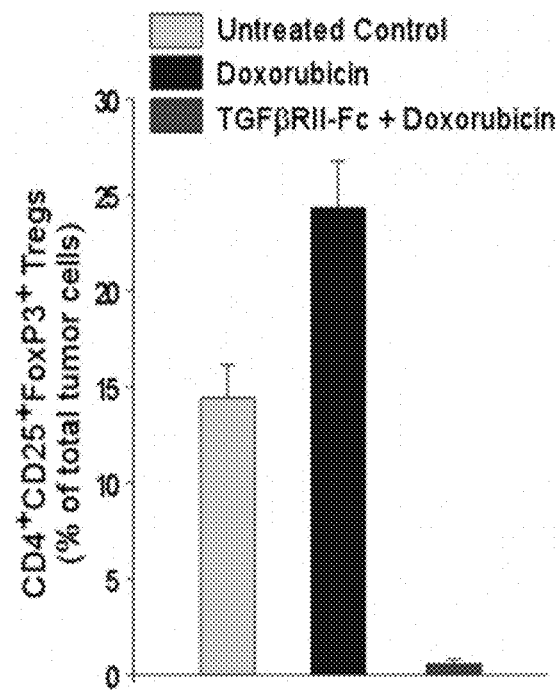
Figure 54F:
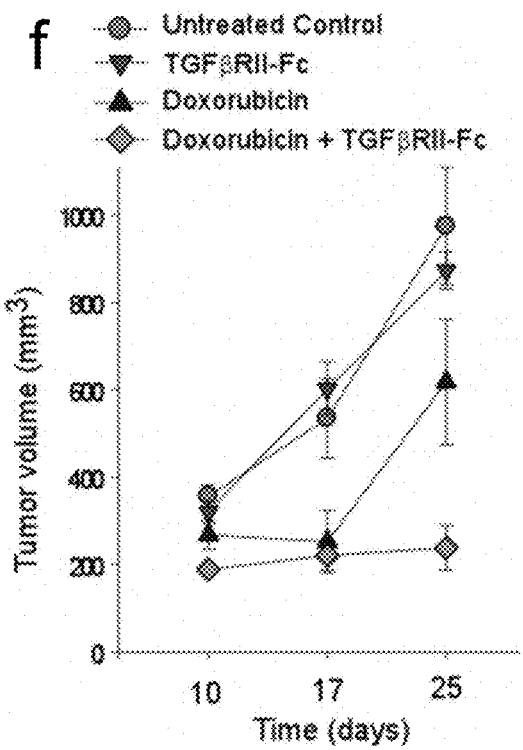

FIGS. 54A-54F show inhibition of TGF-β in the tumor microenvironment reduces 'adaptive' FoxP3$^+$ regulatory T cells and enhances the antitumor efficacy chemotherapy. (FIG. 54A) Tumor growth results in a progressive increase in the level of serum TGF-β. Levels of TGF-β in serum of mice at d0, d14, and d28 following inoculation of $5 \times 10^5$ live MB49 tumor cells were evaluated utilizing ELISA. (FIG. 54B) Tumor cell-autonomous expression of TGF-β is the dominant source of elevated TGF-β in tumor-bearing mice. Tumor cells or draining lymph node cells isolated from either tumor-bearing mice or their tumor-free counterparts were cultured ex vivo in serum-free medium for 24 h and the amount of TGF-β/$10^6$ cells in supernatants was measured by ELISA. (FIG. 54C) TGFβRII:Fc sequesters TGF-β in supernatants of MB49 tumor cells in a concentration-dependent manner. MB49 tumor cells were cultured in the presence of graded concentrations of TGFβRII:Fc (0-400 ng/ml) for 24 h followed by measurement of TGF-β (μg/ml/$10^6$ cells) in supernatants via ELISA. (FIG. 54D) TGF-β induces 'adaptive' FoxP3$^+$ regulatory T cells in the tumor microenvironment. At 5 d following inoculation of MB49 tumor cells, mice were either left untreated (control) or treated with TGFβRII:Fc (1 μg intratumoral; twice weekly) for 3 weeks followed by flow cytometric analyses of intracellular FoxP3 expression in CD4$^+$CD25$^+$ T cells infiltrating the tumors. (FIGS. 54E, 54F). Sequestration of intratumoral TGF-β with TGFβRII:Fc reduces CD4$^+$CD25$^+$FoxP3$^+$ Tregs in tumor tissue and improves the antitumor efficacy of doxorubicin. MB49 tumor-bearing mice were administered doxorubicin (5 mg/kg i.p. weekly×3) with or without twice weekly treatment with TGFβRII:Fc (1 μg intratumoral). The percentage of CD4$^+$CD25$^+$FoxP3$^+$ cells (Tregs) among tumor cells was assessed by flow cytometry (FIG. 54E), and tumor volume was monitored to determine the effect of counteracting tumor-induced TGF-β-mediated immune tolerance on the in vivo antitumor efficacy of doxorubicin (FIG. 54F).

FIGS. 55A-55D show that anti-CD4 antibody-mediated depletion of CD4$^+$ regulatory T cells facilitates chemotherapy-induced activation of tumor-reactive CD8$^+$ T cells and enhances the antitumor efficacy of chemotherapy. (FIG. 55A) In vivo depletion of tumor-infiltrating CD4$^+$CD25$^+$FoxP3$^+$ T cells by treatment of tumor-bearing mice with anti-CD4 antibody. C57BL/6 mice injected with $5 \times 10^5$ MB49 tumor cells s.c. were left untreated (control) or administered an anti-CD4 antibody (Clone GK1.5) i.p. at 5 d and 9 d following tumor challenge. CD4$^+$CD25$^+$FoxP3$^+$ T cells infiltrating tumors isolated from mice at d16 following tumor challenge were detected by flow cytometry. (FIG. 55B) Target-specific depletion of either CD4$^+$ T cells, CD4$^+$CD25$^+$FoxP3$^+$ T cells, or CD8$^+$ T cells by treatment of tumor-bearing mice with anti-CD4 antibody or anti-CD8 antibody. C57BL/6 mice injected s.c. with $5 \times 10^5$ MB49 tumor cells were left untreated or treated with doxorubicin (5 mg/kg i.p. weekly×3) beginning at d7 following tumor inoculation, with or without administration of either anti-CD4 antibody (Clone GK1.5) or anti-CD8 antibody (Clone GK2.43) at d5 and d9 following tumor inoculation. Flow cytometric analyses of peripheral blood mononuclear cells isolated from mice at d16 following tumor challenge determined the percentage of CD4$^+$ T cells or CD8$^+$ T cells among total mononuclear cells, and the percentage of CD4$^+$CD25$^+$FoxP3$^+$ T cells among total CD4$^+$ T cells. (FIG. 55C) Depletion of CD4$^+$ regulatory T cells facilitates chemotherapy-induced activation of tumor-reactive CD8$^+$ T cells. C57BL/6 mice injected s.c. with $5 \times 10^5$ MB49 tumor cells were left untreated or treated with doxorubicin (5 mg/kg i.p. weekly×3) beginning at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8$^+$ T cells from the tumor and draining lymph node in response to in vitro stimulation with MB49 cell lysates. (FIG. 55D) Depletion of CD4$^+$ regulatory T cells augments the in vivo antitumor efficacy of chemotherapy via activation of tumor-reactive CD8$^+$ T cells. C57BL/6 mice injected s.c. with 5×10$^5$ MB49 tumor cells were left untreated or treated with doxorubicin (5 mg/kg i.p. weekly×3) beginning at d7 following tumor inoculation, with or without administration of either anti-CD4 antibody (Clone GK1.5) or anti-CD8 antibody (Clone GK2.43) at d5 and d9 following tumor inoculation. Tumor volume was monitored to determine the effect of depleting either CD4$^+$ T cells or CD8$^+$ T cells on the in vivo antitumor efficacy of doxorubicin.

Figure 56A:
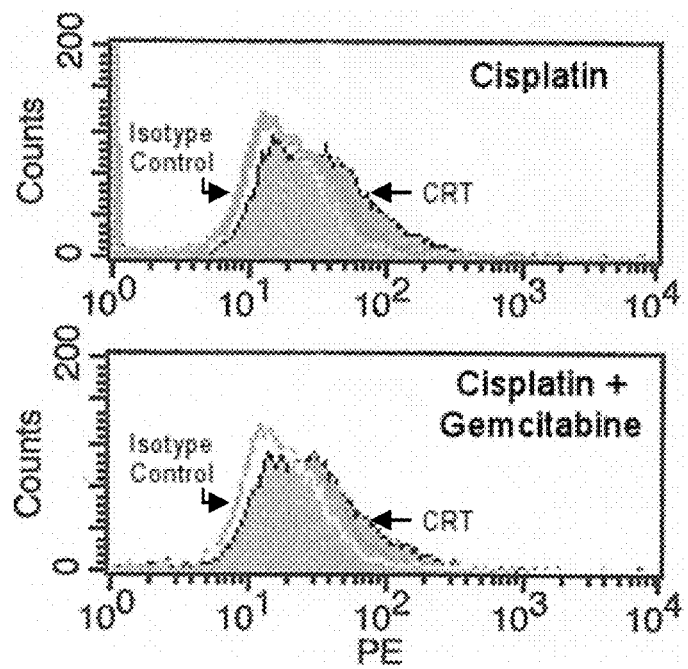
Figure 56B:
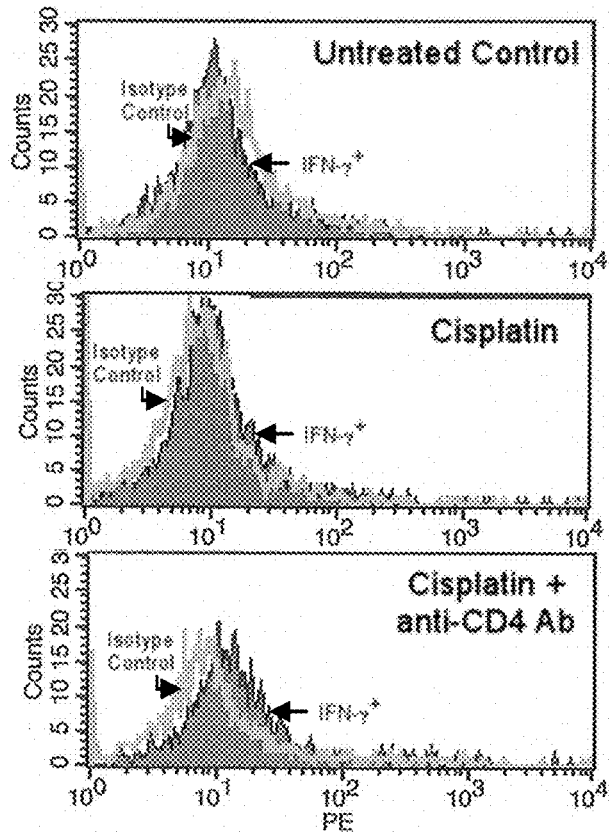
Figure 56C:
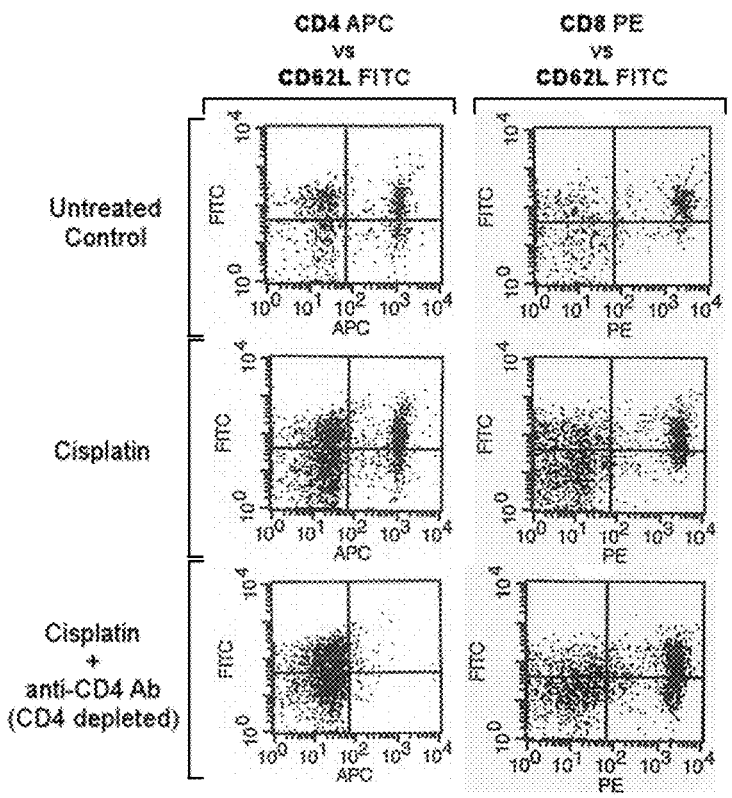

FIGS. 56A-56F show anti-CD4 antibody-mediated depletion of CD4$^+$ regulatory T cells augments and sustains the antitumor effect of chemotherapy by enabling activation of adaptive antitumor immunity. (FIG. 56A) Surface exposure of calreticulin (CRT) in response to treatment of MB49 cancer cells with either cisplatin or the combination of cisplatin and gemcitabine for 4 h. The surface exposure of CRT was determined by immunofluorescence cytometry of untreated control or chemotherapy-treated cells stained with Dylight-labeled anti-CRT antibody or an isotype control (IgG1) antibody. (FIGS. 56B, 56C) Depletion of CD4$^+$ regulatory T cells enables cisplatin-induced activation of tumor-reactive IFN-γ$^+$CD8$^+$ T cells and effector memory (CD8$^+$CD62L$^-$) T cells. C57BL/6 mice injected s.c. with 5×10$^5$ MB49 tumor cells were left untreated or treated with cisplatin (0.5 mg/kg i.p. weekly×4) beginning at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8$^+$ T cells from the tumor and draining lymph node (DLN) in response to in vitro stimulation with MB49 cell lysates (FIG. 56B). The percentage of effector memory T$_{EM}$ cells was determined by flow cytometric analyses of CD8$^+$CD62L$^-$ cells (FIG. 56C). (FIGS. 56D, 56E and 56F) Depletion of CD4$^+$ regulatory T cells augments the in vivo antitumor efficacy of chemotherapy via activation of tumor-reactive CD8$^+$ T cells. C57BL/6 mice injected s.c. with 5×10$^5$ MB49 tumor cells were left untreated or treated with either cisplatin (0.5 mg/kg) or the combination of cisplatin and gemcitabine (i.p. weekly×4) beginning at d7 following tumor inoculation, with or without administration of either anti-CD4 antibody (Clone GK1.5) or anti-CD8 antibody (Clone GK2.43) at d5 and d9 following tumor inoculation. Tumor volume was monitored to determine the effect of depleting either CD4$^+$ T cells or CD8$^+$ T cells on the in vivo antitumor efficacy of chemotherapy and the percentage of mice exhibiting complete tumor-regression by d50 following tumor inoculation. Establishment of adaptive antitumor immunity following regression of primary tumors was determined by re-challenging mice with live MB49 tumor cells in the opposite flank.

FIGS. 57A-57H show that Chemotherapy-induced expression of NKG2D ligands on tumor cells cooperates with depletion of CD4$^+$ regulatory T cells to stimulate CD8$^+$ T cell-mediated tumor regression. (FIG. 57A) Genotoxic chemotherapeutic agents induce expression of mouse NKG2D ligands (Rae-1) on cancer cells. Kinetics of the upregulation of Rae1 transcripts in mouse CT26 colon cancer cells was determined by quantitative real-time PCR following treatment with irinotecan (25 µg/ml) or oxaliplatin (10 µg/ml). Quantitative RT-PCR was carried out using Rae-1 specific primers [sense, 5'-CTAGTGCCACCTGG-GAATTCA-3' (SEQ ID NO: 111); anti-sense, 5'-CATCATT-AGCTGATCTCCAGCTCA-3' (SEQ ID NO: 112)] and probe [5'-6-FAM-CATCAGTGACAGTTACTTCTT-CACCTTCTACACAGAGA-Tamra-3' (SEQ ID NO: 113)]. (FIG. 57B) Genotoxic chemotherapeutic agents induce p53-independent cell surface expression of human NKG2D ligands (MHC-I-related A and B molecules-MICA/MICB) on cancer cells. Isogenic p53-proficient (p53$^{+/+}$) or p53-deficient (p53$^{-/-}$) HCT116 cells were treated with irinotecan (25 µg/ml) for 16 h or left untreated. Irinotecan-induced upregulation of cell surface expression of MICA/B was determined by flow cytometryic analysis of tumor cells labeled with an anti-human MICA/B MAb (R&D Systems). (FIG. 57C) and (FIG. 57D) Induction of NKG2D ligands contributes to the antitumor effect of chemotherapy in vivo. Immunocompetent Balb/C mice injected s.c. with 2×10$^5$ syngeneic CT26 tumor cells were treated with irinotecan (50 mg/kg i.p weekly×3) beginning at d5 following tumor inoculation, with or without pre-treatment with an NKG2D blocking antibody (CX5, eBIOscience) (200 µg i.p.) at 16 h before each dose of chemotherapy. Tumor volume was monitored to determine the effect of NKG2D blockade on the in vivo antitumor efficacy of irinotecan. (FIG. 57E) In vivo depletion of CD4$^+$CD25$^+$FoxP3$^+$ T cells by treatment of tumor-bearing mice with anti-CD4 antibody. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) at d5 and d9 following tumor inoculation. CD4$^+$CD25$^+$FoxP3$^+$ T cells in spleen and draining lymph node isolated from mice at d16 following tumor challenge were detected by flow cytometry. (FIG. 57F) Depletion of CD4$^+$ regulatory T cells facilitates irinotecan-induced activation of tumor-reactive IFN-γ$^+$CD8$^+$ T cells. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) at d5 and d9 following tumor inoculation. Tumor-reactive immune responses were determined by flow cytometric analyses of IFN-γ expression in CD8$^+$ T cells from the tumor and draining lymph node (DLN) in response to in vitro stimulation with either CT26 cell lysates, an irrelevant peptide (Hemagglutinin-HA), or medium alone. (FIG. 57G) and (FIG. 57H) Chemotherapy-induced expression of NKG2D ligands on tumor cells cooperates with depletion of CD4$^+$ regulatory T cells to stimulate CD8$^+$ T cell-mediated tumor regression. Balb/C mice injected with 2×10$^5$ CT26 tumor cells s.c. were left untreated or treated with irinotecan (50 mg/kg i.p weekly×3) beginning at d7 following tumor inoculation, with or without administration of anti-CD4 antibody (Clone GK1.5) and/or anti-CD8 antibody (Clone GK2.43) at d5 and d9 following tumor inoculation. Tumor volume was monitored to determine the effect of depleting CD4$^+$ T cells and/or CD8$^+$ T cells on the in vivo antitumor efficacy of irinotecan.

DETAILED DESCRIPTION OF THE INVENTION

Targeted immunostimulatory antibodies and/or fusion proteins for prevention or treatment of cancer: Chemotherapy is a cornerstone of systemic treatment of patients with most common types of advanced cancers. The vast majority of human cancers harbor genetic alterations and signaling mechanisms that impair the direct death signaling pathways entrained by chemotherapeutic agents. Although chemotherapeutic agents employ diverse mechanisms to directly kill tumor cells, the present invention provides that these agents have immuno-adjuvant effects which activate innate and adaptive antitumor immune responses that are crucial for their antitumor efficacy in vivo. The present invention also provides that antitumor CD8+ T cells play an instrumental role in the in vivo response of tumors to diverse cytotoxic chemotherapeutic agents. Although chemotherapeutic agents can induce "immunogenic" tumor cell death and facilitate cross-presentation of antigens by dendritic cells, tumors create a tolerogenic environment that allows them to suppress the activation of innate and adaptive immune responses and evade immunologic attack by immune effector cells. The present invention provides that strategies to counteract tumor-induced immune tolerance in the tumor microenvironment can enhance the antitumor efficacy of chemotherapy by activating and leveraging T cell-mediated adaptive antitumor immunity against disseminated cancer cells.

The present invention is based on the seminal discovery that targeted immunomodulatory antibodies and fusion proteins can counteract or reverse immune tolerance of cancer cells. Cancer cells are able to escape elimination by chemotherapeutic agents or tumor-targeted antibodies via specific immunosuppressive mechanisms in the tumor microenvironment and such ability of cancer cells is recognized as immune tolerance. By counteracting tumor-induced immune tolerance, the present invention provides effective compositions and methods for cancer treatment, optional in combination with another existing cancer treatment.

The present invention provides compositions and methods for targeted immunostimulatory antibodies and fusion proteins that counteract immune tolerance in the tumor microenvironment and promote T cell-mediated adaptive antitumor immunity for maintenance of durable long-term protection against recurrent or disseminated cancers. These tumor-targeted immunostimulatory molecules are designed to facilitate effective long term T cell-mediated immune responses against tumor cells by at least one of the following:

(i) promoting death of tumor cells via enhancement of antibody-dependent cellular cytotoxicity (ADCC);
(ii) facilitating effective cross-presentation of tumor antigen(s) from dying tumor cells by augmenting maturation of dendritic cells (DCs); and
(iii) increasing activation and proliferation of antitumor CD8+ T cells by negating immune suppression mediated by regulatory T cells and myeloid suppressor cells. These antitumor immune responses may be activated in tandem with the sensitization of tumor cells to immune effector-mediated cytotoxicity, thereby establishing a positive feedback loop that augments tumor cytoreduction and reinforces adaptive antitumor immunity. The tumor-targeted immunostimulatory monoclonal antibodies (mAbs) of the present invention provides the ability to generate and boost antitumor immunity to multiple cross-presented tumor antigens obtained from endogenous tumor cells during the course of therapy (as an in situ tumor vaccine), while simultaneously leveraging the antitumor immune response to eliminate disseminated cancer cells. Accordingly, the targeted immunostimulatory antibodies and fusion proteins of the invention can integrate the hitherto distinct fields of passive and active immunotherapy and provide a novel platform for simultaneously leveraging the synergistic benefits of these strategies to entrain effective innate and adaptive immune responses against targeted cancers.

While passive immunotherapy of cancer with tumor-targeted monoclonal antibodies has demonstrated clinical efficacy, the goal of active therapeutic vaccination to induce T cell-mediated immunity and establish immunological memory against tumor cells has remained challenging. Several tumor-specific and tumor-associated antigens have been identified, yet tumors employ diverse mechanisms to create a tolerogenic environment that allows them to suppress the activation of a T cell-mediated antitumor immune response. The tumor-targeted immunostimulatory antibodies and/or fusion proteins of the invention are designed to overcome such immune tolerance in the tumor microenvironment and activate robust levels of T cell responses for effective cancer immunotherapy or chemo-immunotherapy. Accordingly, the tumor-targeted immunostimulatory antibodies and/or fusion proteins of the invention have broad clinical relevance for advancing the treatment of many types of human cancers.

The tumor-targeted immunostimulatory mAbs and/or fusion proteins of the invention provide their ability to generate and boost antitumor immunity to multiple cross-presented tumor antigens obtained from endogenous tumor cells during the course of therapy (as an in situ tumor vaccine), while simultaneously leveraging the antitumor immune response to eliminate disseminated cancer cells. Accordingly, the tumor-targeted immunostimulatory antibodies and/or fusion proteins of the invention can integrate the hitherto distinct fields of passive and active immunotherapy and provide a novel platform for simultaneously leveraging the synergistic benefits of these strategies to entrain effective innate and adaptive immune responses against targeted cancers. This approach of the present invention is distinguished from and superior to conventional tumor antigen-, allogeneic tumor cell- or DC-based vaccines in at least one of the following aspects: (i) There is no a priori requirement to define, clone and purify individual tumor antigens, since the patient's tumor itself is the in vivo source of antigens; (ii) Multivalent antitumor immune responses that are naturally tailored against antigens from the patient's own tumor are less likely to allow immune escape than a pre-selected tumor antigen; (iii) The activation of antitumor immune responses by the immuno-adjuvant effects of tumor-targeted immunostimulatory antibodies or fusion proteins occurs in tandem with the sensitization of tumor cells to immune effector-mediated cytotoxicity, thereby establishing a positive feedback loop that augments tumor cytoreduction and reinforces adaptive antitumor immunity; and (iv) The molecules of the invention have broad clinical relevance for advancing the treatment of many types of human cancers.

In addition, the targeted immunostimulatory antibodies and/or fusion proteins of the invention are distinguished from and superior to existing therapeutic molecules in at least one of the following aspects: (i) to counteract immune tolerance in the tumor microenvironment and promote T cell-mediated adaptive antitumor immunity for maintenance of long-term protection against recurrent or disseminated cancers (for prevention or treatment of diverse cancers); (ii) to produce immune cell compositions for adoptive cellular therapy of diverse cancers; and (iii) to serve as immune adjuvants or vaccines for prophylaxis of diverse cancers or infectious diseases.

The targeted immunostimulatory antibodies and/or fusion proteins of the invention provide the ability to disrupt immunosuppressive networks in the tumor microenvironment. Tumors employ a wide array of regulatory mechanisms to avoid or suppress the immune response. Cancer cells actively promote immune tolerance in the tumor microenvironment via the expression of cytokines and molecules that inhibit the differentiation and maturation of antigen-presenting dendritic cells. The immunosuppressive cytokines and ligands produced by tumor cells include the following: (i) Transforming growth factor-beta (TGF-β); (ii) Programmed death-1 ligand 1 (PD-L1; B7-H1); (iii) Vascular endothelial growth factor (VEGF); and (iv) Interleukin-10 (IL-10). In addition to blocking dendritic cell (DC) maturation, these molecules promote the development of specialized subsets of immunosuppressive CD4+ T cells (regulatory T cells; Treg cells) and myeloid-derived suppressor cells (MDSC). Tregs are a minority sub-population of CD4+ T cells that constitutively express CD25 [the interleukin-2 (IL-2) receptor α-chain] and the forkhead box P3 (FOXP3) transcription factor. Tregs (CD4+CD25+FoxP3+ cells) maintain immune tolerance by restraining the activation, proliferation, and effector functions of a wide range of immune cells, including CD4+ and CD8+ T cells, natural killer (NK) and NKT cells, B cells and antigen presenting cells (APCs) in vitro and in vivo. The accumulation of Treg cells in the tumor microenvironment reinforces tumor immune tolerance and facilitates tumor progression and metastases. The increased expression of immunosuppressive cytokines (TGF-β; PD-L1) and tumor-infiltrating Tregs is correlated with a reduction of survival of patients with diverse types of cancers. The present invention provides that tumor-induced immune tolerance mediated via Tregs is a crucial determinant of the resistance of cancers to cytotoxic chemotherapeutic agents and tumor-targeted antibodies. The targeted immunostimulatory antibodies and/or fusion proteins of the invention inhibit key immunosuppressive molecules expressed by the targeted tumor cell or tumor-infiltrating Treg cells and myeloid suppressor cells (DCs or MDSC). As such, they provide the targeted ability to inhibit the development or function of Tregs within the tumor microenvironment. In another aspect, they provide the ability to counteract Treg-induced immune suppression in the tumor microenvironment.

The targeted immunostimulatory antibodies and/or fusion proteins of the invention provide the ability to inhibit the development or function of Tregs and myeloid suppressor cells (DCs or MDSC) within the tumor microenvironment. Tregs (CD4+CD25+FoxP3+ cells) express an array of immunosuppressive cytokines and molecules which act in concert to induce immune tolerance and promote tumor progression and metastases. These include: (i) Cytotoxic T-lymphocyte associated protein 4 (CTLA-4; CD152), a co-inhibitory receptor that binds to the ligands CD80 (B7-1) or CD86 (B7-2) on the antigen presenting cell (APC) and inhibits co-stimulation of T cells; (ii) Programmed death-1 ligand 1 (PD-L1; B7-H1), a ligand which engages the co-inhibitory receptor Programmed death-1 (PD-1) and inhibits T cell activation and proliferation. (iii) Transforming growth factor-beta (TGF-β), a cytokine which regulates immune responses by restricting the maturation and antigen-presenting function of dendritic cells, inhibiting the proliferation and activation of naïve T cells, suppressing the expression of cytotoxic molecules (Granzyme A/B, FasL, Apo2L/TRAIL, IFN-γ) in immune effector cells, and promoting the development and function of Tregs; (iv) Receptor activator of nuclear factor-κB ligand (RANKL), a ligand which engages Receptor activator of nuclear factor-κB (RANK) and promotes osteoclast differentiation, Treg development, and tumor metastases. In addition, Tregs express other surface molecules; (v) LAG-3, a CD4-related molecule that binds MHC class II; (vi) glucocorticoid-induced tumor necrosis factor receptor family-related gene (GITR; TNFRSF18); and (vii) IL-10. The targeted immunostimulatory antibodies and/or fusion proteins of the invention provide the ability to bind a targeted molecule expressed by Tregs or myeloid suppressor cells while concurrently sequestering and inhibiting one or more immunosuppressive molecule that promotes their development, survival or function. In one aspect, the targeted immunostimulatory antibodies and/or fusion proteins directly deplete the number of Tregs.

In one embodiment, the present invention provides a molecule including a targeting moiety fused with an immunomodulatory moiety. The targeting moiety specifically binds a target molecule on the tumor cell or tumor microenvironment (tumor stroma, tumor vasculature, or tumor infiltrating immune cell), and the immunomodulatory moiety specifically binds an immunosuppressive molecule expressed by the targeted tumor cell or tumor-infiltrating Treg cells and myeloid suppressor cells (DC or MDSC).

In one embodiment, the present invention provides a molecule including a targeting moiety fused with an immunomodulatory moiety. The targeting moiety specifically binds a target molecule expressed by Treg cells, myeloid suppressor cells (MDSC), or dendritic cells (DC), and the immunomodulatory moiety specifically binds an immunosuppressive molecule that promotes their development, survival or function.

In one embodiment, the present invention provides a molecule including a targeting moiety fused with an immunomodulatory moiety. The targeting moiety specifically binds a target molecule, and the immunomodulatory moiety specifically binds one of the following molecules: (i) Transforming growth factor-beta (TGF-β); (ii) Programmed death-1 ligand 1 (PD-L1) or Programmed death-1 ligand 2 (PD-L2); (iii) Receptor activator of nuclear factor-κB (RANK) ligand (RANKL); (iv) Vascular endothelial growth factor (VEGF); (v) Transforming growth factor-beta receptor (TGF-βR); (vi) Programmed death-1 (PD-1); and (vii) Receptor activator of nuclear factor-κB (RANK).

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-B1), HER2/neu (Erb-B2), CD20, Vascular endothelial growth factor (VEGF), insulin-like growth factor receptor (IGF-1R), TRAIL-receptor, epithelial cell adhesion molecule, carcino-embryonic antigen, Prostate-specific membrane antigen, Mucin-1, CD30, CD33, or CD40.

In one aspect, the targeting moiety specifically binds a component of a regulatory T cell, myeloid suppressor cell, or dendritic cell. In another aspect, the targeting moiety specifically binds one of the following molecules: (i) CD4; (ii) CD25 (IL-2α receptor; IL-2αR); (iii) cytotoxic T-lymphocyte antigen-4 (CTLA-4; CD152); (iv) Interleukin-10 (IL-10); (v) Transforming growth factor-beta receptor (TGF-βR); (vi) Transforming growth factor-beta (TGF-β); (vii) Programmed Death-1 (PD-1); (viii) Programmed death-1 ligand (PD-L1 or PD-L2); (ix) Receptor activator of nuclear factor-κB (RANK); (x) Receptor activator of nuclear factor-κB (RANK) ligand (RANKL); (xi) LAG-3; or (xii) glucocorticoid-induced tumor necrosis factor receptor family-related gene (GITR: TNFRSF18).

In one aspect, the immunomodulatory moiety specifically binds one of the following molecules: (i) Transforming growth factor-beta (TGF-β); (ii) Programmed death-1 ligand (PD-L1 or PD-L2); (iii) Receptor activator of nuclear factor-κB (RANK) ligand (RANKL); or (iv) vascular endothelial growth factor (VEGF).

In one aspect, the immunomodulatory moiety includes a molecule that binds TGF-β. In another aspect, the immunomodulatory moiety includes an extracellular ligand-binding domain of Transforming growth factor-beta receptor TGF-βRII, TGF-βRIIb, or TGF-βRIII. In another aspect, the immunomodulatory moiety includes an extracellular ligand-binding domain of TGF-βRII. In another aspect, the molecule includes a TGF-β-binding amino acid sequence corresponding to SEQ ID NOs: 79-91. In an additional aspect, the immunomodulatory moiety inhibits the activity or function of TGF-β.

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain of TGF-βRII. In another aspect, the molecule includes an amino acid sequence corresponding to SEQ ID NO: 1, 2, 3, 4, 5, 6, 7, 8, 9 or 10.

In one aspect, the targeting moiety includes an antibody, antibody fragment, or polypeptide that specifically binds to Programmed Death-1 (PD-1), Programmed death-1 ligand 1 (PD-L1), or Programmed death-1 ligand 2 (PD-L2). In another aspect, the targeting moiety includes an extracellular ligand-binding domain or ectodomain of Programmed Death-1 (PD-1). In an additional aspect, the immunomodulatory moiety includes an extracellular ligand-binding domain of TGF-βRII. In another aspect, the molecule includes PD-1 ectodomain, immunoglobulin Fc region, and TGFβRII ectodomain. In another aspect, the molecule includes an amino acid sequence corresponding to SEQ ID NO: 11 or 12.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of TGF-βRII. In another aspect, the molecule includes RANK ectodomain, immunoglobulin Fc region, and TGFβRII ectodomain. In another aspect, the molecule includes an amino acid sequence corresponding to SEQ ID NO: 13 or 14.

In one aspect, the immunomodulatory moiety includes a molecule that specifically binds to Programmed death-1 ligand 1 (PD-L1) or Programmed death-1 ligand 2 (PD-L2). In another aspect, the immunomodulatory moiety includes an extracellular ligand-binding domain or ectodomain of Programmed Death-1 (PD-1). In another aspect, the molecule includes a PD-L1-binding amino acid sequence corresponding to SEQ ID NO: 92, 93, or 94. In an additional aspect, the immunomodulatory moiety inhibits the activity or function of Programmed death-1 ligand 1 (PD-L1).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Programmed Death-1 (PD-1). In another aspect, the molecule includes an amino acid sequence corresponding to SEQ ID NO: 15, 16, 17, 18, 19, 20, 21, 22, 23, or 24.

In one aspect, the targeting moiety includes an antibody, antibody fragment, or polypeptide that specifically binds to Receptor activator of nuclear factor-κB (RANK) or Receptor activator of nuclear factor-κB ligand (RANKL). In another aspect, the targeting moiety includes an extracellular ligand-binding domain or ectodomain of Receptor activator of nuclear factor-κB (RANK). In an additional aspect, the immunomodulatory moiety includes an extracellular ligand-binding domain of Programmed Death-1 (PD-1). In another aspect, the molecule includes RANK ectodomain, immunoglobulin Fc region, and PD-1 ectodomain. In another aspect, the molecule includes an amino acid sequence corresponding to SEQ ID NO: 25 or 26.

In one aspect, the immunomodulatory moiety includes a molecule that specifically binds to Receptor activator of nuclear factor-κB ligand (RANKL). In another aspect, the immunomodulatory moiety includes an extracellular ligand-binding domain or ectodomain of Receptor activator of nuclear factor-κB (RANK). In another aspect, the molecule includes a RANKL-binding amino acid sequence corresponding to SEQ ID NO: 95, 96, 97, or 98. In an additional aspect, the immunomodulatory moiety inhibits the activity or function of Receptor activator of nuclear factor-κB ligand (RANKL).

In one aspect, the targeting moiety includes an antibody, antibody fragment, or polypeptide that specifically binds to HER2/neu, EGFR1, CD20, vascular endothelial growth factor (VEGF), cytotoxic T-lymphocyte antigen-4 (CTLA-4), CD25 (IL-2α receptor; IL-2αR), or CD4. In an additional aspect, the immunomodulatory moiety includes an extracellular ligand-binding domain or ectodomain of Receptor activator of nuclear factor-κB (RANK). In another aspect, the molecule includes an amino acid sequence corresponding to SEQ ID NO: 27, 28, 29, 30, 31, 32, 33, 34, 35, or 36.

The present invention provides novel targeted immunosuppressive antibodies and fusion proteins that induce or promote immune tolerance by at least one of the following:
  (i) inhibiting the activation of dendritic cells, T cells, and/or B cells; and
  (ii) promoting the development and/or suppressor function of regulatory T cells and immunosuppressive myeloid DCs. These targeted immunosuppressive molecules of the invention are designed to suppress unwanted or excessive immune or inflammatory responses in order to treat autoimmune or inflammatory diseases or prevent the rejection of a transplanted cell, tissue, or organ.

Targeted immunosuppressive antibodies and/or fusion proteins: The aberrant activation of self-reactive T cells and/or breakdown of the mechanisms of immune tolerance promotes the development of autoimmunity that results in various diseases including type I diabetes mellitus, multiple sclerosis, systemic lupus erythematosus, inflammatory bowel disease, and rheumatoid arthritis. The targeted immunosuppressive antibodies and/or fusion proteins of the invention are designed to suppress unwanted or excessive immune or inflammatory responses and restore or promote immune tolerance. Accordingly, the compositions and methods of the invention have broad clinical relevance for the treatment of diverse autoimmune or inflammatory diseases and preventing the rejection of a transplanted cell, tissue, or organ grafts.

The targeted immunosuppressive antibodies and/or fusion proteins of the invention provides their ability to inhibit the activity of targeted pro-inflammatory cytokines or immune cells while simultaneously promoting immune tolerance via the targeted delivery of immunosuppressive molecules that facilitate the development and/or function of regulatory T cells. These molecules of the present invention are distinguished from and superior to existing therapeutic molecules in at least one of the following aspects: (i) The molecules of the invention enable targeted delivery of immunosuppressive molecules to immune cells or pro-inflammatory molecules in the milieu of the affected cell, tissue or organ; (ii) The molecules of the invention can couple the inhibition of the targeted pro-inflammatory molecule or immune cell with the simultaneous delivery of an immunosuppressive molecule that promotes immune tolerance, thereby improving the suppression of immune effector cells; and (iii) The molecules of the invention can provide a mechanism of simultaneously engaging two independent or synergistic mechanisms of immune tolerance or immune suppression.

Further, the targeted immunosuppressive antibodies and/or fusion proteins of the invention are distinguished from and superior to existing therapeutic molecules in at least one of the following aspects: (i) To suppress unwanted or excessive immune or inflammatory responses in order to treat autoimmune or inflammatory diseases; and (ii) To prevent the rejection of a transplanted cell, tissue, or organ grafts.

In one aspect, the immunomodulatory moiety includes a sequence from Programmed death-1 ligand 1 (PD-L1) or Programmed death-1 ligand 2 (PD-L2). In another aspect, the molecule includes a PD-1-binding amino acid sequence corresponding to SEQ ID NO: 99, 100, or 101. In an additional aspect, the immunomodulatory moiety increases the function of PD-1.

In one aspect, the targeting moiety specifically binds to Tumor Necrosis Factor-α (TNF-α), and the immunomodulatory moiety includes a sequence from Programmed death-1 ligand 1 (PD-L1) or Programmed death-1 ligand 2 (PD-L2). In an additional aspect, the targeting moiety includes an antibody that binds TNF-α, and the immunomodulatory moiety includes a sequence from PD-1 ligand 1 (PD-L1 or B7-H1). In another aspect, the molecule includes an amino acid sequence corresponding to SEQ ID NO: 37. In another aspect, the targeting moiety includes an extracellular ligand-binding domain of tumor necrosis factor receptor 2 (TNFR2), and the immunomodulatory moiety includes a sequence from PD-1 ligand 1 (PD-L1 or B7-H1). In another aspect, the molecule includes TNFR2 Extracellular ligand binding domain, immunoglobulin Fc region, and a sequence from PD-L1. In another aspect, the molecule includes an amino acid sequence corresponding to SEQ ID NO: 38 or 39.

In one aspect, the targeting moiety includes an antibody or antibody fragment that specifically binds to CD20, CD25, or CD4, and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 40, 41, 42, 43, 44, or 45.

In one aspect, the targeting moiety includes the extracellular domain of CTLA-4 and immunoglobulin Fc region (IgG Cγ1), and the immunomodulatory moiety includes a sequence from Programmed death-1 ligand 1 (PD-L1) or Programmed death-1 ligand 2 (PD-L2). In another aspect, the molecule includes an amino acid sequence corresponding to SEQ ID NO: 46 or 47.

In one aspect, the targeting moiety includes transforming growth factor-β (TGF-β) and immunoglobulin Fc region (IgG Cγ1), and the immunomodulatory moiety includes a sequence from Programmed death-1 ligand 1 (PD-L1) or Programmed death-1 ligand 2 (PD-L2). In an additional aspect, the molecule includes an amino acid sequence corresponding to SEQ ID NO: 48 or 49.

In one aspect, the immunomodulatory moiety includes a sequence from transforming growth factor-β (TGF-β). In another aspect, the molecule includes an amino acid sequence corresponding to SEQ ID NO: 99, 100, or 101. In an additional aspect, the immunomodulatory moiety activates the signaling function of transforming growth factor-β (TGF-β) receptor.

In one aspect, the targeting moiety includes an antibody, antibody fragment, or polypeptide that specifically binds to Tumor Necrosis Factor-α (TNF-α), and the immunomodulatory moiety includes a sequence from transforming growth factor-β (TGF-β). In an additional aspect, the targeting moiety includes an antibody that binds TNF-α, and the immunomodulatory moiety includes a sequence from TGF-β. In another aspect, the molecule includes an amino acid sequence corresponding to SEQ ID NO: 50. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from transforming growth factor-β (TGF-β). In another aspect, the molecule includes an amino acid sequence corresponding to SEQ ID NO: 51 or 52.

In one aspect, the targeting moiety includes an antibody or antibody fragment that specifically binds to CD20, CD25 (IL-2α receptor; IL-2αR), or CD4, and the immunomodulatory moiety includes a sequence from transforming growth factor-β (TGF-β). In an additional aspect, the molecule includes an amino acid sequence corresponding to SEQ ID NO: 53, 54, 55, 56, 57 or 58.

In one aspect, the targeting moiety includes an extracellular domain of CTLA-4 and immunoglobulin Fc region (IgG Cγ1), and the immunomodulatory moiety includes a sequence from transforming growth factor-β (TGF-β). In another aspect, the molecule includes an amino acid sequence corresponding to SEQ ID NO: 59 or 60.

In one aspect, the targeting moiety includes an antibody, antibody fragment, or polypeptide that specifically binds to Tumor Necrosis Factor-α (TNF-α), and the immunomodulatory moiety includes an extracellular RANKL-binding domain or ectodomain of Receptor activator of nuclear factor-κB (RANK) or Osteoprotegerin (OPG). In an additional aspect, the targeting moiety includes an antibody that binds TNF-α, and the immunomodulatory moiety includes a sequence from an extracellular RANKL-binding domain or ectodomain of RANK. In another aspect, the molecule includes an amino acid sequence corresponding to SEQ ID NO: 61. In one aspect, the targeting moiety includes an extracellular ligand-binding domain of tumor necrosis factor receptor 2 (TNFR2). In another aspect, the molecule includes TNFR2 Extracellular ligand binding domain, immunoglobulin Fc region, and a sequence from an extracellular RANK-binding domain or ectodomain of RANK. In another aspect, the molecule includes an amino acid sequence corresponding to SEQ ID NO: 62 or 63.

In one aspect, the targeting moiety includes an extracellular domain of CTLA-4 and immunoglobulin Fc region (IgG Cγ1), and the immunomodulatory moiety includes an extracellular RANKL-binding domain or ectodomain of Receptor activator of nuclear factor-κB (RANK) or Osteoprotegerin (OPG). In another aspect, the molecule includes an amino acid sequence corresponding to SEQ ID NO: 64 or 65.

In one aspect, the targeting moiety includes a sequence from transforming growth factor-β (TGF-β) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 66 or 67.

In one aspect, the targeting moiety includes a sequence from Programmed death-1 ligand 1 (PD-L1) and immunoglobulin Fc region (IgG Cγ1), and the immunomodulatory moiety includes an extracellular RANKL-binding domain or ectodomain of Receptor activator of nuclear factor-κB (RANK). In another aspect, the molecule includes an amino acid sequence corresponding to SEQ ID NO: 68 or 69.

In various aspects, the molecule is fused or directly linked to one or more antigen, antigenic determinant, or epitope.

In another embodiment, the present invention provides a composition including the molecule of the invention and a cell, wherein the cell is a tumor cell, immune cell, or dendritic cell.

In another embodiment, the present invention provides a method of counteracting or overcoming immune tolerance. The method includes administering to a subject in need thereof one or more molecule of the invention.

In another embodiment, the present invention provides a method of preventing or treating a neoplastic disease. In one aspect, the neoplastic disease is a non-T cell malignancy which does not express CD4 on the tumor cell. In one embodiment, the method includes administration to a subject in need thereof an antibody that targets and depletes CD4+ regulatory T cells (Tregs) in combination with a cytotoxic anticancer therapy. In one aspect, the antibody that targets and depletes Tregs is an anti-CD4 antibody. In various aspects, the cytotoxic anticancer therapy includes a chemotherapeutic molecule, tumor-targeted antibody, small molecule kinase inhibitor, hormonal agent, or tumor-targeted cytotoxic agent, anti-angiogenic agent or any combination thereof. In another aspect, the cytotoxic anticancer therapy includes ionizing radiation, ultraviolet radiation, cryoablation, thermal ablation, or radiofrequency ablation.

In another embodiment, the method includes administration to a subject in need thereof an antibody or molecule that targets and depletes CD4+ regulatory T cells (Tregs) in combination with an immunostimulatory antibody, fusion protein, peptide or ligand that targets CTLA-4, PD1, PD-1L, RANKL, TGF-β, GITR, 4-1BB, OX-40, or Toll-like receptors (TLR 1-10). In one aspect, the TLR-agonist comprises an activator of TLR-8 or TLR-9. In one aspect, the TLR agonist comprises an immunostimulatory nucleic acid sequence containing CpG nucleotides. In one aspect, the antibody that targets and depletes Tregs is an anti-CD4 antibody.

In another embodiment, the present invention provides a method of preventing or treating a neoplastic disease. The method includes administration to a subject in need thereof one or more molecule of the invention. In various aspects, the subject is administered one or more molecule of the invention in combination with another anticancer therapy. In one aspect, the anticancer therapy includes a chemotherapeutic molecule, antibody, small molecule kinase inhibitor, hormonal agent, cytotoxic agent, targeted therapeutic agent, or anti-angiogenic agent. In another aspect, the anticancer therapy includes ionizing radiation, ultraviolet radiation, cryoablation, thermal ablation, or radiofrequency ablation.

In another aspect, the subject is administered one or more molecule of the invention in combination with an antibody or molecule that inhibits the production or function of regulatory T cells (Tregs) or depletes the number of Tregs. In one aspect, the antibody that targets and depletes Tregs is an anti-CD4 antibody. In another aspect, the molecule that counteracts the function of Tregs is an antibody, fusion protein, peptide or ligand that targets CTLA-4, PD1, PD-1L, RANKL, TGF-β, GITR. In another aspect, the molecule that counteracts the function of Tregs is an antibody or fusion protein or ligand that targets 4-1BB or OX-40. In another aspect, the molecule that counteracts the function of Tregs is an agonist of Toll-like receptors (TLR 1-10). In one aspect, the TLR-agonist comprises an activator of TLR-8 or TLR-9. In one aspect, the TLR agonist is an immunostimulatory nucleic acid sequence containing CpG nucleotides.

In one aspect the chemotherapeutic agent is a topoisomerase-interacting agent, anthracycline, doxorubicin, mitoxantrone, camptothecin, camptothecin analogue, irinotecan, epipodophyilotoxin, ctoposide, alkylating agent, cyclophosphamide, cisplatin, cisplatin analogue, oxaliplatin, antimetabolite, fluoropyrimidine analogue, 5-fluorouracil, gemcitabine, azacytidine, antimicrotubule agent, taxane, paclitaxel, or docetaxel.

In another embodiment, the subject is administered one or more molecule of the invention in combination with any vaccine. In another aspect, the vaccine includes a tumor antigen, tumor-associated antigen, tumor epitope, tumor antigen-containing fusion protein, tumor cell, or dendritic cell. In another aspect, the vaccine includes a pathogen antigen, pathogen-associated antigen, pathogen epitope, or pathogen antigen-containing fusion protein. In one aspect, the vaccine includes a surrogate CD4+ T cell helper epitope from tetanus toxin. In one aspect, the CD4+ T helper sequence contains a domain of tetanus toxin fragment C (pDOM1). In one aspect, the pDOM sequence is fused to a cell-permeabilizing cationic polypeptide (e.g., Arginine-9). In another aspect, the Arg9-pDOM sequence is fused to a specific antigen comprising the vaccine.

In another embodiment, the present invention provides a method for treating immune cells wherein the cells are contacted ex vivo or in vitro with a molecule of the invention. In another embodiment, the present invention provides a method of treatment of a neoplastic disease. The method includes administering to a subject in need thereof a composition of immune cells contacted with a molecule of the invention.

In another embodiment, the present invention provides a method of inducing or promoting immune tolerance. The method includes administering to a subject in need thereof one or more molecule of the invention.

In another embodiment, the present invention provides a method of preventing or treating an autoimmune or inflammatory disease including administering to a subject in need thereof one or more molecule of the invention. In one aspect, the subject is administered one or more molecule of the invention in combination with another anti-inflammatory or immunosuppressive therapy. In another embodiment, the present invention provides a method of treatment of immune cells wherein the cells are contacted ex vivo or in vitro with a molecule of the invention. In another embodiment, the present invention provides a method of treating an autoimmune or inflammatory disease or preventing rejection of grafted cells or tissue. The method includes administering to a subject in need thereof a composition of immune cells contacted with a molecule of the invention.

All publications, patents, and patent applications mentioned in this specification are herein incorporated by reference to the same extent as if each individual publication, patent, or patent application was specifically and individually indicated to be incorporated by reference.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein "immune cells" or "immune effector cells" include T lymphocytes, B lymphocytes, natural killer (NK) cells, NKT cells, monocytes, macrophages, dendritic cells (DC), antigen presenting cells (APC).

As used herein, "neoplasm" or "tumor" including grammatical variations thereof, means new and abnormal growth of tissue, which may be benign or cancerous. In a related aspect, the neoplasm is indicative of a neoplastic disease or disorder, including but not limited, to various cancers. For example, such cancers can include prostate, pancreatic, biliary, colon, rectal, liver, kidney, lung, testicular, breast, ovarian, pancreatic, brain, and head and neck cancers, melanoma, sarcoma, multiple myeloma, leukemia, lymphoma, and the like.

A used herein, "subject," including grammatical variations thereof, means a human or vertebrate animal including a dog, cat, horse, cow, pig, sheep, goat, chicken, monkey, rat, and mouse.

As used herein, "targeting moiety" refers to a molecule that has the ability to localize and bind to a specific molecule or cellular component. The targeting moiety can be an antibody, antibody fragment, scFv, Fc-containing polypeptide, fusion antibody, polypeptide, peptide, aptamer, ligand, nucleic acid, or any combination thereof. In one embodiment, a targeting moiety can bind to a molecule present in a cell or tissue. In one aspect, the targeting moiety can bind a molecule in a diseased cell or tissue, such as a cancer cell or tumor. In, another aspect, the targeting molecule can bind a normal cell or tissue, such as an immune cell. In another aspect, the targeting moiety can bind a cellular or extracellular molecule that modulates the immune response. In another aspect, the targeting moiety binds a growth factor receptor, growth factor, cytokine receptor, cytokine, or cell surface molecule.

In another embodiment, the targeting moiety is a tumor-targeting moiety. The tumor-targeting moiety can bind a component of a tumor cell or bind in the vicinity of a tumor cell (e.g., tumor vasculature or tumor microenvironment). In one embodiment, the tumor targeting moiety binds to a component of a tumor cell, tumor microenvironment, tumor vasculature, tumor-associated lymphocyte, tumor antigen, tumor-associated antigen, tumor cell surface molecule, tumor antigenic determinant, tumor antigen-containing fusion protein, tumor-associated cell, tumor-associated immune cell, or tumor vaccine.

For example, in various embodiments, a targeting moiety is specific for or binds to a molecule or component, which includes but is not limited to, epidermal growth factor receptor (EGFR, EGFR1, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family; AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin 13 receptor alpha2 chain (IL13Ralpha2), Interleukin-6 (IL-6), 1L-6 receptor, Interleukin-4, IL-4 receptor, Cytokine receptors, Class I (hematopoietin family) and Class II (interferon/IL-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, arginine to isoleucine exchange at residue 170 of the alpha-helix of the alpha2-domain in the HLA-A2 gene (HLA-A*201-R170I), MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGE-1, BAGE-2,3,4,5, GAGE-1,2,3,4,5,6,7,8, GnT-V (aberrant N-acetyl giucosaminyl transferase V, MGAT5), HERV-K-MEL, KK-LC, KM-HN-1, LAGE, LAGE-1, CTL-recognized antigen on melanoma (CAMEL), MAGE-A1 (MAGE-1), MAGE-A2, MAGE-A3, MAGE-A4, MAGE-AS, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17, SSX-1,2,3,4, TRP2-1NT2, carcinoembryonic antigen (CEA), Kallikfein 4, mammaglobm-A, OA1, prostate specific antigen (PSA), prostate specific membrane antigen, TRP-1/gp75, TRP-2, adipophilin, interferon inducible protein absent in nielanorna 2 (AIM-2), BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, FRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enoJase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr vims (EBV) proteins (EBV latent membrane proteins—LMP1, LMP2; others), Hepatitis B or C virus proteins, and HIV proteins. A composition of the invention can further include the foregoing as a peptide/polypeptide and/or encoding the same.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell. In one aspect, the targeting moiety specifically binds epidermal growth factor receptor (EGFR1, Erb-B1), HER2/neu (Erb-B2), CD20, Vascular endothelial growth factor (VEGF), insulin-like growth factor receptor (IGF-1R), TRAIL-receptor, epithelial cell adhesion molecule, carcino-embryonic antigen, Prostate-specific membrane antigen, Mucin-1, CD30, CD33, CD40, or a combination thereof.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-I131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb); Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@ 17-1A) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym), Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals—Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab or ImmuRAIT-CEA. Examples of antibodies include those disclosed in U.S. Pat. Nos. 5,736,167, 7,060,808, and 5,821,337.

In one embodiment, the targeting moiety specifically binds a component of a regulatory T cell, myeloid suppressor cell, or dendritic cell. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In one aspect, the targeting moiety is an agonist that increases the function of the targeted molecule. In another aspect, the targeting moiety is an antagonist that inhibits the function of the targeted molecule.

In one aspect, the targeting moiety binds a specific cytokine, cytokine receptor, co-stimulatory molecule, co-inhibitory molecule, or immunomodulatory receptor that modulates the immune system. In another aspect, the targeting moiety specifically binds one of the following molecules: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand 1 (PD-L1; B7-H1); or PD-1 ligand 2 (PD-L2; B7-DC); B7 family; B7-1 (CD80); B7-2 (CD86); B7-H3; B7-H4; GITR/AITR; GITRL/AITRL; BTLA; CD70; CD27; LIGHT; HVEM; Toll-like receptor (TLR) (TLR 1,2,3,4,5,6,7,8,9,10). In one aspect, the targeting moiety is an agonist that increases the function of the targeted molecule. In another aspect, the targeting moiety is an antagonist that inhibits the function of the targeted molecule.

In one aspect, the targeting moiety includes an antibody, antibody fragment, scFv, Fc-containing polypeptide, or peptide that specifically binds a component of a regulatory T cell, myeloid suppressor cell, or dendritic cell. In another aspect, the targeting moiety includes an antibody, antibody fragment, scFv, or Fc-containing polypeptide that specifically binds a cytokine, cytokine receptor, co-stimulatory molecule, or co-inhibitory molecule that modulates the immune system. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); PD-1 ligand 1 (PD-L1; B7-H1); PD-1 ligand 2 (PD-L2; B7-DC); Receptor activator of nuclear factor-κB (RANK); Receptor activator of nuclear factor-κB (RANK) ligand (RANKL); LAG-3; glucocorticoid-induced tumor necrosis factor receptor family-related gone (GITR; TNFRSF18);

Interleukin-4 receptor (IL-4R); tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; B7 family; B7-1 (CD80); B7-2 (CD86); B7-H3; B7-H4; GITR/AITR; GITRL/AITRL; BTLA; CD70; CD27; LIGHT; or HVEM. In one aspect, the targeting moiety is an agonist that increases the function of the targeted molecule. In another aspect, the targeting moiety is an antagonist that inhibits the function of the targeted molecule.

Examples of antibodies which can be incorporated into compositions and methods disclosed herein include, but are not limited, to antibodies such as Zanulimumab (anti-CD4 mAb), Keliximab (anti-CD4 mAb); Ipilimumab (MDX-101; anti-CTLA-4 mAb); Tremilimumab (anti-CTLA-4 mAb); (Daclizumab (anti-CD25/IL-2R mAb); Basiliximab (anti-CD25/IL-2R mAb); MDX-1106 (anti-PD1 mAb); antibody to GITR; GC1008 (anti-TGF-β antibody); metelimumab/CAT-192 (anti-TGF-β antibody); lerdelimumab/CAT-152 (anti-TGF-β antibody); ID11 (anti-TGF-β antibody); Denosumab (anti-RANKL mAb); BMS-663513 (humanized anti-4-1BB mAb); SGN-40 (humanized anti-CD40 mAb); CP870,893 (human anti-CD40 mAb); Infliximab (chimeric anti-TNF mAb; Adalimumab (human anti-TNF mAb); Certolizumab (humanized Fab anti-TNF); Golimumab (anti-TNF); Etanercept (Extracellular domain of TNFR fused to IgG1 Fc); Belatacept (Extracellular domain of CTLA-4 fused to Fc); Abatacept (Extracellular domain of CTLA-4 fused to Fc); Belimumab (anti-B Lymphocyte stimulator); Muromonab-CD3 (anti-CD3 mAb); Otelixizumab (anti-CD3 mAb); Teplizumab (anti-CD3 mAb); Tocilizumab (anti-IL6R mAb); REGN88 (anti-IL6R mAb); Ustekinumab (anti-IL-12/23 mAb); Briakinumab (anti-IL-12/23 mAb); Natalizumab (anti-α4 integrin); Vedolizumab (anti-α4 B7 integrin mAb); T1h (anti-CD6 mAb); Epratuzumab (anti-CD22 mAb); Efalizumab (anti-CD11a mAb); and Atacicept (extracellular domain of transmembrane activator and calcium-modulating ligand interactor fused with Fc).

In one embodiment, the present invention provides a molecule including a targeting moiety fused with an "immunomodulatory moiety". As used herein, "immunomodulatory moiety" refers to a ligand, peptide, polypeptide, or Fc-containing polypeptide that binds a specific component of a regulatory T cell, myeloid suppressor cell, or dendritic cell and modulates the number or function of Tregs or myeloid suppressor cells. In an additional aspect, the "immunomodulatory moiety" specifically binds a cytokine, cytokine receptor, co-stimulatory molecule, or co-inhibitory molecule that modulates the immune system. In another aspect, the immunomodulatory moiety specifically binds one of the following molecules: Transforming growth factor-beta receptor (TGF-βR); Transforming growth factor-beta (TGF-β); Programmed Death-1 (PD-1); PD-1 ligand 1 (PD-L1; B7-H1); PD-1 ligand 2 (PD-L2; B7-DC); Receptor activator of nuclear factor-κB (RANK); or Receptor activator of nuclear factor-κB (RANK) ligand (RANKL); or vascular endothelial growth factor (VEGF). In another aspect, the immunomodulatory moiety specifically binds one of the following molecules: glucocorticoid-induced tumor necrosis factor receptor family-related gene (GITR; AITR; TNFRSF18); GITRL/AITRL; 4-1BB (CD137); 4-1BB ligand (4-1BBL; CD137L); OX40 (CD134; TNR4); OX40 ligand (OX40L); B7-H3; B7-H4; BTLA; CD40; CD40 ligand (CD40L); CD70; CD27; LIGHT; or HVEM. In another aspect, the immunomodulatory moiety specifically binds one of the following molecules: tumor necrosis factor-α (TNF-α); Interleukin-12 (IL-12); IL-12R; Interleukin-10 (IL-10); IL-10R. In another aspect, the immunomodulatory moiety comprises an extracellular domain of CTLA-4. In one aspect, the immunomodulatory moiety is an agonist that increases the function of the bound molecule. In another aspect, the immunomodulatory moiety is an antagonist that inhibits the function of the targeted molecule.

In another aspect, the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); vascular endothelial growth factor receptor (VEGFR1 or VEGFR2); or IL-10R. In another aspect, the immunomodulatory moiety comprises an extracellular domain or ligand-binding sequence of one of the following receptors: tumor necrosis factor receptor 2 (TNFR2); 4-1BB (CD137); OX40 (CD134; TNR4); CD40; IL-12R; or glucocorticoid-induced tumor necrosis factor receptor family-related gene (GITR; AITR; TNFRSF18). In an additional aspect, the extracellular domain of the specific receptor binds the cognate ligand and inhibits the interaction of the ligand with its native receptor.

In another aspect, the immunomodulatory moiety comprises one or more of the following ligands or active ligand fragments: Transforming growth factor-beta (TGF-β); PD-1 ligand 1 (PD-L1); PD-1 ligand 2 (PD-L2); or IL-10. In another aspect, the immunomodulatory moiety comprises one or more of the following ligands or active ligand fragments: 4-1BB ligand (4-1BBL; CD137L); OX40 ligand (OX40L); IL-12; CD40L; or GITRL/AITRL.

In another aspect, the immunomodulatory moiety is fused to the C-terminus of the targeting moiety. In another aspect, the immunomodulatory moiety is fused to the N-terminus of the targeting moiety. In one aspect, the fusion molecule is represented by X-Fc-Y, wherein X is the targeting moiety, Fc is an immunoglobulin Fc region, and Y is the immunomodulatory moiety. In another aspect, the fusion molecule is represented by Y-Fc-X, wherein X is the targeting moiety, and Y is the immunomodulatory moiety. In one aspect, the targeting moiety may additionally be an immunomodulatory moiety.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell, and the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); vascular endothelial growth factor receptor (VEGFR1 or VEGFR2); or IL-10R.

In one aspect, the targeting moiety includes an antibody, antibody fragment, scFv, or Fc-containing polypeptide that specifically binds a component of a tumor cell, tumor antigen, tumor vasculature, tumor microenvironment, or tumor-infiltrating immune cell, and the immunomodulatory moiety comprises one or more of the following ligands or active ligand fragments: 4-1BB ligand (4-1BBL; CD137L); OX40 ligand (OX40L); IL-12; CD40L; or GITRL/AITRL.

In another aspect, the targeting moiety includes an antibody, antibody fragment, scFv, Fc-containing polypeptide or ligand that binds a specific component of a regulatory T cell, myeloid suppressor cell, or dendritic cell, and the immunomodulatory moiety comprises an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); or IL-10R. In another aspect, the immunomodulatory moiety comprises one or more of the following ligands or active ligand fragments: 4-1BB ligand (4-1BBL; CD137L); OX40 ligand (OX40L); IL-12; CD40L; or GITRL/AITRL. In another aspect, the specific targeted component of a regulatory T cell, myeloid suppressor cell, or dendritic cell is one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta (TGF-β); Programmed Death-1 (PD-1); Programmed death-1 ligand (PD-L1 or PD-L2); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R).

In another aspect, the targeting moiety includes an antibody, antibody fragment, scFv, Fc-containing polypeptide or ligand that binds one of the following: CTLA-4; 4-1BB (CD137); OX40 (CD134; TNR4); CD40; IL-12R; or glucocorticoid-induced tumor necrosis factor receptor family-related gene (GITR; AITR; TNFRSF18); and the immunomodulatory moiety comprises a different molecule selected from the following: (i) an extracellular domain or ligand-binding sequence of one of the following receptors: Transforming growth factor-beta receptor (TGF-βRII, TGF-βRIIb, or TGF-βRIII); Programmed Death-1 (PD-1); Receptor activator of nuclear factor-κB (RANK); or IL-10R; or (ii) Fc-containing polypeptide or ligand that binds one of the following: CTLA-4; 4-1BB (CD137); OX40 (CD134; TNR4); CD40; IL-12R; or GITR (AITR; TNFRSF18).

In another aspect, the targeting moiety and immunomodulatory moiety are two different molecules selected from any of the following: an antibody, antibody fragment, scFv, Fc-containing polypeptide or ligand that binds TGF-β, CTLA-4, PD-1, 4-1BB (CD137), OX40 (CD134; TNR4), CD40; IL-12R, or GITR/AITR (TNFRSF18), or Toll-like receptor (TLR); an extracellular domain or ligand-binding sequence of Transforming growth factor-beta receptor (TGF-βRII, TGF-βRIIb, or TGF-βRIII), Programmed Death-1 (PD-1), Receptor activator of nuclear factor-κB (RANK), or IL-10R. In one aspect, the fusion molecule is represented by X-Fc-Y, wherein X is an immunomodulatory targeting moiety and Y is a different immunomodulatory moiety.

In another aspect, the targeting moiety includes an antibody, antibody fragment, scFv, Fc-containing polypeptide that binds one of the following molecules: CD4; CD25 (IL-2α receptor; IL-2αR); or CD20; and the immunomodulatory moiety comprises one of the following ligands or active ligand fragments: Transforming growth factor-beta (TGF-β); PD-1 ligand 1 (PD-L1); PD-1 ligand 2 (PD-L2); or IL-10.

In another aspect, the targeting moiety includes an antibody, antibody fragment, scFv, Fc-containing polypeptide that binds tumor necrosis factor-α (TNF-α), Interleukin-12 (IL-12), IL-6R, B-lymphocyte stimulator, CD11a, CD6, or CD22; and the immunomodulatory moiety comprises one of the following: (i) ligands or active ligand fragments of Transforming growth factor-beta (TGF-β), PD-1 ligand 1 (PD-L1), or IL-10; or (ii) an extracellular domain or ligand-binding fragment of RANK, 4-1BB (CD137), OX40 (CD134; TNR4), CD40, IL-12R or GITR/AITR (TNFRSF18).

In another aspect, the targeting moiety comprises the extracellular domain of CTLA-4 fused to immunoglobulin Fc, and the immunomodulatory moiety comprises one of the following: (i) ligands or active ligand fragments of Transforming growth factor-beta (TGF-β), PD-1 ligand 1 (PD-L1), or IL-10; or (ii) ligand-binding fragment of TNFR2, RANK, 4-1BB (CD137), OX40 (CD134; TNR4), CD40, IL-12R or GITR/AITR (TNFRSF18).

In another aspect, the targeting moiety and immunomodulatory moiety are two different molecules selected from any of the following: an antibody, antibody fragment, scFv, Fc-containing polypeptide that binds tumor necrosis factor-α (TNF-α), Interleukin-12 (IL-12), IL-6R, B-lymphocyte stimulator, CD11a, CD6, or CD22; a ligand-binding fragment of TNFR2, RANK, 4-1BB (CD137), OX40 (CD134; TNR4), CD40, IL-12R or GITR/AITR (TNFRSF18); ligands or active ligand fragments of Transforming growth factor-beta (TGF-β), PD-1 ligand 1 (PD-L1), or IL-10; or CTLA-4-Fc. In one aspect, the fusion molecule is represented by X-Fc-Y, wherein X is the immunomodulatory targeting moiety and Y is a different immunomodulatory moiety.

Antibodies: In one embodiment, the targeting moiety or fusion protein is an immunoglobulin. As used herein, the term "immunoglobulin" includes natural or artificial mono- or polyvalent antibodies including, but not limited to, polyclonal, monoclonal, multispecific, human, humanized or chimeric antibodies, single chain antibodies, Fab fragments. F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin ion can be of any type (e.g., IgG, IgE, IgM, IgD, IgA, and IgY), class (e.g., IgG1, IgG2, IgG3, IgG4, IgA1, and IgA2) or subclass of immunoglobulin molecule.

An antibody as disclosed herein includes an antibody fragment, such as, but not limited to, Fab, Fab' and F(ab') 2, Fd, single-chain Fvs (scFv), single-chain antibodies, disulfide-linked Fvs (sdfv) and fragments including either a VL or VH domain. In one embodiment, the targeting moiety is an antibody or scFv.

An antigen-binding antibody fragment, including single-chain antibody, may include the variable region(s) alone or in combination with the entirety or a portion of the following: hinge region, CH1, CH2, and CH3 domains. An antigen-binding fragment can also include any combination of variable region(s) with a hinge region, CH1, CH2, and CH3 domains. Also includes is a Fc fragment, antigen-Fc fusion proteins, and Fc-targeting moiety. The antibody may be from any animal origin including birds and mammals. In one aspect, the antibody is, or derived from, a human, murine (e.g., mouse and rat), donkey, sheep, rabbit, goat, guinea pig, camel, horse, or chicken. Further, such antibody may be a humanized version of an antibody. The antibody may be monospecific, bispecific, trispecific, or of greater multispecificity.

The antibody herein specifically include a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA. 81:6851-6855). A chimeric antibody of interest herein includes "primatized" antibodies including variable domain antigen-binding sequences derived from a non-human primate (e.g., Old World Monkey, Ape etc.) and human constant region sequences.

Various methods have been employed to produce antibodies. Hybridoma technology, which refers to a cloned cell line that produces a single type of antibody, uses the cells of various species, including mice (murine), hamsters, rats, and humans. Another method to prepare an antibody uses genetic engineering including recombinant DNA techniques. For example, antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen.

In one embodiment, a hybridoma can produce a targeted fusion protein comprising a targeting moiety and an immunomodulatory moiety. In one embodiment, a targeting moiety comprising an antibody, antibody fragment, or polypeptide is linked or fused to an immunomodulatory moiety consisting of a polypeptide, with a linker or without a linker. The linker can be an amino acid linker. In one embodiment, a linker is (GGGGS) n (SEQ ID NO: 123) wherein n is 1, 2, 3, 4, 5, 6, 7, or 8. For example, GGGGSGGGGSGGGGS (SEQ ID NO: 104). In another embodiment, a linker is EPKSCDK (SEQ ID NO: 105). In another embodiment, a linker is IEGRDMD (SEQ. ID. NO: 106). In various aspects, the length of the linker may be modified to optimize binding of the target moiety or the function of the immunomodulatory moiety. In various aspects, the immunomodulatory moiety is a polypeptide that is fused to the C-terminus of the Fc region of the heavy chain of a targeting antibody or Fc-containing fusion protein. In another aspect, the immunomodulatory moiety is a polypeptide that is fused to the C-terminus of the light chain of a targeting antibody. In another aspect, the fusion protein comprises an X-Fc-Y sequence, wherein X is a targeting polypeptide and Y is an immunomodulatory polypeptide.

For example, a hybridoma can produce the polypeptides corresponding to SEQ. ID. NO: 1-69.

An antibody fragment can include a portion of an intact, antibody, e.g., including the antigen-binding or variable region thereof. Examples of antibody fragments include Fab, Fab', F(ab')2, and Fv fragments; Fc fragments or Fc-fusion products; diabodies; linear antibodies; single-chain antibody molecules; and multispecific antibodies formed from antibody fragment(s).

An intact antibody is one which includes an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof tor any other modified Fc (e.g., glycosylation or other engineered Fc).

The intact antibody may have one or more "effector functions" which refer to those biological activities attributable to the Fc region (a native sequence Fc region or amino acid sequence variant Fc region or any other modified Fc region) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g., B cell receptor (BCR); and cross-presentation of antigens by antigen presenting cells or dendritic cells. In one embodiment, the targeting antibody or Fc-containing fusion protein facilitates focused or preferential delivery of a immunomodulatory moiety to a target cell. In another aspect, a targeting antibody can induce death of the targeted cell or sensitize it to immune cell-mediated cytotoxicity. In another aspect, the Fc-fusion protein or antibody can facilitate delivery of the immunomodulatory moiety or immunogenic apoptotic material from antibody-bound tumor targets, or both, to an antigen presenting cells (APC) via interactions between their Fc and Fc receptors (on APC).

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgC3, IgG4, IgA, and IgA2. The heavy-chain constant domains (that correspond to the different classes of antibodies are called alpha ($\alpha$), delta ($\delta$), epsilon ($\epsilon$), gamma ($\gamma$), and mu ($\mu$) respectively. The subunit structures and three-dimensional configurations of different classes of immunoglobulins are well known.

Peptides: In some aspects of the invention the targeting moiety or immunomodulatory moiety is a peptide or polypeptide. A peptide includes any analog, fragment or chemical derivative of a peptide whose amino acid residue sequence is shown herein. Therefore, a present peptide can be subject to various changes, substitutions, insertions, and deletions where such changes provide for certain advantages in its use. In this regard, a peptide of this invention corresponds to, rather than is identical to, the sequence of a recited peptide where one or more changes are made and it retains the ability to function as the unmodified peptide in one or more of the assays.

The term "analog" includes any peptide having an amino acid residue sequence substantially identical to a sequence specifically shown herein in which one or more residues have been conservatively substituted with a functionally similar residue and which displays the activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The term "fragment" refers to any subject polypeptide having an amino acid residue sequence shorter than that of a polypeptide whose amino acid residue sequence is disclosed herein.

As used herein "a tumor targeting peptide" includes polymers containing fewer than 100 amino acids, where the polymer specifically binds to a cellular component of a tumor cell, tumor vasculature, and/or a component of a tumor microenvironment.

A peptide of the present invention can be synthesized by any of the techniques that are known to those skilled in "the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis"* W. H. Freeman Co., San Francisco, 1969; Bodanszky, et al., "Peptide Synthesis", John Wiley & Sons, Second Edition, 1976; J. Meienhofer, "Hormonal Proteins and Peptides". Vol. 2. p. 46, Academic Press (New York), 1983; Merrifield, Adv. Enzymol., 32:221-96, 1969; Fields et al. Int. J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis. Appropriate protective groups usable in such synthesis are described in the above texts and in J. F. W. McOmie, "Protective Groups in Organic Chemistry", Plenum Press, New York, 1973.

Aptamers: In one aspect of the invention, the targeting moiety is an aptamer. In various embodiments, an aptamer is specific for a molecule on a tumor cell, tumor vasculature, and/or a tumor microenvironment. The term "aptamer" includes DNA, RNA or peptides that are selected based on specific binding properties to a particular molecule. For example, an aptamer(s) can be selected for binding a particular gene product in a tumor cell, tumor vasculature, tumor microenvironment, and/or an immune cell, as disclosed herein, where selection is made by methods known in the art and familiar to one of skill in the art. Subsequently, said aptamer(s) can be administered to a subject to modulate or regulate an immune response.

Some aptamers having affinity to a specific protein, DNA, amino acid and nucleotides have been described (e.g., K. Y. Wang, et al., Biochemistry 32:1899-1904 (1993); Pitner et al., U.S. Pat. No. 5,691,145: Gold, et al., Ann. Rev. Biochem. 64:763-797 (1995); Szostak et al., U.S. Pat. No. 5,631,146). High affinity and high specificity binding aptamers have been derived from combinatorial libraries (supra, Gold, et al.). Aptamers may have high affinities, with equilibrium dissociation constants ranging from micromolar to sub-nanomolar depending on the selection used, aptamers may also exhibit high selectivity, for example, showing a thousand fold, discrimination between 7-methyl G and G (Haller and Sarnow, Proc. Natl. Acad. Sci. USA 94:8521-8526 (1997)) or between D and L-tryptophan (supra, Gold et al.). An aptamer can be selected based on the particular molecule targeted (e.g., aptamer targeting EGFR or other cancer markers). Standard procedures for in vitro selection are known, such as SELEX experiments, described at Science 249 (4968) 505-510 (1990), and Nature (London), 346 (6287) 818-822 (1990) which can be followed throughout, or with modifications and improvements known in the art.

The term "therapeutically effective amount" means the amount of the subject compound that will elicit the biological or medical response of a tissue, system, animal or human that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering" should be understood to mean providing a composition in a therapeutically effective amount to the individual in need of treatment. Administration can be intratumoral or systemic (intravenous) administration. Furthermore, in conjunction with vaccination of recipient with pathogen antigen vaccine (e.g., tetanus toxoid). In addition, in conjunction with agent to deplete or inactivate regulatory T cells (e.g., cyclophosphamide) or myeloid suppressor cells (e.g., gemcitabine). In a further example, ex vivo treatment of immune cells and tumor cells for generation of tumor reactive or pathogen antigen reactive immune cells—for adoptive cellular immunotherapy. Administration can be intradermal or subcutaneous.

Furthermore, administration can be in combination with one or more additional therapeutic agents deplete or inactivate regulatory T cells (cyclophosphamide) or myeloid suppressor cells (e.g., gemcitabine). The pharmaceutical compositions of the invention identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., cancer, pathogenic infectious agents, associated conditions thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Counteracting Tumor Immune Tolerance via Antibody-mediated Depletion of CD4$^+$ Regulatory T Cells Facilitates the Activation of Tumor-Reactive CD8$^+$ T Cells and Enhances the In Vivo Antitumor Efficacy of Cytotoxic Anticancer Agents.

Figure 53B:
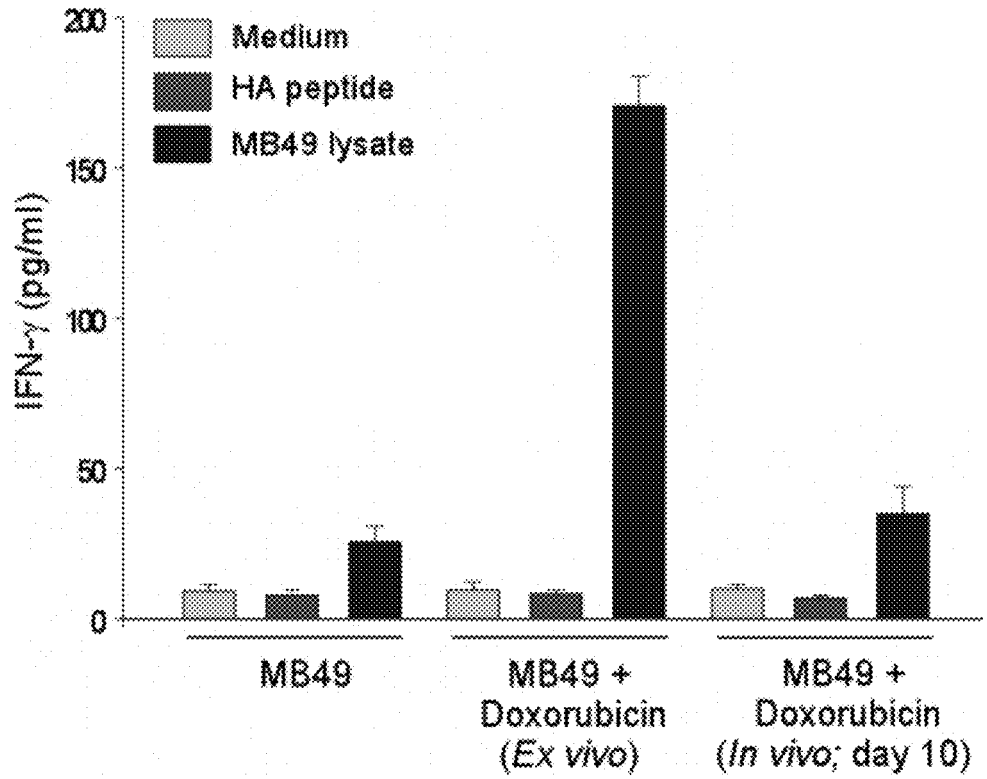
Figure 53C:
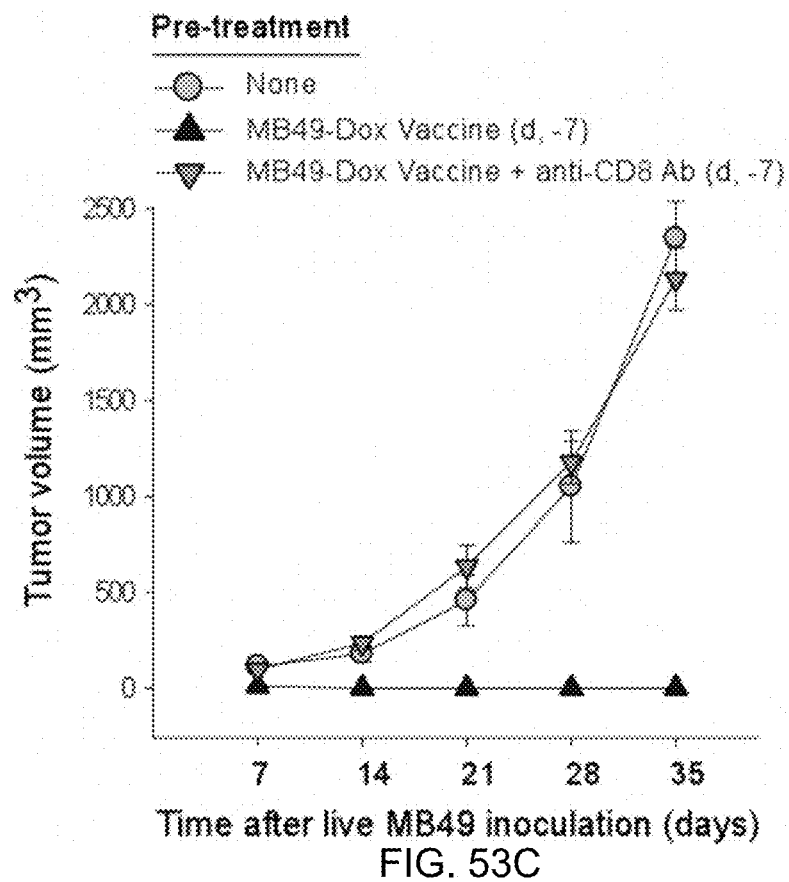

Immunogenic death of tumor cells by chemotherapeutic agents can induce CD8$^+$ T cell-mediated antitumor immunity. In response to specific chemotherapeutic agents, tumor cells exhibit the rapid translocation of intracellular calreticulin (CRT) to the cell surface where its aggregation provides a signal for the recognition and engulfment of dying tumor cells by antigen presenting dendritic cells (DCS). Treatment of mouse MB49 or human SW780 bladder cancer cells with doxorubicin, an anthracycline chemotherapeutic agent, induced rapid surface exposure of CRT that was detected by immunofluorescence cytometry of cells stained with Dylight 488-labeled anti-CRT antibody (FIG. 53A). To determine whether ex vivo treatment with doxorubicin induced an immunogenic death of tumor cells, either untreated live MB49 cells or an equivalent number of MB49 cells that were pre-treated in vitro with doxorubicin were injected into one flank of syngeneic immunocompetent C57BL/6 mice. Unlike mice injected with live tumor cells, mice injected with doxorubicin-treated tumor cells exhibited increased production of IFN-γ by draining lymph node (DLN) cells in response to in vitro re-challenge with MB49 cell lysates (FIG. 53B). Vaccination with doxorubicin-killed MB49 cells generated a tumor-specific immune response since no corresponding increase in IFN-γ secretion by DLN cells was observed following in vitro exposure to an irrelevant peptide (Hemagglutinin-HA). Injection of doxorubicin-treated MB49 tumor cells protected mice against tumor growth upon challenge with untreated live MB49 tumor cells injected into the opposite flank. (FIG. 1C). The protection against tumor growth by vaccination with doxorubicin-treated tumor cells was not observed in mice that were depleted of CD8$^+$ T cells with an anti-CD8 antibody before challenge with live tumor cells (FIG. 53C). These observations indicate that ex vivo treatment with chemotherapeutic agents can induce an immunogenic death of tumor cells that generates CD8$^+$ T cell-mediated adaptive antitumor immunity.

Figure 53D:
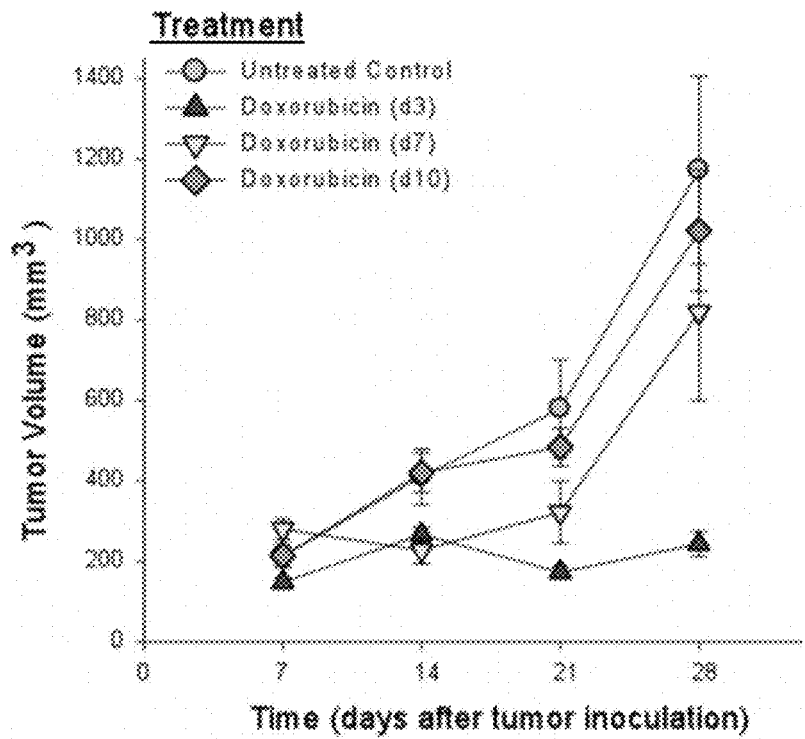

Tumor-induced immune tolerance inhibits activation of CD8$^+$ T cells in response to chemotherapy. To examine whether in vivo treatment with chemotherapeutic agents can activate CD8$^+$ T cell-mediated immune responses in mice with pre-established tumors, C57BL/6 mice were injected with live syngeneic MB49 tumor cells and then administered intratumoral doxorubicin at various time points following tumor inoculation. In contrast to vaccination of naïve mice with doxorubicin-killed MB49 cells, in vivo treatment of mice with established MB49 tumors at d10 following tumor inoculation failed to induce a corresponding increase in IFN-γ secretion by DLN cells in response to in vitro re-challenge with MB49 cell lysates (FIG. 53B). Whereas treatment with doxorubicin on d3 following tumor inoculation was able to arrest tumor growth, delayed administration of the same dose of doxorubicin on d10 failed to inhibit the progressive growth of established MB49 tumors (FIG. 53D). These results indicate that tumor-induced immune tolerance in the microenvironment of established cancers counteracts the activation of adaptive antitumor immunity in response to chemotherapy-induced tumor cell death.

Figure 53E:
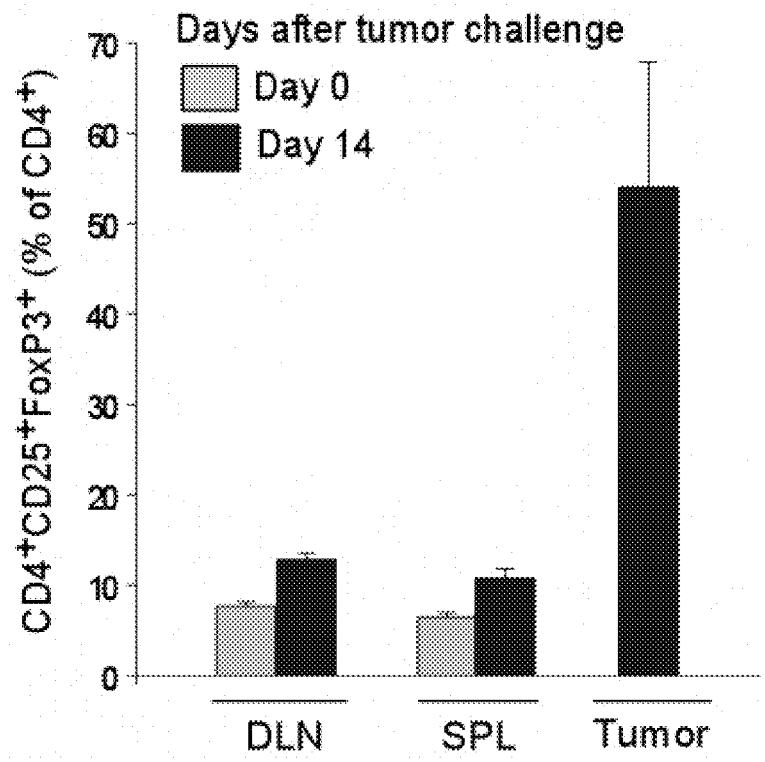
Figure 53F:
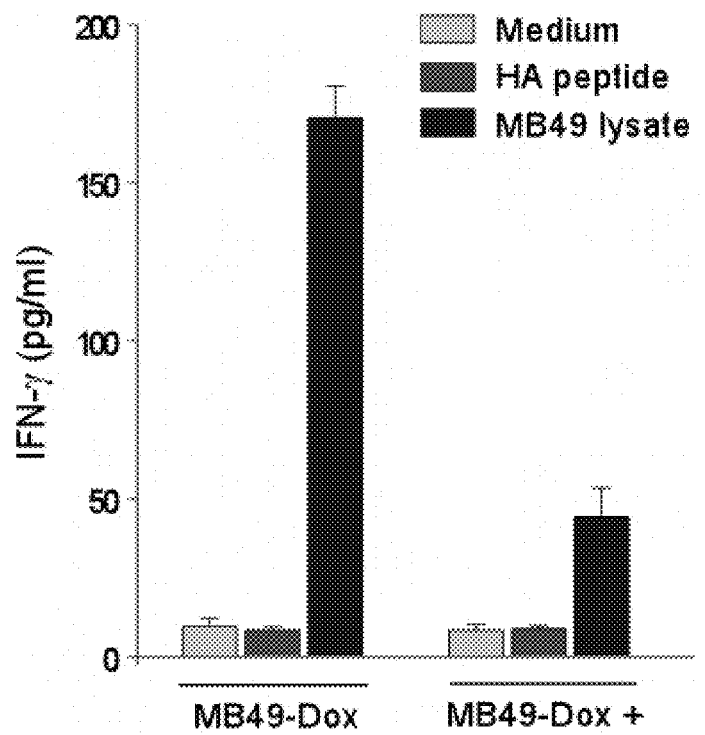
Figure 53G:
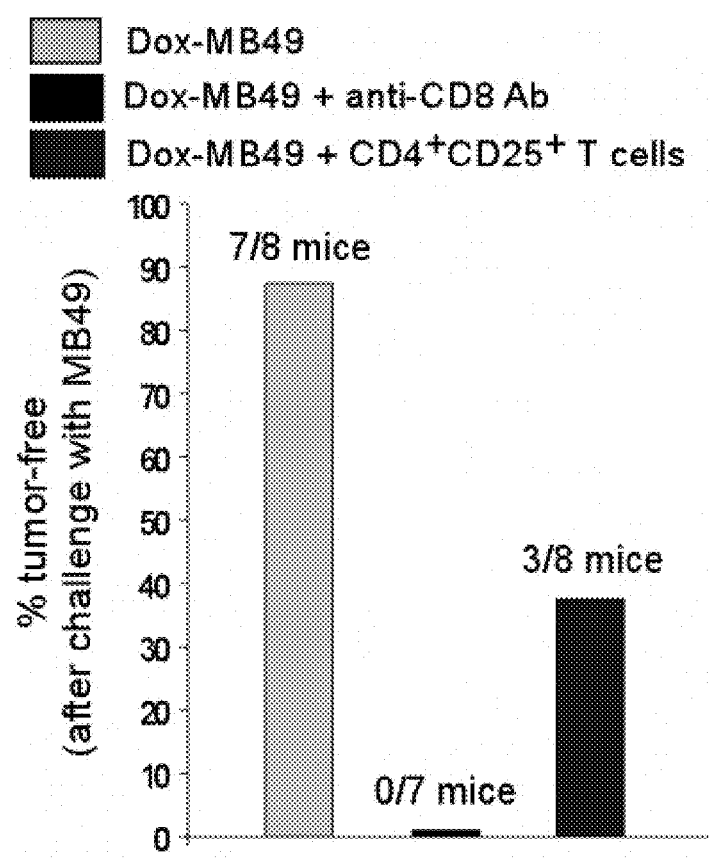

Regulatory T cells (Treg) accumulate in the tumor microenvironment and counteract the ability of chemotherapy to activate CD8$^+$ T cell mediated antitumor immunity. To investigate whether FoxP3$^+$ Tregs are involved in enforcing immune tolerance in the tumor microenvironment, we examined the percentage of CD4$^+$CD25$^+$FoxP3$^+$ cells (Tregs) among CD4$^+$ T lymphocytes in the spleen, draining lymph nodes (DLN), and tumors of immunocompetent C57BL/6 mice at d0 and d14 after tumor inoculation. Whereas tumor-bearing mice exhibited only a minor increase in the percentage of Tregs among CD4$^+$ T cells in the spleen and DLN at d14 following tumor inoculation, a majority of tumor-infiltrating CD4$^+$ T cells at this time were CD4$^+$CD25$^+$FoxP3$^+$ cells (FIG. 53E). To investigate whether Tregs infiltrating the tumor microenvironment can suppress the activation of adaptive antitumor immunity in response to chemotherapy-induced tumor cell death, CD4$^+$CD25$^+$ cells isolated from tumors and DLN of tumor-bearing mice were adoptively transferred into syngeneic C57BL/6 naïve mice before vaccination with doxorubicin-killed MB49 cells. The adoptive transfer of tumor-infiltrating CD4$^+$CD25$^+$ cells into naïve mice inhibited the ability of subsequent in vivo vaccination with doxorubicin-treated MB49 tumor cells to increase production of IFN-γ by draining lymph node (DLN) cells in response to in vitro re-challenge with MB49 cell lysates (FIG. 53F). Consistent with the ability of tumor-infiltrating CD4$^+$CD25$^+$ cells to suppress the tumor-specific immune response, the adoptive transfer of these cells counteracted the protection conferred by vaccination with doxorubicin-treated MB49 cells against tumor growth upon challenge with untreated live MB49 tumor cells (FIG. 53G). These results indicate that the tumor microenvironment fosters the accumulation of FoxP3$^+$ Tregs which counteract the activation of CD8$^+$ T cell mediated antitumor immunity in response to chemotherapy-induced tumor cell death.

Inhibition of TGF-β in the tumor microenvironment reduces tumor-infiltrating FoxP3$^+$ regulatory T cells and enhances the antitumor efficacy chemotherapy. TGF-β induces FoxP3 expression in naïve peripheral CD4$^+$CD25$^-$ FoxP3$^-$ T cells and facilitates their conversion into 'adaptive' FoxP3$^+$ Tregs that share the immunosuppressive ability of natural FoxP3$^+$ Tregs generated in the thymus. Since human cancers frequently become refractory to the growth-inhibitory effect of TGF-β and acquire an ability to increase expression and secretion of TGF-β, we investigated whether this switch enables tumor cells to increase the number of adaptive Tregs in the tumor microenvironment. Examination of serum levels of TGF-β in mice at d0, d14, and d28 following inoculation of live MB49 tumor cells demonstrated that tumor growth resulted in a progressive increase in the level of serum TGF-β (FIG. 54A). To assess the precise source of TGF-β in tumor-bearing mice, the total amount of TGF-β in supernatants of tumor cells or draining lymph node cells isolated from tumor-bearing mice were measured following ex vivo culture in serum-free medium for 24 h. Measurement of the level of TGF-β/10$^6$ cells showed that tumor cells were the dominant source of the increased level of TGF-β in tumor-bearing mice (FIG. 54B). In addition to tumor cell-autonomous expression of TGF-β, T cells from tumor-bearing mice also expressed higher levels of TGF-β compared to their counterparts from tumor-free mice (FIG. 54B). To determine whether the elevation of TGF-β is responsible for the upregulation of Tregs in the tumor microenvironment, tumor-bearing mice were treated with a soluble chimeric protein comprising the extracellular domain of TGFβRII and the Fc portion of the murine IgG1 heavy chain (TGFβRII:Fc). This fusion protein interferes with the binding of TGF-β to endogenous TGFβRII and functions as a stable TGF-β antagonist. ELISA assays confirmed the ability of TGFβRII:Fc to sequester TGF-β in supernatants of MB49 tumor cells in a concentration-dependent manner (FIG. 54C). At 5 d following inoculation of MB49 tumor cells, mice were either left untreated or treated with TGFβRII:Fc (1 μg intratumoral; twice weekly) for 3 weeks followed by flow cytometric analyses of intracellular FoxP3 expression in CD4$^+$CD25$^+$ T cells infiltrating the tumors. In vivo treatment of tumors with TGFβRII: Fc resulted in a significant decline in FoxP3 expression in tumor-infiltrating CD4$^+$ T cells (FIG. 54D) and a dramatic reduction of CD4$^+$CD25$^+$FoxP3$^+$ Tregs in tumor tissue (FIG. 54E). To determine whether inhibition of TGF-β in the tumor microenvironment can improve the antitumor efficacy of chemotherapy, MB49 tumor-bearing mice were administered doxorubicin (5 mg/kg i.p. weekly×3) with or without twice weekly treatment with TGFβRII:Fc (1 μg intratumoral). In contrast to treatment with either doxorubicin or TGFβRII:Fc alone, combined treatment with both agents was able to arrest the growth of MB49 tumors. These results indicate that tumor cell autonomous expression of TGF-β in the tumor microenvironment induces 'adaptive' FoxP3$^+$ Tregs and that counteracting tumor-induced TGF-β-mediated immune tolerance enhances the antitumor efficacy of chemotherapy.

Figure 55A:
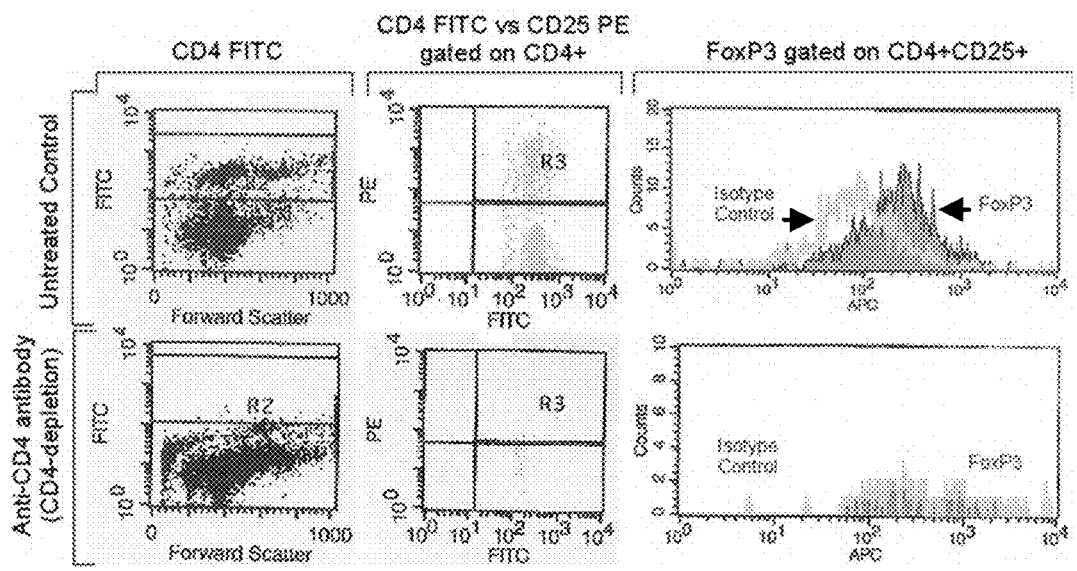
Figure 55B:
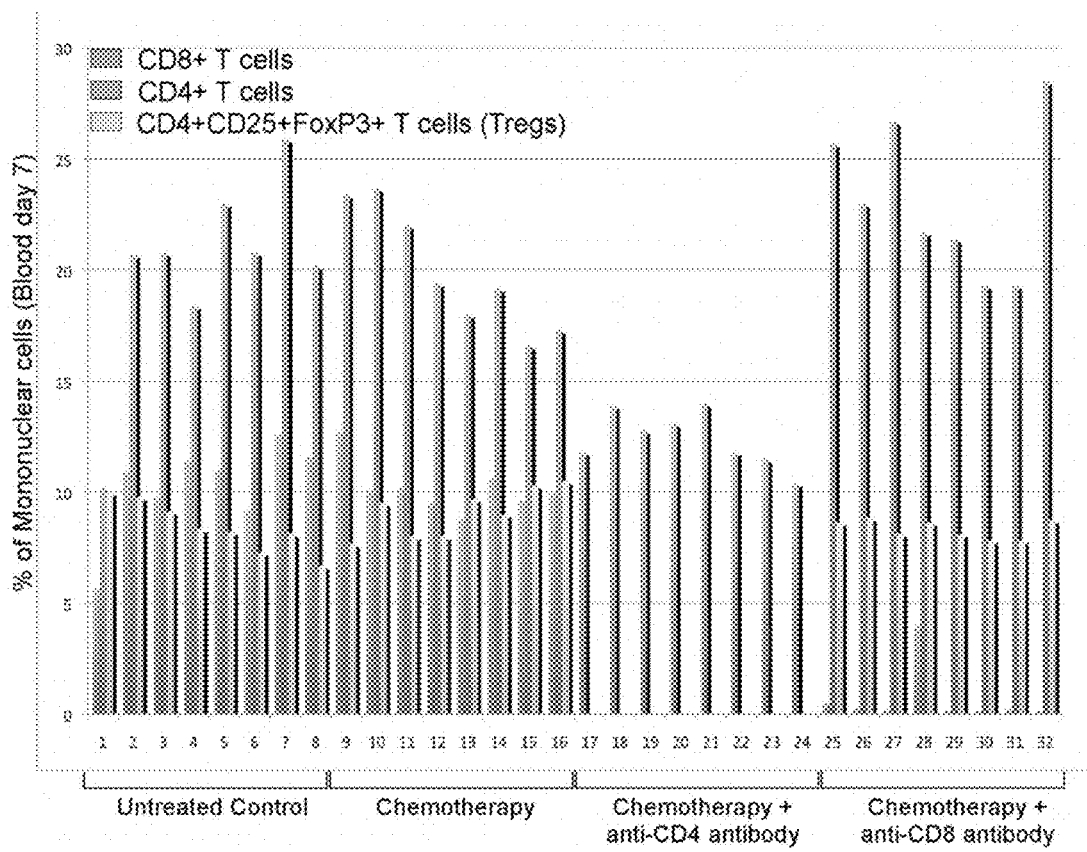
Figure 55C:
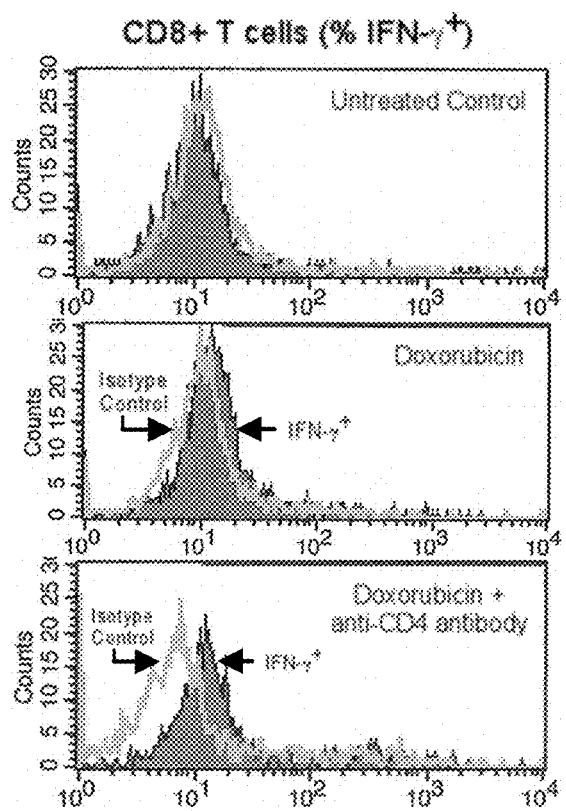
Figure 55D:
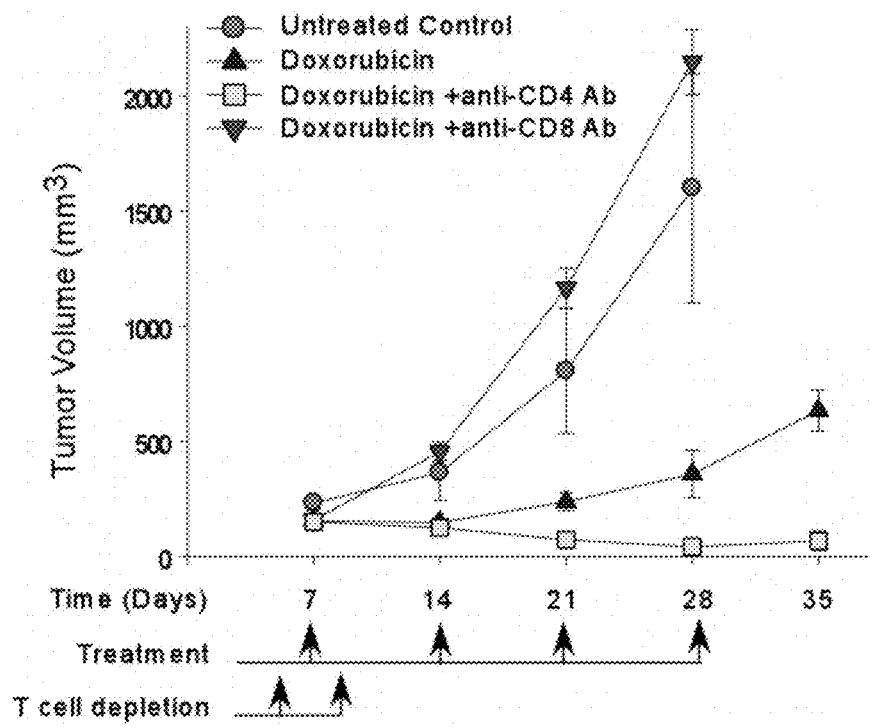

Anti-CD4 antibody-mediated depletion of CD4$^+$ regulatory T cells facilitates chemotherapy-induced activation of tumor-reactive CD8$^+$ T cells and enhances the antitumor efficacy of chemotherapy. To determine whether depletion of CD4$^+$ regulatory T cells can improve the antitumor efficacy of chemotherapy by enhancing the activity of CD8$^+$ T cells in the tumor microenvironment, immunocompetent mice bearing syngeneic tumors were administered an anti-CD4 antibody (Clone GK1.5) to deplete CD4$^+$ T cells or an anti-CD8 antibody (Clone GK2.43) to deplete CD8$^+$ T cells and then treated with specific chemotherapeutic agents. Flow cytometric analyses of peripheral blood mononuclear cells from MB49 tumor-bearing mice at d7 following administration of anti-CD4 antibody or anti-CD8 antibody confirmed the target-specific depletion of either CD4$^+$ T cells or CD8$^+$ T cells, respectively (FIG. 55A). Mice treated with anti-CD4 antibody showed loss of CD4$^+$CD25$^+$FoxP3$^+$ T cells in the peripheral blood as well as among tumor-infiltrating cells (FIGS. 55A, 55B). To determine whether antibody-mediated depletion of CD4$^+$CD25$^+$FoxP3$^+$ cells facilitates chemotherapy-induced activation of tumor-reactive CD8$^+$ T cells in the tumor microenvironment, we evaluated the expression of IFN-γ in CD8$^+$ T cells extracted from the tumor and draining lymph node of MB49 tumor-bearing mice that were left untreated or treated with doxorubicin (with or without anti-CD4 antibody). Flow cytometric analyses showed that CD8$^+$ T cells from untreated mice did not express IFN-γ in response to in vitro re-challenge with MB49 cell lysates (FIG. 55C). Whereas IFN-γ$^+$CD8$^+$ T cells became evident in mice treated with doxorubicin alone, antibody-mediated depletion of CD4$^+$ T cells further enhanced the percentage of tumor-reactive CD8$^+$ T cells that expressed IFN-γ in doxorubicin-treated animals (FIG. 55C). To directly evaluate whether the activation of tumor-reactive CD8$^+$ T cells determines the in vivo antitumor efficacy of chemotherapy, we examined the effect of antibody-mediated depletion of CD8$^+$ T cells or CD4$^+$ T cells on the response of MB49 tumor-bearing mice to systemic treatment with doxorubicin (5 mg/kg). Treatment with doxorubicin alone inhibited the growth of MB49 tumors but failed to arrest tumor progression. Whereas depletion of CD8$^+$ T cells completely impaired the in vivo antitumor efficacy of doxorubicin, depletion of CD4$^+$ T cells enhanced the response to doxorubicin and resulted in tumor regression (FIG. 55D).

Figure 56D:
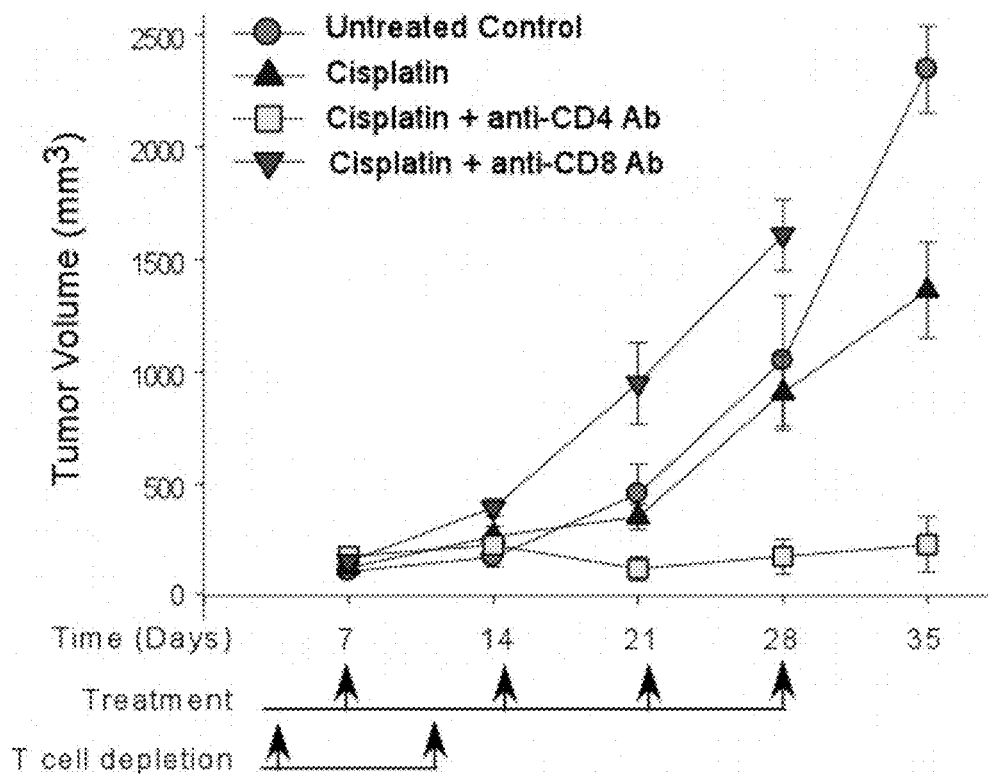
Figure 56E:
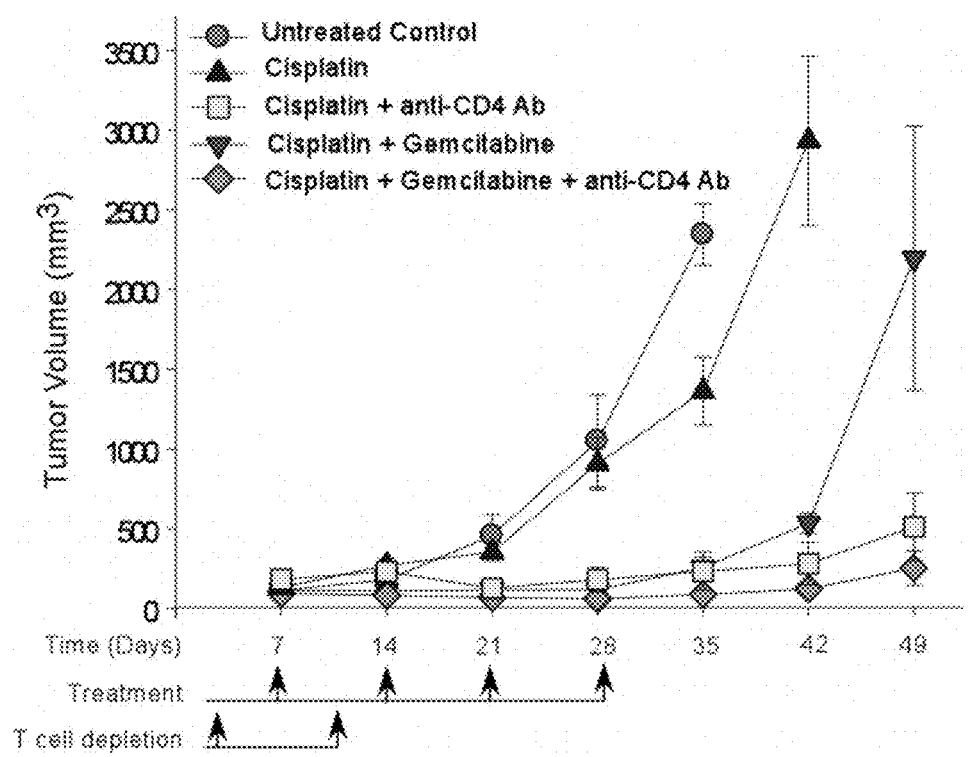
Figure 56F:
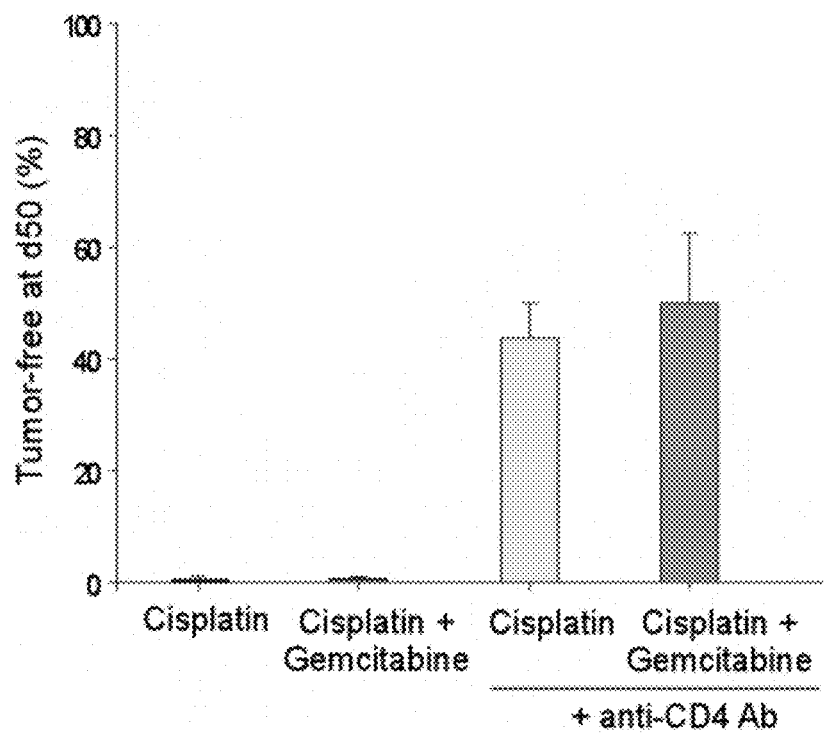

Anti-CD4 antibody-mediated depletion of CD4$^+$ regulatory T cells augments and sustains the antitumor effect of chemotherapy by enabling activation of adaptive antitumor immunity. Whereas tumor cells treated with anthracyclins, such as doxorubicin, are particularly effective in eliciting an antitumor immune response, other chemotherapeutic agents are less effective in inducing immunogenic tumor cell death. The surface exposure of calreticulin is a key determinant of the immunogenicity of tumor cell death in response to chemotherapeutic agents. Compared to the efficient translocation of CRT to the cell surface in response to treatment with doxorubicin (FIG. 1A), treatment of MB49 tumor cells with equitoxic doses of either cisplatin or the combination of cisplatin and gemcitabine was less effective in increasing CRT exposure (FIG. 56A). Whereas tumor-reactive IFN-γ$^+$ CD8$^+$ T cells were evident in tumors of MB49 tumor-bearing mice treated with doxorubicin (FIG. 55C), treatment with cisplatin was unable to induce a corresponding elevation of IFN-γ expression in CD8$^+$ T cells in response to in vitro re-challenge with MB49 cell lysates (FIG. 56B). To examine whether counteraction of Treg-mediated immune tolerance enables the activation of antitumor immunity by cisplatin, immunocompetent tumor-bearing mice were treated with cisplatin following depletion of Tregs with anti-CD4 antibody. Antibody-mediated depletion of CD4$^+$ T cells enhanced the percentage of tumor-reactive IFN-γ$^+$ CD8$^+$ T cells as well as CD8$^+$CD62L$^-$ T cells in cisplatin-treated animals (FIGS. 56B, 56C). Treatment of MB49 tumor-bearing mice with cisplatin partially inhibited tumor growth but failed to arrest tumor progression. Whereas depletion of CD8$^+$ T cells completely negated the in vivo antitumor effect of cisplatin, depletion of CD4$^+$ T cells enhanced the response to cisplatin and arrested tumor growth (FIG. 56D). Although treatment of tumor-bearing mice with the combination of cisplatin and gemcitabine was also able to arrest tumor growth, tumor growth rapidly resumed following termination of therapy with none of the animals (0/8) being tumor-free at d50 following tumor inoculation (FIG. 56E). In contrast, mice depleted of CD4$^+$ T cells exhibited a more sustained response to either single agent or combination chemotherapy, with 7/16 mice exhibiting complete tumor regression. The complete regression of tumors was attended with establishment of adaptive antitumor immunity since none of the cured mice (7/7) developed tumors when re-challenged with live MB49 tumor cells in the opposite flank.

Figure 57A:
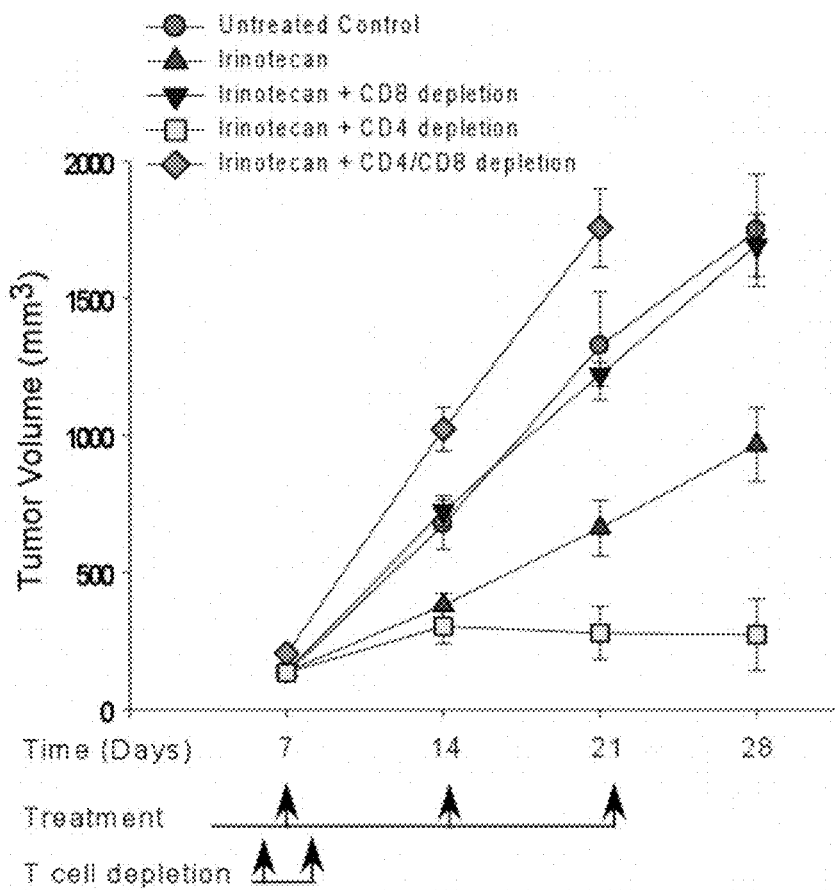
Figure 57B:
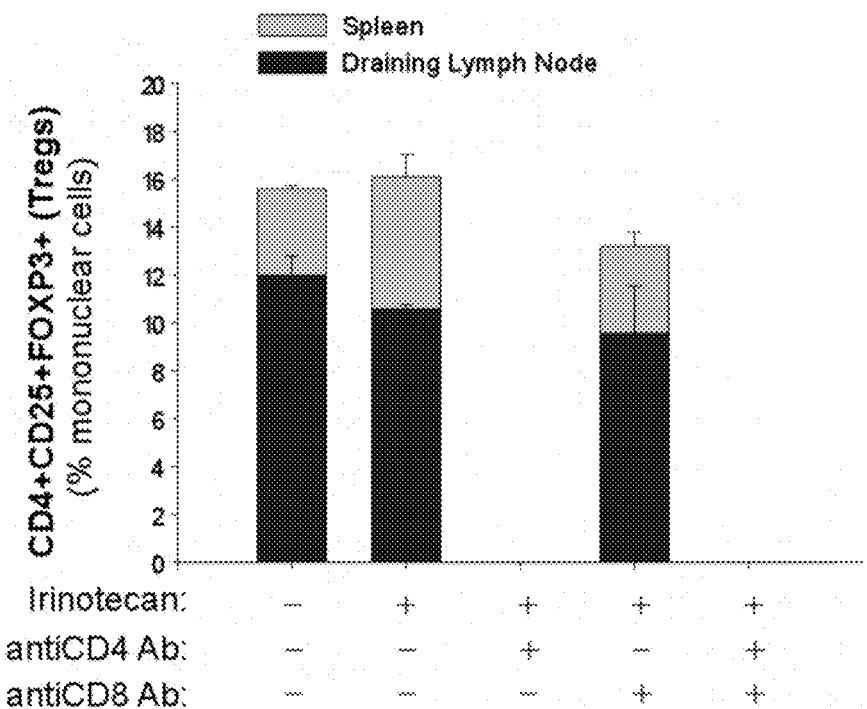
Figure 57C:
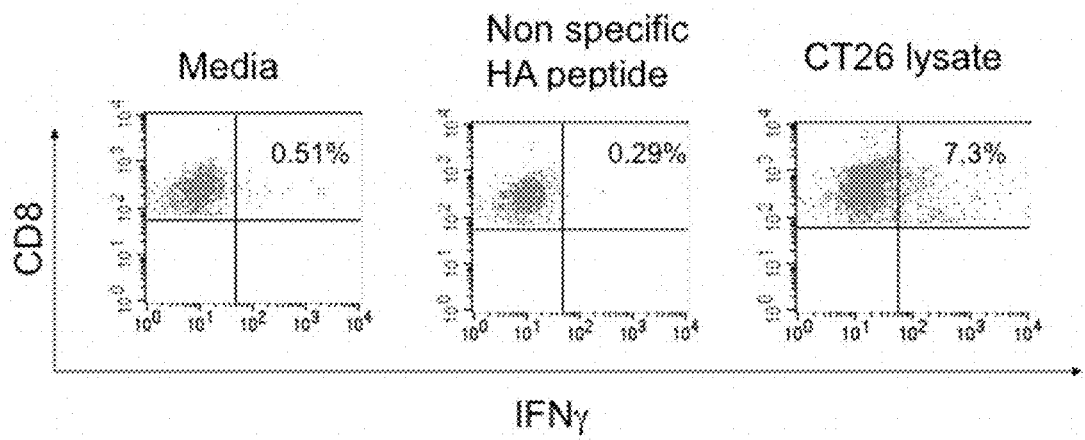
Figure 57D:
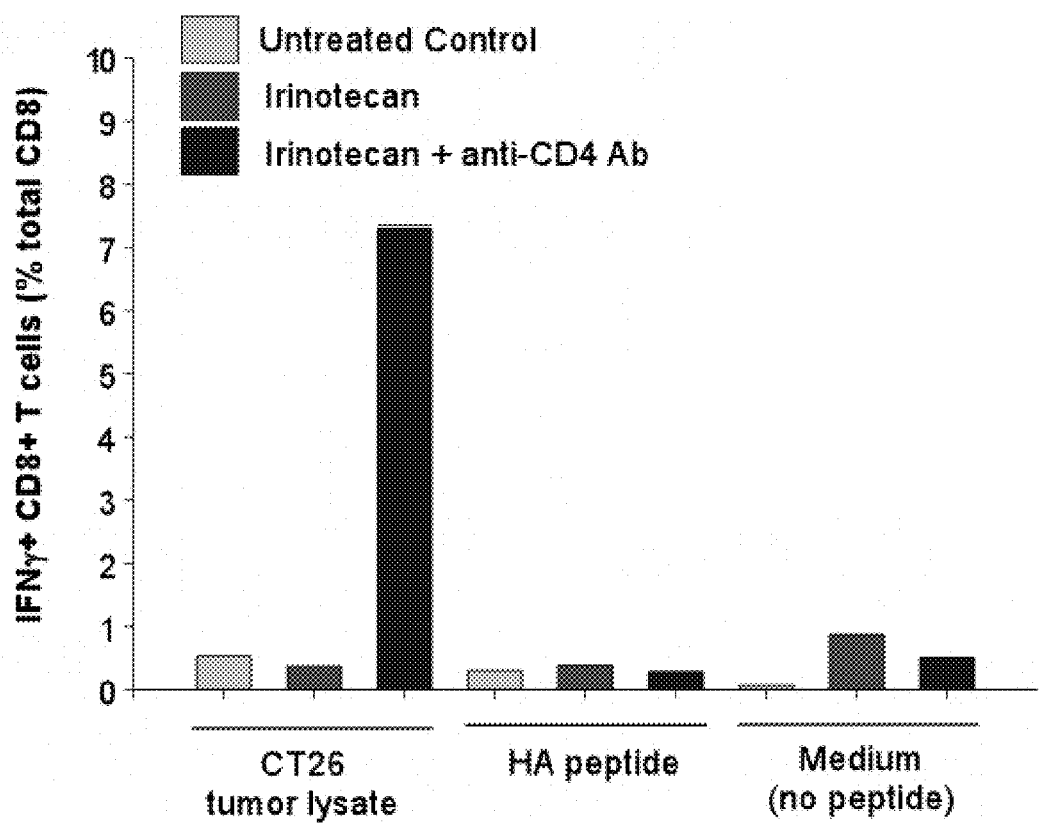
Figure 57E:
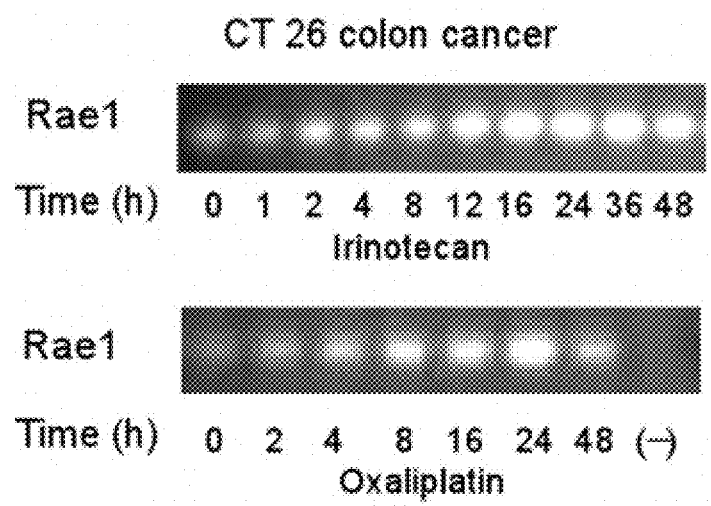
Figure 57F:
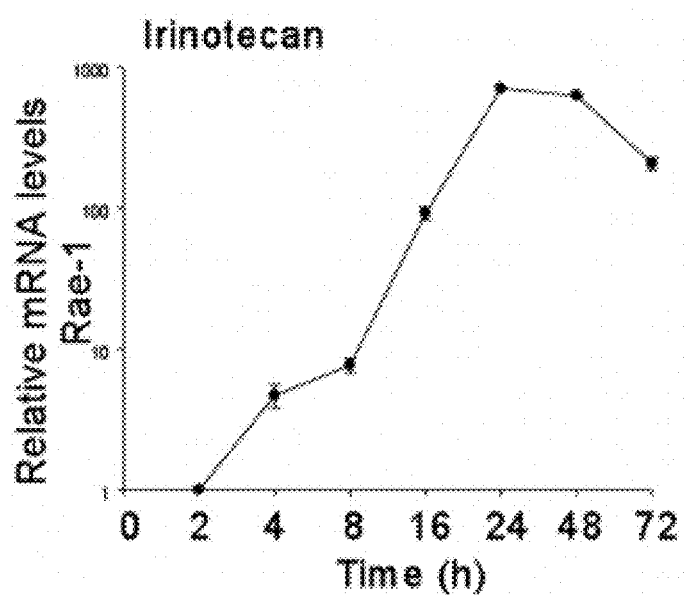
Figure 57G:
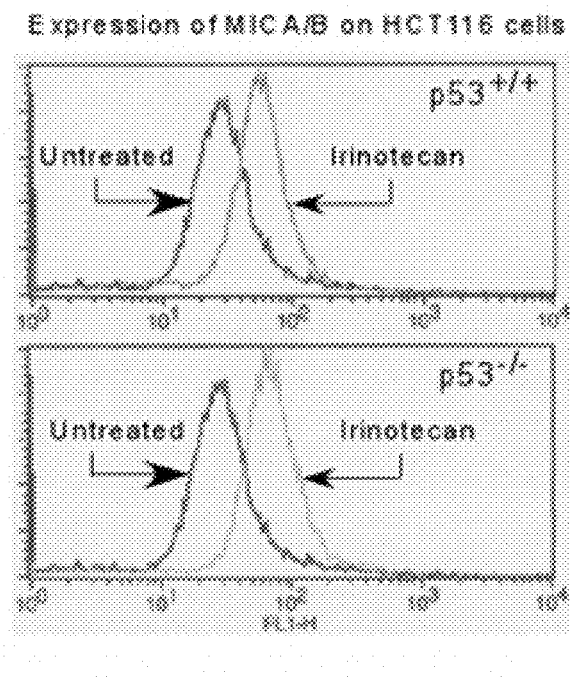
Figure 57H:
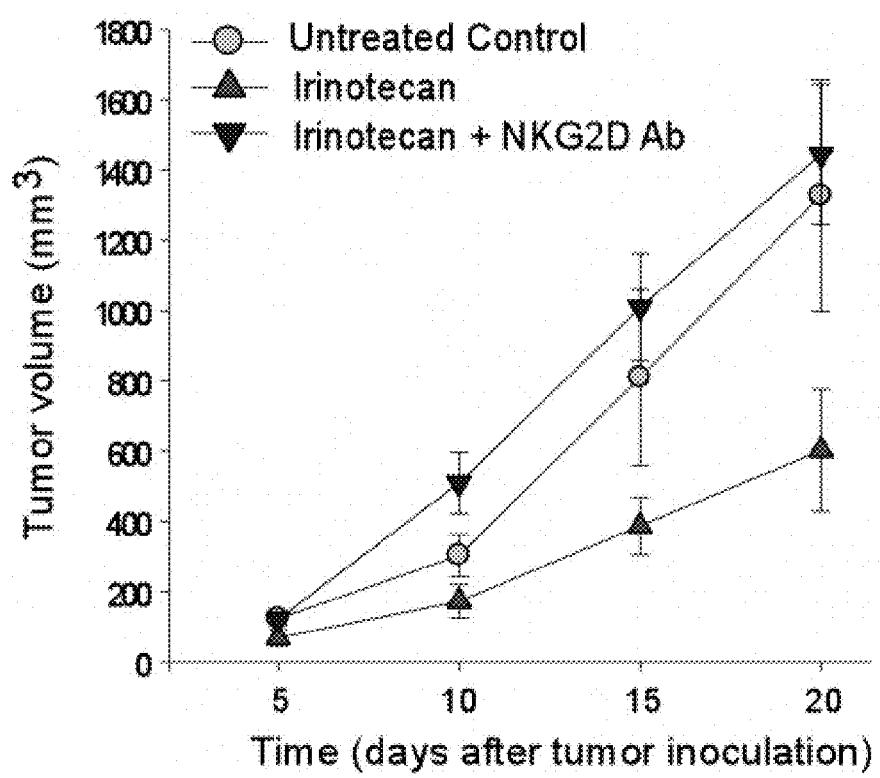

Chemotherapy-induced expression of NKG2D ligands on tumor cells cooperates with depletion of CD$^{4+}$ regulatory T cells to stimulate CD$^{8+}$ T cell-mediated tumor regression. NKG2D (NK group 2, member D) is a lectin-like type II transmembrane stimulatory receptor used by NK cells, γδ-TC$^{R+}$ T cells and αβ-TC$^{R+}$ T cells for immune surveillance of tumors. Expression of mouse and human ligands for NKG2D is upregulated in transformed epithelial cell lines in response to genotoxic stress or stalled DNA replication, via activation of a DNA damage checkpoint pathway initiated by ATM (ataxia telengiectasia, mutated) or ATR (ATM- and Rad3-related) protein kinases. Treatment of CT26 mouse colon cancer cells with genotoxic chemotherapeutic agents resulted in upregulation of mouse NKG2D ligands of the retinoic acid inducible gene family (Rae1) (FIG. 57A). RT-PCR showed that Rae1 mRNA was induced in CT26 cells by 2-4 h, reached a plateau after 16-24 h, and began to decline after 48 h of treatment with either the irinotecan or oxaliplatin (FIG. 57A). Flow cytometric analysis demonstrated that cell surface expression of human NKG2D ligands (MHC-I-related A and B molecules—MICA, MICB) was also upregulated on human colorectal cancer cells (HCT116) in response to treatment with irinotecan (FIG. 53B). Isogenic HCT116 cells that differ only in their p53 status demonstrated that p53 is not required for irinotecan-induced upregulation of MICA/B (FIG. 53B). To examine whether the induction of NKG2D ligands contributes to the antitumor effect of chemotherapy in vivo, immunocompetent Balb/C mice inoculated with syngeneic CT26 tumor cells were treated with irinotecan (50 mg/kg i.p) with or without pre-treatment with an NKG2D blocking antibody (200 μg i.p.). Whereas treatment with irinotecan alone inhibited the growth of CT26 tumors, the antitumor effect of irinotecan was negated by pre-treatment with the NKG2D blocking antibody (FIG. 1C). Since engagement of NKG2D by its ligands provides a costimulatory signal for the activation of CD$^{8+}$ T cells, we investigated whether DNA damage-induced expression of NKG2D ligands on tumor cells cooperates with depletion of CD$^{4+}$ regulatory T cells to stimulate CD$^{8+}$ T cell-mediated tumor regression. Balb/C mice bearing CT26 tumors were administered an anti-CD4 antibody (Clone GK1.5) to deplete CD$^{4+}$ T cells and/or an anti-CD8 antibody (Clone GK2.43) to deplete CD$^{8+}$ T cells and then treated with irinotecan. Flow cytometric analyses confirmed the loss of CD$^{4+}$CD2$^{5+}$FoxP$^{3+}$ T cells in the spleen and draining lymph node of mice treated with anti-CD4 antibody (FIG. 57D). Antibody-mediated depletion of CD$^{4+}$ T cells enhanced the percentage of tumor-reactive IFN-$^{\gamma+}$CD$^{8+}$ T cells in irinotecan-treated animals (FIG. 57E). Whereas treatment of CT26 tumor-bearing mice with irinotecan only slowed tumor growth, depletion of CD$^{4+}$ T cells enhanced the response to irinotecan and arrested tumor growth (FIG. 57F). The ability of CD$^{4+}$ T cell depletion to augment the antitumor efficacy of irinotecan was mediated by CD$^{8+}$ T cells since antibody-mediated depletion of CD$^{8+}$ T cells completely negated the in vivo antitumor effect of chemotherapy in CD$^{4+}$ T cell-depleted mice (FIG. 57F).

These data provide the following insights: (i) activation of tumor-reactive CD8$^+$ T cells in response to immunogenic tumor cell death is a crucial determinant of the antitumor efficacy of chemotherapy in vivo; (ii) tumor-induced Tregs impair the antitumor efficacy of chemotherapy by inhibiting the activation of CD8$^+$ T cells in the tumor microenvironment; and (iii) Counteracting tumor-induced immune tolerance via antibody-mediated depletion of CD4$^+$ regulatory T cells facilitates chemotherapy-induced activation of antitumor immunity with memory, thereby enhancing the antitumor efficacy of chemotherapy; (iv) Strategies to decrease the number or function of CD4+ regulatory T cells in the tumor microenvironment can increase the activation of CD8+ T cells and improve the response of tumors to cytotoxic anticancer agents (chemotherapy, tumor-targeted antibodies, targeted therapeutics, kinase inhibitors) or chemoimmunotherapy (combination of chemotherapeutic agent with immunotherapeutic agents).

Example 2

Exemplary Targeted Immunomodulatory Antibodies and Fusion Proteins

A targeting moiety, including an antibody, can be coupled to an immunomodulatory moiety including a polypeptide derived from the extracellular domain of TGFBR2. Cross-linkers or activating agents for such coupling or conjugation are well known in the art. Alternatively, the fusion proteins of the invention can be synthesized using recombination DNA technology well known in the art where the coding sequences of various portions of the fusion proteins can be linked together at the nucleic acid level. Subsequently the fusion proteins of the invention can be produced using a host cell well known in the art. Examples of targeted immunomodulatory antibodies and fusion proteins are shown in FIGS. 1-33 and briefly described below.

In one embodiment, the present invention provides a molecule including a targeting moiety fused with an immunomodulatory moiety, wherein the targeting moiety specifically binds to a target molecule, and the immunomodulatory moiety specifically binds to Transforming growth factor-beta (TGF-β). SEQ ID NO: 1 provides a fusion protein including anti-HER2/neu antibody and Transforming growth factor-beta receptor II (TGFβ-RII) Extracellular domain (ECD) (FIG. 2). SEQ ID NO: 2 provides a fusion protein including anti-EGFR1 antibody and Transforming growth factor-beta receptor II (TGFβ-RII) Extracellular domain (ECD) (FIG. 3). SEQ ID NO: 3 provides a fusion protein including anti-CD20 antibody and Transforming growth factor-beta receptor II (TGFβ-RII) Extracellular domain (ECD) (FIG. 4). SEQ ID NO: 4 provides a fusion protein including anti-VEGF antibody and Transforming growth factor-beta receptor II (TGFβ-RII) Extracellular domain (ECD) (FIG. 5). SEQ ID NO: 5 provides a fusion protein including anti-human CTLA-4 antibody and Transforming growth factor-beta receptor II (TGFβ-RII) Extracellular domain (ECD) (FIG. 6). SEQ ID NO: 6 provides a fusion protein including IL-2, Fc, and Transforming growth factor-beta receptor II (TGFβ-RII) Extracellular domain (ECD) (FIG. 7). SEQ ID NO: 7 provides a fusion protein including Transforming growth factor-beta receptor II (TGFβ-RII) Extracellular domain (ECD), Fc, and IL-2 (FIG. 7). SEQ ID NO: 8 provides a fusion protein including anti-CD25 antibody and Transforming growth factor-beta receptor II (TGFβ-RII) Extracellular domain (ECD) (FIG. 8A). SEQ ID NO: 9 provides a fusion protein including anti-CD25 antibody and Transforming growth factor-beta receptor II (TGFβ-RII) Extracellular domain (ECD) (FIG. 8B). SEQ ID NO: 10 provides a fusion protein including anti-CD4 antibody and Transforming growth factor-beta receptor II (TGFβ-RII) Extracellular domain (ECD) (FIG. 9). SEQ ID NO: 11 provides a fusion protein including PD-1 Ectodomain, Fc, and Transforming growth factor-beta receptor II (TGFβ-RII) Extracellular domain (ectodomain) (PD-1 ectodomain+Fc+TGFβRII ectodomain; FIG. 10). SEQ ID NO: 12 provides a fusion protein including Transforming growth factor-beta receptor II (TGFβ-RII) Extracellular domain (ectodomain), Fc, and PD-1 Ectodomain (TGFβRII ectodomain+Fc+PD-1 ectodomain; FIG. 10). SEQ ID NO: 13 provides a fusion protein including RANK Ectodomain, Fc, and Transforming growth factor-beta receptor II (TGFβ-RII) Extracellular domain (ectodomain) (RANK ectodomain+Fc+TGFβRII ectodomain; FIG. 11). SEQ ID NO: 14 provides a fusion protein including Transforming growth factor-beta receptor II (TGFβ-RII) Extracellular domain (ectodomain), Fc, and RANK Ectodomain (TGFβRII ectodomain+Fc+RANK ectodomain; FIG. 11).

In another embodiment, the present invention provides a molecule including a targeting moiety fused with an immunomodulatory moiety, wherein the targeting moiety specifically binds to a target molecule, and the immunomodulatory moiety is a molecule that specifically binds to Programmed Death-1 ligand 1 (PD-L1 or B7-H1) or Programmed Death-1 ligand 2 (PD-L2 or B7-DC). SEQ ID NO: 15 provides a fusion protein including anti-HER2/neu antibody and PD-1 Ectodomain (FIG. 13). SEQ ID NO: 16 provides a fusion protein including anti-EGFR1 antibody and PD-1 Ectodomain (FIG. 14). SEQ ID NO: 17 provides a fusion protein including anti-CD20 antibody and PD-1 Ectodomain (FIG. 15). SEQ ID NO: 18 provides a fusion protein including anti-VEGF antibody and PD-1 Ectodomain (FIG. 16). SEQ ID NO: 19 provides a fusion protein including anti-human CTLA-4 antibody and PD-1 Ectodomain (FIG. 17). SEQ ID NO: 20 provides a fusion protein including anti-CD25 antibody and PD-1 Ectodomain (FIG. 18A). SEQ ID NO: 21 provides a fusion protein including anti-CD25 antibody and PD-1 Ectodomain (FIG. 18B). SEQ ID NO: 22 provides a fusion protein including IL-2, Fc, and PD-1 ectodomain (IL-2+Fc+PD-1 ectodomain; FIG. 19). SEQ ID NO: 23 provides a fusion protein including PD-1 ectodomain, Fc, and IL-2 (PD-1 ectodomain+Fc+IL-2; FIG. 19). SEQ ID NO: 24 provides a fusion protein including anti-CD4 antibody and PD-1 Ectodomain (FIG. 20). SEQ ID NO: 25 provides a fusion protein including RANK Ectodomain, Fc, and PD-1 ectodomain (RANK ectodomain+Fc+PD-1 ectodomain; FIG. 21). SEQ ID NO: 26 provides a fusion protein including PD-1 ectodomain, Fc, and RANK Ectodomain (PD-1 ectodomain+Fc+RANK ectodomain; FIG. 21).

In another embodiment, the present invention provides a molecule including a targeting moiety fused with an immunomodulatory moiety, wherein the targeting moiety specifically binds to a target molecule, and the immunomodulatory moiety is a molecule that specifically binds to Receptor activator of NF-KB ligand (RANKL). SEQ ID NO: 27 provides a fusion protein including anti-HER2/neu antibody and RANK Ectodomain (FIG. 23). SEQ ID NO: 28 provides a fusion protein including anti-EGFR1 antibody and RANK Ectodomain (FIG. 24). SEQ ID NO: 29 provides a fusion protein including anti-CD20 antibody and RANK Ectodomain (FIG. 25). SEQ ID NO: 30 provides a fusion protein including anti-VEGF antibody and RANK Ectodomain (FIG. 26). SEQ ID NO: 31 provides a fusion protein including anti-human CTLA-4 antibody and RANK Ectodomain (FIG. 27). SEQ ID NO: 32 provides a fusion protein including anti-CD25 antibody and RANK Ectodomain (FIG. 28A). SEQ ID NO: 33 provides a fusion protein including anti-CD25 antibody and RANK Ectodomain (FIG. 28B). SEQ ID NO: 34 provides a fusion protein including IL-2, Fc, and RANK ectodomain (IL-2+Fc+RANK ectodomain; FIG. 29). SEQ ID NO: 35 provides a fusion protein including RANK ectodomain, Fc, and IL-2 (RANK ectodomain+Fc+IL-2; FIG. 29). SEQ ID NO: 36 provides a fusion protein including anti-CD4 antibody and RANK Ectodomain (FIG. 30).

In another embodiment, the present invention provides a molecule including a targeting moiety fused with an immunomodulatory moiety, wherein the targeting moiety specifically binds to a target molecule, and the immunomodulatory moiety includes a molecule that specifically binds to Programmed death-1 (PD-1). SEQ ID NO: 37 provides a fusion protein including anti-tumor necrosis factor (TNFα) antibody and PD-1 ligand 1 (FIG. 32). SEQ ID NO: 38 provides a fusion protein including TNFR2 Extracellular ligand binding domain, Fc, and PD-1 ligand: (TNFR2 ECD+IgG Cγ1+PD-L1; FIG. 33). SEQ ID NO: 39 provides a fusion protein including PD-1 ligand, Fc, and TNFR2 Extracellular ligand binding domain: (PD-L1+IgG Cγ1-TNFR2 ECD; FIG. 33). SEQ ID NO: 40 provides a fusion protein including anti-CD20 antibody and PD-1 ligand 1 (PD-L1) (FIG. 34). SEQ ID NO: 41 provides a fusion protein including anti-CD25 antibody and PD-1 ligand 1 (PD-L1) (FIG. 35A). SEQ ID NO: 42 provides a fusion protein including anti-CD25 antibody and PD-1 ligand 1 (PD-L1) (FIG. 35B). SEQ ID NO: 43 provides a fusion protein including PD-1 ligand 1 (PD-L1), Fc, and IL-2 (PD-L1-Fc-IL2; FIG. 36). SEQ ID NO: 44 provides a fusion protein including IL-2, Fc, and PD-1 ligand 1 (PD-L1) (IL-2-Fc-PD-L1; FIG. 36). SEQ ID NO: 45 provides a fusion protein including anti-CD4 antibody and PD-1 ligand 1 (PD-L1) (FIG. 37). SEQ ID NO: 46 provides a fusion protein including the extracellular domain of CTLA-4, Immunoglobulin Fc (IgG Cγ1), and a sequence from PD-1 ligand (PD-L1) (Oncostatin M signal peptide+CTLA-4 ECD+IgG Cγ1+PD-L1; FIG. 38). SEQ ID NO: 47 provides a fusion protein including the extracellular domain of PD-1 ligand (PD-L1), immunoglobulin Fc (IgG Cγ1), and a sequence from the extracellular domain of CTLA-4: (PD-L1+IgG Cγ1+CTLA-4 ECD; FIG. 38). SEQ ID NO: 48 provides a fusion protein including Transforming growth factor-β (TGF-β), immunoglobulin Fc (IgG Cγ1), and a sequence from PD-1 ligand 1 (PD-L1) (TGFβ-1+Fc+PD-L1; FIG. 39). SEQ ID NO: 49 provides a fusion protein including a sequence from PD-1 ligand 1 (PD-L1), immunoglobulin Fc (IgG Cγ1), and Transforming growth factor beta (TGF-□β) (PD-L1+Fc+TGFβ-1; FIG. 39).

In another embodiment, the present invention provides a molecule including a targeting moiety fused with an immunomodulatory moiety, wherein the targeting moiety specifically binds to a target molecule, and the immunomodulatory moiety includes a molecule that specifically binds to Transforming growth factor-beta receptor (TGF-βR). SEQ ID NO: 50 provides a fusion protein including an antibody that binds TNF-α, and a sequence from Transforming growth factor-β (TGF-β) (FIG. 41). SEQ ID NO: 51 provides a fusion protein including TNFR2 Extracellular ligand binding domain, Fc, and a sequence from Transforming growth factor-β (TGF-β) (TNFR2 ECD+IgG Cγ1+TGF-β; FIG. 42). SEQ ID NO: 52 provides a fusion protein including a sequence from Transforming growth factor-β (TGF-β), Fc, and TNFR2 Extracellular ligand binding domain: (TGF-β+IgG Cγ1+TNFR2 ECD; FIG. 42). SEQ ID NO: 53 provides a fusion protein including anti-CD20 antibody and a sequence from Transforming growth factor-β (TGF-β) (FIG. 43). SEQ ID NO: 54 provides a fusion protein including anti-CD25 antibody and a sequence from transforming growth factor-β (TGF-β) (FIG. 44A). SEQ ID NO: 55 provides a fusion protein including anti-CD25 antibody and a sequence from transforming growth factor-β (TGF-β) (FIG. 44B). SEQ ID NO: 56 provides a fusion protein including a sequence from Transforming growth factor-β (TGF-β), Fc, and IL-2 (TGF-β+Fc+IL-2; FIG. 45). SEQ ID NO: 57 provides a fusion protein including IL-2, Fc, and Transforming growth factor-β (TGF-β) (IL-2+Fc+TGF-β; FIG. 45). SEQ ID NO: 58 provides a fusion protein including anti-CD4 antibody and a sequence from transforming growth factor-β (TGF-β) (FIG. 46). SEQ ID NO: 59 provides a fusion protein including the extracellular domain of CTLA-4, immunoglobulin Fc (IgG Cγ1), and a sequence from a sequence from transforming growth factor-β (TGF-β) (Oncostatin M signal peptide+CTLA-4 ECD+IgG Cγ1+TGF-β1; FIG. 47). SEQ ID NO: 60 provides a fusion protein including a sequence from Transforming growth factor-β (TGF-β), immunoglobulin Fc (IgG Cγ1), and a sequence from the extracellular domain of CTLA-4: (TGF-β1+IgG Cγ1+CTLA-4 ECD) (FIG. 47).

In another embodiment, the present invention provides a molecule including a targeting moiety fused with an immunomodulatory moiety, wherein the targeting moiety specifically binds to a target molecule, and the immunomodulatory moiety is a molecule that specifically binds to Receptor activator of NF-kB ligand (RANKL). SEQ ID NO: 61 provides a fusion protein including an antibody that binds TNF-α, and a sequence from RANK Ectodomain (FIG. 48). SEQ ID NO: 62 provides a fusion protein including TNFR2 Extracellular ligand binding domain, Fc, and a sequence from RANK Ectodomain (TNFR2 ECD+IgG Cγ1+RANK Ectodomain; FIG. 49). SEQ ID NO: 63 provides a fusion protein including a sequence from RANK Ectodomain, Fc, and TNFR2 Extracellular ligand binding domain: (RANK Ectodomain+IgG Cγ1+TNFR2 ECD; FIG. 49). SEQ ID NO: 64 provides a fusion protein including the extracellular domain of CTLA-4, immunoglobulin Fc (IgG Cγ1), and a sequence from a sequence from RANK Ectodomain (Oncostatin M signal peptide+CTLA-4 ECD+IgG Cγ1+RANK Ectodomain; FIG. 50). SEQ ID NO: 65 provides a fusion protein including a sequence from RANK Ectodomain, immunoglobulin Fc (IgG Cγ1), and a sequence from the extracellular domain of CTLA-4: (RANK Ectodomain+IgG Cγ1+CTLA-4 ECD) (FIG. 50). SEQ ID NO: 66 provides a fusion protein including a sequence from transforming growth factor-β (TGF-β), immunoglobulin Fc region (IgG Cγ1), and an extracellular ligand-binding domain or ectodomain of Receptor activator of nuclear factor-κB (RANK) (TGF-β+IgG Cγ1+RANK Ectodomain; FIG. 51). SEQ ID NO: 67 provides a fusion protein including a sequence from RANK Ectodomain, immunoglobulin Fc (IgG Cγ1), and a sequence from transforming growth factor-β (TGF-β): (RANK Ectodomain+IgG Cγ1+TGF-β) (FIG. 51). SEQ ID NO: 68 provides a fusion protein including a sequence from Programmed death-1 ligand 1 (PD-L1), immunoglobulin Fc region (IgG Cγ1), and an extracellular ligand-binding domain or ectodomain of Receptor activator of nuclear factor-κB (RANK) (PD-L1+IgG Cγ1+RANK Ectodomain; FIG. 52). SEQ ID NO: 69 provides a fusion protein including a sequence from RANK Ectodomain, immunoglobulin Fc (IgG Cγ1), and a sequence from Programmed death-1 ligand 1 (PD-L1): (RANK Ectodomain+IgG Cγ1+PD-L1) (FIG. 52).

Although the invention has been described with reference to the above example, it will be understood that modifications and variations are encompassed within the spirit and scope of the invention. Accordingly, the invention is limited only by the following claims.

What is claimed is:

1. An isolated molecule comprising:
   (a) a targeting moiety comprising an antibody or antibody fragment thereof, comprising amino acids 1-119 of SEQ ID NO: 2 and the amino acid sequence of SEQ ID NO: 71, which specifically binds Epidermal Growth Factor Receptor (EGFR); and
   (b) an immunomodulatory moiety comprising an amino acid sequence of the extracellular domain of Transforming growth factor-beta receptor II (TGF-βRII) comprising the amino acid sequence of SEQ ID NO: 87.

2. The molecule of claim 1, wherein the targeting moiety comprises an antibody fragment selected from a Fab or scFv.

3. The molecule of claim 2, wherein the antibody fragment comprises a light chain domain or a variable heavy chain domain.

4. The molecule of claim 3, wherein the antibody fragment comprises a light chain domain comprising the amino acid sequence of SEQ ID NO: 71.

5. The molecule of claim 4, further comprising a polypeptide linker comprising the amino acid sequence of SEQ ID NO: 104.

6. The molecule of claim 5, wherein the light chain domain comprising the amino acid sequence of SEQ ID NO: 71 is fused to an N-terminus of the polypeptide linker comprising the amino acid sequence of SEQ ID NO: 104.

7. The molecule of claim 6, wherein the immunomodulatory moiety comprising the amino acid sequence of SEQ ID NO: 87 is fused to a C-terminus of the polypeptide linker comprising the amino acid sequence of SEQ ID NO: 104.

8. The molecule of claim 3, wherein the variable heavy chain domain comprises amino acids 1-119 of SEQ ID NO: 2.

9. An isolated molecule comprising:
   (a) a targeting moiety comprising an antibody fragment which specifically binds Epidermal Growth Factor Receptor (EGFR) comprising a light chain domain comprising the amino acid sequence of SEQ ID NO: 71 and a variable heavy chain domain comprising amino acids 1-119 of SEQ ID NO: 2;
   (b) an immunomodulatory moiety comprising an amino acid sequence of the extracellular domain of Transforming growth factor-beta receptor II (TGF-βRII) comprising the amino acid sequence of SEQ ID NO: 87; and
   (c) a polypeptide linker comprising the amino acid sequence of SEQ ID NO: 104;
   wherein the light chain domain comprising the amino acid sequence of SEQ ID NO: 71 is fused to an N-terminus of the polypeptide linker comprising the amino acid of SEQ ID NO: 104, and
   wherein the immunomodulatory moiety comprising the amino acid sequence of SEQ ID NO: 87 is fused to a C-terminus of the polypeptide linker comprising the amino acid sequence of SEQ ID NO: 104.

* * * * *